US012636369B2

(12) United States Patent
Kahvejian et al.

(10) Patent No.: US 12,636,369 B2
(45) Date of Patent: May 26, 2026

(54) COMPOSITIONS COMPRISING CIRCULAR POLYRIBONUCLEOTIDES FOR PROTEIN MODULATION AND USES THEREOF

(71) Applicant: Flagship Pioneering Innovations VI, LLC, Cambridge, MA (US)

(72) Inventors: Avak Kahvejian, Lexington, MA (US); Nicholas McCartney Plugis, Duxbury, MA (US); Alexandra Sophie De Boer, Somerville, MA (US)

(73) Assignee: Flagship Pioneering Innovations VI, LLC, Cambridge, MA (US)

( * ) Notice: Subject to any disclaimer, the term of this patent is extended or adjusted under 35 U.S.C. 154(b) by 1106 days.

(21) Appl. No.: 17/619,614

(22) PCT Filed: Jun. 19, 2020

(86) PCT No.: PCT/US2020/038838

§ 371 (c)(1),
(2) Date: Dec. 16, 2021

(87) PCT Pub. No.: WO2020/257730

PCT Pub. Date: Dec. 24, 2020

(65) Prior Publication Data

US 2022/0305128 A1 Sep. 29, 2022

Related U.S. Application Data

(60) Provisional application No. 62/878,220, filed on Jul. 24, 2019, provisional application No. 62/863,698, filed on Jun. 19, 2019.

(51) Int. Cl.

| | |
|---|---|
| ***A61K 47/54*** | (2017.01) |
| ***A61P 13/08*** | (2006.01) |
| ***A61P 15/00*** | (2006.01) |
| ***A61P 35/00*** | (2006.01) |

(52) U.S. Cl.

CPC ............ *A61K 47/549* (2017.08); *A61P 13/08* (2018.01); *A61P 15/00* (2018.01); *A61P 35/00* (2018.01)

(58) Field of Classification Search

CPC .................................................... A61K 47/549

See application file for complete search history.

(56) References Cited

U.S. PATENT DOCUMENTS

| | | | | |
|---|---|---|---|---|
| 5,426,180 | A * | 6/1995 | Kool | C12Q 1/703 536/24.31 |
| 10,953,033 | B2 | 3/2021 | Stewart et al. | |
| 11,058,706 | B2 | 7/2021 | Stewart et al. | |
| 11,160,822 | B2 | 11/2021 | De Boer et al. | |
| 11,458,156 | B2 | 10/2022 | De Boer et al. | |
| 11,756,183 | B2 | 9/2023 | Jaffrey et al. | |
| 11,981,909 | B2 | 5/2024 | Anderson et al. | |
| 2005/0176940 | A1 | 8/2005 | King | |
| 2015/0299702 | A1 | 10/2015 | Kjems et al. | |
| 2016/0201072 | A1 | 7/2016 | Cigan et al. | |
| 2018/0023079 | A1 | 1/2018 | Dimmeler et al. | |
| 2019/0307785 | A1 | 10/2019 | Stewart et al. | |
| 2019/0345503 | A1 | 11/2019 | Chang et al. | |
| 2019/0359983 | A1 | 11/2019 | O'Neill et al. | |
| 2020/0306286 | A1 | 10/2020 | Stewart et al. | |
| 2021/0292761 | A1 | 9/2021 | Kahvejian et al. | |
| 2022/0088049 | A1 | 3/2022 | Kahvejian et al. | |
| 2022/0142896 | A1 | 5/2022 | Kahvejian et al. | |
| 2022/0143062 | A1 | 5/2022 | Kahvejian et al. | |
| 2022/0257794 | A1 | 8/2022 | De Boer et al. | |
| 2022/0296729 | A1 | 9/2022 | Kahvejian et al. | |
| 2022/0305128 | A1 | 9/2022 | Kahvejian et al. | |
| 2023/0340451 | A1 | 10/2023 | Kahvejian et al. | |

FOREIGN PATENT DOCUMENTS

| | | | | |
|---|---|---|---|---|
| EP | 3054017 | A1 | 8/2016 | |
| WO | WO-2007/016507 | A2 | 2/2007 | |
| WO | WO-2011/088435 | A1 | 7/2011 | |
| WO | WO-2016/149668 | A1 | 9/2016 | |
| WO | WO-2017/214202 | A1 | 12/2017 | |
| WO | WO-2017222911 | A1 * | 12/2017 | ............. A61K 39/39 |
| WO | WO-2018/144854 | A1 | 8/2018 | |
| WO | WO-2019/118919 | A1 | 6/2019 | |
| WO | WO-2020/023655 | A1 | 1/2020 | |
| WO | WO-2020/180751 | A1 | 9/2020 | |
| WO | WO-2020/180752 | A1 | 9/2020 | |
| WO | WO-2020/181013 | A1 | 9/2020 | |
| WO | WO-2020/198403 | A2 | 10/2020 | |
| WO | WO-2020/252436 | A1 | 12/2020 | |
| WO | WO-2020/257727 | A1 | 12/2020 | |
| WO | WO-2020/257730 | A1 | 12/2020 | |
| WO | WO-2021/155171 | A1 | 8/2021 | |
| WO | WO-2021/155175 | A1 | 8/2021 | |
| WO | WO-2021/155177 | A1 | 8/2021 | |
| WO | WO-2021/236930 | A1 | 11/2021 | |
| WO | WO-2021/236952 | A1 | 11/2021 | |

(Continued)

OTHER PUBLICATIONS

Damgaard RB (2021, Cell Death and Differentiation, vol. 28, pp. 423-426) (Year: 2021).*

Delebecque et al., "Organization of intracellular reactions with rationally designed RNA assemblies," Science. 333(6041):470-4 (2011) (5 pages).

International Search Report and Written Opinion for International Patent Application No. PCT/US2020/038838, mailed Sep. 25, 2020 (12 pages).

International Search Report and Written Opinion for International Patent Application No. PCT/US2021/015746, mailed May 19, 2021 (11 pages).

Huang et al., "Circular RNA-protein interactions: functions, mechanisms, and identification," Theranostics. 10(8):3503-3517 (Feb. 2020).

Neklesa et al., "Targeted protein degradation by PROTACs," Pharmacol Ther. 174:138-144 (Jun. 2017).

(Continued)

*Primary Examiner* — Anoop K Singh
*Assistant Examiner* — David A Montanari
(74) *Attorney, Agent, or Firm* — Clark & Elbing LLP

(57) ABSTRACT

This invention relates to compositions comprising circular polyribonucleotides and uses thereof.

14 Claims, 22 Drawing Sheets

Specification includes a Sequence Listing.

(56) References Cited

FOREIGN PATENT DOCUMENTS

| | | | |
|---|---|---|---|
| WO | WO-2021/236980 | A1 | 11/2021 |
| WO | WO-2022/051629 | A1 | 3/2022 |

OTHER PUBLICATIONS

Lakhin et al., "Aptamers: problems, solutions and prospects," Acta Naturae. 5(4):34-43 (Oct. 2013).

Jost et al., "Functional sequestration of microRNA-122 from Heptatitis C Virus by circular RNA sponges," RNA Biology, 15(8):1032-1039 (Feb. 2018).

Dong et al., "In vivo inhibition of circulating tumor cells by two apoptosis-promoting circular aptamers with enhanced specificity," Journal of Controlled Release. 280:99-112 (May 2018).

Jiang et al., "Supramolecularly Engineered Circular Bivalent Aptamer for Enhanced Functional Protein Delivery," Journal of the American Chemical Society 140:6780-6784 (May 2018).

Holdt et al., "Circular RNAs as Therapeutic Agents and Targets," Frontiers in Physiology. 9(1262) (Oct. 2018) (16 pages).

Kuai et al., "Circular Bivalent Aptamers Enable in Vivo Stability and Recognition," J Am Chem Soc. 139(27):9128-9131 (Jun. 2017).

Di Giusto et al., "Construction, stability, and activity of multivalent circular anticoagulant aptamers," J Biol Chem. 279(45):46483-9 (Nov. 2004).

Umekage et al., "In vitro and in vivo production and purification of circular RNA aptamer," J Biotechnol. 139(4):265-72 (Feb. 2009).

Orang et al., "Mechanisms of miRNA-Mediated Gene Regulation from Common Downregulation to mRNA-Specific Upregulation," Int J Genomics. (15 pages) (Aug. 2014).

Hornblower et al., "Minding your caps and tails—considerations for functional mRNA synthesis," New England Biolabs (2023) (5 pages).

Di Giusto et al., "Multitasking by multivalent circular DNA aptamers," ChemBioChem 7(3):535-44 (Feb. 2006).

Esposito et al., "Multifunctional aptamer-miRNA conjugates for targeted cancer therapy," Mol Ther. 22(6):1151-1163 (Jun. 2014).

Chan et al., "Co-expression of anti-NFkappaB RNA aptamers and siRNAs leads to maximal suppression of NFkappaB activity in mammalian cells," Nucleic Acids Res. 34(5) (7 pages) (Mar. 2006).

Thapa et al., "Ubiquitin Signaling Regulates RNA Biogenesis, Processing, and Metabolism," Bioessays. 42(1):e1900171 (Nov. 2019) (10 pages).

* cited by examiner

SEQUENCE LISTING

<160> NUMBER OF SEQ ID NOS: 17

<210> SEQ ID NO 1
<211> LENGTH: 264
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 1
gggagccacc atggactaca aggacgacga cgacaagatc atcgactata aagacgacga 60
cgataaaggt ggcgactata aggacgacga cgacaaagcc attaatagtg actctgagtg 120
tcccctgtcc cacgacgggt actgcctcca cgacggtgtg tgcatgtata ttgaagcatt 180
ggacaagtac gcctgcaact gtgttgttgg ctacatcggg gagcgctgtc agtaccgaga 240
cctgaagtgg tgggaacagc gcca 264

<210> SEQ ID NO 2
<211> LENGTH: 90
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 2
ggaacggcaa ccgggcaaac aaacaatcaa tcaatcaatc aatcaatcaa tcaatcaatc 60
aatcaaacaa acaaaagacc gagagccacc 90

<210> SEQ ID NO 3
<211> LENGTH: 70
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 3
ggaatagccg aaaaacaaaa agatcttgaa actgttttaa ggttggccga tcaaaaacaa 60
aacggctatt 70

<210> SEQ ID NO 4
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: VARIANT
<222> LOCATION: (2)..(2)
<223> OTHER INFORMATION: /replace="Ile"
<220> FEATURE:
<221> NAME/KEY: MOD_RES
<222> LOCATION: (4)..(4)
<223> OTHER INFORMATION: Any amino acid
<220> FEATURE:
<221> NAME/KEY: SITE
<222> LOCATION: (1)..(8)
<223> OTHER INFORMATION: /note="Variant residues given in the sequence have no preference with respect to those in the annotations for variant positions"

<400> SEQUENCE: 4

Asp Val Glu Xaa Asn Pro Gly Pro
1               5

<210> SEQ ID NO 5
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 5
tacgcctgca actgtgttgt 20

<210> SEQ ID NO 6
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 6
tcgatgatct tgtcgtcgtc 20

<210> SEQ ID NO 7
<211> LENGTH: 51
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 7
ucauaaucaa uuuauuauuu ucuuuuauuu uauucacaua auuuuguuuu u 51

<210> SEQ ID NO 8
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 8
auuuuguuuu uaacauuuc 19

<210> SEQ ID NO 9
<211> LENGTH: 70
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 9
ucauaaucaa uuuauuauuu ucuuuuauuu uauucacaua auuuuguuuu uauuuuguuu 60
uuaacauuuc 70

<210> SEQ ID NO 10
<211> LENGTH: 119
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 10
caauaaugga ggcaauggua ugacuccaag ugcuauuguc acagaugaaa uuggcaguau 60
ugaccuuaua cuaaaaggca gggguuaaaa augauuauau acauuuuccu uaaaacacu 119

<210> SEQ ID NO 11
<211> LENGTH: 49
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 11
aaaaaaaaaa gatcttgaaa ctgttttaag gttggccgat cttaaaaaa 49

<210> SEQ ID NO 12
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 12
aaaaaaattc tccgaacgtg tcacgtttca agagaacgtg acacgttcgg agaaaaaaaa 60

<210> SEQ ID NO 13
<211> LENGTH: 232
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"
<220> FEATURE:
<221> NAME/KEY: source
<223> OTHER INFORMATION: /note="Description of Combined DNA/RNA
Molecule: Synthetic polynucleotide"

<400> SEQUENCE: 13
aatagccggu cuacggccau accacccuga acgcgcccga ucucgucuga ucucggaagc 60
uaagcagggu cgggccuggu uaguacuugg augggagacc gccugggaau accgggugcu 120
guaggcgucg acuugccaug uguauguggg uacgaaggaa ggauugguau gugguauauu 180
cguacccaca uacucugaug auccuucggg aucauucaug gcaacggcta tt 232

<210> SEQ ID NO 14
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 14

-continued

```
cgagacgcta cggacttaaa atccgttgac                                    30


<210> SEQ ID NO 15
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15

ggtggctccc tggcgctgtt                                               20


<210> SEQ ID NO 16
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 16

cccggttgcc gttccaatag ccgttttg                                      28


<210> SEQ ID NO 17
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 17

gtttttcggc tattccggtg gctctcggtc t                                  31
```

COMPOSITIONS COMPRISING CIRCULAR POLYRIBONUCLEOTIDES FOR PROTEIN MODULATION AND USES THEREOF

CROSS-REFERENCE TO RELATED APPLICATIONS

The present application claims priority to and benefit from U.S. Provisional Application Nos. 62/863,698, filed Jun. 19, 2019, and 62/878,220, filed Jul. 24, 2019, the entire contents of each of which are herein incorporated by reference.

SEQUENCE LISTING

The instant application contains a Sequence Listing which has been submitted electronically in ASCII format and is hereby incorporated by reference in its entirety. Said ASCII copy, created on Dec. 1, 2021, is named 51509-011003_Sequence_Listing_12_1_21_ST25 and is 6,006 bytes in size.

BACKGROUND

Certain circular polyribonucleotides are ubiquitously present in human tissues and cells, including tissues and cells of healthy individuals.

SUMMARY

This disclosure relates generally to compositions, pharmaceutical compositions, and preparations of circular polyribonucleotides and uses thereof for protein modulation. The circular polyribonucleotides of the disclosure can be used for modulation of a substrate protein. The compositions include, and the methods use, circular polyribonucleotide comprising two conjugation moieties for conjugation to a chemical compound, such as small molecules, each of which binds a target protein or a substrate protein for degradation of the substrate protein. The compositions include, and the methods use, circular polyribonucleotide comprising a conjugation moiety for conjugation to a chemical compound, such as a small molecule, that binds a target protein and a binding site that binds a substrate protein, for degradation of the substrate protein. The compositions include, and the methods use, circular polyribonucleotide comprising a binding site that binds a target protein and a conjugation moiety for conjugation to a chemical compound, such as a small molecule, that binds a binding site that binds a substrate protein, for degradation of the substrate protein. The target protein can be a ubiquitin ligase that ubiquitinates the substrate protein, resulting in degradation of the substrate protein. The substrate protein for degradation can be a pathogenic protein.

In one aspect, the invention features a composition comprising a circular polyribonucleotide comprising a first conjugation moiety and a second conjugation moiety, wherein the first conjugation moiety conjugates the circular polyribonucleotide to a first chemical compound (e.g., a small molecule) that binds to a target protein that modulates a substrate protein and wherein the second conjugation moiety conjugates the circular polyribonucleotide to a second chemical compound that binds the substrate protein.

In a second aspect, the invention features a composition comprising: a) circular polyribonucleotide comprising a first conjugation moiety and a second conjugation moiety, b) a first chemical compound that binds a target protein; c) a second chemical compound that binds a substrate protein; wherein the circular polyribonucleotide is conjugated to the first chemical compound by the first conjugation moiety, the circular polyribonucleotide is conjugated to the second chemical compound by the second conjugation moiety, and the target protein modulates the substrate protein.

In some embodiments, the circular polyribonucleotide is an exogenous, synthetic circular polyribonucleotide, lacks a poly-A sequence, lacks a replication element, is translation incompetent, or any combination thereof.

In some embodiments of these aspects, the first conjugation moiety is a first modified nucleotide and the second conjugation moiety is a second modified nucleotide. In some embodiments, the first modified nucleotide and second modified nucleotide are the same or the first modified nucleotide and second modified nucleotide are different. In some embodiments, the first conjugation moiety is a first modified nucleotide and the second conjugation moiety is a second modified nucleotide. In some embodiments, the first modified nucleotide and second modified nucleotide are the same or the first modified nucleotide and second modified nucleotide are different.

In a third aspect, the invention features a composition comprising a circular polyribonucleotide comprising a conjugation moiety and a binding site conjugation moiety, wherein the conjugation moiety conjugates the circular polyribonucleotide to a chemical compound (e.g., a small molecule) and wherein the binding site binds to a protein.

In a fourth aspect, the invention features a composition comprising: a) circular polyribonucleotide comprising a conjugation moiety and a binding site; and b) a chemical compound; wherein the circular polyribonucleotide is conjugated to the chemical compound by the conjugation moiety, and i) the chemical compound binds a target protein and the binding site binds substrate protein; or ii) the chemical compound binds the substrate protein and the binding site binds the target protein.

In some embodiments, the circular polyribonucleotide is an exogenous, synthetic circular polyribonucleotide, lacks a poly-A sequence, lacks a replication element, is translation incompetent, or any combination thereof.

In some embodiments of these aspects, the binding site: a) is an aptamer; or b) a miRNA binding site. In some embodiments, the conjugation moiety is a modified nucleotide.

In some embodiments of these aspects, the modified nucleotide, the first modified nucleotide, or the second modified nucleotide a) is a modified UTP analog, a modified ATP analog, modified CTP analog, or a modified GTP analog; optionally, wherein the modified UTP analog is a modified UTP analog, 5-Azidomethyl-UTP, 5-Azido-C3-UTP, 5-Azido-PEG4-UTP, 5-Ethynyl-UTP, DBCO-PEG4-UTP, Vinyl-UTP, 8-Azido-ATP, 3'-Azido-2',3'-ddATP, 5-Azido-PEG4-CTP, 5-DBCO-PEG4-CTP, N6-Azidohexyl-3'-dATP, 5-azidopropyl-UTP or 5-DBCO-PEG4-dCpG. In some embodiments, the modified nucleotide, the first modified nucleotide, or the second modified nucleotide comprises a click chemistry moiety.

In some embodiments of these aspects, the chemical compound or the first chemical compound is a small molecule. In some embodiments, the chemical compound or the first chemical compound recruits or binds the target protein. In some embodiments, the chemical compound or the first chemical compound is a target protein ligand. In some embodiments, the chemical compound or the first chemical compound is an LCL161 derivative, VHL-1, pomalidomide, lenalidomide, thalidomide or a derivative thereof, a HIF-1a-derived (R)-hydroxyproline, VHL ligand 2, VL-269, a VH032 derivative, or a hydroxyproline-based ligand. In some embodiments, the chemical compound or the second chemical compound is a small molecule. In some embodiments, the chemical compound or the second chemical compound binds to a misfolded protein. In some embodiments, the chemical compound or the second chemical compound binds to a disease-associated protein. In some embodiments, the chemical compound or the second chemical compound binds to a protein associated with cancer. In some embodiments, the chemical compound or the second chemical compound is a Heat Shock Protein 90 (HSP90) inhibitor, Kinase and Phosphatase inhibitor, MDM2 inhibitor, HDAC inhibitor, Human Lysine Methyltransferase Inhibitor, Angiogenesis inhibitor, or Immunosuppressive compound. In some embodiments, the chemical compound or the second chemical compound binds to a Human BET Bromodomain-containing protein, the aryl hydrocarbon receptor (AHR), REF receptor kinase, FKBP, Androgen Receptor (AR), Estrogen receptor (ER), Thyroid Hormone Receptor, HIV Protease, HIV Integrase, HCV Protease, Acyl-protein Thioesterase-1 and -2 (APTI and APT2), BCR-Abl, c-ABL, EGFR, c-Met, Sirt2, CDK9, FLT3, ALK, BTK, ERalpha, BRD2/3/4, PDE4, ERRalpha, RIPK2, FKBP12, TBK1, BRD9, HER2, AR, TRIM23, or MDM2. In some embodiments, the chemical compound or the second chemical compound is dasatinib, lapatinib, gefitinib, foretinib, Sirt2 inhibitor 3b, Sirt2 inhibitor, SNS-032, AC220, ceritinib, ibrutinib, ibrutinib derivative, 4-OHT, Jq1, PDE4 inhibitor, thiazolidinedione-based ligand, ripk2 inhibitor, bosutinib, OTX015, steel factor, TBK1 inhibitor, HJB97, aminopyrazole analog, RN486, AR antagonist, IACS-73, or nutlin small molecule.

In some embodiments of these aspects, the target protein is an enzyme. In some embodiments, the enzyme is a post-translational modification enzyme. In some embodiments, the target protein modifies the substrate by adding a functional group to the substrate protein. In some embodiments, the target protein modifies a substrate protein by adding a functional group to the substrate protein, wherein the modification is by acetylation, acylation, adenylylation, ADP-ribosylation, alkylation, amidation, amide bond formation, amino acid addition, arginylation, beta-lysine addition, butyrylation, carbamidation, carbonylation, carboxylation, citrullination, C-linked glycosylation, crotonylation, diphthamide formation, deacetylation, demethylation, ethanolamine phosphoglycerol attachment, farnesylation, flavin moiety attachment, formylation, gamma-carboxyglutamic acid, gamma-carboxylation, geranilgeranilation, glutarylation, glutathionylation, glycosylation, GPI-anchor formation, heme C attachment, hydroxylation, hypusine formation, iodination, ISGylation, isoprenylation, lipoylation, malonylation, methylation, myristoylation, N-acylation, N-linked glycosylation, neddylation, nitration, nitrosylation, nucleotide addition, O-acylation, O-linked glycosylation, oxidation, palmitoylation, phosphate ester formation, phosphoramidate formation, phosphorylation, phosphopantetheinylation, polyglutamylation, polyglycylation, polysialylation, prenylation, propionylation, pyroglutamate formation, pyrrolidone carboxylic acid, pyrrolylation, pyruvate, Retinylidene Schiff base formation, S-acylation, S-diacylglycerol, S-glutathionylation, S-linked glycosylation, S-nitrosylation, succinylation, sulfation, S-sulfenylation, S-sulfinylation, succinylation, sumoylation, or ubiquitination, uridylylation. In some embodiments, the target protein is a ubiquitin ligase, wherein the ubiquitin ligase is a HECT, RING-finger, U-box, or PHD-finger ubiquitin ligase. In some embodiments, the ubiquitin ligase is selected from the group consisting of von Rippel-Lindau (VHL); cereblon; XIAP; E3A; MDM2; Anaphase-promoting complex (APC); UBR5 (EDDI); SOCS/BC-box/eloBC/CUL5/RING; LNXp80; CBX4; CBLLI; HACEI; HECTDI; HECTD2; HECTD3; HECWI; HECW2; HERCI; HERC2; HERC3; HERC4; HUWEI; ITCH; NEDD4; NEDD4L; PPIL2; PRPF19; PIASI; PIAS2; PIAS3; PIAS4; RANBP2; RNF4; RBXI; SMURFI; SMURF2; STUBI; TOPORS; TRIP12; UBE3A; UBE3B; UBE3C; UBE4A; UBE4B; UBOX5; UBR5; WWPI; WWP2; Parkin; A20/TNFAIP3; AMFR/gp78; ARA54; beta-TrCPI/BTRC; BRCAI; CBL; CHIP/STUB I; E6; E6AP/UBE3A; F-box protein 15/FBXOIS; FBXW7/Cdc4; GRAIL/RNF128; HOIP/RNF3 l; cIAP-1/HIAP-2; cIAP-2/HIAP-1; cIAP (pan); ITCH/AIP4; KAPI; MARCH8; Mind Bomb 1/MIBI; Mind Bomb 2/MIB2; MuRFl/TRIM63; NDFIPI; NEDD4; NleL; Parkin; RNF2; RNF4; RNF8; RNF168; RNF43; SARTI; Skp2; SMURF2; TRAF-1; TRAF-2; TRAF-3; TRAF-4; TRAF-5; TRAF-6; TRIMS; TRIM21; TRIM32; UBR5; and ZNRF3.

In some embodiments of these aspects, the substrate protein is a disease-associated protein. In some embodiments, the substrate protein is a misfolded protein. In some embodiments, the substrate protein comprises a mutation as compared to a wild-type version of the substrate protein. In some embodiments, the substrate protein is BCR-Abl, c-ABL, EGFR, c-Met, Sirt2, CDK9, FLT3, ALK, BTK, ERalpha, BRD2/3/4, PDE4, ERRalpha, RIPK2, FKBP12, TBK1, BRD9, HER2, AR, TRIM23, MDM2, FoxOl, HDAC, DP-1, E2F, ABL, ALK, AMPK, BRK, BRSK I, BRSK2, BTK, CAMKKI, CAMKK alpha, CAMKK beta, Rb, Suv39HI, SCF, pl9INK4D, GSK-3, pi 8 INK4, myc, cyclin E, CDK2, CDK9, CDG4/6, Cycline D, pl6 INK4A, cdc25A, BMII, SCF, Akt, CHK1/2, CI delta, CKI gamma, C 2, CLK2, CSK, DDR2, DYRKIA/2/3, EF2K, EPH-A2/A4/B1/B2/B3/B4, EIF2A 3, Smad2, Smad3, Smad4, Smad7, p53, p21 Cipl, PAX, Fyn, CAS, C3G, SOS, Tal, Raptor, RACK-I, CRK, Rapl, Rae, KRas, NRas, HRas, GRB2, FAK, PBK, spred, Spry, mTOR, MPK, LKB1, PAK 1/2/4/5/6, PDGFRA, PYK.2, Src, SRPKI, PLC, PKC, PKA, PKB, alpha/beta, PKC alpha/gamma/zeta, PKD, PLK1, PRAK, PRK2, RIPK2, WA VE-2, TSC2, DAPK1, BAD, IMP, C-TAKI, TAKI, TAO1, TBKI, TESKI, TGFBRI, TIE2, TLKI, TrkA, TSSKI, TTBKI/2, TTK, Tpl2/cotl, MEKI, MEK2, PLDL Erk1, Erk2, Erk5, Erk8, p90RSK, PEA-15, SRF, p27 KIPI, TIF 1a, HMGNI, ER81, MKP-3, c-Fos, FGF-Rl, GCK, GSK3 beta, HER4, HIPKI/2/3/, IGF-IR, cdc25, UBF, LAMTOR2, Statl, StaO, CREB, JAK, Src, SNCA, PTEN, NF-kappaB, HECTH9, Bax, HSP70, HSP90, Apaf-1, Cyto c, BCL-2, Bcl-xL, BCL-6, Smac, XIAP, Caspase-9, Caspase-3, Caspase-6, Caspase-7, CDC37, TAB, IKK, TRADD, TRAF2, RIPI, FLIP, TAKI, JNK1/2/3, Lek, A-Raf, B-Raf, C-Raf, MOS, MLK1/3, MN 1/2, MSK1, MST2/3/4, MPSKI, MEKK1, ME K4, MEL, ASKI, MINK I, MKK 1/2/3/4/6/7, NE, 2a/6/7, NUAKI, OSRI, SAP, STK33, Syk, Lyn, PDKI, PHK, PIM 1/2/3, Ataxin-1, mTORCl, MDM2, p21 Wafl, Cyclin D1, Lamin A, Tpl2, Myc, catenin, Wnt, IKK-beta, IKKgamma, IKK-alpha, IKK-epsilon, ELK, p65Re1A, IRAKI, IRA 2, IRAK4, IRR, FADD, TRAF6, TRAF3, MKK3, MKK6, ROCK2, RSKI/2, SGK 1, SmMLCK, SIK2/3, ULKI/2, VEGFRI, WNK 1, YESI, ZAP70, MAP4K3, MAP4K5, MAPKlb, MAPKAP-K2 K3, p38, alpha/beta/delta/gamma MAPK, Aurora A, Aurora B, Aurora C, MCAK, Clip, MAPKAPK, FAK, MARK 1/2/3/4, Mud, SHC, CXCR4, Gap-I, Myc, beta-catenin/TCF, Cbl, BRM, Mel1, BRD2, BRD3, BRD4, AR, RAS, ErbB3, EGFR, IREI, HPKI, RIPK2, ERa, or PCAF/GCN5.

In some embodiments, the composition further comprises the target protein and/or the substrate protein. In further embodiments, a complex is formed. In some embodiments, the complex alters substrate protein interactions with other proteins. In some embodiments, the complex increases activity of the substrate protein. In some embodiments, the complex decreases activity of the substrate protein. In some embodiments, the complex alters localization of the substrate protein. In some embodiments, the complex alters stability of the substrate protein. In some embodiments, the complex promotes degradation of the substrate protein, wherein optionally, the degradation of the substrate protein comprises proteasomal degradation. In some embodiments, the complex promotes ubiquitination of the substrate protein.

In a fifth aspect, the invention features a pharmaceutical composition comprising the composition as disclosed herein and a pharmaceutically acceptable carrier or excipient.

In a sixth aspect, the invention features a pharmaceutical composition comprising the composition of as disclosed herein and a pharmaceutically acceptable excipient and is free of any carrier.

In a seventh aspect, the invention features a method of treating a condition in a subject in need thereof, the method comprising administering to the subject the composition or the pharmaceutical composition of as disclosed herein.

In some embodiments of this aspect, the condition is a cancer or a hyperproliferative disease; a neurodegenerative disease; a metabolic disorder; an inflammatory disorder; an autoimmune disease; an infectious disease; or a genetic disease. In some embodiments, the cancer is a solid tumor (e.g., a reproductive tissue cancer, e.g., cervical cancer or prostate cancer) or a liquid tumor (e.g., lymphoma, e.g., a B cell lymphoma). In some embodiments, wherein administering is intravenous administration or intratumoral administration.

Definitions

The present invention will be described with respect to particular embodiments and with reference to certain figures but the invention is not limited thereto but only by the claims. Terms as set forth hereinafter are generally to be understood in their common sense unless indicated otherwise.

As used herein, the terms "circRNA" or "circular polyribonucleotide" or "circular RNA" are used interchangeably and mean a polyribonucleotide molecule that has a structure having no free ends (i.e., no free 3' and/or 5' ends), for example a polyribonucleotide molecule that forms a circular or end-less structure through covalent or non-covalent bonds.

As used herein, the term "aptamer sequence" is a non-naturally occurring or synthetic oligonucleotide that specifically binds to a target molecule. Typically an aptamer is from 20 to 500 nucleotides. Typically an aptamer binds to its target through secondary structure rather than sequence homology.

As used herein, the term "encryptogen" is a nucleic acid sequence or structure of the circular polyribonucleotide that aids in reducing, evading, and/or avoiding detection by an immune cell and/or reduces induction of an immune response against the circular polyribonucleotide.

As used herein, the term "expression sequence" is a nucleic acid sequence that encodes a product, e.g., a peptide or polypeptide, or a regulatory nucleic acid. An exemplary expression sequence that codes for a peptide or polypeptide comprises a plurality of nucleotide triads, each of which code for an amino acid and is termed as a "codon".

As used herein the term "exogenous", when used with reference to a biomolecule (such as a circular RNA) means that the biomolecule was introduced into a host genome, cell or organism by the hand of man. For example, a circular RNA that is added into an existing genome, cell, tissue or subject using recombinant DNA techniques and/or methods for internalizing a biomolecule into a cell, is exogenous to the existing nucleic acid sequence, cell, tissue or subject, and any progeny of the nucleic acid sequence, cell, tissue or subject that retain the biomolecule.

As used herein, the term "immunoprotein binding site" is a nucleotide sequence that binds to an immunoprotein. In some embodiments, the immunoprotein binding site aids in masking the circular polyribonucleotide as exogenous, for example, the immunoprotein binding site is bound by a protein (e.g., a competitive inhibitor) that prevents the circular polyribonucleotide from being recognized and bound by an immunoprotein, thereby reducing or avoiding an immune response against the circular polyribonucleotide.

As used herein, the term "modified ribonucleotide" means any ribonucleotide analog or derivative that has one or more chemical modifications to the chemical composition of an unmodified natural ribonucleotide, such as a natural unmodified nucleotide adenosine (A), uridine (U), guanine (G), cytidine (C). In some embodiments, the chemical modifications of the modified ribonucleotide are modifications to any one or more functional groups of the ribonucleotide, such as, the sugar the nucleobase, or the internucleoside linkage (e.g. to a linking phosphate/to a phosphodiester linkage/to the phosphodiester backbone).

As used herein, the phrase "quasi-helical structure" refers to a higher order structure of the circular polyribonucleotide, wherein at least a portion of the circular polyribonucleotide folds into a helical structure.

As used herein, the phrase "quasi-double-stranded secondary structure" refers to a higher order structure of the circular polyribonucleotide, wherein at least a portion of the circular polyribonucleotide creates a double strand.

As used herein, the term "regulatory sequence" refers to a nucleic acid sequence that modifies an expression product.

As used herein, the term "repetitive nucleotide sequence" refers to a repetitive nucleic acid sequence within a stretch of DNA or throughout a genome. In some embodiments, the repetitive nucleotide sequence includes poly CA or poly TG sequences. In some embodiments, the repetitive nucleotide sequence includes repeated sequences in the Alu family of introns.

As used herein, the term "replication element" refers to a sequence and/or motifs useful for replication or that initiate transcription of the circular polyribonucleotide.

As used herein, the term "selective translation sequence" refers to a nucleic acid sequence that selectively initiates or activates translation of an expression sequence in the circular polyribonucleotide.

As used herein, the term "stagger sequence" refers to a nucleotide sequence that induces ribosomal pausing during translation. In some embodiments, the stagger sequence is a non-conserved sequence of amino-acids with a strong alpha-helical propensity followed by the consensus sequence –D(V/I)ExNPG P, where x is any amino acid.

As used herein, the term "substantially resistant" refers to one that has at least 50%, 60%, 70%, 75%, 80%, 85%, 90%, 95%, 96%, 97%, 98% or 99% resistance as compared to a reference.

As used herein, the term "complex" refers to an association between at least two moieties (e.g. chemical or biochemical) that have an affinity for one another.

"Polypeptide" and "protein" are used interchangeably and refer to a polymer of two or more amino acids joined by a covalent bond (e.g., an amide bond). Polypeptides as described herein can include full length proteins (e.g., fully processed proteins) as well as shorter amino acid sequences (e.g., fragments of naturally occurring proteins or synthetic polypeptide fragments). Polypeptides can include naturally occurring amino acids (e.g., one of the twenty amino acids commonly found in peptides synthesized in nature, and known by the one letter abbreviations A, R, N, C, D, Q, E, G, H, I, L, K, M, F, P, S, T, W, Y and V) and non-naturally occurring amino acids (e.g., amino acids which is not one of the twenty amino acids commonly found in peptides synthesized in nature, including synthetic amino acids, amino acid analogs, and amino acid mimetics).

As used herein, the term "binding site" refers to a region of the circular polyribonucleotide that interacts with another entity, e.g., a chemical compound, a protein, a nucleic acid, etc.

As used herein, the term "binding moiety" refers to a region of a target that can be bound by a binding site, for example, a region, domain, fragment, epitope, or portion of a nucleic acid (e.g., RNA, DNA, RNA-DNA hybrid), chemical compound, small molecule (e.g., drug), aptamer, polypeptide, protein, lipid, carbohydrate, antibody, virus, virus particle, membrane, multi-component complex, organelle, cell, other cellular moieties, any fragment thereof, and any combination thereof.

As used herein, the term "conjugation moiety" refers to a modified nucleotide comprising a functional group for use in a method of conjugation. As used herein, the term "carrier" means a compound, composition, reagent, or molecule that facilitates the transport or delivery of a composition (e.g., a circular polyribonucleotide) into a cell by a covalent modification of the circular polyribonucleotide, via a partially or completely encapsulating agent, or a combination thereof. Non-limiting examples of carriers include carbohydrate carriers (e.g., an anhydride-modified phytoglycogen or glycogen-type material), nanoparticles (e.g., a nanoparticle that encapsulates or is covalently linked binds to the circular polyribonucleotide), liposomes, fusosomes, ex vivo differentiated reticulocytes, exosomes, protein carriers (e.g., a protein covalently linked to the circular polyribonucleotide), or cationic carriers (e.g., a cationic lipopolymer or transfection reagent).

As used herein, the term "naked delivery" means a formulation for delivery to a cell without the aid of a carrier and without covalent modification to a moiety that aids in delivery to a cell. A naked delivery formulation is free from any transfection reagents, cationic carriers, carbohydrate carriers, nanoparticle carriers, or protein carriers. For example, naked delivery formulation of a circular polyribonucleotide is a formulation that comprises a circular polyribonucleotide without covalent modification and is free from a carrier.

The term "diluent" means a vehicle comprising an inactive solvent in which a composition described herein (e.g., a composition comprising a circular polyribonucleotide) may be diluted or dissolved. A diluent can be an RNA solubilizing agent, a buffer, an isotonic agent, or a mixture thereof. A diluent can be a liquid diluent or a solid diluent. Non-limiting examples of liquid diluents include water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and 1,3-butanediol. Non-limiting examples of solid diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, or powdered sugar.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The following detailed description of the embodiments of the invention will be better understood when read in conjunction with the appended drawings. For the purpose of illustrating the invention, there are shown in the drawings embodiments, which are presently exemplified. It should be understood, however, that the invention is not limited to the precise arrangement and instrumentalities of the embodiments shown in the drawings.

DETAILED DESCRIPTION

Figure 1:
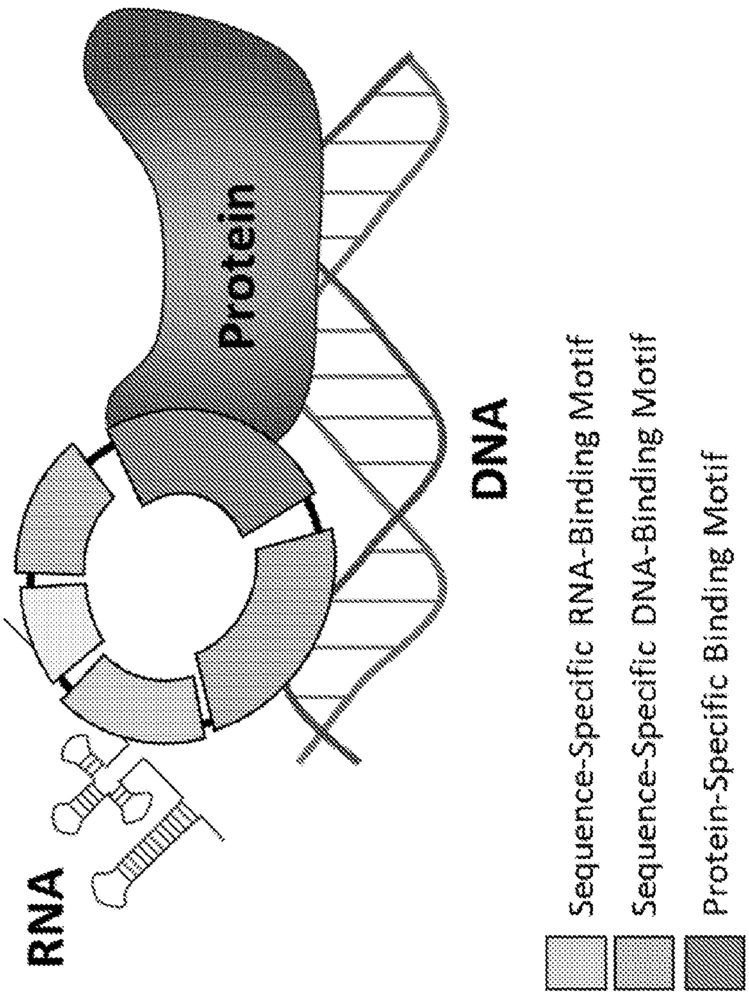
FIG. 1 illustrates an example circular polyribonucleotide molecular scaffold.
Figure 2:
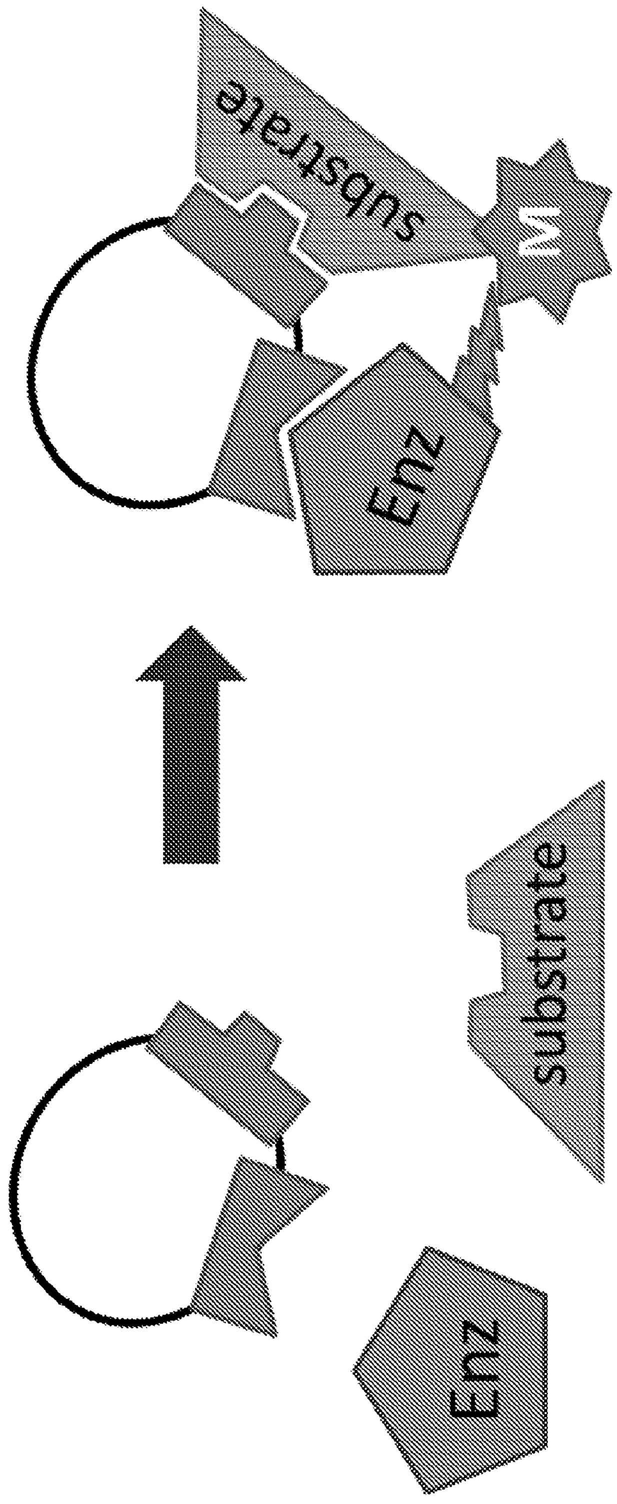
FIG. 2 provides a schematic of a circular RNA that binds an enzyme (Enz) and a substrate (substrate), thereby bringing the two into close proximity and promoting modification (M) of the substrate by the enzyme.

This disclosure relates generally to compositions, pharmaceutical compositions, and preparations of circular polyribonucleotides and uses thereof for protein modulation. The circular polyribonucleotides of the disclosure can be used for modulation of a substrate protein. In some embodiments, circular polyribonucleotides of the disclosure form complexes with target proteins that modify substrate proteins. For example, a circular polyribonucleotide can comprise a conjugation moiety, wherein the conjugation moiety conjugates the circular polyribonucleotide to a chemical compound (e.g., a small molecule). This chemical compound can bind to a target protein, wherein the target protein modulates a substrate protein. This chemical can bind to a substrate protein, wherein the substrate protein is degraded. The circular polyribonucleotide can further comprise a binding site that binds to the substrate protein or can further comprise a second conjugation moiety that is conjugated to a second chemical compound that binds to the substrate protein. The target protein and the substrate protein can be localized to the circular polyribonucleotide, allowing for the target protein to modulate the substrate protein.

Circular Polyribonucleotides

Circular polyribonucleotides (circRNA) described herein are polyribonucleotides that form a continuous structure through covalent or non-covalent bonds.

The present disclosure includes compositions comprising synthetic circRNA and methods of their use. The circular polyribonucleotides of the disclosure can be used for modulation of a substrate protein. Due to the circular structure, circRNA have improved stability, increased half-life, reduced immunogenicity, and/or improved functionality (e.g., of a function described herein) compared to a corresponding linear RNA.

In some embodiments, a circRNA binds a target. In some embodiments, a circRNA binds a substrate. In some embodiments, a circRNA binds a target and binds a substrate of the target. In some embodiments, a circRNA binds a target and mediates modulation of a substrate of the target. In some embodiments, a circRNA brings together a target and its substrate to mediate modification of the substrate, e.g., post-translational modification. In some embodiments, a circRNA brings together a target and its substrate to mediate a cellular process (e.g., alters protein degradation or signal transduction) involving the substrate. In some embodiments, a target is a target protein and a substrate is a substrate protein.

In some embodiments, a circRNA includes comprises a conjugation moiety for binding to chemical compound. The conjugation moiety can be a modified polyribonucleotide. The chemical compound can be conjugated to the circRNA by the conjugation moiety. In some embodiments, the chemical compound binds to a target and mediates modulation of a substrate of the target. In some embodiments, a circRNA binds a substrate of a target and a chemical compound conjugated to the circRNA by the conjugation moiety binds the target to bring together the target and its substrate to mediate modification of the substrate, e.g., post-translational modification. In some embodiments, a circRNA binds a substrate of a target and a chemical compound conjugated to the circRNA by the conjugation moiety binds the target to bring together the target and its substrate to mediate modification of the substrate to mediate a cellular process (e.g., alters protein degradation or signal transduction) involving the substrate. In some embodiments, a target is a target protein and a substrate is a substrate protein.

In some embodiments, the circular polyribonucleotide as describe herein is a bifunctional circular polyribonucleotide. In some embodiments, a bifunctional circular polyribonucleotide herein has the following structure:

$X^1$-circular polyribonucleotide-$X^2$ wherein $X^1$ and $X^2$ independently comprises a molecule (e.g., a chemical compound or a binding site) comprising an E3 ubiquitin ligase binding moiety (UBM) or a molecule (e.g., a chemical compound or a binding site) comprising a protein binding moiety (PBM), or a combination thereof. For example, in some embodiments, $X^1$ comprises an UBM, and $X^2$ comprises a PBM. In some embodiments, $X^1$ and $X^2$ each independently comprise one or more UBMs and one or more PBMs. In some embodiments, each $X^1$ and $X^2$ independently comprises at least about 2, 3, 4, 5, 10, 15, 20, 25, 30, 50, or 100 UBMs and PBMs. In some embodiments, each $X^1$ and $X^2$ independently comprises at most about 2, 3, 4, 5, 10, 15, 20, 25, 30, 50, or 100 UBMs and PBMs. Such two more binding moieties (e.g., UBMs and/or PBMs) can be coupled to each other in a linear or in a branched fashion. An example for a linear configuration of three identical or different UBMs is: $UBM^1$-$UBM^2$-$UBM^3$. An example for a branched configuration of four identical or different UBMs is:

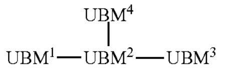

A UBM herein can be any molecule capable of binding (e.g., covalently or non-covalently) an E3 ubiquitin ligase (e.g., a target protein) as described herein. Such E3 ubiquitin ligase can include Rippel-Lindau (VHL); cereblon; XIAP; E3A; MDM2; Anaphase-promoting complex (APC); UBR5 (EDDI); SOCS/BC-box/eloBC/CUL5/RING; LNXp80; CBX4; CBLLI; HACEI; HECTDI; HECTD2; HECTD3; HECWI; HECW2; HERCI; HERC2; HERC3; HERC4; HUWEI; ITCH; NEDD4; NEDD4L; PPIL2; PRPF19; PIASI; PIAS2; PIAS3; PIAS4; RANBP2; RNF4; RBXI; SMURFI; SMURF2; STUBI; TOPORS; TRIP12; UBE3A; UBE3B; UBE3C; UBE4A; UBE4B; UBOX5; UBR5; WWPI; WWP2; Parkin; A20/TNFAIP3; AMFR/gp78; ARA54; beta-TrCPl/BTRC; BRCAI; CBL; CHIP/STUB I; E6; E6AP/UBE3A; F-box protein 15/FBXOIS; FBXW7/Cdc4; GRAIL/RNF128; HOIP/RNF3 l; cIAP-1/HIAP-2; cIAP-2/HIAP-1; cIAP (pan); ITCH/AIP4; KAPI; MARCH8; Mind Bomb 1/MIBI; Mind Bomb 2/MIB2; MuRFl/TRIM63; NDFIPI; NEDD4; NleL; Parkin; RNF2; RNF4; RNF8; RNF168; RNF43; SARTI; Skp2; SMURF2; TRAF-1; TRAF-2; TRAF-3; TRAF-4; TRAF-5; TRAF-6; TRIMS; TRIM21; TRIM32; UBR5; and ZNRF3. Further such examples of E3 ligases include those from Tables 13-27 in EP3458101, which is hereby incorporated by reference in its entirety.

A PBM herein can be any molecule capable of binding (e.g., covalently or non-covalently) a protein (e.g., a target protein) as described herein. Examples of proteins that a PBM herein bind to include a Von Hippel-Lindau E3 ubiquitin ligase, a cereblon E3 ubiquitin ligase, an MDM2 E3 ubiquitin ligase binding moiety, or an inhibitor of apoptosis (IAP).

In some embodiments, a UBM or a PBM binds to single protein, e.g, a ligase. In other embodiments, a UBM or a PBM herein is configured to bind to 2 or more identical or different proteins. Such binding to multiple proteins can occur either simultaneously or sequentially. Further examples of proteins include, but are not limited to, E3 ligases from Tables 13-27 in EP3458101, which is hereby incorporated by reference in its entirety.

In one embodiment, a circRNA comprises a lncRNA or a sequence of a lncRNA, e.g., a circRNA comprises a sequence of a naturally occurring, non-circular lncRNA or a fragment thereof. In one embodiment, a lncRNA or a sequence of a lncRNA is circularized, with or without a spacer sequence, to form a synthetic circRNA.

In one embodiment, a circRNA has ribozyme activity. In one embodiment, a circRNA can be used to act as a ribozyme and cleave pathogenic or endogenous RNA, DNA, small molecules, or proteins. In one embodiment, a circRNA has enzymatic activity. In one embodiment circRNA is able to specifically recognize and cleave proteins.

In one embodiment, a circRNA is an immolating or self-cleaving or cleavable circRNA.

In one embodiment, a circRNA is a transcriptionally/replication competent circRNA. This circRNA can encode any type of RNA. In one embodiment, a synthetic circRNA has an anti-sense miRNA and a transcriptional element. In one embodiment, after transcription, linear functional miRNAs are generated from a circRNA.

In one embodiment, a circRNA has one or more of the above attributes in combination with a translating element.

In some embodiments, a circRNA comprises at least one modified nucleotide. In some embodiments, a circRNA comprises at least 10%, 20%, 30%, 40%, 50%, 60%, 70%, or 80% modified nucleotides. In some embodiments, a circRNA comprises substantially all (e.g., greater than 80%, 85%, 90%, 95%, 97%, 98%, or 99%, or about 100%) modified nucleotides. In some embodiments, a circRNA comprises modified nucleotides and a portion of unmodified contiguous nucleotides, which can be referred to as a hybrid modified circRNA. A portion of unmodified contiguous nucleotides can be an unmodified binding site configured to bind a protein, DNA, RNA, or a cell target in a hybrid modified circRNA. A portion of unmodified contiguous nucleotides can be an unmodified IRES in a hybrid modified circRNA. In other embodiments, a circRNA lacks modified nucleotides, which can be referred to as an unmodified circRNA.

In some embodiments, the circRNA is an exogenous, synthetic circular polyribonucleotide. In some embodiments, the circRNA lacks a poly-A sequence, a replication element, or both. In some embodiments, the circular polyribonucleotide as disclosed herein is translation incompetent.

Binding Sites

In some embodiments, a circRNA comprises one binding site. In some embodiments, a circRNA comprises at least two binding sites. For example, a circRNA comprises 2, 3, 4, 5, 6, 7, 8, 9, 10, 11, 12, 13, 14, 15, 16, 17, 18, 19, 20, or more binding sites. In some embodiments, circRNA described herein is a molecular scaffold that binds one or more targets. Each target is, but is not limited to, a different or the same target protein. In some embodiments, circRNA described herein is a molecular scaffold that binds one or more substrates of a target. Each substrate is, but is not limited to, a different or the same as the target protein. In some embodiments, a circRNA described herein is a molecular scaffold that binds one or more targets and one or more substrates of the target. In some embodiments, a circRNA described herein is an aptamer that binds one or more targets and one or more substrates of the target. In some embodiments, a circRNA comprises a conjugation moiety that is conjugated to a chemical compound, wherein the chemical compound binds to the target. In some embodiments, a circRNA comprises a conjugation moiety that binds to a chemical compound, wherein the chemical compound binds to the substrate. In some embodiments, the target is a target protein. In some embodiments, the substrate is a substrate protein. In some embodiments, the circular polyribonucleotide comprises a conjugation moiety that binds to a chemical compound and an aptamer that binds to a target (e.g., a target protein). In some embodiments, the circular polyribonucleotide comprises a conjugation moiety that binds to a chemical compound and an aptamer that binds to a substrate (e.g., a substrate protein).

Conjugation Moiety

A circRNA can comprise a conjugation moiety. In some embodiments, a circRNA comprises a conjugation moiety that is conjugated to a chemical compound, wherein the chemical compound binds to a target. In some embodiments, a circRNA comprises a conjugation moiety that is conjugated to a chemical compound, wherein the chemical compound binds to a substrate. A target can be a target protein. A substrate can be a substrate protein. The target protein can modulate the substrate protein. In some embodiments, the circular polyribonucleotide comprises a conjugation moiety and an an aptamer.

A conjugation moiety can be a modified nucleotide that facilitates conjugation to chemical compound. A conjugation moiety can be a modified nucleotide comprising a functional group that can be conjugated to a chemical compound. A conjugation moiety can be incorporated, for example, at an internal site of a circular polynucleotide, or at a 5' end, 3' end, or internal site of a linear polynucleotide. A conjugation moiety can be a nucleotide analog, e.g., bromodeoxyuridine. A conjugation moiety can be a functional group, e.g., an azide group or an alkyne group. A conjugation moiety can be a hapten group, e.g., comprising digoxigenin, 2,4-dinitrophenyl, biotin, avidin, or are selected from azoles, nitroaryl compounds, benzofurazans, triterpenes, ureas, thioureas, rotenones, oxazoles, thiazoles, coumarins, cyclolignans, heterobiaryl compounds, azoaryl compounds or benzodiazepines.

A conjugation moiety can be conjugated via a chemical reaction, e.g., using click chemistry or a Staudinger reaction to chemical compound. The conjugation moiety can be a single modified nucleotide of choice (e.g., modified A, C, G, U, or T containing an azide at the 2'-position) that is incorporated site-specifically under optimized conditions (e.g., via solid-phase chemical synthesis). The conjugation moiety can be a plurality of nucleotides containing an azide at the 2'-position that are incorporated, for example, by substituting a nucleotide during an in vitro transcription reaction (e.g., substituting UTP for 5-azido-C3-UTP). Non-limiting examples of conjugation moeities include modified UTP analogs, 5-Azidomethyl-UTP, 5-Azido-C3-UTP, 5-Azido-PEG4-UTP, 5-Ethynyl-UTP, DBCO-PEG4-UTP, Vinyl-UTP, 8-Azido-ATP, 3'-Azido-2',3'-ddATP, 5-Azido-PEG4-CTP, 5-DBCO-PEG4-CTP, N6-Azidohexyl-3'-dATP, 5-azidopropyl-UTP, and 5-DBCO-PEG4-dCpG.

In some embodiments, a circRNA comprises a plurality of conjugation moieties. For example, the circRNA comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 70, 80, 90 or 100 or more conjugation moieties or any number therein between. In some embodiments, the plurality of conjugation moieties are the same. In some embodiments, the plurality of conjugation moieties are different. In some embodiments, a circRNA comprises a first conjugation moiety and a second conjugation moiety. In some embodiments, a circRNA comprises a first conjugation moiety that is conjugated to a first chemical compound and a second conjugation moiety that is conjugated to a second chemical compound, wherein the first chemical compound binds to a target and the second chemical compound binds to a substrate of the target.

Protein Binding Sites

In some embodiments, the circular polyribonucleotide comprises one or more binding sites that bind to a protein. The protein binding site can bind to a circular polyribonucleotide (circRNA)-binding motif of a protein. The protein can be substrate protein. The protein can be target protein.

In some embodiments, a protein binding site comprises a chemical compound (e.g., a chemical compound conjugated to the circRNA via a conjugation moiety). In some embodiments, a protein binding site comprises a protein binding sequence (e.g., an RNA sequence comprising a protein sequence-binding motif). In some embodiments, the protein binding sequence targets or localizes a circular polyribonucleotide to a specific substrate protein of a target protein. In some embodiments, the protein binding sequence specifically binds an arginine-rich region of a protein. In some embodiments, circular polyribonucleotides disclosed herein comprise a protein binding sequence that binds to protein substrate of an enzyme. In some embodiments, circular polyribonucleotides disclosed herein comprise a protein binding sequence that binds to disease-associated protein. In some embodiments, circular polyribonucleotides disclosed herein comprise a protein binding sequence that binds to protein associated with cancer. In some embodiments, circular polyribonucleotides disclosed herein comprise a protein binding sequence that binds to misfolded protein. In some embodiments, a protein binding site comprises a nucleic acid sequence that can bind to a protein such as BCR-Abl, c-ABL, EGFR, c-Met, Sirt2, CDK9, FLT3, ALK, BTK, ERalpha, BRD2/3/4, PDE4, ERRalpha, RIPK2, FKBP12, TBK1, BRD9, HER2, AR, TRIM23, or MDM2.

In some instances, a protein binding site binds to portion of a protein comprising a span of at least 6 amino acids, for example, least 8, 9, 10, 12, 15, 20, 25, 30, 40, 50, or 100 amino acids. In some instances, a protein binding site binds to a portion of a protein comprising a contiguous stretch of amino acids. In some instances, a protein binding site binds to a portion of a protein comprising a non-contiguous stretch of amino acids. In some instances, a protein binding site binds to a portion of a protein comprising a site of a mutation or functional mutation, including a deletion, addition, swap, or truncation of the amino acids in a polypeptide sequence.

In some instances, a protein binding site of the circular polyribonucleotide binds to a polypeptide, protein, or fragment thereof. In some embodiments, a binding site binds to a domain, a fragment, an epitope, a region, or a portion of a polypeptide, protein, or fragment thereof. For example, a protein binding site binds to a domain, a fragment, an epitope, a region, or a portion of an isolated polypeptide, a polypeptide of a cell, a purified polypeptide, or a recombinant polypeptide. For example, a protein binding site binds to a domain, a fragment, an epitope, a region, or a portion of an antibody or fragment thereof. For example, a binding site binds to a domain, a fragment, an epitope, a region, or a portion of a transcription factor. For example, a protein binding site binds to a domain, a fragment, an epitope, a region, or a portion of a receptor. For example, a binding site binds to a domain, a fragment, an epitope, a region, or a portion of a transmembrane receptor. Protein binding sites may bind to a domain, a fragment, an epitope, a region, or a portion of isolated, purified, and/or recombinant polypeptides. Protein binding sites may bind to a domain, a fragment, an epitope, a region, or a portion of a mixture of analytes (e.g., a lysate). For example, a protein binding site binds to a domain, a fragment, an epitope, a region, or a portion of from a plurality of cells or from a lysate of a single cell.

In some embodiments, a protein binding site binds to a domain, a fragment, an epitope, a region, or a portion of a membrane bound protein. Exemplary membrane bound proteins include, but are not limited to, GPCRs (e.g. adrenergic receptors, angiotensin receptors, cholecystokinin receptors, muscarinic acetylcholine receptors, neurotensin receptors, galanin receptors, dopamine receptors, opioid receptors, erotonin receptors, somatostatin receptors, etc.), ion channels (e.g., nicotinic acetylcholine receptors, sodium channels, potassium channels, etc.), receptor tyrosine kinases, receptor serine/threonine kinases, receptor guanylate cyclases, growth factor and hormone receptors (e.g., epidermal growth factor (EGF) receptor), and others. The binding site may bind to a domain, a fragment, an epitope, a region, or a portion of a mutant or modified variants of membrane-bound proteins. For example, some single or multiple point mutations of GPCRs retain function and are involved in disease (See, e.g., Stadel et al., (1997) Trends in Pharmacological Review 18:430-37).

A protein binding site can bind to a domain, a fragment, an epitope, a region, or a portion of a member of a specific binding pair (e.g., a ligand). A protein binding site can bind to a domain, a fragment, an epitope, a region, or a portion of monovalent (monoepitopic) or polyvalent (polyepitopic). A binding moiety can be antigenic or haptenic. A protein binding site can bind to a domain, a fragment, an epitope, a region, or a portion of a single molecule or a plurality of molecules that share at least one common epitope or determinant site. A protein binding site can bind to a domain, a fragment, an epitope, a region, or a portion of a part of a cell (e.g., a bacteria cell, a plant cell, or an animal cell).

In some instances, a protein binding site binds to a domain, a fragment, an epitope, a region, or a portion of a molecule found in a sample from a host. A sample from a host includes a body fluid (e.g., urine, blood, plasma, serum, saliva, semen, stool, sputum, cerebral spinal fluid, tears, mucus, and the like). A sample can be examined directly or may be pretreated. Samples include a quantity of a substance from a living thing or formerly living things. A sample can be natural, recombinant, synthetic, or not naturally occurring. A binding site can bind to any of the above that is expressed from a cell naturally or recombinantly, in a cell lysate or cell culture medium, an in vitro translated sample, or an immunoprecipitation from a sample (e.g., a cell lysate).

In some instances, a protein binding site binds to a protein expressed in a cell-free system or in vitro. For example, a protein binding site binds to a protein in a cell extract. In some instances, a protein binding site binds to a protein in a cell extract with a DNA template, and reagents for transcription and translation. Exemplary sources of cell extracts that can be used include wheat germ, *Escherichia coli*, rabbit reticulocyte, hyperthermophiles, hybridomas, *Xenopus* oocytes, insect cells, and mammalian cells (e.g., human cells). Exemplary cell-free methods that can be used to express target polypeptides (e.g., to produce target polypeptides on an array) include Protein in situ arrays (PISA), Multiple spotting technique (MIST), Self-assembled mRNA translation, Nucleic acid programmable protein array (NAPPA), nanowell NAPPA, DNA array to protein array (DAPA), membrane-free DAPA, nanowell copying and OP-microintaglio printing, and pMAC-protein microarray copying (See Kilb et al., Eng. Life Sci. 2014, 14, 352-364).

In some instances, a protein binding site of a circRNA is synthesized in situ (e.g., on a solid substrate of an array) from a DNA template. In some instances, a plurality of binding sites is synthesized in situ from a plurality of corresponding DNA templates in parallel or in a single reaction. Exemplary methods for in situ protein expression include those described in Stevens, Structure 8(9): R177-R185 (2000); Katzen et al., Trends Biotechnol. 23(3):150-6. (2005); He et al., Curr. Opin. Biotechnol. 19(1):4-9. (2008); Ramachandran et al., Science 305(5680):86-90. (2004); He et al., Nucleic Acids Res. 29(15):E73-3 (2001); Angenendt et al., Mol. Cell Proteomics 5(9): 1658-66 (2006); Tao et al, Nat Biotechnol 24(10):1253-4 (2006); Angenendt et al., Anal. Chem. 76(7):1844-9 (2004); Kinpara et al., J. Biochem. 136(2):149-54 (2004); Takulapalli et al., J. Proteome Res. 11(8):4382-91 (2012); He et al., Nat. Methods 5(2):175-7 (2008); Chatterjee and J. LaBaer, Curr Opin Biotech 17(4):334-336 (2006); He and Wang, Biomol Eng 24(4):375-80 (2007); and He and Taussig, J. Immunol. Methods 274(1-2):265-70 (2003).

In some embodiments, circRNA further comprises other binding motifs for binding other intracellular molecules. FIG. 1 shows an example of a circular polyribonucleotide with a sequence-specific RNA-binding motif, sequence-specific DNA-binding motif, and protein-specific binding motif.

RNA Binding Sites

In some embodiments, the circular polyribonucleotide further comprises one or more RNA binding sites. In some embodiments, the circular polyribonucleotide includes RNA binding sites that modify expression of an endogenous gene and/or an exogenous gene. In some embodiments, the RNA binding site modulates expression of a host gene. The RNA binding site can include a sequence that hybridizes to an endogenous gene (e.g., a sequence for a miRNA, siRNA, mRNA, lncRNA, RNA, DNA, an antisense RNA, gRNA as described herein), a sequence that hybridizes to an exogenous nucleic acid such as a viral DNA or RNA, a sequence that hybridizes to an RNA, a sequence that interferes with gene transcription, a sequence that interferes with RNA translation, a sequence that stabilizes RNA or destabilizes RNA such as through targeting for degradation, or a sequence that modulates a DNA- or RNA-binding factor.

In some embodiments, the RNA binding site is one of a tRNA, lncRNA, lincRNA, miRNA, rRNA, snRNA, microRNA, siRNA, piRNA, snoRNA, snRNA, exRNA, scaRNA, Y RNA, and hnRNA binding site. RNA binding sites are well-known to persons of ordinary skill in the art.

The length of the RNA binding site may be between about 5 to 30 nucleotides, between about 10 to 30 nucleotides, or about 11, 12, 13, 14, 15, 16, 17, 18, 19, 20, 21, 22, 23, 24, 25, 26, 27, 28, 29, 30, or more nucleotides. The degree of identity of the RNA binding site to a target of interest can be at least 75%, at least 80%, at least 85%, at least 90%, or at least 95%.

The RNA binding site can comprise a sequence that is substantially complementary, or fully complementary, to all or a fragment of an endogenous gene or gene product (e.g., mRNA). The complementary sequence can complement sequences at the boundary between introns and exons to prevent the maturation of newly-generated nuclear RNA transcripts of specific genes into mRNA for transcription. The complementary sequence may be specific to genes by hybridizing with the mRNA for that gene and prevent its translation. The RNA binding site can comprise a sequence that is antisense or substantially antisense to all or a fragment of an endogenous gene or gene product, such as DNA, RNA, or a derivative or hybrid thereof.

In some embodiments, the circular polyribonucleotide further comprises a RNA binding site that has an RNA or RNA-like structure typically between about 5-5000 base pairs (depending on the specific RNA structure, e.g., miRNA 5-30 bps, lncRNA 200-500 bps) and has a nucleobase sequence identical (complementary) or nearly identical (substantially complementary) to a coding sequence in an expressed target gene within the cell.

In some embodiments, a RNA binding site comprises a chemical compound (e.g., a chemical compound conjugated to the circRNA via a conjugation moiety).

DNA Binding Sites

In some embodiments, the circular polyribonucleotide further comprises a DNA binding site, such as a sequence for a guide RNA (gRNA). In some embodiments, the circular polyribonucleotide comprises a guide RNA or a complement to a gRNA sequence. A gRNA short synthetic RNA composed of a "scaffold" sequence necessary for binding to the incomplete effector moiety and a user-defined ~20 nucleotide targeting sequence for a genomic target. Guide RNA sequences can have a length of between 17-24 nucleotides (e.g., 19, 20, or 21 nucleotides) and complementary to the targeted nucleic acid sequence. Custom gRNA generators and algorithms can be used in the design of effective guide RNA. Gene editing can be achieved using a chimeric "single guide RNA" ("sgRNA"), an engineered (synthetic) single RNA molecule that mimics a naturally occurring crRNA-tracrRNA complex and contains both a tracrRNA (for binding the nuclease) and at least one crRNA (to guide the nuclease to the sequence targeted for editing). Chemically modified sgRNA can be effective in genome editing.

The gRNA can recognize specific DNA sequences (e.g., sequences adjacent to or within a promoter, enhancer, silencer, or repressor of a gene).

In some embodiments, the gRNA is part of a CRISPR system for gene editing. For gene editing, the circular polyribonucleotide can be designed to include one or multiple guide RNA sequences corresponding to a desired target DNA sequence. The gRNA sequences may include at least 10, 11, 12, 13, 14, 15, 16, 17, 18, 19, 20, 21, 22, 23, 24, 25, 26, 27, 28, 29, 30 or more nucleotides for interaction with Cas9 or other exonuclease to cleave DNA, e.g., Cpf1 interacts with at least about 16 nucleotides of gRNA sequence for detectable DNA cleavage.

In some embodiments, the circular polyribonucleotide includes sequences that bind a major groove of in duplex DNA. In one such instance, the specificity and stability of a triplex structure created by the circular polyribonucleotide and duplex DNA is afforded via Hoogsteen hydrogen bonds, which are different from those formed in classical Watson-Crick base pairing in duplex DNA. In one instance, the circular polyribonucleotide binds to the purine-rich strand of a target duplex through the major groove.

In some embodiments, triplex formation occurs in two motifs, distinguished by the orientation of the circular polyribonucleotide with respect to the purine-rich strand of the target duplex. In some instances, polypyrimidine sequence stretches in a circular polyribonucleotides bind to the polypurine sequence stretches of a duplex DNA via Hoogsteen hydrogen bonding in a parallel fashion (i.e. in the same 5' to 3', orientation as the purine-rich strand of the duplex), whereas the polypurine stretches (R) bind in an antiparallel fashion to the purine strand of the duplex via reverse-Hoogsteen hydrogen bonds. In the antiparallel strand, a purine motif comprises triplets of G:G-C, A:A-T, or T:A-T; whereas in the parallel, a pyrimidine motif comprises canonical triples of C+:G-C or T:A-T triplets (where C+ represents a protonated cytosine on the N3 position). Antiparallel GA and GT sequences in a circular polyribonucleotide may form stable triplexes at neutral pH, while parallel CT sequences in a circular polyribonucleotide may bind at acidic pH. N3 on cytosine in the circular polyribonucleotide may be protonated. Substitution of C with 5-methyl-C may permit binding of CT sequences in the circular polyribonucleotide at physiological pH as 5-methyl-C has a higher pK than does cytosine. For both purine and pyrimidine motifs, contiguous homopurine-homopyrimidine sequence stretches of at least 10 base pairs aid circular polyribonucleotide binding to duplex DNA, since shorter triplexes may be unstable under physiological conditions, and interruptions in sequences can destabilize the triplex structure. In some embodiments, the DNA duplex target for triplex formation includes consecutive purine bases in one strand. In some embodiments, a target for triplex formation comprises a homopurine sequence in one strand of the DNA duplex and a homopyrimidine sequence in the complementary strand.

In some embodiments, a triplex comprising a circular polyribonucleotide is a stable structure. In some embodiments, a triplex comprising a circular polyribonucleotide exhibits an increased half-life, e.g., increased by about 5%, 10%, 15%, 20%, 25%, 30%, 35%, 40%, 45%, 50%, or greater, e.g., persistence for at least about 1 hr to about 30 days, or at least about 2 hrs, 6 hrs, 12 hrs, 18 hrs, 24 hrs, 2 days, 3, days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 60 days, or longer or any time there between.

In some embodiments, a DNA binding site comprises a chemical compound (e.g., a chemical compound conjugated to the circRNA via a conjugation moiety).

Other Binding Sites

In some embodiments, the circRNA further comprises binding site that binds to one of a small molecule, an aptamer, a lipid, a carbohydrate, a virus particle, a membrane, a multi-component complex, a cell, a cellular moiety, or any fragment thereof binding site. In some embodiments, the circular polyribonucleotide further comprises one or more binding sites that bind to a lipid. In some embodiments, the circular polyribonucleotide comprises one or more binding sites that bind to a carbohydrate. In some embodiments, the circular polyribonucleotide further comprises one or more binding sites that bind to a carbohydrate. In some embodiments, the circular polyribonucleotide further comprises one or more binding sites that bind to a membrane. In some embodiments, the circular polyribonucleotide further comprises one or more binding sites that bind to a multi-component complex, e.g., ribosome, nucleosome, transcription machinery, etc. In some embodiments, a binding site comprises a chemical compound (e.g., a chemical compound conjugated to the circRNA via a conjugation moiety).

Modifications

In some aspects, the invention described herein comprises compositions and methods of using and making modified circular polyribonucleotides, and delivery of modified circular polyribonucleotides. The term "modified nucleotide" can refer to any nucleotide analog or derivative that has one or more chemical modifications to the chemical composition of an unmodified natural ribonucleotide, such as a natural unmodified nucleotide adenosine (A), uridine (U), guanine (G), cytidine (C) as shown by the chemical formulae in TABLE 1, and monophosphate. The chemical modifications of the modified ribonucleotide can be modifications to any one or more functional groups of the ribonucleotide, such as, the sugar the nucleobase, or the internucleoside linkage (e.g. to a linking phosphate/to a phosphodiester linkage/to the phosphodiester backbone).

TABLE 1

| Unmodified Natural Ribonucleosides | | |
| --- | --- | --- |
| Ribonucleoside | IUPAC name | Chemical Formula |
| Adenosine | (2R,3R,4S,5R)-2-(6-amino-9H-purin-9-yl)-5-(hydroxymethyl)oxolane-3,4-diol | 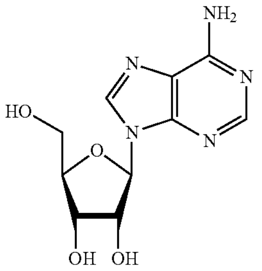 $C_{10}H_{13}N_5O_4$ |
| Uridine | 1-[(3R,4S,5R)-3,4-dihydroxy-5-(hydroxymethyl)oxolan-2-yl]pyrimidine-2,4-dione | 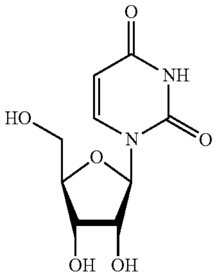 $C_9H_{12}N_2O_6$ |
| Guanine | 2-amino-9H-purin-6(1H)-one | 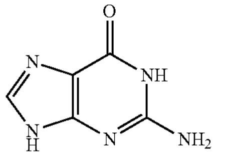 $C_5H_5N_5O$ |
| Cytidine | 4-amino-1-[(2R,3R,4S,5R)-3,4-dihydroxy-5-(hydroxymethyl)oxolan-2-yl]pyrimidin-2(1H)-one | 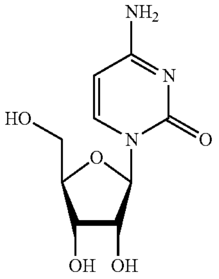 $C_9H_{13}N_3O_5$ |

The circular polyribonucleotide can include one or more substitutions, insertions and/or additions, deletions, and covalent modifications with respect to reference sequences, in particular, the parent polyribonucleotide, are included within the scope of this invention. In some embodiments, the circular polyribonucleotide includes one or more post-transcriptional modifications (e.g., capping, cleavage, polyadenylation, splicing, poly-A sequence, methylation, acylation, phosphorylation, methylation of lysine and arginine residues, acetylation, and nitrosylation of thiol groups and tyrosine residues, etc). The circular polyribonucleotide can include any useful modification, such as to the sugar, the nucleobase, or the internucleoside linkage (e.g., to a linking phosphate/to a phosphodiester linkage/to the phosphodiester backbone). One or more atoms of a pyrimidine nucleobase can be replaced or substituted with optionally substituted amino, optionally substituted thiol, optionally substituted alkyl (e.g., methyl or ethyl), or halo (e.g., chloro or fluoro). In certain embodiments, modifications (e.g., one or more modifications) are present in each of the sugar and the internucleoside linkage. Modifications can be modifications of ribonucleic acids (RNA) to deoxyribonucleic acids (DNA), threose nucleic acids (TNA), glycol nucleic acids (GNA), peptide nucleic acids (PNA), locked nucleic acids (LNA) or hybrids thereof). Additional modifications are described herein.

In some embodiments, the circular polyribonucleotide includes at least one N(6)methyladenosine (m6A) modification to increase translation efficiency.

In some embodiments, the modification may include a chemical or cellular induced modification. For example, some nonlimiting examples of intracellular RNA modifications are described by Lewis and Pan in "RNA modifications and structures cooperate to guide RNA-protein interactions" from Nat Reviews Mol Cell Biol, 2017, 18:202-210.

"Pseudouridine" refers, in another embodiment, to $m^1acp^3\Psi$ (1-methyl-3-(3-amino-3-carboxypropyl) pseudouridine. In another embodiment, the term refers to $m^1\Psi$ (1-methylpseudouridine). In another embodiment, the term refers to Ψm (2'-O-methylpseudouridine. In another embodiment, the term refers to m5D (5-methyldihydrouridine). In another embodiment, the term refers to $m^3\Psi$ (3-methylpseudouridine). In another embodiment, the term refers to a pseudouridine moiety that is not further modified. In another embodiment, the term refers to a monophosphate, diphosphate, or triphosphate of any of the above pseudouridines. In another embodiment, the term refers to any other pseudouridine known in the art. Each possibility represents a separate embodiment of the present invention.

In some embodiments, chemical modifications to the ribonucleotides of the circular polyribonucleotide can enhance immune evasion. Modifications include, for example, end modifications, e.g., 5'-end modifications (phosphorylation (mono-, di- and tri-), conjugation, inverted linkages, etc.), 3'-end modifications (conjugation, DNA nucleotides, inverted linkages, etc.), base modifications (e.g., replacement with stabilizing bases, destabilizing bases, or bases that base pair with an expanded repertoire of partners), removal of bases (abasic nucleotides), or conjugated bases. The modified ribonucleotide bases can also include 5-methylcytidine and pseudouridine. In some embodiments, base modifications can modulate expression, immune response, stability, subcellular localization, to name a few functional effects, of the circular polyribonucleotide. In some embodiments, the modification includes a bi-orthogonal nucleotide, e.g., an unnatural base.

In some embodiments, sugar modifications (e.g., at the 2' position or 4' position) or replacement of the sugar one or more ribonucleotides of the circular polyribonucleotide can, as well as backbone modifications, include modification or replacement of the phosphodiester linkages. Non-limiting examples of circular polyribonucleotide include circular polyribonucleotide with modified backbones or non-natural internucleoside linkages, such as those modified or replaced of the phosphodiester linkages. Circular polyribonucleotides having modified backbones include, among others, those that do not have a phosphorus atom in the backbone. For the purposes of this application, and as sometimes referenced in the art, modified RNA that do not have a phosphorus atom in their internucleoside backbone can also be considered to be oligonucleosides. In particular embodiments, the circular polyribonucleotide will include ribonucleotides with a phosphorus atom in its internucleoside backbone.

Modified circular polyribonucleotide backbones can include, for example, phosphorothioates, chiral phosphorothioates, phosphorodithioates, phosphotriesters, aminoalkylphosphotriesters, methyl and other alkyl phosphonates such as 3'-alkylene phosphonates and chiral phosphonates, phosphinates, phosphoramidates such as 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included. In some embodiments, the circular polyribonucleotide can be negatively or positively charged.

The modified nucleotides, which can be incorporated into the circular polyribonucleotide, can be modified on the internucleoside linkage (e.g., phosphate backbone). Herein, in the context of the polynucleotide backbone, the phrases "phosphate" and "phosphodiester" are used interchangeably. Backbone phosphate groups can be modified by replacing one or more of the oxygen atoms with a different substituent. Further, the modified nucleosides and nucleotides can include the wholesale replacement of an unmodified phosphate moiety with another internucleoside linkage as described herein. Examples of modified phosphate groups include, but are not limited to, phosphorothioate, phosphoroselenates, boranophosphates, boranophosphate esters, hydrogen phosphonates, phosphoramidates, phosphorodiamidates, alkyl or aryl phosphonates, and phosphotriesters. Phosphorodithioates have both non-linking oxygens replaced by sulfur. The phosphate linker can also be modified by the replacement of a linking oxygen with nitrogen (bridged phosphoramidates), sulfur (bridged phosphorothioates), and carbon (bridged methylene-phosphonates).

The α-thio substituted phosphate moiety is provided to confer stability to RNA and DNA polymers through the unnatural phosphorothioate backbone linkages. Phosphorothioate DNA and RNA have increased nuclease resistance and subsequently a longer half-life in a cellular environment. Phosphorothioate linked to the circular polyribonucleotide is expected to reduce the innate immune response through weaker binding/activation of cellular innate immune molecules.

In some embodiments, a modified nucleoside includes an α-thio-nucleoside (e.g., 5'-O-(l-thiophosphate)-adenosine, 5'-O-(l-thiophosphate)-cytidine (α-thio-cytidine), 5'-O-(l-thiophosphate)-guanosine, 5'-O-(l-thiophosphate)-uridine, or 5'-O-(l-thiophosphate)-pseudouridine). Other internucleoside linkages can include internucleoside linkages which do not contain a phosphorous atom.

In some embodiments, the circular polyribonucleotide can include one or more cytotoxic nucleosides. For example, cytotoxic nucleosides can be incorporated into circular polyribonucleotide, such as bifunctional modification. Cytotoxic nucleoside can include, but are not limited to, adenosine arabinoside, 5-azacytidine, 4'-thio-aracytidine, cyclopentenylcytosine, cladribine, clofarabine, cytarabine, cytosine arabinoside, 1-(2-C-cyano-2-deoxy-beta-D-arabino-pentofuranosyl)-cytosine, decitabine, 5-fluorouracil, fludarabine, floxuridine, gemcitabine, a combination of tegafur and uracil, tegafur ((R,S)-5-fluoro-1-(tetrahydrofuran-2-yl)pyrimidine-2,4(1H,3H)-dione), troxacitabine, tezacitabine, 2'-deoxy-2'-methylidenecytidine (DMDC), and 6-mercaptopurine. Additional examples include fludarabine phosphate, N4-behenoyl-1-beta-D-arabinofuranosylcytosine, N4-octadecyl-1-beta-D-arabinofuranosylcytosine, N4-palmitoyl-1-(2-C-cyano-2-deoxy-beta-D-arabino-pentofuranosyl) cytosine, and P-4055 (cytarabine 5'-elaidic acid ester).

The circular polyribonucleotide can be uniformly modified along the entire length of the molecule. For example, one or more or all types of nucleotide (e.g., naturally-occurring nucleotides, purine or pyrimidine, or any one or more or all of A, G, U, C, I, pU) can be uniformly modified in the circular polyribonucleotide, or in a given predetermined sequence region thereof. In some embodiments, the circular polyribonucleotide includes a pseudouridine. In some embodiments, the circular polyribonucleotide includes an inosine, which can aid in the immune system characterizing the circular polyribonucleotide as endogenous versus viral RNA. The incorporation of inosine can also mediate improved RNA stability/reduced degradation.

In some embodiments, all nucleotides in the circular polyribonucleotide (or in a given sequence region thereof) are modified. In some embodiments, the modification can include an m6A, which can augment expression; an inosine, which can attenuate an immune response; pseudouridine, which can increase RNA stability, or translational read-through (stop codon=coding potential), an m5C, which can increase stability; and a 2,2,7-trimethylguanosine, which aids subcellular translocation (e.g., nuclear localization).

Different sugar modifications, nucleotide modifications, and/or internucleoside linkages (e.g., backbone structures) can exist at various positions in the circular polyribonucleotide. One of ordinary skill in the art will appreciate that the nucleotide analogs or other modification(s) can be located at any position(s) of the circular polyribonucleotide, such that the function of the circular polyribonucleotide is not substantially decreased. A modification can also be a non-coding region modification. The circular polyribonucleotide can include from about 1% to about 100% modified nucleotides (either in relation to overall nucleotide content, or in relation to one or more types of nucleotide, i.e. any one or more of A, G, U or C) or any intervening percentage (e.g., from 1% to 20%>, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%).

In some embodiments, the circular polyribonucleotide provided herein is a modified circular polyribonucleotide. For example, a completely modified circular polyribonucleotide comprises all or substantially all modified adenosine residues, all or substantially all modified uridine residues, all or substantially all modified guanine residues, all or substantially all modified cytidine residues, or any combination thereof. In some embodiments, the circular polyribonucleotide provided herein is a hybrid modified circular polyribonucleotide. A hybrid modified circular polyribonucleotide can have at least one modified nucleotide and can have a portion of contiguous unmodified nucleotides. This unmodified portion of the hybrid modified circular polyribonucleotide can have at least about 5, 10, 15, or 20 contiguous unmodified nucleotides, or any number therebetween. In some embodiments, the unmodified portion of the hybrid modified circular polyribonucleotide has at least about 30, 40, 40, 60, 70, 80, 90, 100, 110, 120, 130, 140, 150, 160, 180, 200, 220, 250, 280, 300, 320, 350, 380, 400, 420, 450, 500, 550, 600, 650, 700, 750, 800, 850, 900, or 1000 contiguous unmodified nucleotides, or any number therebetween. In some embodiments, the hybrid modified circular polyribonucleotide has 1, 2, 3, 4, 5, 6, 7, 8, 9, 10, or more unmodified portions. In some embodiments, the hybrid modified circular polyribonucleotide has at least 1, 2, 3, 4, 5, 6, 7, 8, 9, 10, 12, 15, 20, 30, 40, 50, 70, 80, 100, 120, 150, 200, 250, 300, 400, 500, 600, 700, 800, 900, 1000, or more modified nucleotides. In some embodiments, the hybrid modified circular polyribonucleotide has at least 1%, 2%, 5%, 7%, 8%, 10%, 12%, 15%, 18%, 20%, 25%, 30%, 35%, 40%, 45%, 50%, 55%, 60%, 65%, 70%, 80%, 90%, 95%, or 99% but less than 100% nucleotides that are modified. In some embodiments, the unmodified portion comprises a binding site. In some embodiments, the unmodified portion comprises a binding site configured to bind a protein, DNA, RNA, or a cell target. In some embodiments, the unmodified portion comprises an IRES.

In some embodiments, the hybrid modified circular polyribonucleotide has a lower immunogenicity than a corresponding unmodified circular polyribonucleotide. In some embodiments, the hybrid modified circular polyribonucleotide has an immunogenicity that is at least about 1.1, 1.2, 1.3, 1.5, 1.6, 1.8, 2, 2.2, 2.5, 2.8, 3, 3.2, 3.3, 3.5, 3.8, 4.0, 4.2, 4.5, 4.8, 5.0, 5.5, 6.0, 6.5, 7.0, 7.5, 8.0, 8.5, 9.0, 9.5, or 10.0 fold lower than a corresponding unmodified circular polyribonucleotide. In some embodiments, the immunogenicity as described herein is assessed by the level of expression or signaling or activation of at least one of RIG-I, TLR-3, TLR-7, TLR-8, MDA-5, LGP-2, OAS, OASL, PKR, and IFN-beta. In some embodiments, the hybrid modified circular polyribonucleotide has a higher half-life than a corresponding unmodified circular polyribonucleotide. In some embodiments, the hybrid modified circular polyribonucleotide has a half-life that is at least about 1.1, 1.2, 1.3, 1.5, 1.6, 1.8, 2, 2.2, 2.5, 2.8, 3, 3.2, 3.3, 3.5, 3.8, 4.0, 4.2, 4.5, 4.8, 5.0, 5.5, 6.0, 6.5, 7.0, 7.5, 8.0, 8.5, 9.0, 9.5, or 10.0 fold higher than a corresponding unmodified circular polyribonucleotide. In some embodiments, the half-life is measured by introducing the circular polyribonucleotide or the corresponding circular polyribonucleotide into a cell and measuring a level of the introduced circular polyribonucleotide or corresponding circular polyribonucleotide inside the cell.

In some embodiments, the hybrid modified circular polyribonucleotide comprises one or more expression sequences. In some embodiments, the one or more expression sequences of the hybrid modified circular polyribonucleotide has a translation efficiency similar to or higher than a corresponding unmodified circular polyribonucleotide. In some embodiments, the one or more expression sequences of the hybrid modified circular polyribonucleotide have a translation efficiency of that is at least about 0.7, 0.8, 0.9, 1.0, 1.1, 1.2, 1.3, 1.5, 1.6, 1.8, 2, 2.2, 2.5, 2.8, or 3 fold higher than a corresponding unmodified circular polyribonucleotide. In some embodiments, the one or more expression sequences of the hybrid modified circular polyribonucleotide have a higher translation efficiency than a corresponding circular polyribonucleotide having a portion comprising a modified nucleotide (e.g., the portion corresponds to the unmodified portion of the hybrid modified circular polyribonucleotide). In some embodiments, one or more expression sequences of the circular polyribonucleotide are configured to have a higher translation efficiency than a corresponding circular polyribonucleotide having a first portion comprising more than 10%, or at least 20%, 30%, 40%, 50%, 60%, 70%, 80%, 90%, or 100% modified nucleotides. In some embodiments, the one or more expression sequences of the hybrid modified circular polyribonucleotide has a translation efficiency that is at least about 1.1, 1.2, 1.3, 1.5, 1.6, 1.8, 2, 2.2, 2.5, 2.8, 3, 3.2, 3.3, 3.5, 3.8, 4.0, 4.2, 4.5, 4.8, 5.0, 5.5, 6.0, 6.5, 7.0, 7.5, 8.0, 8.5, 9.0, 9.5, or 10.0 fold higher than a corresponding circular polyribonucleotide having a portion comprising a modified nucleotide (e.g., the portion corresponds to the unmodified portion of the hybrid modified circular polyribonucleotide). As described herein, in some embodiments, the translation efficiency is measured either in a cell comprising the circular polyribonucleotide or the corresponding circular polyribonucleotide, or in an in vitro translation system (e.g., rabbit reticulocyte lysate).

In some embodiments, the hybrid modified circular polyribonucleotide has a binding site that is unmodified, e.g., having no modified nucleotides. In some embodiments, the hybrid modified circular polyribonucleotide has a binding site configured to bind to a protein, DNA, RNA, or cell target that is unmodified, e.g., having no modified nucleotides. In some embodiments, the hybrid modified circular polyribonucleotide has an internal ribosome entry site (IRES) that is unmodified, e.g., having no modified nucleotides. In some embodiments, the hybrid modified circular polyribonucleotide has no more than 10% of the nucleotides in the binding site that are modified nucleotides. In some embodiments, the hybrid modified circular polyribonucleotide has no more than 10% of the nucleotides in the binding site configured to bind to a protein, DNA, RNA, or cell target that are modified nucleotides. In some embodiments, the hybrid modified circular polyribonucleotide has no more than 10% of the nucleotides in the internal ribosome entry site (IRES) that are modified nucleotides. In some embodiments, a hybrid modified circular polyribonucleotide has modified nucleotides throughout except the binding site. In some embodiments, a hybrid modified circular polyribonucleotide has modified nucleotides throughout except the binding site configured to bind a protein, DNA, RNA, or a cell target. In some embodiments, a hybrid modified circular polyribonucleotide has modified nucleotides throughout except the IRES element. In other embodiments, the hybrid modified circular polyribonucleotide has modified nucleotides throughout except the IRES element and one or more other portions. Without wishing to be bound by a certain theory, the unmodified IRES element renders the hybrid modified circular polyribonucleotide translation competent, e.g., having a translation efficiency for the one or more expression sequences that is similar to or higher than a corresponding circular polyribonucleotide that does not have any modified nucleotides.

In some embodiments, the hybrid modified circular polyribonucleotide has modified nucleotides, e.g., 5' methylcytidine and pseudouridine, throughout the circular polyribonucleotide except the IRES element or a binding site configured to bind a protein, DNA, RNA, or a cell target. In these cases, the hybrid modified circular polyribonucleotide has a higher a lower immunogenicity as compared to a corresponding circular polyribonucleotide that does not comprise 5' methylcytidine and pseudouridine. In some embodiments, the hybrid modified circular polyribonucleotide has an immunogenicity that is at least about 1.1, 1.2, 1.3, 1.5, 1.6, 1.8, 2, 2.2, 2.5, 2.8, 3, 3.2, 3.3, 3.5, 3.8, 4.0, 4.2, 4.5, 4.8, 5.0, 5.5, 6.0, 6.5, 7.0, 7.5, 8.0, 8.5, 9.0, 9.5, or 10.0 fold lower than a corresponding unmodified circular polyribonucleotide. In some embodiments, the immunogenicity as described herein is assessed by expression or signaling or activation of at least one of RIG-I, TLR-3, TLR-7, TLR-8, MDA-5, LGP-2, OAS, OASL, PKR, and IFN-beta. In some embodiments, the hybrid modified circular polyribonucleotide has n higher half-life than a corresponding unmodified circular polyribonucleotide, e.g., a corresponding circular polyribonucleotide that does not comprise 5' methylcytidine and pseudouridine. In some embodiments, the hybrid modified circular polyribonucleotide has a higher half-life that is at least about 1.1, 1.2, 1.3, 1.5, 1.6, 1.8, 2, 2.2, 2.5, 2.8, 3, 3.2, 3.3, 3.5, 3.8, 4.0, 4.2, 4.5, 4.8, 5.0, 5.5, 6.0, 6.5, 7.0, 7.5, 8.0, 8.5, 9.0, 9.5, or 10.0 fold higher than a corresponding unmodified circular polyribonucleotide. In some embodiments, the half-life is measured by introducing the circular polyribonucleotide or the corresponding circular polyribonucleotide into a cell and measuring a level of the introduced circular polyribonucleotide or corresponding circular polyribonucleotide inside the cell.

In some cases, the hybrid modified circular polyribonucleotide as described herein has similar immunogenicity as compared to a corresponding circular polyribonucleotide that is otherwise the same but completely modified. For instance, a hybrid modified circular polyribonucleotide that has 5' methylcytidine and pseudouridine throughout except its IRES element can have similar immunogenicity or lower immunogenicity as compared to a corresponding circular polyribonucleotide that is otherwise the same but has 5' methylcytidine and pseudouridine throughout and no unmodified cytidine and uridine. In some embodiments, the hybrid modified circular polyribonucleotide that has 5' methylcytidine and pseudouridine throughout except its IRES element has translation efficiency that is similar to or higher than the translation efficiency of a corresponding circular polyribonucleotide that is otherwise the same but has 5' methylcytidine and pseudouridine throughout and no unmodified cytidine and uridine.

Other Circular Polyribonucleotide Features

In some embodiments, the circular polyribonucleotide comprises one or more of the elements as described herein in addition to comprising a sequence encoding a protein (e.g., a therapeutic protein) and/or at least one binding site. In some embodiments, the circular polyribonucleotide lacks a poly-A tail. In some embodiments, the circular polyribonucleotide lacks a replication element. In some embodiments, the circular polyribonucleotide lacks an IRES. In some embodiments, the circular polyribonucleotide lacks a cap. In some embodiments, the circular polyribonucleotide comprises any feature or any combination of features as disclosed in WO2019/118919, which is hereby incorporated by reference in its entirety.

For example, the circular polyribonucleotide comprises a sequence that encodes a peptide or polypeptide.

In some embodiments, the circular polyribonucleotide comprises one or more RNA sequences, each of which can encode a polypeptide. The polypeptide can be produced in substantial amounts. As such, the polypeptide can be any proteinaceous molecule that can be produced. A polypeptide can be a polypeptide that can be secreted from a cell, or localized to the cytoplasm, nucleus or membrane compartment of a cell.

In some embodiments, the circular polyribonucleotide includes a sequence encoding a protein e.g., a therapeutic protein. Some examples of therapeutic proteins can include, but are not limited to, an protein replacement, protein supplementation, vaccination, antigens (e.g., tumor antigens, viral, and bacterial), hormones, cytokines, antibodies, immunotherapy (e.g., cancer), cellular reprogramming/transdifferentiation factor, transcription factors, chimeric antigen receptor, transposase or nuclease, immune effector (e.g., influences susceptibility to an immune response/signal), a regulated death effector protein (e.g., an inducer of apoptosis or necrosis), a non-lytic inhibitor of a tumor (e.g., an inhibitor of an oncoprotein), an epigenetic modifying agent, epigenetic enzyme, a transcription factor, a DNA or protein modification enzyme, a DNA-intercalating agent, an efflux pump inhibitor, a nuclear receptor activator or inhibitor, a proteasome inhibitor, a competitive inhibitor for an enzyme, a protein synthesis effector or inhibitor, a nuclease, a protein fragment. Further examples of peptides are described in paragraphs [0151]-[0153] of WO2019/118919, which is hereby incorporated by reference in its entirety.

In some embodiments, the circular polyribonucleotide as disclosed herein is translation incompetent.

For example, the circular polyribonucleotide comprises a regulatory element, e.g., a sequence that modifies expression of an expression sequence within the circular polyribonucleotide. A regulatory element may include a sequence that is located adjacent to an expression sequence that encodes an expression product. A regulatory element may be operably linked to the adjacent sequence. A regulatory element may increase an amount of product expressed as compared to an amount of the expressed product when no regulatory element is present. In addition, one regulatory element can increase an amount of products expressed for multiple expression sequences attached in tandem. Hence, one regulatory element can enhance the expression of one or more expression sequences. Multiple regulatory elements can also be used, for example, to differentially regulate expression of different expression sequences. In some embodiments, a regulatory element as provided herein can include a selective translation sequence. As used herein, the term "selective translation sequence" refers to a nucleic acid sequence that selectively initiates or activates translation of an expression sequence in the circular polyribonucleotide, for instance, certain riboswitch aptazymes. A regulatory element can also include a selective degradation sequence. As used herein, the term "selective degradation sequence" refers to a nucleic acid sequence that initiates degradation of the circular polyribonucleotide, or an expression product of the circular polyribonucleotide. In some embodiments, the regulatory element is a translation modulator. A translation modulator can modulate translation of the expression sequence in the circular polyribonucleotide. A translation modulator can be a translation enhancer or suppressor. In some embodiments, a translation initiation sequence can function as a regulatory element. Further examples of regulatory elements are described in paragraphs [0154]-[0161] of WO2019/118919, which is hereby incorporated by reference in its entirety.

In some embodiments, the circular polyribonucleotide comprises a sequence encoding a protein (e.g., a therapeutic protein) and/or at least one binding site, and comprises a translation initiation sequence, e.g., a start codon. In some embodiments, the translation initiation sequence includes a Kozak or Shine-Dalgarno sequence. In some embodiments, the circular polyribonucleotide includes the translation initiation sequence, e.g., Kozak sequence, adjacent to an expression sequence. In some embodiments, the translation initiation sequence is a non-coding start codon. In some embodiments, the translation initiation sequence, e.g., Kozak sequence, is present on one or both sides of each expression sequence, leading to separation of the expression products. In some embodiments, the circular polyribonucleotide includes at least one translation initiation sequence adjacent to an expression sequence. In some embodiments, the translation initiation sequence provides conformational flexibility to the circular polyribonucleotide. In some embodiments, the translation initiation sequence is within a substantially single stranded region of the circular polyribonucleotide. Further examples of translation initiation sequences are described in paragraphs [0163]-[0165] of WO2019/118919, which is hereby incorporated by reference in its entirety.

In some embodiments, a circular polyribonucleotide described herein comprises an internal ribosome entry site (IRES) element. A suitable IRES element to include in a circular polyribonucleotide can be an RNA sequence capable of engaging an eukaryotic ribosome. Further examples of an IRES are described in paragraphs [0166]-[0168] of WO2019/118919, which is hereby incorporated by reference in its entirety.

A circular polyribonucleotide can include one or more expression sequences (e.g., a therapeutic protein), and each expression sequence may or may not have a termination element. Further examples of termination elements are described in paragraphs [0169]-[0170] of WO2019/118919, which is hereby incorporated by reference in its entirety.

A circular polyribonucleotide of the disclosure can comprise a stagger element. The term "stagger element" refers to a moiety, such as a nucleotide sequence, that induces ribosomal pausing during translation. In some embodiments, the stagger element is a non-conserved sequence of amino-acids with a strong alpha-helical propensity followed by the consensus sequence –D(V/I)ExNPGP, where x=any amino acid. In some embodiments, the stagger element may include a chemical moiety, such as glycerol, a non nucleic acid linking moiety, a chemical modification, a modified nucleic acid, or any combination thereof.

In some embodiments, the circular polyribonucleotide includes at least one stagger element adjacent to an expression sequence. In some embodiments, the circular polyribonucleotide includes a stagger element adjacent to each expression sequence. In some embodiments, the stagger element is present on one or both sides of each expression sequence, leading to separation of the expression products, e.g., peptide(s) and/or polypeptide(s). In some embodiments, the stagger element is a portion of the one or more expression sequences. In some embodiments, the circular polyribonucleotide comprises one or more expression sequences, and each of the one or more expression sequences is separated from a succeeding expression sequence by a stagger element on the circular polyribonucleotide. In some embodiments, the stagger element prevents generation of a single polypeptide (a) from two rounds of translation of a single expression sequence or (b) from one or more rounds of translation of two or more expression sequences. In some embodiments, the stagger element is a sequence separate from the one or more expression sequences. In some embodiments, the stagger element comprises a portion of an expression sequence of the one or more expression sequences.

Examples of stagger elements are described in paragraphs [0172]-[0175] of WO2019/118919, which is hereby incorporated by reference in its entirety.

In some embodiments, the circular polyribonucleotide comprises one or more regulatory nucleic acid sequences or comprises one or more expression sequences that encode regulatory nucleic acid, e.g., a nucleic acid that modifies expression of an endogenous gene and/or an exogenous gene. In some embodiments, the expression sequence of a circular polyribonucleotide as provided herein can comprise a sequence that is antisense to a regulatory nucleic acid like a non-coding RNA, such as, but not limited to, tRNA, lncRNA, miRNA, rRNA, snRNA, microRNA, siRNA, piRNA, snoRNA, snRNA, exRNA, scaRNA, Y RNA, and hnRNA.

Exemplary regulatory nucleic acids are described in paragraphs [0177]-[0194] of WO2019/118919, which is hereby incorporated by reference in its entirety.

In some embodiments, the translation efficiency of a circular polyribonucleotide as provided herein is greater than a reference, e.g., a linear counterpart, a linear expression sequence, or a linear circular polyribonucleotide. In some embodiments, a circular polyribonucleotide as provided herein has the translation efficiency that is at least about 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 250%, 300%, 350%, 400%, 450%, 500%, 600%, 70%, 800%, 900%, 1000%, 2000%, 5000%, 10000%, 100000%, or more greater than that of a reference. In some embodiments, a circular polyribonucleotide has a translation efficiency 10% greater than that of a linear counterpart. In some embodiments, a circular polyribonucleotide has a translation efficiency 300% greater than that of a linear counterpart.

In some embodiments, the circular polyribonucleotide produces stoichiometric ratios of expression products. Rolling circle translation continuously produces expression products at substantially equivalent ratios. In some embodiments, the circular polyribonucleotide has a stoichiometric translation efficiency, such that expression products are produced at substantially equivalent ratios. In some embodiments, the circular polyribonucleotide has a stoichiometric translation efficiency of multiple expression products, e.g., products from 2, 3, 4, 5, 6, 7, 8, 9, 10, 11, 12, or more expression sequences.

In some embodiments, once translation of the circular polyribonucleotide is initiated, the ribosome bound to the circular polyribonucleotide does not disengage from the circular polyribonucleotide before finishing at least one round of translation of the circular polyribonucleotide. In some embodiments, the circular polyribonucleotide as described herein is competent for rolling circle translation. In some embodiments, during rolling circle translation, once translation of the circular polyribonucleotide is initiated, the ribosome bound to the circular polyribonucleotide does not disengage from the circular polyribonucleotide before finishing at least 2 rounds, at least 3 rounds, at least 4 rounds, at least 5 rounds, at least 6 rounds, at least 7 rounds, at least 8 rounds, at least 9 rounds, at least 10 rounds, at least 11 rounds, at least 12 rounds, at least 13 rounds, at least 14 rounds, at least 15 rounds, at least 20 rounds, at least 30 rounds, at least 40 rounds, at least 50 rounds, at least 60 rounds, at least 70 rounds, at least 80 rounds, at least 90 rounds, at least 100 rounds, at least 150 rounds, at least 200 rounds, at least 250 rounds, at least 500 rounds, at least 1000 rounds, at least 1500 rounds, at least 2000 rounds, at least 5000 rounds, at least 10000 rounds, at least 105 rounds, or at least 106 rounds of translation of the circular polyribonucleotide.

In some embodiments, the rolling circle translation of the circular polyribonucleotide leads to generation of polypeptide product that is translated from more than one round of translation of the circular polyribonucleotide ("continuous" expression product). In some embodiments, the circular polyribonucleotide comprises a stagger element, and rolling circle translation of the circular polyribonucleotide leads to generation of polypeptide product that is generated from a single round of translation or less than a single round of translation of the circular polyribonucleotide ("discrete" expression product). In some embodiments, the circular polyribonucleotide is configured such that at least 10%, 20%, 30%, 40%, 50%, at least 60%, at least 70%, at least 80%, at least 90%, at least 95%, at least 96%, at least 97%, at least 98%, at least 99%, or 100% of total polypeptides (molar/molar) generated during the rolling circle translation of the circular polyribonucleotide are discrete polypeptides. In some embodiments, the amount ratio of the discrete products over the total polypeptides is tested in an in vitro translation system. In some embodiments, the in vitro translation system used for the test of amount ratio comprises rabbit reticulocyte lysate. In some embodiments, the amount ratio is tested in an in vivo translation system, such as a eukaryotic cell or a prokaryotic cell, a cultured cell or a cell in an organism.

In some embodiments, the circular polyribonucleotide comprises untranslated regions (UTRs). UTRs of a genomic region comprising a gene may be transcribed but not translated. In some embodiments, a UTR may be included upstream of the translation initiation sequence of an expression sequence described herein. In some embodiments, a UTR may be included downstream of an expression sequence described herein. In some instances, one UTR for first expression sequence is the same as or continuous with or overlapping with another UTR for a second expression sequence. In some embodiments, the intron is a human intron. In some embodiments, the intron is a full-length human intron, e.g., ZKSCAN1.

Exemplary untranslated regions are described in paragraphs [0197]-[201] of WO2019/118919, which is hereby incorporated by reference in its entirety.

In some embodiments, the circular polyribonucleotide may include a poly-A sequence. Exemplary poly-A sequences are described in paragraphs [0202]-[0205] of WO2019/118919, which is hereby incorporated by reference in its entirety. In some embodiments, the circular polyribonucleotide lacks a poly-A sequence.

In some embodiments, the circular polyribonucleotide comprises one or more riboswitches. Exemplary riboswitches are described in paragraphs [0232]-[0252] of WO2019/118919, which is hereby incorporated by reference in its entirety.

In some embodiments, the circular polyribonucleotide comprises an aptazyme. Exemplary aptazymes are described in paragraphs [0253]-[0259] of WO2019/118919, which is hereby incorporated by reference in its entirety.

In some embodiments, the circular polyribonucleotide comprises one or more RNA binding sites. microRNAs (or miRNA) can be short noncoding RNAs that bind to the 3'UTR of nucleic acid molecules and down-regulate gene expression either by reducing nucleic acid molecule stability or by inhibiting translation. The circular polyribonucleotide may comprise one or more microRNA target sequences, microRNA sequences, or microRNA seeds. Such sequences may correspond to any known microRNA, such as those taught in US Publication US2005/0261218 and US Publication US2005/0059005, the contents of which are incorporated herein by reference in their entirety. Further examples of RNA binding sites are described in paragraphs [0206]-[0215] of WO2019/118919, which is hereby incorporated by reference in its entirety.

In some embodiments, the circular polyribonucleotide includes one or more protein binding sites that enable a protein, e.g., a ribosome, to bind to an internal site in the RNA sequence. Further examples of protein binding sites are described in paragraphs [0218]-[0221] of WO2019/118919, which is hereby incorporated by reference in its entirety.

In some embodiments, the circular polyribonucleotide comprises an encryptogen to reduce, evade or avoid the innate immune response of a cell. In one aspect, provided herein are circular polyribonucleotide which when delivered to cells (e.g., contacting), results in a reduced immune response from the host as compared to the response triggered by a reference compound, e.g. a linear polynucleotide corresponding to the described circular polyribonucleotide or a circular polyribonucleotide lacking an encryptogen. In some embodiments, the circular polyribonucleotide has less immunogenicity than a counterpart lacking an encryptogen.

In some embodiments, an encryptogen enhances stability. There is growing body of evidence about the regulatory roles played by the UTRs in terms of stability of a nucleic acid molecule and translation. The regulatory features of a UTR may be included in the encryptogen to enhance the stability of the circular polyribonucleotide.

In some embodiments, 5' or 3'UTRs can constitute encryptogens in a circular polyribonucleotide. For example, removal or modification of UTR AU rich elements (AREs) may be useful to modulate the stability or immunogenicity of the circular polyribonucleotide.

In some embodiments, removal of modification of AU rich elements (AREs) in expression sequence, e.g., translatable regions, can be useful to modulate the stability or immunogenicity of the circular polyribonucleotide In some embodiments, an encryptogen comprises miRNA binding site or binding site to any other non-coding RNAs. For example, incorporation of miR-142 sites into the circular polyribonucleotide described herein may not only modulate expression in hematopoietic cells, but also reduce or abolish immune responses to a protein encoded in the circular polyribonucleotide.

In some embodiments, an encyptogen comprises one or more protein binding sites that enable a protein, e.g., an immunoprotein, to bind to the RNA sequence. By engineering protein binding sites into the circular polyribonucleotide, the circular polyribonucleotide may evade or have reduced detection by the host's immune system, have modulated degradation, or modulated translation, by masking the circular polyribonucleotide from components of the host's immune system. In some embodiments, the circular polyribonucleotide comprises at least one immunoprotein binding site, for example to evade immune reponses, e.g., CTL responses. In some embodiments, the immunoprotein binding site is a nucleotide sequence that binds to an immunoprotein and aids in masking the circular polyribonucleotide as exogenous.

In some embodiments, an encryptogen comprises one or more modified nucleotides. Exemplary modifications can include any modification to the sugar, the nucleobase, the internucleoside linkage (e.g. to a linking phosphate/to a phosphodiester linkage/to the phosphodiester backbone), and any combination thereof that can prevent or reduce immune response against the circular polyribonucleotide. Some of the exemplary modifications provided herein are described in details above.

In some embodiments, the circular polyribonucleotide includes one or more modifications as described elsewhere herein to reduce an immune response from the host as compared to the response triggered by a reference compound, e.g. a circular polyribonucleotide lacking the modifications. In particular, the addition of one or more inosine has been shown to discriminate RNA as endogenous versus viral. See for example, Yu, Z. et al. (2015) RNA editing by ADAR1 marks dsRNA as "self". Cell Res. 25, 1283-1284, which is incorporated by reference in its entirety.

In some embodiments, the circular polyribonucleotide includes one or more expression sequences for shRNA or an RNA sequence that can be processed into siRNA, and the shRNA or siRNA targets RIG-I and reduces expression of RIG-I. RIG-I can sense foreign circular RNA and leads to degradation of foreign circular RNA. Therefore, a circular polynucleotide harboring sequences for RIG-I-targeting shRNA, siRNA or any other regulatory nucleic acids can reduce immunity, e.g., host cell immunity, against the circular polyribonucleotide.

In some embodiments, the circular polyribonucleotide lacks a sequence, element or structure, that aids the circular polyribonucleotide in reducing, evading or avoiding an innate immune response of a cell. In some such embodiments, the circular polyribonucleotide may lack a polyA sequence, a 5' end, a 3' end, phosphate group, hydroxyl group, or any combination thereof.

In some embodiments, the circular polyribonucleotide comprises a spacer sequence. In some embodiments, elements of a polyribonucleotide may be separated from one another by a spacer sequence or linker. Exemplary of spacer sequences are described in paragraphs [0293]-[0302] of WO2019/118919, which is hereby incorporated by reference in its entirety.

The circular polyribonucleotide described herein may also comprise a non-nucleic acid linker. Exemplary non-nucleic acid linkers are described in paragraphs [0303]-[0307] of WO2019/118919, which is hereby incorporated by reference in its entirety.

In some embodiments, the circular polyribonucleotide further includes another nucleic acid sequence. In some embodiments, the circular polyribonucleotide may comprise other sequences that include DNA, RNA, or artificial nucleic acids. The other sequences may include, but are not limited to, genomic DNA, cDNA, or sequences that encode tRNA, mRNA, rRNA, miRNA, gRNA, siRNA, or other RNAi molecules. In some embodiments, the circular polyribonucleotide includes an siRNA to target a different locus of the same gene expression product as the circular polyribonucleotide. In some embodiments, the circular polyribonucleotide includes an siRNA to target a different gene expression product than a gene expression product that is present in the circular polyribonucleotide.

In some embodiments, the circular polyribonucleotide lacks a 5'-UTR. In some embodiments, the circular polyribonucleotide lacks a 3'-UTR. In some embodiments, the circular polyribonucleotide lacks a poly-A sequence. In some embodiments, the circular polyribonucleotide lacks a termination element. In some embodiments, the circular polyribonucleotide lacks an internal ribosomal entry site. In some embodiments, the circular polyribonucleotide lacks degradation susceptibility by exonucleases. In some embodiments, the fact that the circular polyribonucleotide lacks degradation susceptibility can mean that the circular polyribonucleotide is not degraded by an exonuclease, or only degraded in the presence of an exonuclease to a limited extent, e.g., that is comparable to or similar to in the absence of exonuclease. In some embodiments, the circular polyribonucleotide is not degraded by exonucleases. In some embodiments, the circular polyribonucleotide has reduced degradation when exposed to exonuclease. In some embodiments, the circular polyribonucleotide lacks binding to a cap-binding protein In some embodiments, the circular polyribonucleotide lacks a 5' cap.

In some embodiments, the circular polyribonucleotide lacks a 5'-UTR and is competent for protein expression from its one or more expression sequences. In some embodiments, the circular polyribonucleotide lacks a 3'-UTR and is competent for protein expression from its one or more expression sequences. In some embodiments, the circular polyribonucleotide lacks a poly-A sequence and is competent for protein expression from its one or more expression sequences. In some embodiments, the circular polyribonucleotide lacks a termination element and is competent for protein expression from its one or more expression sequences. In some embodiments, the circular polyribonucleotide lacks an internal ribosomal entry site and is competent for protein expression from its one or more expression sequences. In some embodiments, the circular polyribonucleotide lacks a cap and is competent for protein expression from its one or more expression sequences. In some embodiments, the circular polyribonucleotide lacks a 5'-UTR, a 3'-UTR, and an IRES, and is competent for protein expression from its one or more expression sequences. In some embodiments, the circular polyribonucleotide comprises one or more of the following sequences: a sequence that encodes one or more miRNAs, a sequence that encodes one or more replication proteins, a sequence that encodes an exogenous gene, a sequence that encodes a therapeutic, a regulatory element (e.g., translation modulator, e.g., translation enhancer or suppressor), a translation initiation sequence, one or more regulatory nucleic acids that targets endogenous genes (e.g., siRNA, lncRNAs, shRNA), and a sequence that encodes a therapeutic mRNA or protein.

As a result of its circularization, the circular polyribonucleotide may include certain characteristics that distinguish it from linear RNA. For example, the circular polyribonucleotide is less susceptible to degradation by exonuclease as compared to linear RNA. As such, the circular polyribonucleotide can be more stable than a linear RNA, especially when incubated in the presence of an exonuclease. The increased stability of the circular polyribonucleotide compared with linear RNA can make the circular polyribonucleotide more useful as a cell transforming reagent to produce polypeptides (e.g., antigens and/or epitopes to elicit antibody responses). The increased stability of the circular polyribonucleotide compared with linear RNA can make the circular polyribonucleotide easier to store for long than linear RNA. The stability of the circular polyribonucleotide treated with exonuclease can be tested using methods standard in art which determine whether RNA degradation has occurred (e.g., by gel electrophoresis).

Moreover, unlike linear RNA, the circular polyribonucleotide can be less susceptible to dephosphorylation when the circular polyribonucleotide is incubated with phosphatase, such as calf intestine phosphatase.

In some embodiments, the circular polyribonucleotide comprises particular sequence characteristics. For example, the circular polyribonucleotide may comprise a particular nucleotide composition. In some such embodiments, the circular polyribonucleotide may include one or more purine (adenine and/or guanosine) rich regions. In some such embodiments, the circular polyribonucleotide may include one or more purine poor regions. In some embodiments, the circular polyribonucleotide may include one or more AU rich regions or elements (AREs). In some embodiments, the circular polyribonucleotide may include one or more adenine rich regions.

In some embodiments, the circular polyribonucleotide may include one or more repetitive elements described elsewhere herein. In some embodiments, the circular polyribonucleotide comprises one or more modifications described elsewhere herein.

A circular polyribonucleotide may include one or more substitutions, insertions and/or additions, deletions, and covalent modifications with respect to reference sequences. For example, circular polyribonucleotides with one or more insertions, additions, deletions, and/or covalent modifications relative to a parent polyribonucleotide are included within the scope of this disclosure. Exemplary modifications are described in paragraphs [0310]-[0325] of WO2019/118919, which is hereby incorporated by reference in its entirety.

In some embodiments, the circular polyribonucleotide comprises a higher order structure, e.g., a secondary or tertiary structure. In some embodiments, complementary segments of the circular polyribonucleotide fold itself into a double stranded segment, held together with hydrogen bonds between pairs, e.g., A-U and C-G. In some embodiments, helices, also known as stems, are formed intramolecularly, having a double-stranded segment connected to an end loop. In some embodiments, the circular polyribonucleotide has at least one segment with a quasi-double-stranded secondary structure.

In some embodiments, one or more sequences of the circular polyribonucleotide include substantially single stranded vs double stranded regions. In some embodiments, the ratio of single stranded to double stranded may influence the functionality of the circular polyribonucleotide.

In some embodiments, one or more sequences of the circular polyribonucleotide that are substantially single stranded. In some embodiments, one or more sequences of the circular polyribonucleotide that are substantially single stranded may include a protein- or RNA-binding site. In some embodiments, the circular polyribonucleotide sequences that are substantially single stranded may be conformationally flexible to allow for increased interactions. In some embodiments, the sequence of the circular polyribonucleotide is purposefully engineered to include such secondary structures to bind or increase protein or nucleic acid binding.

In some embodiments, the circular polyribonucleotide sequences that are substantially double stranded. In some embodiments, one or more sequences of the circular polyribonucleotide that are substantially double stranded may include a conformational recognition site, e.g., a riboswitch or aptazyme. In some embodiments, the circular polyribonucleotide sequences that are substantially double stranded may be conformationally rigid. In some such instances, the conformationally rigid sequence may sterically hinder the circular polyribonucleotide from binding a protein or a nucleic acid. In some embodiments, the sequence of the circular polyribonucleotide is purposefully engineered to include such secondary structures to avoid or reduce protein or nucleic acid binding.

There are 16 possible base-pairings, however of these, six (AU, GU, GC, UA, UG, CG) may form actual base-pairs. The rest are called mismatches and occur at very low frequencies in helices. In some embodiments, the structure of the circular polyribonucleotide cannot easily be disrupted without impact on its function and lethal consequences, which provide a selection to maintain the secondary structure. In some embodiments, the primary structure of the stems (i.e., their nucleotide sequence) can still vary, while still maintaining helical regions. The nature of the bases is secondary to the higher structure, and substitutions are possible as long as they preserve the secondary structure. In some embodiments, the circular polyribonucleotide has a quasi-helical structure. In some embodiments, the circular polyribonucleotide has at least one segment with a quasi-helical structure. In some embodiments, the circular polyribonucleotide includes at least one of a U-rich or A-rich sequence or a combination thereof. In some embodiments, the U-rich and/or A-rich sequences are arranged in a manner that would produce a triple quasi-helix structure. In some embodiments, the circular polyribonucleotide has a double quasi-helical structure. In some embodiments, the circular polyribonucleotide has one or more segments (e.g., 2, 3, 4, 5, 6, or more) having a double quasi-helical structure. In some embodiments, the circular polyribonucleotide includes at least one of a C-rich and/or G-rich sequence. In some embodiments, the C-rich and/or G-rich sequences are arranged in a manner that would produce triple quasi-helix structure. In some embodiments, the circular polyribonucleotide has an intramolecular triple quasi-helix structure that aids in stabilization.

In some embodiments, the circular polyribonucleotide has two quasi-helical structure (e.g., separated by a phosphodiester linkage), such that their terminal base pairs stack, and the quasi-helical structures become colinear, resulting in a "coaxially stacked" substructure.

In some embodiments, the circular polyribonucleotide comprises a tertiary structure with one or more motifs, e.g., a pseudoknot, a g-quadruplex, a helix, and coaxial stacking.

Further examples of structure of circular polyribonucleotides as disclosed herein are described in paragraphs [0326]-[0333] of WO2019/118919, which is hereby incorporated by reference in its entirety.

In some embodiments, the circular polyribonucleotide comprises a translating element. CircRNA described herein that contain a translating element can translate RNA into proteins. Protein expression can be facilitated by a circRNA containing a sequence-specific RNA-binding motif, sequence-specific DNA-binding motif, protein-specific binding motif, and regulatory RNA motif. The regulatory RNA motif can initiate RNA transcription and protein expression.

In some embodiments, the circular polyribonucleotide includes at least one cleavage sequence. In some embodiments, the cleavage sequence is adjacent to an expression sequence. In some embodiments, the circular polyribonucleotide includes a cleavage sequence, such as in an immolating circRNA or cleavable circRNA or self-cleaving circRNA. In some embodiments, the circular polyribonucleotide comprises two or more cleavage sequences, leading to separation of the circular polyribonucleotide into multiple products, e.g., miRNAs, linear RNAs, smaller circular polyribonucleotide, etc.

In some embodiments, the cleavage sequence includes a ribozyme RNA sequence. A ribozyme (from ribonucleic acid enzyme, also called RNA enzyme or catalytic RNA) is an RNA molecule that catalyzes a chemical reaction. Many natural ribozymes catalyze either the hydrolysis of one of their own phosphodiester bonds, or the hydrolysis of bonds in other RNA, but they have also been found to catalyze the aminotransferase activity of the ribosome. Catalytic RNA can be "evolved" by in vitro methods. Similar to riboswitch activity discussed above, ribozymes and their reaction products can regulate gene expression. In some embodiments, a catalytic RNA or ribozyme can be placed within a larger non-coding RNA such that the ribozyme is present at many copies within the cell for the purposes of chemical transformation of a molecule from a bulk volume. In some embodiments, aptamers and ribozymes can both be encoded in the same non-coding RNA.

In some embodiments, circRNA described herein comprises immolating circRNA or cleavable circRNA or self-cleaving circRNA. CircRNA can deliver cellular components including, for example, RNA, lncRNA, lincRNA, miRNA, tRNA, rRNA, snoRNA, ncRNA, siRNA, or shRNA. In some embodiments, circRNA includes miRNA separated by (i) self-cleavable elements; (ii) cleavage recruitment sites; (iii) degradable linkers; (iv) chemical linkers; and/or (v) spacer sequences. In some embodiments, circRNA includes siRNA separated by (i) self-cleavable elements; (ii) cleavage recruitment sites (e.g., ADAR); (iii) degradable linkers (e.g., glycerol); (iv) chemical linkers; and/or (v) spacer sequences. Non-limiting examples of self-cleavable elements include hammerhead, splicing element, hairpin, hepatitis delta virus (HDV), Varkud Satellite (VS), and glmS ribozymes. Non-limiting examples of circRNA immolating applications are listed in TABLE 2.

TABLE 2

| Process | MOA (example) |
|---|---|
| miRNA delivery | microRNAs in a circular form with sell cleavage element (e.g. hammerhead), cleavage recruitment (e.g. ADAR) or degradable linker (glycerol) |
| siRNA delivery | siRNAs in a circular form with sell cleavage element (e.g. hammerhead), cleavage recruitment (e.g. ADAR) or degradabale linker (glycerol) |

In some embodiments, the circular polyribonucleotide is at least about 20 nucleotides, at least about 30 nucleotides, at least about 40 nucleotides, at least about 50 nucleotides, at least about 75 nucleotides, at least about 100 nucleotides, at least about 200 nucleotides, at least about 300 nucleotides, at least about 400 nucleotides, at least about 500 nucleotides, at least about 1,000 nucleotides, at least about 2,000 nucleotides, at least about 5,000 nucleotides, at least about 6,000 nucleotides, at least about 7,000 nucleotides, at least about 8,000 nucleotides, at least about 9,000 nucleotides, at least about 10,000 nucleotides, at least about 12,000 nucleotides, at least about 14,000 nucleotides, at least about 15,000 nucleotides, at least about 16,000 nucleotides, at least about 17,000 nucleotides, at least about 18,000 nucleotides, at least about 19,000 nucleotides, or at least about 20,000 nucleotides. In some embodiments, the circular polyribonucleotide may be of a sufficient size to accommodate a binding site for a ribosome. One of skill in the art can appreciate that the maximum size of a circular polyribonucleotide can be as large as is within the technical constraints of producing a circular polyribonucleotide, and/or using the circular polyribonucleotide. While not being bound by theory, it is possible that multiple segments of RNA may be produced from DNA and their 5' and 3' free ends annealed to produce a "string" of RNA, which ultimately may be circularized when only one 5' and one 3' free end remains. In some embodiments, the maximum size of a circular polyribonucleotide may be limited by the ability of packaging and delivering the RNA to a target. In some embodiments, the size of a circular polyribonucleotide is a length sufficient to encode useful polypeptides, and thus, lengths of at least 20,000 nucleotides, at least 15,000 nucleotides, at least 10,000 nucleotides, at least 7,500 nucleotides, or at least 5,000 nucleotides, at least 4,000 nucleotides, at least 3,000 nucleotides, at least 2,000 nucleotides, at least 1,000 nucleotides, at least 500 nucleotides, at least t 400 nucleotides, at least 300 nucleotides, at least 200 nucleotides, at least 100 nucleotides may be useful.

In some embodiments, the circular polyribonucleotide is capable of replicating or replicates in a cell from an aquaculture animal (fish, crabs, shrimp, oysters etc.), a mammalian cell, e.g., a cell from a pet or zoo animal (cats, dogs, lizards, birds, lions, tigers and bears etc.), a cell from a farm or working animal (horses, cows, pigs, chickens etc.), a human cell, cultured cells, primary cells or cell lines, stem cells, progenitor cells, differentiated cells, germ cells, cancer cells (e.g., tumorigenic, metastic), non-tumorigenic cells (normal cells), fetal cells, embryonic cells, adult cells, mitotic cells, non-mitotic cells, or any combination thereof. In some embodiments, the invention includes a cell comprising the circular polyribonucleotide described herein, wherein the cell is a cell from an aquaculture animal (fish, crabs, shrimp, oysters etc.), a mammalian cell, e.g., a cell from a pet or zoo animal (cats, dogs, lizards, birds, lions, tigers and bears etc.), a cell from a farm or working animal (horses, cows, pigs, chickens etc.), a human cell, a cultured cell, a primary cell or a cell line, a stem cell, a progenitor cell, a differentiated cell, a germ cell, a cancer cell (e.g., tumorigenic, metastic), a non-tumorigenic cell (normal cells), a fetal cell, an embryonic cell, an adult cell, a mitotic cell, a non-mitotic cell, or any combination thereof.

Stability and Half Life

In some embodiments, a circular polyribonucleotide provided herein has increased half-life over a reference, e.g., a linear polyribonucleotide having the same nucleotide sequence that is not circularized (linear counterpart). In some embodiments, the circular polyribonucleotide is substantially resistant to degradation, e.g., exonuclease degradation. In some embodiments, the circular polyribonucleotide is resistant to self-degradation. In some embodiments, the circular polyribonucleotide lacks an enzymatic cleavage site, e.g., a dicer cleavage site. Further examples of stability and half life of circular polyribonucleotides as disclosed herein are described in paragraphs [0308]-[0309] of WO2019/118919, which is hereby incorporated by reference in its entirety.

In some embodiments, the circular polyribonucleotide has a half-life of at least that of a linear counterpart, e.g., linear expression sequence, or linear circular polyribonucleotide. In some embodiments, the circular polyribonucleotide has a half-life that is increased over that of a linear counterpart. In some embodiments, the half-life is increased by about 5%, 10%, 15%, 20%, 25%, 30%, 35%, 40%, 45%, 50%, or greater. In some embodiments, the circular polyribonucleotide has a half-life or persistence in a cell for at least about 1 hr to about 30 days, or at least about 2 hrs, 6 hrs, 12 hrs, 18 hrs, 24 hrs, 2 days, 3, days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 60 days, or longer or any time therebetween. In certain embodiments, the circular polyribonucleotide has a half-life or persistence in a cell for no more than about 10 mins to about 7 days, or no more than about 1 hr, 2 hrs, 3 hrs, 4 hrs, 5 hrs, 6 hrs, 7 hrs, 8 hrs, 9 hrs, 10 hrs, 11 hrs, 12 hrs, 13 hrs, 14 hrs, 15 hrs, 16 hrs, 17 hrs, 18 hrs, 19 hrs, 20 hrs, 21 hrs, 22 hrs, 24 hrs, 36 hrs, 48 hrs, 60 hrs, 72 hrs, 4 days, 5 days, 6 days, 7 days, or any time therebetween. In some embodiments, the circular polyribonucleotide has a half-life or persistence in a cell while the cell is dividing. In some embodiments, the circular polyribonucleotide has a half-life or persistence in a cell post division. In certain embodiments, the circular polyribonucleotide has a half-life or persistence in a dividing cell for greater than about about 10 minutes to about 30 days, or at least about 1 hr, 2 hrs, 3 hrs, 4 hrs, 5 hrs, 6 hrs, 7 hrs, 8 hrs, 9 hrs, 10 hrs, 11 hrs, 12 hrs, 13 hrs, 14 hrs, 15 hrs, 16 hrs, 17 hrs, 18 hrs, 24 hrs, 2 days, 3, days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 60 days, or longer or any time therebetween.

In some embodiments, at least about 10%, 20%, 30%, 40%, 50%, 60%, 70%, 80%, 90%, or 95% of an amount of the circular polyribonucleotide persists for a time period of at least about 3, 4, 5, 6, 7, 8, 9, 10, 12, 14, or 16 days in a cell.

In some embodiments, the circular polyribonucleotide is non-immunogenic in a mammal, e.g., a human.

Production Methods

In some embodiments, the circular polyribonucleotide includes a deoxyribonucleic acid sequence that is non-naturally occurring and can be produced using recombinant technology (e.g., derived in vitro using a DNA plasmid), chemical synthesis, or a combination thereof.

It is within the scope of the disclosure that a DNA molecule used to produce an RNA circle can comprise a DNA sequence of a naturally-occurring original nucleic acid sequence, a modified version thereof, or a DNA sequence encoding a synthetic polypeptide not normally found in nature (e.g., chimeric molecules or fusion proteins, such as fusion proteins comprising multiple antigens and/or epitopes). DNA and RNA molecules can be modified using a variety of techniques including, but not limited to, classic mutagenesis techniques and recombinant techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof.

The circular polyribonucleotide may be prepared according to any available technique including, but not limited to chemical synthesis and enzymatic synthesis. In some embodiments, a linear primary construct or linear mRNA may be cyclized, or concatemerized to create a circular polyribonucleotide described herein. The mechanism of cyclization or concatemerization may occur through methods such as, but not limited to, chemical, enzymatic, splint ligation), or ribozyme catalyzed methods. The newly formed 5'-/3'-linkage may be an intramolecular linkage or an intermolecular linkage.

Methods of making the circular polyribonucleotides described herein are described in, for example, Khudyakov & Fields, Artificial DNA: Methods and Applications, CRC Press (2002); in Zhao, Synthetic Biology: Tools and Applications, (First Edition), Academic Press (2013); and Egli & Herdewijn, Chemistry and Biology of Artificial Nucleic Acids, (First Edition), Wiley-VCH (2012).

Various methods of synthesizing circular polyribonucleotides are also described in the art (see, e.g., U.S. Pat. Nos. 6,210,931, 5,773,244, 5,766,903, 5,712,128, 5,426,180, US Publication No. US20100137407, International Publication No. WO1992001813 and International Publication No. WO2010084371; the contents of each of which are herein incorporated by reference in their entireties).

In some embodiments, the circular polyribonucleotides is purified, e.g., free ribonucleic acids, linear or nicked RNA, DNA, proteins, etc are removed. In some embodiments, the circular polyribonucleotides may be purified by any known method commonly used in the art. Examples of nonlimiting purification methods include, column chromatography, gel excision, size exclusion, etc.

Circularization

In some embodiments, a linear circular polyribonucleotide may be cyclized, or concatemerized. In some embodiments, the linear circular polyribonucleotide may be cyclized in vitro prior to formulation and/or delivery. In some embodiments, the linear circular polyribonucleotide may be cyclized within a cell.

Extracellular Circularization

In some embodiments, the linear circular polyribonucleotide is cyclized, or concatemerized using a chemical method to form a circular polyribonucleotide. In some chemical methods, the 5'-end and the 3'-end of the nucleic acid (e.g., a linear circular polyribonucleotide) includes chemically reactive groups that, when close together, may form a new covalent linkage between the 5'-end and the 3'-end of the molecule. The 5'-end may contain an NHS-ester reactive group and the 3'-end may contain a 3'-amino-terminated nucleotide such that in an organic solvent the 3'-amino-terminated nucleotide on the 3'-end of a linear RNA molecule will undergo a nucleophilic attack on the 5'-NHS-ester moiety forming a new 5'-/3'-amide bond.

In some embodiments, a DNA or RNA ligase may be used to enzymatically link a 5'-phosphorylated nucleic acid molecule (e.g., a linear circular polyribonucleotide) to the 3'-hydroxyl group of a nucleic acid (e.g., a linear nucleic acid) forming a new phosphorodiester linkage. In an example reaction, a linear circular polyribonucleotide is incubated at 37° C. for 1 hour with 1-10 units of T4 RNA ligase (New England Biolabs, Ipswich, MA) according to the manufacturer's protocol. The ligation reaction may occur in the presence of a linear nucleic acid capable of base-pairing with both the 5'- and 3'-region in juxtaposition to assist the enzymatic ligation reaction. In some embodiments, the ligation is splint ligation. For example, a splint ligase, like SplintR® ligase, can be used for splint ligation. For splint ligation, a single stranded polynucleotide (splint), like a single stranded RNA, can be designed to hybridize with both termini of a linear polyribonucleotide, so that the two termini can be juxtaposed upon hybridization with the single-stranded splint. Splint ligase can thus catalyze the ligation of the juxtaposed two termini of the linear polyribonucleotide, generating a circular polyribonucleotide.

In some embodiments, a DNA or RNA ligase may be used in the synthesis of the circular polynucleotides. As a non-limiting example, the ligase may be a circ ligase or circular ligase.

In some embodiments, either the 5'- or 3'-end of the linear circular polyribonucleotide can encode a ligase ribozyme sequence such that during in vitro transcription, the resultant linear circular polyribonucleotide includes an active ribozyme sequence capable of ligating the 5'-end of the linear circular polyribonucleotide to the 3'-end of the linear circular polyribonucleotide. The ligase ribozyme may be derived from the Group I Intron, Hepatitis Delta Virus, Hairpin ribozyme or may be selected by SELEX (systematic evolution of ligands by exponential enrichment). The ribozyme ligase reaction may take 1 to 24 hours at temperatures between 0 and 37° C.

In some embodiments, a linear circular polyribonucleotide may be cyclized or concatermerized by using at least one non-nucleic acid moiety. In one aspect, the at least one non-nucleic acid moiety may react with regions or features near the 5' terminus and/or near the 3' terminus of the linear circular polyribonucleotide in order to cyclize or concatermerize the linear circular polyribonucleotide. In another aspect, the at least one non-nucleic acid moiety may be located in or linked to or near the 5' terminus and/or the 3' terminus of the linear circular polyribonucleotide. The non-nucleic acid moieties contemplated may be homologous or heterologous. As a non-limiting example, the non-nucleic acid moiety may be a linkage such as a hydrophobic linkage, ionic linkage, a biodegradable linkage and/or a cleavable linkage. As another non-limiting example, the non-nucleic acid moiety is a ligation moiety. As yet another non-limiting example, the non-nucleic acid moiety may be an oligonucleotide or a peptide moiety, such as an apatamer or a non-nucleic acid linker as described herein.

In some embodiments, a linear circular polyribonucleotide may be cyclized or concatermerized due to a non-nucleic acid moiety that causes an attraction between atoms, molecular surfaces at, near or linked to the 5' and 3' ends of the linear circular polyribonucleotide. As a non-limiting example, one or more linear circular polyribonucleotides may be cyclized or concatermized by intermolecular forces or intramolecular forces. Non-limiting examples of intermolecular forces include dipole-dipole forces, dipole-induced dipole forces, induced dipole-induced dipole forces, Van der Waals forces, and London dispersion forces. Non-limiting examples of intramolecular forces include covalent bonds, metallic bonds, ionic bonds, resonant bonds, agnostic bonds, dipolar bonds, conjugation, hyperconjugation and antibonding.

In some embodiments, the linear circular polyribonucleotide may comprise a ribozyme RNA sequence near the 5' terminus and near the 3' terminus. The ribozyme RNA sequence may covalently link to a peptide when the sequence is exposed to the remainder of the ribozyme. In one aspect, the peptides covalently linked to the ribozyme RNA sequence near the 5' terminus and the 3 'terminus may associate with each other causing a linear circular polyribonucleotide to cyclize or concatemerize. In another aspect, the peptides covalently linked to the ribozyme RNA near the 5' terminus and the 3' terminus may cause the linear primary construct or linear mRNA to cyclize or concatemerize after being subjected to ligated using various methods known in the art such as, but not limited to, protein ligation. Non-limiting examples of ribozymes for use in the linear primary constructs or linear RNA of the present invention or a non-exhaustive listing of methods to incorporate and/or covalently link peptides are described in US patent application No. US20030082768, the contents of which is here in incorporated by reference in its entirety.

In some embodiments, the linear circular polyribonucleotide may include a 5' triphosphate of the nucleic acid converted into a 5' monophosphate, e.g., by contacting the 5' triphosphate with RNA 5' pyrophosphohydrolase (RppH) or an ATP diphosphohydrolase (apyrase). Alternately, converting the 5' triphosphate of the linear circular polyribonucleotide into a 5' monophosphate may occur by a two-step reaction comprising: (a) contacting the 5' nucleotide of the linear circular polyribonucleotide with a phosphatase (e.g., Antarctic Phosphatase, Shrimp Alkaline Phosphatase, or Calf Intestinal Phosphatase) to remove all three phosphates; and (b) contacting the 5' nucleotide after step (a) with a kinase (e.g., Polynucleotide Kinase) that adds a single phosphate.

In some embodiments, the circularization efficiency of the circularization methods provided herein is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 95%, or 100%. In some embodiments, the circularization efficiency of the circularization methods provided herein is at least about 40%.

In some embodiment, the circular polyribonucleotide includes at least one splicing element. Exemplary splicing elements are described in paragraphs [0270]-[0275] of WO2019/118919, which is hereby incorporated by reference in its entirety.

Other Circularization Methods

In some embodiments, linear circular polyribonucleotides may include complementary sequences, including either repetitive or nonrepetitive nucleic acid sequences within individual introns or across flanking introns. Repetitive nucleic acid sequence are sequences that occur within a segment of the circular polyribonucleotide. In some embodiments, the circular polyribonucleotide includes a repetitive nucleic acid sequence. In some embodiments, the repetitive nucleotide sequence includes poly CA or poly UG sequences. In some embodiments, the circular polyribonucleotide includes at least one repetitive nucleic acid sequence that hybridizes to a complementary repetitive nucleic acid sequence in another segment of the circular polyribonucleotide, with the hybridized segment forming an internal double strand. In some embodiments, repetitive nucleic acid sequences and complementary repetitive nucleic acid sequences from two separate circular polyribonucleotides hybridize to generate a single circularized polyribonucleotide, with the hybridized segments forming internal double strands. In some embodiments, the complementary sequences are found at the 5' and 3' ends of the linear circular polyribonucleotides. In some embodiments, the complementary sequences include about 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, or more paired nucleotides.

In some embodiments, chemical methods of circularization may be used to generate the circular polyribonucleotide. Such methods may include, but are not limited to click chemistry (e.g., alkyne and azide based methods, or clickable bases), olefin metathesis, phosphoramidate ligation, hemiaminal-imine crosslinking, base modification, and any combination thereof.

In some embodiments, enzymatic methods of circularization may be used to generate the circular polyribonucleotide. In some embodiments, a ligation enzyme, e.g., DNA or RNA ligase, may be used to generate a template of the circular polyribonuclease or complement, a complementary strand of the circular polyribonuclease, or the circular polyribonuclease.

Circularization of the circular polyribonucleotide may be accomplished by methods known in the art, for example, those described in “RNA circularization strategies in vivo and in vitro” by Petkovic and Muller from Nucleic Acids Res, 2015, 43(4): 2454-2465, and “In vitro circularization of RNA” by Muller and Appel, from RNA Biol, 2017, 14(8): 1018-1027.

The circular polyribonucleotide may encode a sequence and/or motifs useful for replication. Exemplary replication elements include binding sites for RNA polymerase. Other types of replication elements are described in paragraphs [0280]-[0286] of WO2019/118919, which is hereby incorporated by reference in its entirety. In some embodiments, the circular polyribonucleotide as disclosed herein lacks a replication element, e.g., lacks an RNA-dependent RNA polymerase binding site.

In some embodiments, the circular polyribonucleotide lacks a poly-A sequence and a replication element.

Chemical Compound

A circRNA disclosed herein can be conjugated to a chemical compound by a conjugation moiety. A chemical compound can recruit a target or a substrate. A chemical compound can be a UBM or a PBM as described herein. The target can be a target protein. The substrate can be substrate protein of the target protein. The chemical compound can be a target protein ligand. A chemical compound can be a molecule selected for its ability to interact with a collection of functional groups.

A chemical compound can be a small molecule. A chemical compound can bind to a substrate protein, such as compound that binds to Human BET Bromodomain-containing proteins, the aryl hydrocarbon receptor (AHR), REF receptor kinase, FKBP, Androgen Receptor (AR), Estrogen receptor (ER), Thyroid Hormone Receptor, HIV Protease, HIV Integrase, HCV Protease, and Acyl-protein Thioesterase-1 and -2 (APTI and APT2). A chemical compound can be selected from the group consisting of Heat Shock Protein 90 (HSP90) inhibitors, Kinase and Phosphatase inhibitors, MDM2 inhibitors, HDAC inhibitors, Human Lysine Methyltransferase Inhibitors, Angiogenesis inhibitors, and immunosuppressive compounds, which can bind to the substrate. Examples of small molecules that bind to proteins include, but are not limited to 4-hydroxytamoxifen (4-OHT), AC220, Afatinib, an aminopyrazole analog, an AR antagonist, BI-7273, Bosutinib, Ceritinib, Chloroalkane, Dasatinib, Foretinib, Gefitinib, a HIF-1α-derived (R)-hydroxyproline, HJB97, a hydroxyproline-based ligand, IACS-7e, Ibrutinib, an ibrutinib derivative, Jq1, Lapatinib, an LCL161 derivative, Lenalidomide, a nutlin small molecule, OTX015, a PDE4 inhibitor, Pomalidomide, a ripk2 inhibitor, RN486, Sirt2 inhibitor 3b, SNS-032, Steel factor, a TBK1 inhibitor, Thalidomide, a thalidomide derivative, a Thiazolidinedione-based ligand, a VH032 derivative, VHL ligand 2, VHL-1, VL-269, and derivatives thereof.

Non-limiting examples of small molecules that are conjugated to circular RNAs of the disclosure that bind to exemplary target proteins are provided in TABLE 4. Non-limiting examples of chemical compounds that are conjugated to circular RNAs of the disclosure that bind to exemplary substrate proteins are provided in TABLE 3.

TABLE 3

| Exemplary Chemical Compounds | Examplary Target Protein(s) |
|---|---|
| An LCL161 derivative | IAP |
| VHL-1 | VHL |
| Pomalidomide | CRBN |
| Thalidomide | CRBN |
| Lenalidomide | CRBN |
| A thalidomide derivative | CRBN |
| A HIF-1α-derived (R)-hydroxyproline | VHL |
| VHL ligand 2 | VHL |
| VL-269 | VHL |
| VH 032 | VHL |
| A VH 032 derivative | VHL |
| A hydroxyproline-based ligand | VHL |

TABLE 4

| Exemplary Chemical Compounds | Examplary Substrate Protein(s) |
|---|---|
| Dasatinib | BCR-Abl; c-ABL |
| Lapatinib | EGFR |
| Gefitinib | EGFR |
| Foretinib | c-met |
| Sirt2 inhibitor 3b | sirt2 |
| SNS-032 | CDK9 |
| AC220 | FLT3 |
| Ceritinib | ALK |
| Ibrutinib | BTK |
| 4-OHT | ERalpha |
| Jq1 | BRD2/3/4 |
| A PDE4 inhibitor | PDE4 |
| Chloroalkane | GFP-halotag7 |
| A Thiazolidinedione- | ERRalpha |
| based ligand | RIPK2 |
| A ripk2 inhibitor | c-ABL; BCR-ABL |
| Bosutinib | BRD2/3/4 |
| OTX015 | FKBP12 |
| Steel factor | TBK1 |
| A TBK1 inhibitor | BRD9 |
| BI-7273 | wild type EGFR; |
| Lapatinib | Exon 20 insertion |
| Geftinib | EGFR; HER2 |
| Afatinib | Exon 19 deletion |
| Foretinib | EGFR; L858R EGFR |
| Sirt 2 inhibitor 3b | EGFR |
| HJB97 | c-Met |
| SNS-032 | Sirt2 |
| An aminopyrazole analog | BRD2/3/4 |
| AC220 | CDK9 |
| RN486 | CDK9 |
| Ceritinib | FLT3 |
| An adrenergic receptor | BTK |
| antagonist | ALK |
| An androgen receptor | Adrenergic receptors |
| antagonist | Androgen receptors |
| IACS-7e | TRIM24 |
| An ibrutinib derivative | wild-type BTK; C481S BTK |
| A nutlin small molecule | MDM2 |

In some embodiments, a chemical compound binds to a target protein, wherein the target protein is an enzyme. The chemical compound can bind to post-translational modifying enzyme. The chemical compound can bind to a nitrosylase, an acetyltransferase, a deacetylase, a factor that modulates SUMOylation, a methyltransferase, a kinase, a phosphatase, a glycosyltransferase, a glycoside hydrolase, or a sulfotransferase. In some embodiments, the chemical compound binds to a factor that modulates, for example, acetylation, acylation, adenylylation, ADP-ribosylation, alkylation, amidation, amide bond formation, amino acid addition, arginylation, beta-lysine addition, butyrylation, carbamidation, carbonylation, carboxylation, citrullination, C-linked glycosylation, crotonylation, diphthamide formation, deacetylation, demethylation, ethanolamine phosphoglycerol attachment, farnesylation, flavin moiety attachment, formylation, gamma-carboxyglutamic acid, gamma-carboxylation, geranilgeranilation, glutarylation, glutathionylation, glycosylation, GPI-anchor formation, heme C attachment, hydroxylation, hypusine formation, iodination, ISGylation, isoprenylation, lipoylation, malonylation, methylation, myristoylation, N-acylation, N-linked glycosylation, neddylation, nitration, nitrosylation, nucleotide addition, O-acylation, O-linked glycosylation, oxidation, palmitoylation, phosphate ester formation, phosphoramidate formation, phosphorylation, phosphopantetheinylation, polyglutamylation, polyglycylation, polysialylation, prenylation, propionylation, pyroglutamate formation, pyrrolidone carboxylic acid, pyrrolylation, pyruvate, Retinylidene Schiff base formation, S-acylation, S-diacylglycerol, S-glutathionylation, S-linked glycosylation, S-nitrosylation, SUMOylation, succinylation, sulfation, S-sulfenylation, S-sulfinylation, succinylation, ubiquitination, uridylylation, or a combination thereof. For example, a chemical compound can bind to a ubiquitin ligase, thereby generating a complex. Examples of ligands that can bind to ubiquitin ligases include, but are not limited to, a HIF-1α-derived (R)-hydroxyproline, a hydroxyproline-based ligand, an LCL161 derivative, lenalidomide, pomalidomide, thalidomide, a thalidomide derivative, a VH032 derivative, VHL-1, VHL ligand 2, VL-269, and derivatives thereof.

In some embodiments, a chemical compound binds to a substrate protein, wherein the substrate protein is a disease associated protein. The chemical compound can bind to protein associated with cancer. The chemical compound can bind to a misfolded protein. For example, a chemical compound can bind to a substrate, thereby generating a complex.

In some embodiments, a circRNA comprises a first conjugation moiety that is conjugated to a first chemical compound and a second conjugation moiety that is conjugated to a second chemical compound, wherein the first chemical compound binds to a target protein and the second chemical compound binds to a substrate protein of the target protein. In some embodiments, a circRNA comprises a first conjugation moiety that is conjugated to a first chemical compound and a second conjugation moiety that is conjugated to a second chemical compound, wherein the first chemical compound is bound to a target protein and the second chemical compound is bound to a substrate protein of the target protein, thereby forming a complex.

In some embodiments, a circRNA comprises a plurality of chemical compounds moieties. For example, the circRNA comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 70, 80, 90 or 100 or more chemical compounds or any number therein between. In some embodiments, the plurality of chemical compounds are the same. In some embodiments, the plurality of chemical compounds are different. In some embodiments, a circRNA comprises a first conjugation moiety and a second conjugation moiety. In some embodiments, a circRNA comprises a first conjugation moiety that is conjugated to a first chemical compound and a second conjugation moiety that is conjugated to a second chemical compound, wherein the first chemical compound binds to a target and the second chemical compound binds to a substrate of the target.

Conjugation to a Conjugation Moiety of a Circular Polyribonucleotide

A circRNA of the disclosure can be conjugated, for example, to a chemical compound (e.g., a small molecule), an antibody or fragment thereof, a peptide, a protein, an aptamer, a drug, or a combination thereof. In some embodiments, a small molecule is conjugated to a circRNA, thereby generating a circRNA comprising a small molecule. In some embodiments, two molecules are conjugated to a circRNA. Such two molecules can be identical or different. In instances where a circRNA is conjugated to two different molecules, e.g., a first chemical compound and a second chemical compound, such two different molecules can bind to biological molecules, e.g., molecules present in biological systems, such as proteins, nucleic acids, metabolites, etc. In some embodiments, a first chemical compound binds to a target molecule, and a second chemical compound can bind to a substrate molecule.

A circRNA of the disclosure can comprise a conjugation moiety to facilitate conjugation a chemical compound as described herein. A conjugation moiety is incorporated, for example, at an internal site of a circular polynucleotide, or at a 5' end, 3' end, or internal site of a linear polynucleotide. A conjugation moiety can be incorporated chemically or enzymatically. For example, a conjugation moiety is incorporated during solid phase oligonucleotide synthesis, cotranscriptionally (e.g., with a tolerant RNA polymerase) or posttranscriptionally (e.g., with an RNA methyltransferase). A conjugation moiety can be a nucleotide analog, e.g., bromodeoxyuridine. A conjugation moiety can comprise a reactive or functional group, e.g., an azide group or an alkyne group. A conjugation moiety can be capable of undergoing a chemoselective and/or biorthogonal reaction. Thus, in some embodiments, a conjugation moiety can be a hapten group, e.g., comprising digoxigenin, 2,4-dinitrophenyl, biotin, avidin, or are selected from azoles, nitroaryl compounds, benzofurazans, triterpenes, ureas, thioureas, rotenones, oxazoles, thiazoles, coumarins, cyclolignans, heterobiaryl compounds, azoaryl compounds or benzodiazepines. A conjugation moiety can comprise a diarylethene photoswitch capable of undergoing reversible electrocyclic rearrangement. A conjugation moiety can comprise a nucleophile, a carbanion, and/or an α,β-unsaturated carbonyl compound. In some instances, conjugation can include functional group modifications such as mesylate formation, sulfur alkylation, NHS ester formation, carbamate formation, carbonate formation, amide bond formation, or any combination thereof.

Thus, as described herein, a circRNA can be conjugated to one or more molecules covalently or non-covalently, or a combination thereof.

In some embodiments, where a circRNA is conjugated covalently, a circRNA can be conjugated via a chemical reaction, e.g., using click chemistry, Staudinger ligation, transition-metal catalyzed reactions, e.g., Pd-catalyzed C—C bond formation (e.g., Suzuki-Miyaura reaction), Michael addition, olefin metathesis, or inverse electron demand Diels-Alder. Click chemistry can utilize pairs of functional groups that rapidly and selectively react ("click") with each other in appropriate reaction conditions. Non-limiting click chemistry reactions include azide-alkyne cycloaddition, copper-catalyzed 1,3-dipolar azide-alkyne cycloaddition (CuAAC), ruthenium-catalyzed azide-alkyne cycloaddition (RuAAC), strain-promoted Azide-Alkyne Click Chemistry reaction (SPAAC), tetrazine-alkene (e.g., trans-cyclooctene) ligation, or photo-click reactions (e.g., alkene-tetrazole photoreactions). Other types of conjugation chemistry can include Schiff-base formation, peptide ligation, isopeptide bond formation, etc.

Non-limiting examples of functionalized nucleotides include modified UTP analogs, modified ATP analogs, modified CTP analogs, and/or modified GTP analogs, and any combinations thereof. In some instances, functionalized nucleotides include azide and/or alkene functional groups. Examples of such modified nucleotides include azide modified UTP analogs, 5-Azidomethyl-UTP, 5-Azido-C3-UTP, 5-Azido-PEG4-UTP, 5-Ethynyl-UTP, DBCO-PEG4-UTP, Vinyl-UTP, 8-Azido-ATP, 3'-Azido-2',3'-ddATP, 5-Azido-PEG4-CTP, 5-DBCO-PEG4-CTP, N6-Azidohexyl-3'-dATP, 5-DBCO-PEG4-dCpG and 5-azidopropyl-UTP. In some embodiments, a circRNA comprises at least one 5-Azidomethyl-UTP, 5-Azido-C3-UTP, 5-Azido-PEG4-UTP, 5-Ethynyl-UTP, DBCO-PEG4-UTP, Vinyl-UTP, 8-Azido-ATP, 5-Azido-PEG4-CTP, 5-DBCO-PEG4-CTP, or 5-azidopropyl-UTP.

A single modified nucleotide of choice (e.g., modified A, C, G, U, or T containing an azide at the 2'-position) can be incorporated site-specifically under optimized conditions (e.g., via solid-phase chemical synthesis). A plurality of nucleotides containing an azide at the 2'-position can be incorporated, for example, by substituting a nucleotide during an in vitro transcription reaction (e.g., substituting UTP for 5-azido-C3-UTP).

A circRNA conjugate can be generated using a copper-catalyzed click reaction, e.g., copper-catalyzed 1,3-dipolar azide-alkyne cycloaddition (CuAAC) of an alkyne-functionalized small molecule and an azide-functionalized polyribonucleic acid. A linear RNA can be conjugated with a small molecule. For example, a linear RNA can be modified at its 3'-end by a poly(A) polymerase with an azido-derivatized nucleotide. The azide can be conjugated to a small molecule via copper-catalyzed or strain-promoted azide-alkyne click reaction, and the linear RNA can be circularized.

A circRNA conjugate can be generated using a Staudinger reaction. For example, a circular RNA comprising an azide-functionalized circular RNA can be conjugated with an alkyne-functionalized small molecule in the presence of triphenylphosphine-3,3',3"-trisulfonic acid (TPPTS).

A circRNA conjugate can be generated using a Suzuki-Miyaura reaction. For example, a circRNA comprising a halogenated nucleotide analog can be subjected to Suzuki-Miyaura reaction in the presence of a cognate reactive partner. A a circRNA comprising 5-Iodouridine triphosphate (IUTP), for example, can be used in a catalytic system with $Pd(OAc)_2$ and 2-aminopyrimidine-4,6-diol (ADHP) or dimethylamino-substituted ADHP (DMADHP) to functionalize iodouridine-labeled circRNA in the presence of various boronic acid and ester substrates. In another example, a circRNA comprising 8-bromoguanosine is reacted with arylboronic acids in the presence of a catalytic system made of $Pd(OAc)_2$ and a water-soluble triphenylphosphan-3,3',3"-trisulfonateligand.

A circRNA conjugate can be generated using Michael addition, for example, via reaction of an an electron-rich Michael Donor with an α,β-unsaturated compound (Michael Acceptor).

Target

A chemical compound conjugated to conjugation moiety of a circRNA can bind to a target. A binding site (e.g., an aptamer) of a circular polyribonucleotide can bind to a target. Targets include, but are not limited to, nucleic acids (e.g., RNAs, DNAs, RNA-DNA hybrids), small molecules (e.g., drugs), aptamers, polypeptides, proteins, lipids, carbohydrates, antibodies, viruses, virus particles, membranes, multi-component complexes, organelles, cells, other cellular moieties, any fragments thereof, and any combination thereof (See, e.g., Fredriksson et al., (2002) Nat Biotech 20:473-77; Gullberg et al., (2004) PNAS, 101:8420-24). For example, a target is a single-stranded RNA, a double-stranded RNA, a single-stranded DNA, a double-stranded DNA, a DNA or RNA comprising one or more double stranded regions and one or more single stranded regions, an RNA-DNA hybrid, a small molecule, an aptamer, a polypeptide, a protein, a lipid, a carbohydrate, an antibody, an antibody fragment, a mixture of antibodies, a virus particle, a membrane, a multi-component complex, a cell, a cellular moiety, any fragment thereof, or any combination thereof. A target can be a target protein.

In some embodiments, a target is a polypeptide, a protein, or any fragment thereof. For example, a target is a purified polypeptide, an isolated polypeptide, a fusion tagged polypeptide, a polypeptide attached to or spanning the membrane of a cell or a virus or virion, a cytoplasmic protein, an intracellular protein, an extracellular protein, a kinase, a tyrosine kinase, a serine/threonine kinase, a phosphatase, an aromatase, a phosphodiesterase, a cyclase, a helicase, a protease, an oxidoreductase, a reductase, a transferase, a hydrolase, a lyase, an isomerase, a glycosylase, a extracellular matrix protein, a ligase, a ubiquitin ligase, an ion transporter, a channel, a pore, an apoptotic protein, a cell adhesion protein, a pathogenic protein, an aberrantly expressed protein, an transcription factor, a transcription regulator, a translation protein, an epigenetic factor, an epigenetic regulator, a chromatin regulator, a chaperone, a secreted protein, a ligand, a hormone, a cytokine, a chemokine, a nuclear protein, a receptor, a transmembrane receptor, a receptor tyrosine kinase, a G-protein coupled receptor, a growth factor receptor, a nuclear receptor, a hormone receptor, a signal transducer, an antibody, a membrane protein, an integral membrane protein, a peripheral membrane protein, a cell wall protein, a globular protein, a fibrous protein, a glycoprotein, a lipoprotein, a chromosomal protein, a proto-oncogene, an oncogene, a tumor-suppressor gene, any fragment thereof, or any combination thereof. In some embodiments, a target is a heterologous polypeptide. In some embodiments, a target is a protein overexpressed in a cell using molecular techniques, such as transfection. In some embodiments, a target is a recombinant polypeptide. For example, a target is in a sample produced from bacterial (e.g., *E. coli*), yeast, mammalian, or insect cells (e.g., proteins overexpressed by the organisms). In some embodiments, a target is a polypeptide with a mutation, insertion, deletion, or polymorphism. In some embodiments, a target is a polypeptide naturally expressed by a cell (e.g., a healthy cell or a cell associated with a disease or condition). In some embodiments, a target is an antigen, such as a polypeptide used to immunize an organism or to generate an immune response in an organism, such as for antibody production.

A target protein can comprise an enzyme that modulates a substrate, e.g., a substrate protein. In some embodiments, a target protein modulates a substrate protein by post-translational modification, for example, acetylation, acylation, adenylylation, ADP-ribosylation, alkylation, amidation, amide bond formation, amino acid addition, arginylation, beta-lysine addition, butyrylation, carbamidation, carbonylation, carboxylation, citrullination, C-linked glycosylation, crotonylation, diphthamide formation, deacetylation, demethylation, ethanolamine phosphoglycerol attachment, farnesylation, flavin moiety attachment, formylation, gamma-carboxyglutamic acid, gamma-carboxylation, geranilgeranilation, glutarylation, glutathionylation, glycosylation, GPI-anchor formation, heme C attachment, hydroxylation, hypusine formation, iodination, ISGylation, isoprenylation, lipoylation, malonylation, methylation, myristoylation, N-acylation, N-linked glycosylation, neddylation, nitration, nitrosylation, nucleotide addition, O-acylation, O-linked glycosylation, oxidation, palmitoylation, phosphate ester formation, phosphoramidate formation, phosphorylation, phosphopantetheinylation, polyglutamylation, polyglycylation, polysialylation, prenylation, propionylation, pyroglutamate formation, pyrrolidone carboxylic acid, pyrrolylation, pyruvate, Retinylidene Schiff base formation, S-acylation, S-diacylglycerol, S-glutathionylation, S-linked glycosylation, S-nitrosylation, SUMOylation, succinylation, sulfation, S-sulfenylation, S-sulfinylation, ubiquitination, uridylylation, or a combination thereof. Examples of substrate proteins include, but are not limited to, an adrenergic receptor, ALK, an androgen receptor, BCR-ABL, BRD2, BRD3, BRD4, BRD9, BTK, c-ABL, c-Met, CDK9, EGFR, ERalpha, ERRalpha, FLT3, FKBP12, GFP-halotag7, HER2, MDM2, p53, PDE4, RIPK2, sirt2, TBK1, TRIM24, or a combination thereof.

In some embodiments, a target protein is a ubiquitin ligase, an E3 ubiquitin ligase, a HECT ubiquitin ligase, a RING-finger ubiquitin ligase, a U-box ubiquitin ligase, a PHD-finger ubiquitin ligase, or a combination thereof. In some embodiments, a target protein is a ubiquitin ligase adaptor protein/complex, a proteasome adaptor protein/complex, or a proteasome protein/complex, such as RNP1, RPN10, RPN13, p62, Rad23/HR23, Dsk2/PLIC/Ubiquilin, and Ddi1. In some embodiments, a target protein is a ubiquitin adaptor that can direct substrates to autophagic vacuoles, such as p62/SQSTM-1/Sequestosome-1, neighbor of BRCA1 gene 1 (NBR1), HDAC6, ESCRT-0 complex, ESCRT-I complex, ESCRT-II complex, and ESCRT-III complex. In some embodiments, a target is a molecule that directs a substrate protein to a lysosome by endocytosis (e.g., an endocytic receptor), a molecule that directs a substrate protein to a lysosome by phagocytosis (e.g., a phagocytic receptor), a molecule that directs a substrate protein to a lysosome via autophagy, a molecule that directs a substrate protein to a lysosome via macroautophagy, a molecule that directs a substrate protein to a lysosome via microautophagy, a molecule that directs a substrate protein to a lysosome via chaperone-mediated autophagy, a molecule that directs a substrate protein to a lysosome via a multivesicular body pathway.

Further examples of target proteins include, but are not limited to, AFF4, AMFR, ANAPC11, ANKIB1, APC/C, AREL1, ARIH1, ARIH2, BARD1, beta-TrCP1, BFAR, BIRC2, BIRC3, BIRC7, BIRC8, BMI1, BRAP, BRCA1, c-IAP1CBL, CBLB, CBLC, CBLL1, CCDC36, CCNB1IP1, Cereblon (CRBN), CGRRF1, CHFR, CHIP, CNOT4, CUL9, CYHR1, DCST1, DTX1, DTX2, DTX3, DTX3L, DTX4, DZIP3, E4F1, E6AP, FANCL, G2E3, gp78, HACE1, HECTD1, HECTD2, HECTD3, HECTD4, HECW1, HECW2, HERC1, HERC2, HERC3, HERC4, HERC5, HERC6, HLTF, HOIL-IL, HOIP, HUL5, HUWE1, IAP, IRF2BP1, IRF2BP2, IRF2BPL, Itch, KCMF1, KMT2C, KMT2D, LNX1, LNX2, LONRF1, LONRF2, LONRF3, LRSAM1, LTN1, LUBAC, MAEA, MAP3K1, MARCH1, MARCH10, MARCH11, MARCH2, MARCH3, MARCH4, MARCH5, MARCH6, MARCH7, MARCH8, MARCH9, Mdm2, MDM4, MECOM, MEX3A, MEX3B, MEX3C, MEX3D, MGRN1, MIB1, MIB2, MID1, MID2, MKRN1, MKRN2, MKRN3, MKRN4P, MNAT1, MSL2, MUL1, MYCBP2, MYLIP, NEDD4, NEDD4L, NEURL1, NEURL1B, NEURL3, NFX1, NFXL1, NHLRC1, NOSIP, NSMCE1, Parkin, PARK2, PCGF1, PCGF2, PCGF3, PCGF5, PCGF6, PDZRN3, PDZRN4, PELI1, PELI2, PELI3, PEX10, PEX12, PEX2, PHF7, PHRF1, PJA1, PJA2, PLAG1, PLAGL1, PML, PPIL2, PRPF19, pVHL, RAD18, RAG1, RAPSN, RBBP6, RBCK1, RBX1, RC3H1, RC3H2, RCHY1, RFFL, RFPL1, RFPL2, RFPL3, RFPL4A, RFPL4AL1, RFPL4B, RFWD2, RFWD3, RING1, RLF, RLIM, RMND5A, RMND5B, RNF10, RNF103, RNF11, RNF111, RNF112, RNF113A, RNF113B, RNF114, RNF115, RNF121, RNF122, RNF123, RNF125, RNF126, RNF128, RNF13, RNF130, RNF133, RNF135, RNF138, RNF139, RNF14, RNF141, RNF144A, RNF144B, RNF145, RNF146, RNF148, RNF149, RNF150, RNF151, RNF152, RNF157, RNF165, RNF166, RNF167, RNF168, RNF169, RNF17, RNF170, RNF175, RNF180, RNF181, RNF182, RNF183, RNF185, RNF186, RNF187, RNF19A, RNF19B, RNF2, RNF20, RNF207, RNF208, RNF212, RNF212B, RNF213, RNF214, RNF215, RNF216, RNF217, RNF219, RNF220, RNF222, RNF223, RNF224, RNF225, RNF24, RNF25, RNF26, RNF31, RNF32, RNF34, RNF38, RNF39, RNF4, RNF40, RNF41, RNF43, RNF44, RNF5, RNF6, RNF7, RNF8, RNFT1, RNFT2, Rsp5, RSPRY1, San1, SCAF11, SCF, SHARPIN, SH3RF1, SH3RF2, SH3RF3, SHPRH, SIAH1, SIAH2, SIAH3, SMURF1, SMURF2, STUB1, SYVN1, TMEM129, Topors, TRAF2, TRAF3, TRAF4, TRAF5, TRAF6, TRAF7, TRAIP, TRIM10, TRIM11, TRIM13, TRIM15, TRIM17, TRIM2, TRIM21, TRIM22, TRIM23, TRIM24, TRIM25, TRIM26, TRIM27, TRIM28, TRIM3, TRIM31, TRIM32, TRIM33, TRIM34, TRIM35, TRIM36, TRIM37, TRIM38, TRIM39, TRIM4, TRIM40, TRIM41, TRIM42, TRIM43, TRIM43B, TRIM45, TRIM46, TRIM47, TRIM48, TRIM49, TRIM49B, TRIM49C, TRIM49D1, TRIM5, TRIM50, TRIM51, TRIM52, TRIM54, TRIM55, TRIM56, TRIM58, TRIM59, TRIM6, TRIM60, TRIM61, TRIM62, TRIM63, TRIM64, TRIM64B, TRIM64C, TRIM65, TRIM67, TRIM68, TRIM69, TRIM7, TRIM71, TRIM72, TRIM73, TRIM74, TRIM75P, TRIM77, TRIM8, TRIM9, TRIML1, TRIML2, TRIP12, TTC3, UBE3A, UBE3B, UBE3C, UBE3D, UBE4A, UBE4B, UBOX5, UBR1, UBR2, UBR3, UBR4, UBR5, UBR7, UHRF1, UHRF2, UNK, UNKL, VHL, VPS11, VPS18, VPS41, VPS8, WDR59, WDSUB1, WWP1, WWP2, XIAP, ZBTB12, ZFP91, ZFPL1, ZNF280A, ZNF341, ZNF511, ZNF521, ZNF598, ZNF645, ZNRF1, ZNRF2, ZNRF3, ZNRF4, Zswim2, and ZXDC. For example, a target protein is selected from the group consisting of von Rippel-Lindau (VHL); cereblon; XIAP; E3A; MDM2; Anaphase-promoting complex (APC); UBR5 (EDDI); SOCS/BC-box/eloBC/CUL5/RING; LNXp80; CBX4; CBLLI; HACEI; HECTDI; HECTD2; HECTD3; HECWI; HECW2; HERCI; HERC2; HERC3; HERC4; HUWEI; ITCH; NEDD4; NEDD4L; PPIL2; PRPF19; PIASI; PIAS2; PIAS3; PIAS4; RANBP2; RNF4; RBXI; SMURFI; SMURF2; STUBI; TOPORS; TRIP12; UBE3A; UBE3B; UBE3C; UBE4A; UBE4B; UBOX5; UBR5; WWPI; WWP2; Parkin; A20/TNFAIP3; AMFR/gp78; ARA54; beta-TrCPl/BTRC; BRCAI; CBL; CHIP/STUB I; E6; E6AP/UBE3A; F-box protein 15/FBXOIS; FBXW7/Cdc4; GRAIL/RNF128; HOIP/RNF3 1; cIAP-1/HIAP-2; cIAP-2/HIAP-1; cIAP (pan); ITCH/AIP4; KAPI; MARCH8; Mind Bomb 1/MIBI; Mind Bomb 2/MIB2; MuRFl/TRIM63; NDFIPI; NEDD4; NleL; Parkin; RNF2; RNF4; RNF8; RNF168; RNF43; SARTI; Skp2; SMURF2; TRAF-1; TRAF-2; TRAF-3; TRAF-4; TRAF-5; TRAF-6; TRIMS; TRIM21; TRIM32; UBR5; and ZNRF3

Further examples of target proteins include, but are not limited to, E3 ligases from Tables 13-27 in EP3458101, which is hereby incorporated by reference in its entirety.

In some embodiments, a target is an antibody. An antibody can specifically bind to a particular spatial and polar organization of another molecule. An antibody can be monoclonal, polyclonal, or a recombinant antibody, and can be prepared by techniques that are well known in the art such as immunization of a host and collection of sera (polyclonal) or by preparing continuous hybrid cell lines and collecting the secreted protein (monoclonal), or by cloning and expressing nucleotide sequences, or mutagenized versions thereof, coding at least for the amino acid sequences required for specific binding of natural antibodies. A naturally occurring antibody can be a protein comprising at least two heavy (H) chains and two light (L) chains inter-connected by disulfide bonds. Each heavy chain can be comprised of a heavy chain variable region ($V_H$) and a heavy chain constant region. The heavy chain constant region can comprise three domains, $C_{H1}$, $C_{H2}$ and $C_{H3}$. Each light chain can comprise a light chain variable region ($V_L$) and a light chain constant region. The light chain constant region can comprise one domain, $C_L$. The $V_H$ and $V_L$ regions can be further subdivided into regions of hypervariability, termed complementary determining regions (CDR), interspersed with regions that are more conserved, termed framework regions (FR). Each $V_H$ and $V_L$ can be composed of three CDRs and four FRs arranged from amino terminus to carboxy-terminus in the following order: $FR_1$, $CDR_1$, $FR_2$, $CDR_2$, $FR_3$, $CDR_3$, and $FR_4$. The constant regions of the antibodies may mediate the binding of the immunoglobulin to host tissues or factors, including various cells of the immune system (e.g., effector cells) and the first component (C1 q) of the classical complement system. The antibodies can be of any isotype (e.g., IgG, IgE, IgM, IgD, IgA and IgY), class (e.g., $lgG_1$, $lgG_2$, $lgG_3$, $lgG_4$, $lgA_1$ and $lgA_2$), subclass or modified version thereof. Antibodies may include a complete immunoglobulin or fragments thereof. An antibody fragment can refer to one or more fragments of an antibody that retain the ability to specifically bind to a binding moiety, such as an antigen. In addition, aggregates, polymers, and conjugates of immunoglobulins or their fragments are also included so long as binding affinity for a particular molecule is maintained. Examples of antibody fragments include a Fab fragment, a monovalent fragment consisting of the $V_L$, $V_H$, $C_L$ and $C_{H1}$ domains; a $F(ab)_2$ fragment, a bivalent fragment comprising two Fab fragments linked by a disulfide bridge at the hinge region; an Fd fragment consisting of the $V_H$ and $C_{H1}$ domains; an Fv fragment consisting of the VL and $V_H$ domains of a single arm of an antibody; a single domain antibody (dAb) fragment (Ward et al., (1989) Nature 341:544-46), which consists of a $V_H$ domain; and an isolated CDR and a single chain Fragment (scFv) in which the $V_L$ and $V_H$ regions pair to form monovalent molecules (known as single chain Fv (scFv); See, e.g., Bird et al., (1988) Science 242:423-26; and Huston et al., (1988) PNAS 85:5879-83). Thus, antibody fragments can include Fab, $F(ab)_2$, scFv, Fv, dAb, and the like. Although the two domains $V_L$ and $V_H$ are coded for by separate genes, they can be joined, using recombinant methods, by an artificial peptide linker that enables them to be made as a single protein chain. Such single chain antibodies include one or more antigen binding moieties. An antibody can be a polyvalent antibody, for example, bivalent, trivalent, tetravalent, pentavalent, hexavalanet, heptavalent, or octavalent antibodies. An antibody can be a multi-specific antibody. For example, bispecific, trispecific, tetraspecific, pentaspecific, hexaspecific, heptaspecific, or octaspecific antibodies are generated, e.g., by recombinantly joining a combination of any two or more antigen binding agents (e.g., Fab, $F(ab)_2$, scFv, Fv, IgG). Multi-specific antibodies can be used to bring two or more targets into close proximity, e.g., degradation machinery and a target substrate to degrade, or a ubiquitin ligase and a substrate to ubiquitinate. These antibody fragments can be obtained using conventional techniques known to those of skill in the art, and the fragments can be screened for utility in the same manner as are intact antibodies. Antibodies can be human, humanized, chimeric, isolated, dog, cat, donkey, sheep, any plant, animal, or mammal.

In some embodiments, a target is a polymeric form of ribonucleotides and/or deoxyribonucleotides (adenine, guanine, thymine, or cytosine), such as DNA or RNA (e.g., mRNA). DNA includes double-stranded DNA found in linear DNA molecules (e.g., restriction fragments), viruses, plasmids, and chromosomes. In some embodiments, a polynucleotide target is single-stranded, double stranded, small interfering RNA (siRNA), messenger RNA (mRNA), transfer RNA (tRNA), a chromosome, a gene, a noncoding genomic sequence, genomic DNA (e.g., fragmented genomic DNA), a purified polynucleotide, an isolated polynucleotide, a hybridized polynucleotide, a transcription factor binding site, mitochondrial DNA, ribosomal RNA, a eukaryotic polynucleotide, a prokaryotic polynucleotide, a synthesized polynucleotide, a ligated polynucleotide, a recombinant polynucleotide, a polynucleotide containing a nucleic acid analogue, a methylated polynucleotide, a demethylated polynucleotide, any fragment thereof, or any combination thereof. In some embodiments, a target is a recombinant polynucleotide. In some embodiments, a target is a heterologous polynucleotide. For example, a target is a polynucleotide produced from bacterial (e.g., *E. coli*), yeast, mammalian, or insect cells (e.g., polynucleotides heterologous to the organisms). In some embodiments, a target is a polynucleotide with a mutation, insertion, deletion, or polymorphism.

In some embodiments, a target is an aptamer. An aptamer is an isolated nucleic acid molecule that binds with high specificity and affinity to a binding moiety, such as a protein. An aptamer is a three dimensional structure held in certain conformation(s) that provides chemical contacts to specifically bind its given target. Although aptamers are nucleic acid based molecules, there is a fundamental difference between aptamers and other nucleic acid molecules such as genes and mRNA. In the latter, the nucleic acid structure encodes information through its linear base sequence and thus this sequence is of importance to the function of information storage. In complete contrast, aptamer function, which is based upon the specific binding of a target molecule, is not entirely dependent on a conserved linear base sequence (a non-coding sequence), but rather a particular secondary/tertiary/quaternary structure. Any coding potential that an aptamer may possess is entirely fortuitous and plays no role whatsoever in the binding of an aptamer to its cognate target. Aptamers must also be differentiated from the naturally occurring nucleic acid sequences that bind to certain proteins. These latter sequences are naturally occurring sequences embedded within the genome of the organism that bind to a specialized sub-group of proteins that are involved in the transcription, translation, and transportation of naturally occurring nucleic acids (e.g., nucleic acid-binding proteins). Aptamers on the other hand are short, isolated, non-naturally occurring nucleic acid molecules. While aptamers can be identified that bind nucleic acid-binding proteins, in most cases such aptamers have little or no sequence identity to the sequences recognized by the nucleic acid-binding proteins in nature. More importantly, aptamers can bind virtually any protein (not just nucleic acid-binding proteins) as well as almost any partner of interest including small molecules, carbohydrates, peptides, etc. For most partners, even proteins, a naturally occurring nucleic acid sequence to which it binds does not exist. For those partners that do have such a sequence, e.g., nucleic acid-binding proteins, such sequences will differ from aptamers as a result of the relatively low binding affinity used in nature as compared to tightly binding aptamers. Aptamers are capable of specifically binding to selected partners and modulating the partner's activity or binding interactions, e.g., through binding, aptamers may block their partner's ability to function. The functional property of specific binding to a partner is an inherent property an aptamer. A typical aptamer is 6-35 kDa in size (20-100 nucleotides), binds its partner with micromolar to sub-nanomolar affinity, and may discriminate against closely related targets (e.g., aptamers may selectively bind related proteins from the same gene family). In some embodiments, an aptamer is from 250-500 nucleotides. Aptamers are capable of using commonly seen intermolecular interactions such as hydrogen bonding, electrostatic complementarities, hydrophobic contacts, and steric exclusion to bind with a specific partner. Aptamers have a number of desirable characteristics for use as therapeutics and diagnostics including high specificity and affinity, low immunogenicity, biological efficacy, and excellent pharmacokinetic properties. An aptamer can comprise a molecular stem and loop structure formed from the hybridization of complementary polynucleotides that are covalently linked (e.g., a hairpin loop structure). The stem comprises the hybridized polynucleotides and the loop is the region that covalently links the two complementary polynucleotides.

In some embodiments, a target is a small molecule. For example, a small molecule is a macrocyclic molecule, an inhibitor, a drug, or chemical compound. In some embodiments, a small molecule contains no more than five hydrogen bond donors. In some embodiments, a small molecule contains no more than ten hydrogen bond acceptors. In some embodiments, a small molecule has a molecular weight of 500 Daltons or less. In some embodiments, a small molecule has a molecular weight of from about 180 to 500 Daltons. In some embodiments, a small molecule contains an octanol-water partition coefficient lop P of no more than five. In some embodiments, a small molecule has a partition coefficient log P of from −0.4 to 5.6. In some embodiments, a small molecule has a molar refractivity of from 40 to 130. In some embodiments, a small molecule contains from about 20 to about 70 atoms. In some embodiments, a small molecule has a polar surface area of 140 Angstroms$^2$ or less.

In some embodiments, a target is a cell. For example, a target is an intact cell, a cell treated with a compound (e.g., a drug), a fixed cell, a lysed cell, or any combination thereof. In some embodiments, a target is a single cell. In some embodiments, a target is a plurality of cells.

Substrate

A target can modulate a substrate. A chemical compound conjugated to a conjugation moiety of a circRNA can bind to a substrate. A binding site in a circular polyribonucleotide can bind to a substrate. Substrates include, but are not limited to, nucleic acids (e.g., RNAs, DNAs, RNA-DNA hybrids), small molecules (e.g., drugs), aptamers, polypeptides, proteins, lipids, carbohydrates, antibodies, viruses, virus particles, membranes, multi-component complexes, organelles, cells, other cellular moieties, any fragments thereof, and any combination thereof. (See, e.g., Fredriksson et al., (2002) Nat Biotech 20:473-77; Gullberg et al., (2004) PNAS, 101:8420-24). For example, a substrate is a single-stranded RNA, a double-stranded RNA, a single-stranded DNA, a double-stranded DNA, a DNA or RNA comprising one or more double stranded regions and one or more single stranded regions, an RNA-DNA hybrid, a small molecule, an aptamer, a polypeptide, a protein, a lipid, a carbohydrate, an antibody, an antibody fragment, a mixture of antibodies, a virus particle, a membrane, a multi-component complex, a cell, a cellular moiety, any fragment thereof, or any combination thereof. A substrate can be a substrate protein. The substrate protein can be modified by a target protein, which can modulate a cellular process involving the substrate protein.

A substrate protein can be a single protein. A substrate protein can be a protein aggregate. In some embodiments, a substrate protein is a protein, organelle, lipoprotein, glycoprotein, phosphoprotein, hemoprotein, flavoprotein, metalloprotein, ribonucleoprotein, or any combination thereof. A substrate protein can be associated with a disease or condition. For example, a substrate protein is a disease-associated protein. In some embodiments, a substrate protein is a misfolded protein. In some embodiments, a substrate protein comprises a mutation as compared to a wild-type version of the substrate protein. Substrate proteins include, but are not limited to, adrenergic receptors, ALK, androgen receptors, BCR-ABL, BRD2, BRD3, BRD4, BRD9, BTK, c-ABL, c-Met, CDK9, EGFR, ERalpha, ERRalpha, FLT3, FKBP12, GFP-halotag7, HER2, MDM2, p53, PDE4, RIPK2, sirt2, TBK1, TRIM24, and combinations thereof. A substrate protein can be selected from the group consisting of FoxOl, HDAC, DP-1, E2F, ABL, ALK, AMPK, BRK, BRSK I, BRSK2, BTK, CAMKKI, CAMKK alpha, CAMKK beta, Rb, Suv39HI, SCF, pl9INK4D, GSK-3, pi 8 INK4, myc, cyclin E, CDK2, CDK9, CDG4/6, Cycline D, pl6 INK4A, cdc25A, BMII, SCF, Akt, CHK1/2, CI delta, CKI gamma, C 2, CLK2, CSK, DDR2, DYRKIA/2/3, EF2K, EPH-A2/A4/B1/B2/B3/B4, EIF2A 3, Smad2, Smad3, Smad4, Smad7, p53, p21 Cipl, PAX, Fyn, CAS, C3G, SOS, Tal, Raptor, RACK-I, CRK, Rapl, Rae, KRas, NRas, HRas, GRB2, FAK, PBK, spred, Spry, mTOR, MPK, LKB1, PAK 1/2/4/5/6, PDGFRA, PYK.2, Src, SRPKI, PLC, PKC, PKA, PKB, alpha/beta, PKC alpha/gamma/zeta, PKD, PLK1, PRAK, PRK2, RIPK2, WA VE-2, TSC2, DAPK1, BAD, IMP, C-TAKI, TAKI, TAO1, TBKI, TESKI, TGFBRI, TIE2, TLKI, TrkA, TSSKI, TTBKI/2, TTK, Tpl2/cotl, MEKI, MEK2, PLDL Erk1, Erk2, Erk5, Erk8, p90RSK, PEA-15, SRF, p27 KIPI, TIF 1a, HMGNI, ER81, MKP-3, c-Fos, FGF-Rl, GCK, GSK3 beta, HER4, HIPKI/2/3/, IGF-IR, cdc25, UBF, LAMTOR2, Statl, StaO, CREB, JAK, Src, SNCA, PTEN, NF-kappaB, HECTH9, Bax, HSP70, HSP90, Apaf-1, Cyto c, BCL-2, Bcl-xL, BCL-6, Smac, XIAP, Caspase-9, Caspase-3, Caspase-6, Caspase-7, CDC37, TAB, IKK, TRADD, TRAF2, RIPI, FLIP, TAKI, JNK1/2/3, Lek, A-Raf, B-Raf, C-Raf, MOS, MLK1/3, MN 1/2, MSK1, MST2/3/4, MPSKI, MEKK1, ME K4, MEL, ASKI, MINK I, MKK 1/2/3/4/6/7, NE, 2a/6/7, NUAKI, OSRI, SAP, STK33, Syk, Lyn, PDKI, PHK, PIM 1/2/3, Ataxin-1, mTORCl, MDM2, p21 Wafl, Cyclin D1, Lamin A, Tpl2, Myc, catenin, Wnt, IKK-beta, IKKgamma, IKK-alpha, IKK-epsilon, ELK, p65Re1A, IRAKI, IRA 2, IRAK4, IRR, FADD, TRAF6, TRAF3, MKK3, MKK6, ROCK2, RSKI/2, SGK 1, SmMLCK, SIK2/3, ULKI/2, VEGFRI, WNK 1, YESI, ZAP70, MAP4K3, MAP4K5, MAPKlb, MAPKAP-K2 K3, p38, alpha/beta/delta/gamma MAPK, Aurora A, Aurora B, Aurora C, MCAK, Clip, MAPKAPK, FAK, MARK 1/2/3/4, Mud, SHC, CXCR4, Gap-I, Myc, beta-catenin/TCF, Cbl, BRM, Mel1, BRD2, BRD3, BRD4, AR, RAS, ErbB3, EGFR, IREI, HPKI, RIPK2, and ERa, PCAF/GCN5, including all variants, mutations, splice variants, indels and fusions thereof.

Substrate proteins can be modified by a post-translational modification of a peptide sequence, e.g., acetylation, acylation, adenylylation, ADP-ribosylation, alkylation, amidation, amide bond formation, amino acid addition, arginylation, beta-lysine addition, butyrylation, carbamidation, carbonylation, carboxylation, citrullination, C-linked glycosylation, crotonylation, diphthamide formation, deacetylation, demethylation, ethanolamine phosphoglycerol attachment, farnesylation, flavin moiety attachment, formylation, gamma-carboxyglutamic acid, gamma-carboxylation, geranilgeranilation, glutarylation, glutathionylation, glycosylation, GPI-anchor formation, heme C attachment, hydroxylation, hypusine formation, iodination, ISGylation, isoprenylation, lipoylation, malonylation, methylation, myristoylation, N-acylation, N-linked glycosylation, neddylation, nitration, nitrosylation, nucleotide addition, O-acylation, O-linked glycosylation, oxidation, palmitoylation, phosphate ester formation, phosphoramidate formation, phosphorylation, phosphopantetheinylation, polyglutamylation, polyglycylation, polysialylation, prenylation, propionylation, pyroglutamate formation, pyrrolidone carboxylic acid, pyrrolylation, pyruvate, Retinylidene Schiff base formation, S-acylation, S-diacylglycerol, S-glutathionylation, S-linked glycosylation, S-nitrosylation, succinylation, sulfation, S-sulfenylation, S-sulfinylation, succinylation, sumoylation, ubiquitination, uridylylation, or a combination thereof.

For example, a substrate protein is marked for degradation via ubiquitination. Substrate proteins can be marked for degradation by the attachment of ubiquitin to the amino group of the side chain of a lysine residue. Additional ubiquitins can then be added to form a polyubiquitin chain. Such polyubiquinated proteins can then be directed to, for example, a proteasome, autophagosome, or lysosome for degradation.

In some embodiments, a substrate is an antibody. An antibody can specifically bind to a particular spatial and polar organization of another molecule. An antibody can be monoclonal, polyclonal, or a recombinant antibody, and can be prepared by techniques that are well known in the art such as immunization of a host and collection of sera (polyclonal) or by preparing continuous hybrid cell lines and collecting the secreted protein (monoclonal), or by cloning and expressing nucleotide sequences, or mutagenized versions thereof, coding at least for the amino acid sequences required for specific binding of natural antibodies. A naturally occurring antibody can be a protein comprising at least two heavy (H) chains and two light (L) chains inter-connected by disulfide bonds. Each heavy chain can be comprised of a heavy chain variable region ($V_H$) and a heavy chain constant region. The heavy chain constant region can comprise three domains, $C_{H1}$, $C_{H2}$ and $C_{H3}$. Each light chain can comprise a light chain variable region ($V_L$) and a light chain constant region. The light chain constant region can comprise one domain, $C_L$. The $V_H$ and $V_L$ regions can be further subdivided into regions of hypervariability, termed complementary determining regions (CDR), interspersed with regions that are more conserved, termed framework regions (FR). Each $V_H$ and $V_L$ can be composed of three CDRs and four FRs arranged from amino-terminus to carboxy-terminus in the following order: $FR_1$, $CDR_1$, $FR_2$, $CDR_2$, $FR_3$, $CDR_3$, and $FR_4$. The constant regions of the antibodies may mediate the binding of the immunoglobulin to host tissues or factors, including various cells of the immune system (e.g., effector cells) and the first component (C1 q) of the classical complement system. The antibodies can be of any isotype (e.g., IgG, IgE, IgM, IgD, IgA and IgY), class (e.g., $lgG_1$, $lgG_2$, $lgG_3$, $lgG_4$, $lgA_1$ and $lgA_2$), subclass or modified version thereof. Antibodies may include a complete immunoglobulin or fragments thereof. An antibody fragment can refer to one or more fragments of an antibody that retain the ability to specifically bind to a binding moiety, such as an antigen. In addition, aggregates, polymers, and conjugates of immunoglobulins or their fragments are also included so long as binding affinity for a particular molecule is maintained. Examples of antibody fragments include a Fab fragment, a monovalent fragment consisting of the $V_L$, $V_H$, $C_L$ and $C_{H1}$ domains; a $F(ab)_2$ fragment, a bivalent fragment comprising two Fab fragments linked by a disulfide bridge at the hinge region; an Fd fragment consisting of the $V_H$ and $C_{H1}$ domains; an Fv fragment consisting of the $V_L$ and $V_H$ domains of a single arm of an antibody; a single domain antibody (dAb) fragment (Ward et al., (1989) Nature 341:544-46), which consists of a $V_H$ domain; and an isolated CDR and a single chain Fragment (scFv) in which the $V_L$ and $V_H$ regions pair to form monovalent molecules (known as single chain Fv (scFv); See, e.g., Bird et al., (1988) Science 242:423-26; and Huston et al., (1988) PNAS 85:5879-83). Thus, antibody fragments include Fab, $F(ab)_2$, scFv, Fv, dAb, and the like. Although the two domains $V_L$ and $V_H$ are coded for by separate genes, they can be joined, using recombinant methods, by an artificial peptide linker that enables them to be made as a single protein chain. Such single chain antibodies include one or more antigen binding moieties. An antibody can be a polyvalent antibody, for example, bivalent, trivalent, tetravalent, pentavalent, hexavalanet, heptavalent, or octavalent antibodies. An antibody can be a multi-specific antibody. For example, bispecific, trispecific, tetraspecific, pentaspecific, hexaspecific, heptaspecific, or octaspecific antibodies can be generated, e.g., by recombinantly joining a combination of any two or more antigen binding agents (e.g., Fab, $F(ab)_2$, scFv, Fv, IgG). Multi-specific antibodies can be used to bring two or more targets into close proximity. These antibody fragments can be obtained using conventional techniques known to those of skill in the art, and the fragments can be screened for utility in the same manner as are intact antibodies. Antibodies can be human, humanized, chimeric, isolated, dog, cat, donkey, sheep, any plant, animal, or mammal.

In some embodiments, a substrate is a polymeric form of ribonucleotides and/or deoxyribonucleotides (adenine, guanine, thymine, or cytosine), such as DNA or RNA (e.g., mRNA). DNA includes double-stranded DNA found in linear DNA molecules (e.g., restriction fragments), viruses, plasmids, and chromosomes. In some embodiments, a substrate is single-stranded, double stranded, small interfering RNA (siRNA), messenger RNA (mRNA), transfer RNA (tRNA), a chromosome, a gene, a noncoding genomic sequence, genomic DNA (e.g., fragmented genomic DNA), a purified polynucleotide, an isolated polynucleotide, a hybridized polynucleotide, a transcription factor binding site, mitochondrial DNA, ribosomal RNA, a eukaryotic polynucleotide, a prokaryotic polynucleotide, a synthesized polynucleotide, a ligated polynucleotide, a recombinant polynucleotide, a polynucleotide containing a nucleic acid analogue, a methylated polynucleotide, a demethylated polynucleotide, any fragment thereof, or any combination thereof. In some embodiments, a target is a recombinant polynucleotide. In some embodiments, a substrate is a heterologous polynucleotide. For example, a substrate is a polynucleotide produced from bacterial (e.g., *E. coli*), yeast, mammalian, or insect cells (e.g., polynucleotides heterologous to the organisms). In some embodiments, a substrate is a polynucleotide with a mutation, insertion, deletion, or polymorphism.

In some embodiments, substrate is an aptamer. As described herein, an aptamer is an isolated nucleic acid molecule that binds with high specificity and affinity to a binding moiety, such as a protein. Aptamers have a number of desirable characteristics for use as therapeutics and diagnostics including high specificity and affinity, low immunogenicity, biological efficacy, and excellent pharmacokinetic properties. An aptamer can comprise a molecular stem and loop structure formed from the hybridization of complementary polynucleotides that are covalently linked (e.g., a hairpin loop structure). The stem comprises the hybridized polynucleotides and the loop is the region that covalently links the two complementary polynucleotides.

In some embodiments, a substrate is a small molecule. For example, a small molecule can be a macrocyclic molecule, an inhibitor, a drug, or chemical compound. In some embodiments, a small molecule contains no more than five hydrogen bond donors. In some embodiments, a small molecule contains no more than ten hydrogen bond acceptors. In some embodiments, a small molecule has a molecular weight of 500 Daltons or less. In some embodiments, a small molecule has a molecular weight of from about 180 to 500 Daltons. In some embodiments, a small molecule contains an octanol-water partition coefficient lop P of no more than five. In some embodiments, a small molecule has a partition coefficient log P of from −0.4 to 5.6. In some embodiments, a small molecule has a molar refractivity of from 40 to 130. In some embodiments, a small molecule contains from about 20 to about 70 atoms. In some embodiments, a small molecule has a polar surface area of 140 Angstroms$^2$ or less.

In some embodiments, a substrate is a cell. For example, a substrate is an intact cell, a cell treated with a compound (e.g., a drug), a fixed cell, a lysed cell, or any combination thereof. In some embodiments, a substrate is a single cell. In some embodiments, a target is a plurality of cells.

Modulation of a Substrate

A circRNA as disclosed herein can modulate a cellular process by modifying a substrate. In some embodiments, a circRNA includes comprises a conjugation moiety for binding to chemical compound. The conjugation moiety can be a modified polyribonucleotide. The chemical compound can be conjugated to the circRNA by the conjugation moiety. In some embodiments, the chemical compound binds to a target and mediates modulation of a substrate of the target. In some embodiments, a first chemical compound binds to a target and a second chemical compound binds to a substrate and the target mediates modulation of a substrate. In some embodiments, a circRNA binds a substrate of a target and a chemical compound conjugated to the circRNA by the conjugation moiety binds the target to bring together the target and its substrate to mediate modification of the substrate, e.g., post-translational modification. In some embodiments, a circRNA binds a substrate of a target and a chemical compound conjugated to the circRNA by the conjugation moiety binds the target to bring together the target and its substrate to mediate modification of the substrate to mediate a cellular process (e.g., alters protein degradation or signal transduction) involving the substrate. In some embodiments, a target is a target protein and a substrate is a substrate protein.

In some embodiments, the circular polyribonucleotide as disclosed herein persists in a cell or subject. In some embodiments, the circular polyribonucleotide as disclosed herein persists in a cell or subject longer than a small molecule. In some embodiments, the circular polyribonucleotide as disclosed herein persists in a cell or subject longer than a corresponding proteolysis targeting chimera small molecule.

Modulation of a substrate protein comprises, for example, chemical modification of a substrate protein. In some embodiments, modulation of a substrate protein comprises post-translational modification of a peptide sequence, e.g., acetylation, acylation, adenylylation, ADP-ribosylation, alkylation, amidation, amide bond formation, amino acid addition, arginylation, beta-lysine addition, butyrylation, carbamidation, carbonylation, carboxylation, citrullination, C-linked glycosylation, crotonylation, diphthamide formation, deacetylation, demethylation, ethanolamine phosphoglycerol attachment, farnesylation, flavin moiety attachment, formylation, gamma-carboxyglutamic acid, gamma-carboxylation, geranilgeranilation, glutarylation, glutathionylation, glycosylation, GPI-anchor formation, heme C attachment, hydroxylation, hypusine formation, iodination, ISGylation, isoprenylation, lipoylation, malonylation, methylation, myristoylation, N-acylation, N-linked glycosylation, neddylation, nitration, nitrosylation, nucleotide addition, O-acylation, O-linked glycosylation, oxidation, palmitoylation, phosphate ester formation, phosphoramidate formation, phosphorylation, phosphopantetheinylation, polyglutamylation, polyglycylation, polysialylation, prenylation, propionylation, pyroglutamate formation, pyrrolidone carboxylic acid, pyrrolylation, pyruvate, Retinylidene Schiff base formation, S-acylation, S-diacylglycerol, S-glutathionylation, S-linked glycosylation, S-nitrosylation, succinylation, sulfation, S-sulfenylation, S-sulfinylation, succinylation, sumoylation, ubiquitination, uridylylation, or a combination thereof.

Modulation of a substrate protein can alter the biological activity of the substrate protein. In some embodiments, modulation of a substrate protein promotes or inhibits interaction of two or more molecules (e.g., proteins), promotes or inhibits formation of a complex (e.g., a protein complex), or promotes or inhibits of an enzymatic reaction. In some embodiments, modulation of a substrate protein alters the stability of a molecule (e.g., the substrate protein), or promotes or inhibits synthesis of a molecule (e.g., promotes or inhibits transcription, translation, or enzymatic processing). In some embodiments, modulation of a substrate protein promotes or inhibits of ubiquitination, e.g., ubiquitination of one of the one or more proteins. In some embodiments, modulation of a substrate protein promotes or inhibits degradation of a protein, e.g., degradation of one or more target proteins via proteasomal degradation or lysosomal degradation. In some embodiments, modulation of a substrate protein promotes or inhibits a signal transduction pathway, results in a conformational change, (e.g., a conformational change of a substrate protein protein), results in increased or decreased biological activity of the substrate protein, or alters localization of the substrate protein (e.g., alters sub-cellular localization). In some embodiments, modulation of a substrate protein alters a disease or condition, e.g., reduces a disease or condition in a subject. In some embodiments, modulation of a substrate protein promotes or inhibits DNA damage repair (e.g., increases or decreases the accuracy of DNA damage repair, or increases or decreases the processive efficiency of DNA damage repair). In some embodiments, modulation of a substrate protein promotes or inhibits cell cycle progression, promotes or inhibits cell division (e.g., inhibits cell division of a disease-associated cell subset), promotes or inhibits apoptosis (e.g., apoptosis of a disease-associated cell subset). In some embodiments, modulation of a substrate protein promotes or inhibits epigenetic modifications (e.g., DNA methylation or histone modification). In some embodiments, modulation of a substrate protein promotes or inhibits gene expression by promoting or inhibiting epigenetic modifications.

In some embodiments, a circRNA described herein is used to promote degradation of one or more substrate proteins. A circRNA of the disclosure can be used, for example, to direct one or more substrate proteins to degradation machinery, to bring one or more substrate proteins in close proximity with degradation machinery, to bring one or more substrate proteins in close proximity with an enzyme that can mark the substrate protein for degradation, to reduce stability of a substrate protein (e.g., shorten the substrate protein half-life), to promote association of a substrate protein with an adaptor protein that is involved in a degradation process, to promote association of a substrate protein with a sorting agent that can sort the substrate protein into a degradative pathway, or a combination thereof. Substrate proteins can be degraded, for example, by a proteasomal pathway, a lysosomal pathway, an autophagic pathway, or a combination thereof.

Ubiquitination can be a multi-step reaction which involves subsequent action of three types of enzymes: E1 ubiquitin-activating, E2 ubiquitin-conjugating enzymes and E3 ubiquitin-ligases. Ubiquitin can be bound to a substrate protein as a monomer at a single (monoubiquitination) or multiple (multi-monoubiquitination) Lys residues. A ubiquitin moiety can be further polymerized by additional ubiquitins (polyubiquitination) via any of its seven Lys residues (Lys6, Lys11, Lys27, Lys29, Lys33, Lys48, and Lys63), or the N-terminal methionine (Men). A single ubiquitin polymer can comprise one type of ubiquitin linkages (homotypic), or mixed ubiquitin linkages (heterotypic), in which a ubiquitin is joined to other ubiquitins through two or more different linkages. In some cases, ubiquitin is also be modified at two or more sites, forming a branched polymer. Ubiquitin on substrate proteins can be modified by ubiquitin-like modifiers such as SUMO, NEDD8, and ISG15, or small molecule chemicals such as phosphate and acetate. The ubiquitin linkages and their modifications can generate distinct structures and recruit specific downstream effectors. Ubiquitin chains can bind to adaptors which can decode the distinct structures of ubiquitin chains and transfer the information on the substrate proteins to downstream machinery.

Ubiquitinated substrate proteins can be degraded by a proteasome. For example, adaptors (e.g., RNP1, RPN10, RPN13, p62, Rad23/HR23, Dsk2/PLIC/Ubiquilin, Ddi1) can deliver ubiquitinated substrate proteins to the proteasome. The substrate protein can then be deubiquitinated and threaded into the interior of the proteasome, where it can be degraded by chymotrypsin-, trypsin-, and caspase-like proteolytic activities.

Ubiquitinated substrate proteins can also be delivered to autophagosomes and/or lysosomes for degradation. For example, some ubiquitin adaptors link the substrate proteins to autophagic vacuoles (e.g., p62/SQSTM-1/Sequestosome-1, neighbor of BRCA1 gene 1 (NBR1), HDAC6, ESCRT-0 complex, ESCRT-I complex, ESCRT-II complex, ESCRT-III complex). These adaptors can direct ubiquitinated substrate proteins to autophagic vacuoles, e.g., by binding ubiquitin on substrate proteins using ubiquitin binding domains and LC3 on autophagic vacuoles using LIR domains.

In some embodiments, ubiquitinated substrate proteins are not degraded by the proteasome but are modulated in other ways. The diversity of possible effects of ubiquitination can be related to the number of ubiquitin modifications present on a substrate protein (e.g., monoubiquitination or multi-monoubiquitination), characteristics of polyubiquitin chains, e.g., linear versus branched, type of linkages present (e.g., Lys6, Lys11, Lys27, Lys29, Lys33, Lys48, Lys63, Met1), homotypic versus heterotypic chains, modifications by ubiquitin-like modifiers such as SUMO, NEDD8, and ISG15, or small molecule chemicals such as phosphate and acetate, and downstream effectors, e.g., ubiquitin adaptors which can decode the distinct structures of ubiquitin chains.

Ubiquitination of a substrate protein can affect, for example, cell cycle regulation, DNA damage responses, substrate trafficking (e.g., trafficking of proteins to or from the plasma membrane), endocytosis, innate immunity, and intracellular signaling. For example, ubiquitination of a substrate protein can increase or decrease biological activity, increase or decrease interaction with a partner, or increase or decrease activation of a signal transduction pathway. Ubiquitination of substrate proteins can have effects that include but are not limited to modulation of immune and inflammatory signaling processes (e.g., modulation of NF-κB transcription factor activation, modulation of T and B cell development, modulation of cytokine signaling, modulation of TNF signaling pathways, modulation of NOD-like receptor signaling, modulation of TLR signaling, modulation of IL-1B signaling, modulation of RIG-I-like receptor signaling), modulation of cell death, modulation of embryonic development, modulation of autoimmune disease, modulation of JNK phosphorylation, modulation of Wnt signaling, and combinations thereof.

In some embodiments, a circRNA described herein is used to promote ubiquitination of a substrate protein (e.g., for proteasomal and/or lysosomal degradation). In some embodiments, a circRNA described herein is used to promote ubiquitination of a substrate protein without further administering a ubiquitin ligase (e.g., the circRNA associated degradation uses endogenous ubiquitin ligase). In some embodiments, a circRNA comprises a first binding site that binds a substrate protein, and a second binding site that binds a ubiquitin ligase. In some embodiments, a circRNA comprises a first binding site that binds a substrate protein, and a conjugation moiety bound to a small molecule that binds a ubiquitin ligase. In some embodiments, a circRNA comprises a conjugation moiety bound to a small molecule that binds a substrate protein, and a binding site that binds a ubiquitin ligase. A circRNA of the disclosure binds, for example, an E3 ubiquitin ligase, a HECT ubiquitin ligase, a RING-finger ubiquitin ligase, a U-box ubiquitin ligase, a PHD-finger ubiquitin ligase, or a combination thereof. For example, a circRNA of the disclosure binds one or more ubiquitin ligases including, but not limited to, AFF4, AMFR, ANAPC11, ANKIB1, APC/C, AREL1, ARIH1, ARIH2, BARD1, beta-TrCP1, BFAR, BIRC2, BIRC3, BIRC7, BIRC8, BMI1, BRAP, BRCA1, c-IAP1CBL, CBLB, CBLC, CBLL1, CCDC36, CCNB1IP1, Cereblon (CRBN), CGRRF1, CHFR, CHIP, CNOT4, CUL9, CYHR1, DCST1, DTX1, DTX2, DTX3, DTX3L, DTX4, DZIP3, E4F1, E6AP, FANCL, G2E3, gp78, HACE1, HECTD1, HECTD2, HECTD3, HECTD4, HECW1, HECW2, HERC1, HERC2, HERC3, HERC4, HERC5, HERC6, HLTF, HOIL-IL, HOIP, HUL5, HUWE1, IAP, IRF2BP1, IRF2BP2, IRF2BPL, Itch, KCMF1, KMT2C, KMT2D, LNX1, LNX2, LONRF1, LONRF2, LONRF3, LRSAM1, LTN1, LUBAC, MAEA, MAP3K1, MARCH1, MARCH10, MARCH11, MARCH2, MARCH3, MARCH4, MARCH5, MARCH6, MARCH7, MARCH8, MARCH9, Mdm2, MDM4, MECOM, MEX3A, MEX3B, MEX3C, MEX3D, MGRN1, MIB1, MIB2, MID1, MID2, MKRN1, MKRN2, MKRN3, MKRN4P, MNAT1, MSL2, MUL1, MYCBP2, MYLIP, NEDD4, NEDD4L, NEURL1, NEURL1B, NEURL3, NFX1, NFXL1, NHLRC1, NOSIP, NSMCE1, Parkin, PARK2, PCGF1, PCGF2, PCGF3, PCGF5, PCGF6, PDZRN3, PDZRN4, PELI1, PELI2, PELI3, PEX10, PEX12, PEX2, PHF7, PHRF1, PJA1, PJA2, PLAG1, PLAGL1, PML, PPIL2, PRPF19, pVHL, RAD18, RAG1, RAPSN, RBBP6, RBCK1, RBX1, RC3H1, RC3H2, RCHY1, RFFL, RFPL1, RFPL2, RFPL3, RFPL4A, RFPL4AL1, RFPL4B, RFWD2, RFWD3, RING1, RLF, RLIM, RMND5A, RMND5B, RNF10, RNF103, RNF11, RNF111, RNF112, RNF113A, RNF113B, RNF114, RNF115, RNF121, RNF122, RNF123, RNF125, RNF126, RNF128, RNF13, RNF130, RNF133, RNF135, RNF138, RNF139, RNF14, RNF141, RNF144A, RNF144B, RNF145, RNF146, RNF148, RNF149, RNF150, RNF151, RNF152, RNF157, RNF165, RNF166, RNF167, RNF168, RNF169, RNF17, RNF170, RNF175, RNF180, RNF181, RNF182, RNF183, RNF185, RNF186, RNF187, RNF19A, RNF19B, RNF2, RNF20, RNF207, RNF208, RNF212, RNF212B, RNF213, RNF214, RNF215, RNF216, RNF217, RNF219, RNF220, RNF222, RNF223, RNF224, RNF225, RNF24, RNF25, RNF26, RNF31, RNF32, RNF34, RNF38, RNF39, RNF4, RNF40, RNF41, RNF43, RNF44, RNF5, RNF6, RNF7, RNF8, RNFT1, RNFT2, Rsp5, RSPRY1, San1, SCAF11, SCF, SHARPIN, SH3RF1, SH3RF2, SH3RF3, SHPRH, SIAH1, SIAH2, SIAH3, SMURF1, SMURF2, STUB1, SYVN1, TMEM129, Topors, TRAF2, TRAF3, TRAF4, TRAF5, TRAF6, TRAF7, TRAIP, TRIM10, TRIM11, TRIM13, TRIM15, TRIM17, TRIM2, TRIM21, TRIM22, TRIM23, TRIM24, TRIM25, TRIM26, TRIM27, TRIM28, TRIM3, TRIM31, TRIM32, TRIM33, TRIM34, TRIM35, TRIM36, TRIM37, TRIM38, TRIM39, TRIM4, TRIM40, TRIM41, TRIM42, TRIM43, TRIM43B, TRIM45, TRIM46, TRIM47, TRIM48, TRIM49, TRIM49B, TRIM49C, TRIM49D1, TRIM5, TRIM50, TRIM51, TRIM52, TRIM54, TRIM55, TRIM56, TRIM58, TRIM59, TRIM6, TRIM60, TRIM61, TRIM62, TRIM63, TRIM64, TRIM64B, TRIM64C, TRIM65, TRIM67, TRIM68, TRIM69, TRIM7, TRIM71, TRIM72, TRIM73, TRIM74, TRIM75P, TRIM77, TRIM8, TRIM9, TRIML1, TRIML2, TRIP12, TTC3, UBE3A, UBE3B, UBE3C, UBE3D, UBE4A, UBE4B, UBOX5, UBR1, UBR2, UBR3, UBR4, UBR5, UBR7, UHRF1, UHRF2, UNK, UNKL, VHL, VPS11, VPS18, VPS41, VPS8, WDR59, WDSUB1, WWP1, WWP2, XIAP, ZBTB12, ZFP91, ZFPL1, ZNF280A, ZNF341, ZNF511, ZNF521, ZNF598, ZNF645, ZNRF1, ZNRF2, ZNRF3, ZNRF4, Zswim2, ZXDC, proteins coded for by the aforementioned genes, or combinations thereof. For example, a circRNA of the disclosure binds one or more ubiquitin ligases selected from the group consisting of von Rippel-Lindau (VHL); cereblon; XIAP; E3A; MDM2; Anaphase-promoting complex (APC); UBR5 (EDDI); SOCS/BC-box/eloBC/CUL5/RING; LNXp80; CBX4; CBLLI; HACEI; HECTDI; HECTD2; HECTD3; HECWI; HECW2; HERCI; HERC2; HERC3; HERC4; HUWEI; ITCH; NEDD4; NEDD4L; PPIL2; PRPF19; PIASI; PIAS2; PIAS3; PIAS4; RANBP2; RNF4; RBXI; SMURFI; SMURF2; STUBI; TOPORS; TRIP12; UBE3A; UBE3B; UBE3C; UBE4A; UBE4B; UBOX5; UBR5; WWPI; WWP2; Parkin; A20/TNFAIP3; AMFR/gp78; ARA54; beta-TrCPl/BTRC; BRCAI; CBL; CHIP/STUB I; E6; E6AP/UBE3A; F-box protein 15/FBXOIS; FBXW7/Cdc4; GRAIL/RNF128; HOIP/RNF3 1; cIAP-1/HIAP-2; cIAP-2/HIAP-1; cIAP (pan); ITCH/AIP4; KAPI; MARCH8; Mind Bomb 1/MIBI; Mind Bomb 2/MIB2; MuRFl/TRIM63; NDFIPI; NEDD4; NleL; Parkin; RNF2; RNF4; RNF8; RNF168; RNF43; SARTI; Skp2; SMURF2; TRAF-1; TRAF-2; TRAF-3; TRAF-4; TRAF-5; TRAF-6; TRIMS; TRIM21; TRIM32; UBR5; and ZNRF3. A circRNA of the disclosure binds one or more ubiquitin ligases including, but not limited to, E3 ligases from Tables 13-27 in EP3458101, which is hereby incorporated by reference in its entirety.

In some embodiments, a circRNA described herein is used to direct a substrate protein to proteasomal degradation without binding an E3 ubiquitin ligase. For example, a circRNA comprises a first binding site that binds a substrate protein, and a second binding site that directs the substrate protein to a proteasome (e.g., via binding a ubiquitin ligase adaptor protein/complex, a proteasome adaptor protein/ complex, or a proteasome protein/complex). A circRNA of the disclosure binds, for example, RNP1, RPN10, RPN13, p62, Rad23/HR23, Dsk2/PLIC/Ubiquilin, Ddi1, or a combination thereof. A circRNA of the disclosure binds, for example, FoxOl, HDAC, DP-1, E2F, ABL, ALK, AMPK, BRK, BRSK I, BRSK2, BTK, CAMKKI, CAMKK alpha, CAMKK beta, Rb, Suv39HI, SCF, pl91NK4D, GSK-3, pi 8 INK4, myc, cyclin E, CDK2, CDK9, CDG4/6, Cycline D, pl6 INK4A, cdc25A, BMII, SCF, Akt, CHK1/2, CI delta, CKI gamma, C 2, CLK2, CSK, DDR2, DYRKIA/2/3, EF2K, EPH-A2/A4/B1/B2/B3/B4, EIF2A 3, Smad2, Smad3, Smad4, Smad7, p53, p21 Cipl, PAX, Fyn, CAS, C3G, SOS, Tal, Raptor, RACK-I, CRK, Rapl, Rae, KRas, NRas, HRas, GRB2, FAK, PBK, spred, Spry, mTOR, MPK, LKB1, PAK 1/2/4/5/6, PDGFRA, PYK.2, Src, SRPKI, PLC, PKC, PKA, PKB, alpha/beta, PKC alpha/gamma/zeta, PKD, PLK1, PRAK, PRK2, RIPK2, WA VE-2, TSC2, DAPK1, BAD, IMP, C-TAKI, TAKI, TAO1, TBKI, TESKI, TGFBRI, TIE2, TLKI, TrkA, TSSKI, TTBKI/2, TTK, Tpl2/cotl, MEKI, MEK2, PLDL Erk1, Erk2, Erk5, Erk8, p90RSK, PEA-15, SRF, p27 KIPI, TIF 1a, HMGNI, ER81, MKP-3, c-Fos, FGF-Rl, GCK, GSK3 beta, HER4, HIPKI/2/3/, IGF-IR, cdc25, UBF, LAMTOR2, Statl, StaO, CREB, JAK, Src, SNCA, PTEN, NF-kappaB, HECTH9, Bax, HSP70, HSP90, Apaf-1, Cyto c, BCL-2, Bcl-xL, BCL-6, Smac, XIAP, Caspase-9, Caspase-3, Caspase-6, Caspase-7, CDC37, TAB, IKK, TRADD, TRAF2, RIPI, FLIP, TAKI, JNK1/2/3, Lek, A-Raf, B-Raf, C-Raf, MOS, MLK1/3, MN 1/2, MSK1, MST2/3/4, MPSKI, MEKK1, ME K4, MEL, ASKI, MINK I, MKK 1/2/3/4/6/7, NE, 2a/6/7, NUAKI, OSRI, SAP, STK33, Syk, Lyn, PDKI, PHK, PIM 1/2/3, Ataxin-1, mTORCl, MDM2, p21 Wafl, Cyclin D1, Lamin A, Tpl2, Myc, catenin, Wnt, IKK-beta, IKKgamma, IKK-alpha, IKK-epsilon, ELK, p65Re1A, IRAKI, IRA 2, IRAK4, IRR, FADD, TRAF6, TRAF3, MKK3, MKK6, ROCK2, RSKI/2, SGK 1, SmMLCK, SIK2/3, ULKI/2, VEGFRI, WNK 1, YESI, ZAP70, MAP4K3, MAP4K5, MAPKlb, MAPKAP-K2 K3, p38, alpha/beta/delta/gamma MAPK, Aurora A, Aurora B, Aurora C, MCAK, Clip, MAPKAPK, FAK, MARK 1/2/3/4, Mucl, SHC, CXCR4, Gap-I, Myc, beta-catenin/TCF, Cbl, BRM, Mell, BRD2, BRD3, BRD4, AR, RAS, ErbB3, EGFR, IREI, HPKI, RIPK2, ERa, or PCAF/GCN5, including all variants, mutations, splice variants, indels and fusions thereof.

In some embodiments, a circRNA described herein is used to promote lysosomal degradation of a substrate protein. Lysosomes are membrane-enclosed organelles that can contain an array of digestive enzymes to degrade their contents. Substrate proteins can be delivered to lysosomes, for example, via endocytosis, phagocytosis, autophagy, macroautophagy, microautophagy, chaperone-mediated autophagy, or the multivesicular body pathway. Endocytosis and phagocytosis can deliver substrate proteins from an extracellular environment to lysosomes, e.g., via processes initiated by ligation of one or more endocytic or phagocytic receptors. Autophagy can deliver substrate proteins from an intracellular environment to lysosomes. In macroautophagy, proteins can be sequestered in vesicles that form in the cytosol and then fuse with lysosomes to transfer their contents for degradation. In microautophagy, proteins can be trapped inside vesicles that form directly through the invagination of the lysosomal membrane. These vesicles can then pinch off into the lysosomal lumen for degradation. In chaperone-mediated autophagy, substrate protein proteins in the cytosol can be recognized through the binding of a constitutive chaperone, the heat shock-cognate protein of 70 KDa (hsc70), to a pentapeptide motif present in the substrate protein. After substrate protein binding, the substrate protein can be translocated into the lysosomal lumen and degraded. Multivesicular bodies (MVBs) are a specialized subset of endosomes that contain membrane-bound intraluminal vesicles. These vesicles can form by budding into the lumen of the MVB. Sorting mechanisms can determine which MVB contents can be degraded via fusion with lysosomes, and which MVB contents can be recycled to the plasma membrane.

In some embodiments, a circRNA described herein is used to promote lysosomal degradation of a substrate protein. For example, a circRNA comprises a first binding site that binds a substrate protein, and a second binding site that directs the substrate protein to a lysosome. A circRNA of the disclosure can bind, for example, a ubiquitin ligase adaptor, or a second substrate that is trafficked to lysosomes, e.g., p62/SQSTM-1/Sequestosome-1, neighbor of BRCA1 gene 1 (NBR1), HDAC6, ESCRT-0 complex, ESCRT-I complex, ESCRT-II complex, or ESCRT-III complex. In some embodiments, a circRNA described herein is used to direct a substrate protein to a lysosome via endocytosis. For example, a circRNA comprises a first binding site that binds a substrate protein, and a second binding site that directs the substrate protein to an endocytic receptor. In some embodiments, a circRNA described herein is used to direct a substrate protein to a lysosome via phagocytosis. For example, a circRNA comprises a first binding site that binds a substrate protein, and a second binding site site binds to and directs the circular polyribonucleotide bound to the substrate protein to a phagocytic receptor. In some embodiments, a circRNA described herein is used to direct a substrate protein to a lysosome via autophagy, e.g., via macroautophagy, microautophagy, chaperone-mediated autophagy, the multivesicular body pathway, or a combination thereof. For example, a circRNA comprises a first binding site that binds a substrate protein, and a second binding site that binds a factor that modulates an autophagy pathway, e.g., is involved in initiating an autophagy pathway or sorting substrates to the lysosome.

In some embodiments, a circRNA described herein is used to promote or inhibit nitrosylation of a substrate protein. For example, a circRNA comprises a first binding site that binds a substrate protein, and a second binding site that binds a factor involved in nitrosylation. Examples of factors involved in nitrosylation include, but are not limited to, nitrosylases, denitrosylases, NOS1, NOS2, NOS3, nNOS, iNOS, eNOS, hemoglobin, cytoglobin, neuroglobin, cytochrome C, ceruloplasmin, thioredoxin, GAPDH, caspase 3, CDK5, glutathione glypican 1, AE1, caspase 3, HDAC, SIRT-1, DNA-PK, X-linked inhibitor of apoptosis, and dynamin-related protein 1.

In some embodiments, a circRNA described herein is used to promote or inhibit acetylation of a substrate protein. For example, a circRNA can comprise a first binding site that binds a substrate protein, and a second binding site that binds an acetyltransferase or a deacetylase. A circRNA of the disclosure binds, for example, a lysine acetyltransferase, a histone acetyltransferase, a deacetylase, or a combination thereof. For example a circRNA of the disclosure binds one or more factors that modulate acetylation, including, but not limited to, proteins encoded by ATAT1, CLOCK, CREBBP, ELP3, EP300, ESCO1, ESCO2, GTF3C4, HAT1, KAT14, KAT2A, KAT2B, MCM3AP, NCOA1, NCOA2, NCOA3, TAF1, HDAC1, HDAC2, HDAC3, HDAC4, HDAC5, HDAC6, HDAC7, HDAC8, HDAC8, HDAC9, HDAC10, HDAC11, SIRT1, SIRT2, SIRT3, SIRT4, SIRT5, SIRT6, and SIRT7.

In some embodiments, a circRNA described herein is used to promote or inhibit SUMOylation of a substrate protein. For example, a circRNA comprises a first binding site that binds a substrate protein, and a second binding site that binds a factor that modulates SUMOylation. For example, a circRNA of the disclosure binds one or more factors that modulate SUMOylation, including, but not limited to, SAE1, SAE2, UBA2, UBE2I, SUMO1, SUMO2, SUMO3, SUMO4, Senp, Ubc9, proteins encoded by the aforementioned genes, or a combination thereof.

In some embodiments, a circRNA described herein is used to promote or inhibit methylation of a substrate protein. For example, a circRNA comprises a first binding site that binds a substrate protein, and a second binding site that binds a methyltransferase. A circRNA of the disclosure binds, for example, a seven beta-strand methyltransferase, a SET methyltransferase, a SPOUT methyltransferase, a radical SAM methyltransferase, a MetH activating methyltransferase, a homocysteine methyltransferase, a membrane methyltransferase, a precorrin-like methyltransferrase, a TYW3 methyltransferase, a demethylase, or a combination thereof. For example, a circRNA of the disclosure binds one or more factors that modulate methylation, including, but not limited to, proteins encoded by AS3MT, ASH1L, ASMT, ASMTL, ATPSCKMT, BCDIN3D, BMT2, BUD23, CAMKMT, CARNMT1, CIAPIN1, CMTR1, CMTR2, COMT, COMTD1, COQ3, COQ5, DIMT1, DNMT1, DOT1L, DOT1L, EEF1AKMT1, EEF2KMT, EHMT1, EHMT2, EZH1, EZH2, FAM173A, FAM86B1, FAM86B2, FASN, FBL, FBLL1, FTSJ1, FTSJ3, GAMT, GNMT, GSTCD, HEMK1, HENMT1, HNMT, INMT, KMT2A, KMT2B, KMT2C, KMT2D, KMT2E, KMT5A, KMT5B, KMT5C, LCMT1, LCMT2, MECOM, MEPCE, MRM2, N6AMT1, NDUFAF5, NDUFAF7, NNMT, NSD1, NSD2, NSD3, PCMT1, PCMTD1, PCMTD2, PNMT, PRDM16, PRDM2, PRDM6, PRDM8, PRDM9, RNMT, RRP8, SETD1A, SETD1B, SETD2, SETD7, SETDB1, SETDB2, SMYD1, SMYD2, SMYD3, SUV39H1, SUV39H2, TFB1M, TFB2M, TGS1, THUMPD2, THUMPD3, TPMT, TRDMT1, ZCCHC4, KDM1A, JMJD1C, KDM1B, KDM2A, KDM2B, KDM3A, KDM3B, KDM4A, KDM4B, KDM4C, KDM4D, KDM4E, KDM4F, KDM5A, KDM5B, KDM5C, KDM5D, KDM6A, KDM6B, KDM7A, KDM8, PHF2, PHF8, and UTY.

In some embodiments, a circRNA described herein is used to promote or inhibit phosphorylation of a substrate protein. For example, a circRNA comprises a first binding site that binds a substrate protein, and a second binding site that binds a kinase or a phosphatase. A circRNA of the disclosure binds, for example, a kinase, a protein kinase, a serine/threonine kinase, a tyrosine kinase, a receptor tyrosine kinase, a lipid kinase, a phosphatidylinositol kinase, a sphingosine kinase, a carbohydrate kinase, a thymidine kinase, a histidine kinase, a phosphatase, a tyrosine phosphatase, a serine/threonine phosphatase, a dual-specificity phosphatase, a histidine phosphatase, a phosphoprotein protein phosphatase, a lipid phosphatase, a haloacid dehalogenase, or a combination thereof. For example a circRNA of the disclosure can bind one or kinases, including, but not limited to, A6, A6ps1, A6ps2, A6r, AAK1, ABL, ACK, ACTR2, ACTR2B, ADCK1, ADCK2, ADCK3, ADCK4, ADCK5, AKT1, AKT2, AKT3, ALK, ALK1, ALK2, ALK4, ALK7, AlphaK1, AlphaK2, AlphaK3, AMPKal, AMPKa2, ANKRD3, ANPa, ANPb, ARAF, ARAFps, ARG, ATM, ATR, AurA, AurAps1, AurAps2, AurB, AurBpsl, AurC, AXL, BARK1, BARK2, BCKDK, BCR, BIKE, BLK, BMPR1A, BMPR1Aps1, BMPR1Aps2, BMPR1B, BMPR2, BMX, BRAF, BRAFps, BRD2, BRD3, BRD4, BRDT, BRK, BRSK1, BRSK2, BTK, BUB1, BUBR1, CaMK1a, CaMK1b, CaMK1d, CaMK1g, CaMK2a, CaMK2b, CaMK2d, CaMK2g, CaMK4, CaMKK1, CaMKK2, caMLCK, CASK, CCK4, CCRK, CDC2, CDC7, CDK10, CDK11, CDK2, CDK3, CDK4, CDK4ps, CDK5, CDK5ps, CDK6, CDK7, CDK7ps, CDK8, CDK8ps, CDK9, CDKL1, CDKL2, CDKL3, CDKL4, CDKL5, CGDps, ChaK1, ChaK2, CHED, CHK1, CHK2, CHK2ps1, CHK2ps2, CK1a, CK1a2, CK1aps1, CK1aps2, CK1aps3, CK1d, CK1e, CK1g1, CK1g2, CK1g2ps, CK1g3, CK2a1, CK2a1-rs, CK2a2, CLIK1, CLIK1L, CLK1, CLK2, CLK2ps, CLK3, CLK3ps, CLK4, COT, CRIK, CRK7, CSK, CTK, CYGD, CYGF, DAPK1, DAPK2, DAPK3, DCAMKL1, DCAMKL2, DCAMKL3, DDR1, DDR2, DLK, DMPK1, DMPK2, DNAPK, DRAK1, DRAK2, DYRK1A, DYRK1B, DYRK2, DYRK3, DYRK4, eEF2K, EGFR, EphAl, EphA10, EphA2, EphA3, EphA4, EphA5, EphA6, EphA7, EphA8, EphBl, EphB2, EphB3, EphB4, EphB6, Erk1, Erk2, Erk3, Erk3ps1, Erk3ps2, Erk3ps3, Erk3ps4, Erk4, Erk5, Erk7, FAK, FASTK, FER, FERps, FES, FGFR1, FGFR2, FGFR3, FGFR4, FGR, FLT1, FLT1ps, FLT3, FLT4, FMS, FRAP, FRK, Fused, FYN, G11, GAK, GCK, GCN2, GPRK4, GPRK5, GPRK6, GPRK6ps, GPRK7, GSK3A, GSK3B, H11, Haspin, HCK, HER2/ErbB2, HER3/ErbB3, HER4/ErbB4, HH498, HIPK1, HIPK2, HIPK3, HIPK4, HPK1, HRI, HRIps, HSER, HUNK, ICK, IGF1R, IKKa, IKKb, IKKe, ILK, INSR, IRAK1, IRAK2, IRAK3, IRAK4, IRE1, IRE2, IRR, ITK, JAK1, JAK2, JAK3, JNK1, JNK2, JNK3, KDR, KHS1, KHS2, KIS, KIT, KSGCps, KSR1, KSR2, LATS1, LATS2, LCK, LIMK1, LIMK2, LIMK2ps, LKB1, LMR1, LMR2, LMR3, LOK, LRRK1, LRRK2, LTK, LYN, LZK, MAK, MAP2K1, MAP2K1ps, MAP2K2, MAP2K2ps, MAP2K3, MAP2K4, MAP2K5, MAP2K6, MAP2K7, MAP3K1, MAP3K2, MAP3K3, MAP3K4, MAP3K5, MAP3K6, MAP3K7, MAP3K8, MAPKAPK2, MAPKAPK3, MAPKAPK5, MAPKAPKpsl, MARK1, MARK2, MARK3, MARK4, MARKps01, MARKps02, MARKps03, MARKps04, MARKps05, MARKps07, MARKps08, MARKps09, MARKps10, MARKps11, MARKps12, MARKps13, MARKps15, MARKps16, MARKps17, MARKps18, MARKps19, MARKps20, MARKps21, MARKps22, MARKps23, MARKps24, MARKps25, MARKps26, MARKps27, MARKps28, MARKps29, MARKps30, MAST1, MAST2, MAST3, MAST4, MASTL, MELK, MER, MET, MISR2, MLK1, MLK2, MLK3, MLK4, MLKL, MNK1, MNK1ps, MNK2, MOK, MOS, MPSK1, MPSK1ps, MRCKa, MRCKb, MRCKps, MSK1, MSK2, MSSK1, MST1, MST2, MST3, MST3ps, MST4, MUSK, MYO3A, MYO3B, MYT1, NDR1, NDR2, NEK1, NEK10, NEK11, NEK2, NEK2ps1, NEK2ps2, NEK2ps3, NEK3, NEK4, NEK4ps, NEK5, NEK6, NEK7, NEK8, NEK9, NIK, NIM1, NLK, NRBP1, NRBP2, NuaK1, NuaK2, Obscn, OSR1, p38a, p38b, p38d, p38g, p70S6K, p70S6Kb, p70S6Kps1, p70S6Kps2, PAK1, PAK2, PAK2ps, PAK3, PAK4, PAK5, PAK6, PASK, PBK, PCTAIRE1, PCTAIRE2, PCTAIRE3, PDGFRa, PDGFRb, PDHK1, PDHK2, PDHK3, PDHK4, PDK1, PEK, PFTAIRE1, PFTAIRE2, PHKg1, PHKg1ps1, PHKg1ps2, PHKg1ps3, PHKg2, PI3K, PI4K2A, PI4KB, PIK3C2A, PIK3C2B, PIK3C2G, PIK3C2G, PIK3C3, PIK3CA, PIK3CG, PIK3R4, PIM1, PIM2, PIM3, PINK1, PIP4K2A, PIP5K1A, PIP5K1B, PIP5K1C, PITSLRE, PKACa, PKACb, PKACg, PKCa, PKCb, PKCd, PKCe, PKCg, PKCh, PKCi, PKCips, PKCt, PKCz, PKD1, PKD2, PKD3, PKG1, PKG2, PKN1, PKN2, PKN3, PKR, PLK1, PLK1ps1, PLK1ps2, PLK2, PLK3, PLK4, PRKX, PRKXps, PRKY, PRP4, PRP4ps, PRPK, PSKH1, PSKHlps, PSKH2, PYK2, QIK, QSK, RAF1, RAF 1ps, RET, RHOK, RIOK1, RIOK2, RIOK3, RIOK3ps, RIPK1, RIPK2, RIPK3, RNAseL, ROCK1, ROCK2, RON, ROR1, ROR2, ROS, RSK1, RSK2, RSK3, RSK4, RSKL1, RSKL2, RYK, RYKps, SAKps, SBK, SCYL1, SCYL2, SCYL2ps, SCYL3, SGK, SgK050ps, SgK069, SgK071, SgK085, SgK110, SgK196, SGK2, SgK22, SgK269, SgK288, SGK3, SgK307, SgK384ps, SgK396, SgK424, SgK493, SgK494, SgK495, SgK49, SIK, skMLCK, SLK, Slob, SMG1, smMLCK, SNRK, SPEG, SPHK1, SPHK2, SRC, SRM, SRPK1, SRPK2, SRPK2ps, SSTK, STK33, STK33ps, STLK3, STLK5, STLK6, STLK6ps1, STLK6-rs, SuRTK106, SYK, TAF1, TAF1L, TAK1, TAO1, TAO2, TAO3, TBCK, TBK1, TEC, TESK1, TESK2, TGFbR1, TGFbR2, TIE1, TIE2, TIF1a, TIF1b, TIF1g, TLK1, TLK1ps, TLK2, TLK2ps1, TLK2ps2, TNK1, Trad, Trb1, Trb2, Trb3, Trio, TRKA, TRKB, TRKC, TRRAP, TSSK1, TSSK2, TSSK3, TSSK4, TSSKps1, TSSKps2, TTBK1, TTBK2, TTK, TTN, TXK, TYK2, TYRO3, TYRO3ps, ULK1, ULK2, ULK3, ULK4, VACAMKL, VRK1, VRK2, VRK3, VRK3ps, Wee1, Wee1B, Wee1Bps, Wee1ps1, Wee1ps2, Wnk1, Wnk2, Wnk3, Wnk4, YANK1, YANK2, YANK3, YES, YESps, YSK1, ZAK, ZAP70, ZC1/HGK, ZC2/TNIK, ZC3/MINK, ZC4/NRK, and proteins encoded by the aformentioned genes.

In some embodiments, a circRNA of the disclosure binds one or phosphatases, including, but not limited to phosphatases encoded by ACP1, ANP32A, ANP32B, ANP32C, ANP32D, ANP32E, AUXI, BPNT1, CABIN1, CDC14A, CDC14B, CDC14C, CDC25A, CDC25B, CDC25C, CDKN3, CHP, CNEP1, CTDSPL2, CTPTP1, CTPTP2, CTPTPL, DOLPP1, DUPD1, DUSP1, DUSP10, DUSP11, DUSP12, DUSP13, DUSP14, DUSP15, DUSP16, DUSP18, DUSP19, DUSP2, DUSP21, DUSP22, DUSP23, DUSP26, DUSP27, DUSP28, DUSP3, DUSP4, DUSP5, DUSP6, DUSP7, DUSP8, DUSP9, EPM2A, EYA1, EYA2, EYA3, EYA4, GAK, HACD1, HDDC2, HDHD1A, HDHD2, HDHD3, ILKAP, IMPA1, IMPA2, IMPAD1, INPP1, INPP5A, INPP5B, INPP5D, INPP5E, INPP5F, INPPL1, ITPA, LHPP, LOC283871, LPPR1, LPPR2, LPPR3, LPPR4, MDSP, MINPP1, MTM1, MTMR1, MTMR10, MTMR11, MTMR12, MTMR2, MTMR3, MTMR4, MTMR6, MTMR7, MTMR8, MTMR9, NUDT10, NUDT11, NUDT14, NUDT3, NUDT4, OCRL, PAP2D, PDP2, PDXP, PHACTR1, PHACTR2, PHACTR3, PHACTR4, PIB5PA, PNKP, PPA1, PPA2, PPAP2A, PPAP2B, PPAP2C, PPAPDC1A, PPAPDC1B, PPAPDC2, PPAPDC3, PPEF1, PPEF2, PPM1A, PPM1B, PPM1D, PPM1E, PPM1F, PPM1G, PPM1H, PPM1J, PPM1K, PPM1L, PPM1M, PPM1N, PPP1CA, PPP1CB, PPP1CC, PPP1R11, PPP1R12A, PPP1R12B, PPP1R12C, PPP1R14A, PPP1R14B, PPP1R14C, PPP1R14D, PPP1R16A, PPP1R16B, PPP1R1A, PPP1R1B, PPP1R1C, PPP1R2, PPP1R3A, PPP1R3B, PPP1R3C, PPP1R3D, PPP1R3F, PPP1R7, PPP1R8, PPP2CA, PPP2CB, PPP2R1A, PPP2R1B, PPP2R2A, PPP2R2B, PPP2R2C, PPP2R2D, PPP2R3A, PPP2R3B, PPP2R3C, PPP2R4, PPP2R5A, PPP2R5B, PPP2R5C, PPP2R5D, PPP2R5E, PPP3CA, PPP3CB, PPP3CC, PPP3R1, PPP3R2, PPP4C, PPP4R1, PPP5C, PPP6C, PPTC7, PRG2, PSPH, PSPH, PTEN, PTEN2, PTN4, PTP4A1, PTP4A2, PTP4A3, PTPC1, PTPM1, PTPN1, PTPN11, PTPN12, PTPN13, PTPN14, PTPN18, PTPN2, PTPN20A, PTPN20B, PTPN21, PTPN22, PTPN23, PTPN3, PTPN5, PTPN6, PTPN7, PTPN9, PTPRA-1, PTPRA-2, PTPRB, PTPRC-1, PTPRC-2, PTPRD-1, PTPRD-2, PTPRE-1, PTPRE-2, PTPRF-1, PTPRF-2, PTPRG-1, PTPRG-2, PTPRH, PTPRJ, PTPRK-1, PTPRK-2, PTPRM-1, PTPRM-2, PTPRN, PTPRN2, PTPRO, PTPRQ, PTPRR, PTPRS-1, PTPRS-2, PTPRT-1, PTPRT-2, PTPRU-1, PTPRU-2, PTPRZ1-1, PTPRZ1-2, RNGTT, RP11, SACM1L, SAMHD1, SAPS1, SAPS2, SAPS3, SBF1, SBF2, SET, SGPP1, SGPP2, SKIP, SSH1, SSH2, SSH3, STYX, STYXL1, SYNJ1, SYNJ2, TENC1, TIMM50, TNS1, TNS3, TPTE, TPTE2, and UBLCP1.

In some embodiments, a circRNA described herein is used to promote or inhibit glycosylation of a substrate protein. For example, a circRNA comprises a first binding site that binds a substrate protein, and a second binding site that binds a glycosyltransferase, a glycoside hydrolase, or a sulfotransferase. For example a circRNA of the disclosure binds one or more glycosyltransferases, including, but not limited to glycosyltransferases encoded by A3GALT2, A4GALT, A4GNT, ABO, ALG1, ALG10, ALG10B, ALG11, ALG12, ALG13, ALG14, ALG1L, ALG1L2, ALG2, ALG3, ALG5, ALG6, ALG8, ALG9, B3GALNT1, B3GALNT2, B3GALT1, B3GALT2, B3GALT4, B3GALT5, B3GALT6, B3GAT1, B3GAT2, B3GAT3, B3GLCT, B3GNT2, B3GNT3, B3GNT4, B3GNT5, B3GNT6, B3GNT7, B3GNT8, B3GNT9, B3GNTL1, B4GALNT1, B4GALNT2, B4GALNT3, B4GALNT4, B4GALT1, B4GALT2, B4GALT3, B4GALT4, B4GALT5, B4GALT6, B4GALT7, C1GALT1, CHPF, CHPF, CHPF2, CHPF2, CHSY1, CHSY1, CHSY3, CHSY3, COLGALT1, COLGALT2, CSGALNACT1, CSGALNACT2, DPM1, EOGT, EXT1, EXT2, EXTL1, EXTL2, EXTL3, FUT1, FUT10, FUT11, FUT2, FUT3, FUT4, FUT5, FUT6, FUT7, FUT8, FUT9, GALNT1, GALNT10, GALNT11, GALNT12, GALNT13, GALNT14, GALNT15, GALNT16, GALNT17, GALNT18, GALNT2, GALNT3, GALNT4, GALNT5, GALNT6, GALNT7, GALNT8, GALNT9, GALNTL5, GALNTL6, GBGT1, GCNT1, GCNT2, GCNT3, GCNT4, GCNT7, GLT1D1, GLT6D1, GLT8D1, GLT8D2, GTDC1, GXYLT1, GXYLT2, GYG1, GYG2, GYS1, GYS2, HAS1, HAS2, HAS3, LARGE1, LARGE2, LFNG, MFNG, MGAT1, MGAT2, MGAT3, MGAT4A, MGAT4B, MGAT4C, MGAT4D, MGAT5, MGAT5B, OGT, PIGA, PIGB, PIGM, PIGV, PIGZ, POFUT1, POFUT2, POGLUT1, POGLUT2, POGLUT3, POMGNT1, POMGNT2, POMT1, POMT2, PYGB, PYGL, PYGM, RFNG, RXYLT1, ST3GAL1, ST3GAL2, ST3GAL3, ST3GAL4, ST3GAL5, ST3GAL6, ST6GAL1, ST6GAL2, ST6GALNAC1, ST6GALNAC2, ST6GALNAC3, ST6GALNAC4, ST6GALNAC5, ST6GALNAC6, ST8SIA1, ST8SIA2, ST8SIA3, ST8SIA4, ST8SIA5, ST8SIA6, STT3A, STT3B, UGCG, UGGT1, UGGT2, UGT1A, UGT1A1, UGT1A10, UGT1A11P, UGT1A12P, UGT1A13P, UGT1A2P, UGT1A3, UGT1A4, UGT1A5, UGT1A6, UGT1A7, UGT1A8, UGT1A9, UGT2A1, UGT2A2, UGT2A3, UGT2B10, UGT2B11, UGT2B15, UGT2B17, UGT2B24P, UGT2B25P, UGT2B26P, UGT2B27P, UGT2B28, UGT2B29P, UGT2B4, UGT2B7, UGT3A1, UGT3A2, UGT8, XXYLT1, XYLT1, and XYLT2.

In some embodiments, a circRNA of the disclosure binds one or more glycoside hydrolases, including, but not limited to glycoside hydrolases encoded by AGL, AMY1A, AMY1B, AMY1C, AMY2A, AMY2B, AMYP1, CEMIP, CEMIP2, CHI3L1, CHI3L2, CHIA, CHID1, CHIT1, CTBS, EDEM1, EDEM2, EDEM3, FUCA1, FUCA2, GAA, GANAB, GANC, GBA3, GBE1, GLA, GLB1, GLB1L, GLB1L2, GLB1L3, HEXA, HEXB, HEXD, HPSE, HPSE2, HYAL1, HYAL2, HYAL3, HYAL4, HYAL6P, KL, KLB, LALBA, LCT, LCTL, LYG1, LYG2, LYZ, LYZL1, LYZL2, LYZL4, LYZL6, MAN1A1, MAN1A2, MAN1B1, MAN1C1, MAN2A1, MAN2A2, MAN2B1, MAN2B2, MAN2C1, MANBA, MANBAL, MANEA, MANEAL, MGAM, MGAM2, MYORG, NAGA, NEU1, NEU2, NEU3, NEU4, OGA, OVGP1, SI, SLC3A1, SLC3A2, SPACA3, SPACA5, SPACA5B, and SPAM1.

Pharmaceutical Compositions

The present invention includes any compositions disclosed herein in combination with one or more pharmaceutically acceptable excipients. A pharmaceutically acceptable excipient can be a non-carrier excipient. A non-carrier excipient serves as a vehicle or medium for a composition, such as a circular polyribonucleotide as described herein. A non-carrier excipient serves as a vehicle or medium for a composition, such as a linear polyribonucleotide as described herein. Non-limiting examples of a non-carrier excipient include solvents, aqueous solvents, non-aqueous solvents, dispersion media, diluents, dispersions, suspension aids, surface active agents, isotonic agents, thickening agents, emulsifying agents, preservatives, polymers, peptides, proteins, cells, hyaluronidases, dispersing agents, granulating agents, disintegrating agents, binding agents, buffering agents (e.g., phosphate buffered saline (PBS)), lubricating agents, oils, and mixtures thereof. A non-carrier excipient can be any one of the inactive ingredients approved by the United States Food and Drug Administration (FDA) and listed in the Inactive Ingredient Database that does not exhibit a cell-penetrating effect. Pharmaceutical compositions may optionally comprise one or more additional active substances, e.g. therapeutically and/or prophylactically active substances. Pharmaceutical compositions of the present invention may be sterile and/or pyrogen-free. General considerations in the formulation and/or manufacture of pharmaceutical agents may be found, for example, in Remington: The Science and Practice of Pharmacy 21st ed., Lippincott Williams & Wilkins, 2005 (incorporated herein by reference).

The pharmaceutical compositions described herein can be used in therapeutic and veterinary methods to treat a subject. In some embodiments, pharmaceutical compositions (e.g., comprising a circular polyribonucleotide as described herein) provided herein are suitable for administration to a subject, wherein the subject is a non-human animal, for example, suitable for veterinary use. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, any animals, such as humans and/or other primates; mammals, including commercially relevant mammals, e.g., pet and live-stock animals, such as cattle, pigs, horses, sheep, goats, cats, dogs, mice, and/or rats; and/or birds, including commercially relevant birds such as parrots, poultry, chickens, hen or roosters, ducks, geese, and/or turkeys; zoo animals, e.g., a feline; non-mammal animals, e.g., reptiles, fish, amphibians, etc.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product.

In some embodiments, the pharmaceutically acceptable carrier or excipient is a sugar (e.g., sucrose, lactose, mannitol, maltose, sorbitol or fructose), a neutral salt (e.g., sodium chloride, magnesium sulfate, magnesium chloride, potassium sulfate, sodium carbonate, sodium sulfite, potassium acid phosphate, or sodium acetate), an acidic component (e.g., fumaric acid, maleic acid, adipic acid, citric acid or ascorbic acid), an alkaline component (e.g., tris(hydroxymethyl) aminomethane (TRIS), meglumine, tribasic or dibasic phosphates of sodium or potassium), or an amino acid (e.g., glycine or arginine).

The circular polyribonucleotide described herein may also be included in pharmaceutical compositions with a delivery carrier.

Pharmaceutical compositions described herein may be formulated for example to include a pharmaceutical excipient or carrier. A pharmaceutical carrier can be a membrane, lipid biylar, and/or a polymeric carrier, e.g., a liposome, such as a nanoparticle, e.g., a lipid nanoparticle, and delivered by known methods, such as via partial or full encapsulation of the modified circular polyribonucleotide, to a subject in need thereof (e.g., a human or non-human agricultural or domestic animal, e.g., cattle, dog, cat, horse, poultry). Such methods include, but not limited to, transfection (e.g., lipid-mediated, cationic polymers, calcium phosphate, dendrimers); electroporation or other methods of membrane disruption (e.g., nucleofection), viral delivery (e.g., lentivirus, retrovirus, adenovirus, AAV), microinjection, microprojectile bombardment ("gene gun"), fugene, direct sonic loading, cell squeezing, optical transfection, protoplast fusion, impalefection, magnetofection, exosome-mediated transfer, lipid nanoparticle-mediated transfer, and any combination thereof. Methods of delivery are also described, e.g., in Gori et al., Delivery and Specificity of CRISPR/Cas9 Genome Editing Technologies for Human Gene Therapy. Human Gene Therapy. July 2015, 26(7): 443-451. doi: 10.1089/hum.2015.074; and Zuris et al. Cationic lipid-mediated delivery of proteins enables efficient protein-based genome editing in vitro and in vivo. Nat Biotechnol. 2014 Oct. 30; 33(1):73-80.

In some embodiments, the circular polyribonucleotide or pharmaceutical composition is delivered as a naked delivery formulation. A naked delivery formulation delivers a circular polyribonucleotide as disclosed herein to a cell without the aid of a carrier and without covalent modification or partial or complete encapsulation of the circular polyribonucleotide.

A naked delivery formulation is a formulation that is free from a carrier and wherein the circular polyribonucleotide as described herein is without a covalent modification that binds a moiety that aids in delivery to a cell or without partial or complete encapsulation of the circular polyribonucleotide. In some embodiments, a circular polyribonucleotide without covalent modification bound to a moiety that aids in delivery to a cell is not covalently bound to a protein, small molecule, a particle, a polymer, or a biopolymer that aids in delivery to a cell.

In some embodiments, a naked delivery formulation may be free of any or all of: transfection reagents, cationic carriers, carbohydrate carriers, nanoparticle carriers, or protein carriers. For example, a naked delivery formulation may be free from phtoglycogen octenyl succinate, phytoglycogen beta-dextrin, anhydride-modified phytoglycogen beta-dextrin, lipofectamine, polyethylenimine, poly(trimethylenimine), poly(tetramethylenimine), polypropylenimine, aminoglycoside-polyamine, dideoxy-diamino-b-cyclodextrin, spermine, spermidine, poly(2-dimethylamino)ethyl methacrylate, poly(lysine), poly(histidine), poly(arginine), cationized gelatin, dendrimers, chitosan, 1,2-Dioleoyl-3-Trimethylammonium-Propane(DOTAP), N-[1-(2,3-dioleoyloxy) propyl]-N,N,N-trimethylammonium chloride (DOTMA), 1-[2-(oleoyloxy)ethyl]-2-oleyl-3-(2-hydroxyethyl)imidazolinium chloride (DOTIM), 2,3-dioleyloxy-N-[2(sperminecarboxamido)ethyl]-N,N-dimethyl-1-propanaminium trifluoroacetate (DOSPA), 3B—[N—(N\N'-Dimethylaminoethane)-carbamoyl]Cholesterol Hydrochloride (DC-Cholesterol HCl), diheptadecylamidoglycyl spermidine (DOGS), N,N-distearyl-N,N-dimethylammonium bromide (DDAB), N-(1,2-dimyristyloxyprop-3-yl)-N,N-dimethyl-N-hydroxyethyl ammonium bromide (DMRIE), N,N-dioleyl-N,N-dimethylammonium chloride (DODAC), human serum albumin (HSA), low-density lipoprotein (LDL), high-density lipoprotein (HDL), or globulin.

A naked delivery formulation may comprise a non-carrier excipient. In some embodiments, a non-carrier excipient may comprise an inactive ingredient. In some embodiments, a non-carrier excipient may comprise a buffer, for example PBS. In some embodiments, a non-carrier excipient may be a solvent, a non-aqueous solvent, a diluent (e.g., a parenterally acceptable diluent), a suspension aid, a surface active agent, an isotonic agent, a thickening agent, an emulsifying agent, a preservative, a polymer, a peptide, a protein, a cell, a hyaluronidase, a dispersing agent, a granulating agent, a disintegrating agent, a binding agent, a buffering agent, a lubricating agent, or an oil.

In some embodiments, a naked delivery formulation may comprise a diluent (e.g., a parenterally acceptable diluent). A diluent may be a liquid diluent or a solid diluent. In some embodiments, a diluent may be an RNA solubilizing agent, a buffer, or an isotonic agent. Examples of an RNA solubilizing agent include water, ethanol, methanol, acetone, formamide, and 2-propanol. Examples of a buffer include 2-(N-morpholino)ethanesulfonic acid (MES), Bis-Tris, 2-[(2-amino-2-oxoethyl)-(carboxymethyl)amino]acetic acid (ADA), N-(2-Acetamido)-2-aminoethanesulfonic acid (ACES), piperazine-N,N'-bis(2-ethanesulfonic acid) (PIPES), 2-[[1,3-dihydroxy-2-(hydroxymethyl)propan-2-yl] amino]ethanesulfonic acid (TES), 3-(N-morpholino)propanesulfonic acid (MOPS), 4-(2-hydroxyethyl)-1-piperazineethanesulfonic acid (HEPES), Tris, Tricine, Gly-Gly, Bicine, or phosphate. Examples of an isotonic agent include glycerin, mannitol, polyethylene glycol, propylene glycol, trehalose, or sucrose.

The invention is further directed to a host or host cell comprising the circular polyribonucleotide described herein. In some embodiments, the host or host cell is a plant, insect, bacteria, fungus, vertebrate, mammal (e.g., human), or other organism or cell.

In some embodiments, the circular polyribonucleotide is non-immunogenic in the host. In some embodiments, the circular polyribonucleotide has a decreased or fails to produce a response by the host's immune system as compared to the response triggered by a reference compound, e.g., a linear polynucleotide corresponding to the described circular polyribonucleotide or a circular polyribonucleotide lacking an encryptogen. Some immune responses include, but are not limited to, humoral immune responses (e.g., production of antigen-specific antibodies) and cell-mediated immune responses (e.g., lymphocyte proliferation).

In some embodiments, a host or a host cell is contacted with (e.g., delivered to or administered to) the circular polyribonucleotide. In some embodiments, the host is a mammal, such as a human. The amount of the circular polyribonucleotide, expression product, or both in the host can be measured at any time after administration.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are packaged injectables, vials, or ampoules. Aqueous suspension compositions can be packaged in single-dose non-reclosable containers. Multiple-dose reclosable containers can be used, for example, in combination with or without a preservative. Formulations for injection can be presented in unit dosage form, for example, in ampoules, or in multi-dose containers with a preservative.

Delivery

The circular polyribonucleotide described herein may be included in pharmaceutical compositions with a delivery carrier. The circular polyribonucleotide described herein may be included in a pharmaceutical composition with a pharmaceutical excipient and free of any carrier.

Pharmaceutical compositions described herein can be formulated for example including a pharmaceutical excipient or carrier. A pharmaceutical carrier may be a membrane, lipid bilayer, and/or a polymeric carrier, e.g., a liposome or particle such as a nanoparticle, e.g., a lipid nanoparticle, and delivered by known methods to a subject in need thereof (e.g., a human or non-human agricultural or domestic animal, e.g., cattle, dog, cat, horse, poultry). Such methods include, but not limited to, transfection (e.g., lipid-mediated, cationic polymers, calcium phosphate); electroporation or other methods of membrane disruption (e.g., nucleofection), fusion, and viral delivery (e.g., lentivirus, retrovirus, adenovirus, AAV).

The invention is further directed to a host or host cell comprising the circular polyribonucleotide described herein. In some embodiments, the host or host cell is a plant, insect, bacteria, fungus, vertebrate, mammal (e.g., human), or other organism or cell.

A method of delivering a modified circular polyribonucleotide molecule as described herein to a cell, tissue or subject, comprises administering the pharmaceutical composition as described herein to the cell, tissue, or subject.

In some embodiments, the method of delivering is an in vivo method. For example, a method of delivering a circular polyribonucleotide as described herein comprises parenterally administering to a subject in need thereof, the pharmaceutical composition as described herein to the subject in need thereof. As another example, a method of delivering a circular polyribonucleotide to a cell or tissue of a subject, comprises administering parenterally to the cell or tissue the pharmaceutical composition as described herein. In some embodiments, the circular polyribonucleotide is in an amount effective to elicit a biological response in the subject. In some embodiments, the circular polyribonucleotide is an amount effective to have a biological effect on the cell or tissue in the subject. In some embodiments, the pharmaceutical composition as described herein comprises a carrier. In some embodiments the pharmaceutical composition as described herein comprises a diluent and is free of any carrier. In some embodiments, parenteral administration is intravenously, intramuscularly, ophthalmically, or topically.

In some embodiments, the pharmaceutical composition is administered orally. In some embodiments the pharmaceutical composition is administered nasally. In some embodiments, the pharmaceutical composition is administered by inhalation. In some embodiments the pharmaceutical composition is administered topically. In some embodiments the pharmaceutical composition is administered ophthalmically. In some embodiments the pharmaceutical composition is administered rectally. In some embodiments the pharmaceutical composition is administered by injection. The administration can be systemic administration or local administration. In some embodiments the pharmaceutical composition is administered parenterally. In some embodiments the pharmaceutical composition is administered intravenously, intraarterially, intraperotoneally, intradermally, intracranially, intrathecally, intralymphaticly, subcutaneously, intramuscularly, or intratumorally. In some embodiments, the pharmaceutical composition is administered via intraocular administration, intracochlear (inner ear) administration, or intratracheal administration. In some embodiments, any of the methods of delivery as described herein are performed with a carrier. In some embodiments, any methods of delivery as described herein are performed without the aid of a carrier or cell penetrating agent.

Cell and Vesicle-Based Carriers

A circular polyribonucleotide described herein may be delivered (e.g., administered) in a vesicle or other membrane-based carrier.

In some embodiments, the circular polyribonucleotide, composition thereof, or pharmaceutical composition thereof is delivered to a cell as described herein, in or via a cell, vesicle or other membrane-based carrier. In some embodiments, the circular polyribonucleotide, composition thereof, or pharmaceutical composition thereof is formulated in liposomes or other similar vesicles. Liposomes are spherical vesicle structures composed of a uni- or multilamellar lipid bilayer surrounding internal aqueous compartments and a relatively impermeable outer lipophilic phospholipid bilayer. Liposomes may be anionic, neutral or cationic. Liposomes are biocompatible, nontoxic, can deliver both hydrophilic and lipophilic drug molecules, protect their cargo from degradation by plasma enzymes, and transport their load across biological membranes and the blood brain barrier (BBB) (see, e.g., Spuch and Navarro, Journal of Drug Delivery, vol. 2011, Article ID 469679, 12 pages, 2011. doi:10.1155/2011/469679 for review).

Vesicles can be made from several different types of lipids; however, phospholipids are most commonly used to generate liposomes as drug carriers. Methods for preparation of multilamellar vesicle lipids are known in the art (see for example U.S. Pat. No. 6,693,086, the teachings of which relating to multilamellar vesicle lipid preparation are incorporated herein by reference). Although vesicle formation can be spontaneous when a lipid film is mixed with an aqueous solution, it can also be expedited by applying force in the form of shaking by using a homogenizer, sonicator, or an extrusion apparatus (see, e.g., Spuch and Navarro, Journal of Drug Delivery, vol. 2011, Article ID 469679, 12 pages, 2011. doi:10.1155/2011/469679 for review). Extruded lipids can be prepared by extruding through filters of decreasing size, as described in Templeton et al., Nature Biotech, 15:647-652, 1997, the teachings of which relating to extruded lipid preparation are incorporated herein by reference.

Lipid nanoparticles are another example of a carrier that provides a biocompatible and biodegradable delivery system for a circular polyribonucleotide or the pharmaceutical composition thereof as described herein. Nanostructured lipid carriers (NLCs) are modified solid lipid nanoparticles (SLNs) that retain the characteristics of the SLN, improve drug stability and loading capacity, and prevent drug leakage. Polymer nanoparticles (PNPs) are an important component of drug delivery. These nanoparticles can effectively direct drug delivery to specific targets and improve drug stability and controlled drug release. Lipid—polymer nanoparticles (PLNs), a new type of carrier that combines liposomes and polymers, may also be employed. These nanoparticles possess the complementary advantages of PNPs and liposomes. A PLN is composed of a core—shell structure; the polymer core provides a stable structure, and the phospholipid shell offers good biocompatibility. As such, the two components increase the drug encapsulation efficiency rate, facilitate surface modification, and prevent leakage of water-soluble drugs. For a review, see, e.g., Li et al. 2017, Nanomaterials 7, 122; doi:10.3390/nano7060122.

Additional non-limiting examples of carriers include carbohydrate carriers (e.g., an anhydride-modified phytoglycogen or glycogen-type material), protein carriers (e.g., a protein covalently linked to the circular polyribonucleotide), or cationic carriers (e.g., a cationic lipopolymer or transfection reagent). Non-limiting examples of carbohydrate carriers include phtoglycogen octenyl succinate, phytoglycogen beta-dextrin, and anhydride-modified phytoglycogen beta-dextrin. Non-limiting examples of cationic carriers include lipofectamine, polyethylenimine, poly(trimethylenimine), poly(tetramethylenimine), polypropylenimine, aminoglycoside-polyamine, dideoxy-diamino-b-cyclodextrin, spermine, spermidine, poly(2-dimethylamino)ethyl methacrylate, poly (lysine), poly(histidine), poly(arginine), cationized gelatin, dendrimers, chitosan, 1,2-Dioleoyl-3-Trimethylammonium-Propane(DOTAP), N-[1-(2,3-dioleoyloxy)propyl]-N,N,N-trimethylammonium chloride (DOTMA), 1-[2-(oleoyloxy) ethyl]-2-oleyl-3-(2-hydroxyethyl)imidazolinium chloride (DOTIM), 2,3-dioleyloxy-N-[2(sperminecarboxamido) ethyl]-N,N-dimethyl-1-propanaminium trifluoroacetate (DOSPA), 3B—[N—(N\N'-Dimethylaminoethane)-carbamoyl]Cholesterol Hydrochloride (DC-Cholesterol HCl), diheptadecylamidoglycyl spermidine (DOGS), N,N-distearyl-N,N-dimethylammonium bromide (DDAB), N-(1,2-dimyristyloxyprop-3-yl)-N,N-dimethyl-N-hydroxyethyl ammonium bromide (DMRIE), and N,N-dioleyl-N,N-dimethylammonium chloride (DODAC). Non-limiting examples of protein carriers include human serum albumin (HSA), low-density lipoprotein (LDL), high-density lipoprotein (HDL), or globulin.

Exosomes can also be used as drug delivery vehicles for a circular polyribonucleotide or a pharmaceutical composition thereof described herein. For a review, see Ha et al. July 2016. Acta Pharmaceutica Sinica B. Volume 6, Issue 4, Pages 287-296; https://doi.org/10.1016/j.apsb.2016.02.001.

Ex vivo differentiated red blood cells can also be used as a carrier for a circular polyribonucleotide or a pharmaceutical composition thereof described herein. See, e.g., WO2015073587; WO2017123646; WO2017123644; WO2018102740; w02016183482; WO2015153102; WO2018151829; WO2018009838; Shi et al. 2014. Proc Natl Acad Sci USA. 111(28): 10131-10136; U.S. Pat. No. 9,644,180; Huang et al. 2017. Nature Communications 8: 423; Shi et al. 2014. Proc Natl Acad Sci USA. 111(28): 10131-10136.

Fusosome compositions, e.g., as described in WO2018208728, can also be used as carriers to deliver the circular polyribonucleotide or pharmaceutical composition thereof described herein.

Virosomes and virus-like particles (VLPs) can also be used as carriers to the circular polyribonucleotideor pharmaceutical composition thereof described herein to a cell (e.g., an isolated cell).

In some embodiments, the circular polyribonucleotide is non-immunogenic in the host. In some embodiments, the circular polyribonucleotide has a decreased or fails to produce a response by the host's immune system as compared to the response triggered by a reference compound, e.g., a linear polynucleotide corresponding to the described circular polyribonucleotide, unmodified circular polyribonucleotide, or a circular polyribonucleotide lacking an encryptogen. Some immune responses include, but are not limited to, humoral immune responses (e.g., production of antigen-specific antibodies) and cell-mediated immune responses (e.g., lymphocyte proliferation).

In some embodiments, a host or a host cell is contacted with (e.g., delivered to or administered to) the circular polyribonucleotide. In some embodiments, the host is a mammal, such as a human. The amount of the circular polyribonucleotide, expression product, or both in the host can be measured at any time after administration. In certain embodiments, a time course of host growth in a culture is determined. If the growth is increased or reduced in the presence of the circular polyribonucleotide, the circular polyribonucleotide or expression product or both is identified as being effective in increasing or reducing the growth of the host.

Applications

Circular polyribonucleotides described herein can be administered to a cell, tissue or subject (e.g., a mammal, e.g., a human) in need thereof, e.g., to modulate cellular function, e.g., gene expression in the cell, tissue or subject. The invention also contemplates methods of modulating cellular function, e.g., gene expression, comprising administering to a cell, tissue or subject in need thereof a circular polyribonucleotide described herein. The administered circular polyribonucleotides can be modified circular polyribonucleotides. In some embodiments, the administered circular polyribonucleotides are completely modified circular polyribonucleotides. In some embodiments, the administered circular polyribonucleotides are hybrid modified circular polyribonucleotides. In other embodiments, the administered circular polyribonucleotides are unmodified circular polyribonucleotides. The administered circular polyribonucleotides can comprise a conjugation moiety.

A circular polyribonucleotide of the disclosure can be used for treating a disease or condition in a subject in need thereof. A disease or condition can be, for example, a hyperproliferative disease, a cancer, a neurodegenerative disease, a metabolic disorder, an inflammatory disorder, an infectious disease, a genetic disease, or a combination thereof. A cancer can be, for example, a solid tumor or a liquid tumor. A solid tumor can be reproductive tissue cancer. A reproductive tissue cancer can be prostate cancer or cervical cancer. A liquid tumor can be a lymphoma. A lymphoma can be a B cell lymphoma. In some embodiments, the circular polyribonucleotide of the disclosure is administered intravenously to treat the disease or condition. In some embodiments, the circular polyribonucleotide of the disclosure is administered by intratumoral injection to treat the cancer.

Pharmaceutical compositions described herein can be administered for prophylactic and/or therapeutic treatments. In therapeutic applications, the compositions can be administered to a subject already suffering from a disease or condition, in an amount sufficient to cure or at least partially reduce the symptoms of the disease or condition, or to cure, heal, improve, ameliorate, or reduce the condition. Compositions can also be administered to lessen a likelihood of developing, contracting, or worsening a condition. Amounts effective for this use can vary based on the severity and course of the disease or condition, previous therapy, the subject's health status, weight, and response to the drugs, and the judgment of the treating physician.

Therapeutic agents described herein can be administered before, during, or after the occurrence of a disease or condition, and the timing of administering the composition containing a therapeutic agent can vary. For example, the compositions can be used as a prophylactic and can be administered continuously to subjects with a propensity to conditions or diseases in order to lessen a likelihood of the occurrence of the disease or condition. The compositions can be administered to a subject during or as soon as possible after the onset of the symptoms.

Pharmaceutical compositions provided herein can be administered in conjunction with other therapies, for example, chemotherapy, radiation, surgery, anti-inflammatory agents, and selected vitamins. The other agents can be administered prior to, after, or concomitantly with the pharmaceutical compositions.

All references and publications cited herein are hereby incorporated by reference.

The following examples are provided to further illustrate some embodiments of the present invention, but are not intended to limit the scope of the invention; it will be understood by their exemplary nature that other procedures, methodologies, or techniques known to those skilled in the art can alternatively be used.

Numbered Embodiments #1

[1] A composition comprising a circular polyribonucleotide comprising a conjugation moiety, wherein the conjugation moiety conjugates the circular polyribonucleotide to a chemical compound (e.g., a small molecule) that binds a target protein to modulate a substrate protein.

[2] A composition comprising a circular polyribonucleotide comprising a first conjugation moiety and a second conjugation moiety, wherein the first conjugation moiety conjugates the circular polyribonucleotide to a first chemical compound (e.g., a small molecule) that binds to a target protein that modulates a substrate protein and wherein the second conjugation moiety conjugates the circular polyribonucleotide to a second chemical compound that binds the substrate protein.

[3] A composition comprising:
a) a circular polyribonucleotide comprising a conjugation moiety; and
b) a chemical compound that binds a target protein;
wherein the circular polyribonucleotide is conjugated to the chemical compound by the conjugation moiety and the target protein modulates a substrate protein.

[4] A composition comprising:
a) a circular polyribonucleotide comprising a first conjugation moiety and a second conjugation moiety;
b) a first chemical compound that binds a target protein; and
c) a second chemical compound that binds a substrate protein;
wherein the circular polyribonucleotide is conjugated to the first chemical compound by the first conjugation moiety, the circular polyribonucleotide is conjugated to the second chemical compound by the second conjugation moiety, and the target protein modulates the substrate protein.

[5] A composition of any one of the preceding embodiments, further comprising the target protein bound to the chemical compound to form a complex.

[6] A composition of any one of the preceding embodiments, further comprising the target protein bound to the first chemical compound and the substrate protein bound to the second chemical compound to form a complex.

[7] A composition comprising:

a) a circular polyribonucleotide comprising a conjugation moiety;

b) a chemical compound; and c) a target protein that modulates a substrate protein;

wherein the conjugation moiety is conjugated to the chemical compound and the chemical compound is bound to the target protein to form a complex.

[8] A composition comprising:

a) a circular polyribonucleotide comprising a conjugation moiety and a binding site;

b) a chemical compound; and c) a target protein that modulates a substrate protein;

wherein the binding site is bound to the target protein, the conjugation moiety is conjugated to the chemical compound, and the chemical compound is bound to the substrate protein to form a complex.

[9] A composition comprising:

a) a circular polyribonucleotide comprising a first conjugation moiety and a second conjugation moiety;

b) a first chemical compound that binds a target protein;

c) a second chemical compound that binds a substrate protein; and d) the target protein that modulates the substrate protein;

wherein the first conjugation moiety is conjugated to the first chemical compound, the second conjugation moiety is conjugated to the second chemical compound, and the first chemical compound is bound to the target protein to form a complex.

[10] A composition comprising:

a) a circular polyribonucleotide comprising a conjugation moiety;

b) a chemical compound that binds to a target protein that modulates a substrate protein;

c) the target protein; and d) the substrate protein;

wherein the conjugation moiety is conjugated to the chemical compound, the chemical compound is bound to the target protein, and the target protein is bound to the substrate protein to form a complex.

[11] A composition comprising:

a) a circular polyribonucleotide comprising a first conjugation moiety and a second conjugation moiety;

b) a first chemical compound that binds a target protein that modulates a substrate protein;

c) a second chemical compound that binds the substrate protein;

d) the target protein; and e) the substrate protein;

wherein the first conjugation moiety is conjugated to the first chemical compound, the second conjugation moiety is conjugated to the second the chemical compound, the first chemical compound is bound to the target protein, and second chemical compound is bound to the substrate protein to form a complex.

[12] The composition of any one of the preceding embodiments, wherein the circular polyribonucleotide further comprises a binding site that binds to the substrate protein or the target protein.

[13] The composition of embodiment [12], wherein substrate comprises a circular polyribonucleotide (circRNA)-binding motif.

[14] A composition comprising:

a) a first circular polyribonucleotide comprising a first conjugation moiety;

b) a second circular polyribonucleotide comprising a second conjugation moiety;

b) a first chemical compound that binds a target protein that modulates a substrate protein;

c) a second chemical compound that binds the substrate protein;

d) the target protein; and e) the substrate protein;

wherein the first conjugation moiety is conjugated to the first chemical compound, the first chemical compound is bound to the target protein, the second conjugation moiety is conjugated to the second the chemical compound, and second chemical compound is bound to the substrate protein.

[15] The composition of embodiment [14], wherein the substrate protein is bound to the target protein to form a complex.

[16] The composition of any one of the preceding embodiments, wherein the conjugation moiety is a modified nucleotide.

[17] The composition of any one of the preceding embodiments, wherein the first conjugation moiety is a first modified nucleotide and the second conjugation moiety is a second modified nucleotide.

[18] The composition of embodiment [17], wherein the first modified nucleotide and second modified nucleotide are the same.

[19] The composition of embodiment [17], wherein the first modified nucleotide and second modified nucleotide are different.

[20] The composition of any one of the preceding embodiments, wherein the modified nucleotide is a modified UTP analog, 5-Azidomethyl-UTP, 5-Azido-C3-UTP, 5-Azido-PEG4-UTP, 5-Ethynyl-UTP, DBCO-PEG4-UTP, Vinyl-UTP, 8-Azido-ATP, 3'-Azido-2',3'-ddATP, 5-Azido-PEG4-CTP, 5-DBCO-PEG4-CTP, N6-Azidohexyl-3'-dATP, 5-azidopropyl-UTP or 5-DBCO-PEG4-dCpG.

[21] The composition of any one of the preceding embodiments, wherein the first modified nucleotide is a modified UTP analog, 5-Azidomethyl-UTP, 5-Azido-C3-UTP, 5-Azido-PEG4-UTP, 5-Ethynyl-UTP, DBCO-PEG4-UTP, Vinyl-UTP, 8-Azido-ATP, 3'-Azido-2',3'-ddATP, 5-Azido-PEG4-CTP, 5-DBCO-PEG4-CTP, N6-Azidohexyl-3'-dATP, 5-azidopropyl-UTP or 5-DBCO-PEG4-dCpG, and the second modified nucleotide is a modified UTP analog, 5-Azidomethyl-UTP, 5-Azido-C3-UTP, 5-Azido-PEG4-UTP, 5-Ethynyl-UTP, DBCO-PEG4-UTP, Vinyl-UTP, 8-Azido-ATP, 3'-Azido-2',3'-ddATP, 5-Azido-PEG4-CTP, 5-DBCO-PEG4-CTP, N6-Azidohexyl-3'-dATP, 5-azidopropyl-UTP or 5-DBCO-PEG4-dCpG.

[22] The composition of any one of the preceding embodiments, wherein the chemical compound or the first chemical compound is a small molecule.

[23] The composition of any one of the preceding embodiments, wherein the chemical compound or the first chemical compound recruits the target protein.

[24] The composition of any one of the preceding embodiments, wherein the chemical compound or the first chemical compound is a target protein ligand.

[25] The composition of any one of the preceding embodiments, wherein the chemical compound or the first chemical compound is an LCL161 derivative, VHL-1, pomalidomide, lenalidomide, thalidomide or a derivative thereof, a HIF-1a-derived (R)-hydroxyproline, VHL ligand 2, VL-269, a VH032 derivative, or a hydroxyproline-based ligand.

[26] The composition of any one the preceding embodiments, wherein the circular polyribonucleotide is conjugated to one or more additional chemical compounds.

[27] The composition of embodiment [26], wherein the one or more additional chemical compounds are the same.

[28] The composition of embodiment [26], wherein the one or more additional chemical compounds are different.

[29] The composition of any one of the preceding embodiments, wherein the second chemical compound is a small molecule.

[30] The composition of any one of the preceding embodiments, wherein the second chemical compound binds to a misfolded protein.

[31] The composition of any one of the preceding embodiments, wherein the second chemical compound binds to a disease-associated protein.

[32] The composition of any one of the preceding embodiments, wherein the second chemical compound binds to a protein associated with cancer.

[33] The composition of any one of the preceding embodiments, wherein the second chemical compound binds to BCR-Abl, c-ABL, EGFR, c-Met, Sirt2, CDK9, FLT3, ALK, BTK, ERalpha, BRD2/3/4, PDE4, ERRalpha, RIPK2, FKBP12, TBK1, BRD9, HER2, AR, TRIM23, or MDM2.

[34] The composition of any one of the preceding embodiments, wherein the second chemical compound binds to GFP-halotag7.

[35] The composition of any one of the preceding embodiments, wherein the second chemical compound is dasatinib, lapatinib, gefitinib, foretinib, Sirt2 inhibitor 3b, Sirt2 inhibitor, SNS-032, AC220, ceritinib, ibrutinib, ibrutinib derivative, 4-OHT, Jq1, PDE4 inhibitor, thiazolidinedione-based ligand, ripk2 inhibitor, bosutinib, OTX015, steel factor, TBK1 inhibitor, HJB97, aminopyrazole analog, RN486, AR antagonist, IACS-73, or nutlin small molecule.

[36] The composition of any one of the preceding embodiments, wherein the second chemical compound is chloroalkane.

[37] The composition of any one of the preceding embodiments, wherein the target protein is an enzyme.

[38] The composition of any one of the preceding embodiments, wherein the target protein is a post-translational modification enzyme.

[39] The composition of any one of the preceding embodiments, wherein the target protein modifies the substrate by adding a functional group to the substrate protein.

[40] The composition of any one of the preceding embodiments, wherein the target protein modifies the substrate protein by acetylation, acylation, adenylylation, ADP-ribosylation, alkylation, amidation, amide bond formation, amino acid addition, arginylation, beta-lysine addition, butyrylation, carbamidation, carbonylation, carboxylation, citrullination, C-linked glycosylation, crotonylation, diphthamide formation, deacetylation, demethylation, ethanolamine phosphoglycerol attachment, farnesylation, flavin moiety attachment, formylation, gamma-carboxyglutamic acid, gamma-carboxylation, geranilgeranilation, glutarylation, glutathionylation, glycosylation, GPI-anchor formation, heme C attachment, hydroxylation, hypusine formation, iodination, ISGylation, isoprenylation, lipoylation, malonylation, methylation, myristoylation, N-acylation, N-linked glycosylation, neddylation, nitration, nitrosylation, nucleotide addition, O-acylation, O-linked glycosylation, oxidation, palmitoylation, phosphate ester formation, phosphoramidate formation, phosphorylation, phosphopantetheinylation, polyglutamylation, polyglycylation, polysialylation, prenylation, propionylation, pyroglutamate formation, pyrrolidone carboxylic acid, pyrrolylation, pyruvate, Retinylidene Schiff base formation, S-acylation, S-diacylglycerol, S-glutathionylation, S-linked glycosylation, S-nitrosylation, succinylation, sulfation, S-sulfenylation, S-sulfinylation, succinylation, sumoylation, or ubiquitination, uridylylation.

[41] The composition of any one of the preceding embodiments, wherein the target protein is a ubiquitin ligase.

[42] The composition of embodiment [41], wherein the ubiquitin ligase is a HECT, RING-finger, U-box, or PHD-finger ubiquitin ligase.

[43] The composition of any one of embodiment [41] or [42], wherein the ubiquitin ligase is TAP, VHL, or CRBN.

[44] The composition of any one of the preceding embodiments, wherein modulation of the substrate protein modulates a cellular process.

[45] The composition of any one of the preceding embodiments, wherein degradation of the substrate protein modulates a cellular process.

[46] The composition of any one of the preceding embodiments, wherein the cellular process is DNA damage repair, cell division, apoptosis, cell cycle regulation, signal transduction, transcriptional activity, or epigenetic regulation.

[47] The composition of any one of the preceding embodiments, wherein the cellular process is associated with pathogenesis of a disease or condition.

[48] The composition of any one of the preceding embodiments, wherein the substrate protein is a disease-associated protein.

[49] The composition of any one of the preceding embodiments, wherein the substrate protein is a misfolded protein.

[50] The composition of any one of the preceding embodiments, wherein the substrate protein comprises a mutation as compared to a wild-type version of the substrate protein.

[51] The composition of any one of the preceding embodiments, wherein the substrate protein is BCR-Abl, c-ABL, EGFR, c-Met, Sirt2, CDK9, FLT3, ALK, BTK, ERalpha, BRD2/3/4, PDE4, ERRalpha, RIPK2, FKBP12, TBK1, BRD9, HER2, AR, TRIM23, or MDM2.

[52] The composition of any one of the preceding embodiments, wherein the complex alters substrate protein interactions with other proteins.

[53] The composition of any one of the preceding embodiments, wherein the complex increases activity of the substrate protein.

[54] The composition of any one of the preceding embodiments, wherein the complex decreases activity of the substrate protein.

[55] The composition of any one of the preceding embodiments, wherein the complex alters localization of the substrate protein.

[56] The composition of any one of the preceding embodiments, wherein the complex alters stability of the substrate protein.

[57] The composition of any one of the preceding embodiments, wherein the complex promotes degradation of the substrate protein.

[58] The composition of any one of the preceding embodiments, wherein the degradation of the substrate protein comprises proteasomal degradation.

[59] The composition of any one of the preceding embodiments, wherein the complex promotes ubiquitination of the substrate protein.

[60] The composition of any one of the preceding embodiments, wherein the circular polyribonucleotide is translation incompetent or translation defective.

[61] The composition of any one of the preceding embodiments, wherein the circular polyribonucleotide further comprises at least one structural element selected from the group consisting of:

a) an encryptogen;

b) a splicing element;

c) a regulatory sequence;

d) a replication sequence;

e) a quasi-double-stranded secondary structure;

f) a quasi-helical structure; and g) an expression sequence.

[62] The composition of any one of the preceding embodiments, wherein the quasi-helical structure comprises at least one double-stranded RNA segment with at least one non-double-stranded segment.

[63] The composition of any one of the preceding embodiments, wherein the quasi-helical structure comprises a first sequence and a second sequence linked with a repetitive sequence.

[64] The composition of any one of the preceding embodiments, wherein the encryptogen comprises a splicing element.

[64] The composition of any one of the preceding embodiments, wherein the circular polyribonucleic acid comprises at least one modified nucleic acid.

[65] The composition of any one of the preceding embodiments, wherein the at least one modified nucleic acid is selected from the group consisting of 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), 2'-O—N-methylacetamido (2'-O-NMA), a locked nucleic acid (LNA), an ethylene nucleic acid (ENA), a peptide nucleic acid (PNA), a 1',5'-anhydrohexitol nucleic acid (HNA), a morpholino, a methylphosphonate nucleotide, a thiolphosphonate nucleotide, and a 2'-fluoro N3-P5'-phosphoramidite.

[66] The composition of any one of the preceding embodiments, wherein the encryptogen comprises at least one modified nucleic acid.

[67] The composition of any one of the preceding embodiments, wherein the encryptogen comprises a protein binding site.

[68] The composition of any one of the preceding embodiments, wherein the encryptogen comprises an immunoprotein binding site.

[69] The composition of any one of the preceding embodiments, wherein the circular polyribonucleic acid has at least 2× lower immunogenicity than a counterpart lacking the encryptogen, as assessed by expression, signaling, or activation of at least one of RIG-I, TLR-3, TLR-7, TLR-8, MDA-5, LGP-2, OAS, OASL, PKR, and IFN-beta.

[70] The composition of any one of the preceding embodiments, wherein the circular polyribonucleic acid has a size of about 20 bases to about 20 kb.

[71] The composition of any one of the preceding embodiments, wherein the circular polyribonucleic acid is synthesized through circularization of a linear polynucleotide.

[72] The composition of any one of the preceding embodiments, wherein the circular polyribonucleic acid is substantially resistant to degradation.

[73] The composition of any one of the preceding embodiments, wherein the circular polyribonucleic acid comprises one or more expression sequences.

[74] A pharmaceutical composition comprising the composition of any one of the preceding embodiments and a pharmaceutically acceptable carrier or excipient.

[75] A method of modulating a substrate protein, the method comprising:

providing the composition or the pharmaceutical composition of any one of preceding embodiments; and administering the composition or the pharmaceutical composition to a subject having the substrate protein.

[76] A method of treating a condition in a subject in need thereof, the method comprising administering to the subject the composition or the pharmaceutical composition of any one of the preceding embodiments.

[77] The method of embodiment [77], wherein the condition is a cancer or a hyperproliferative disease.

[78] The method of embodiment [77], wherein the condition is a neurodegenerative disease.

[79] The method of embodiment [77], wherein the condition is a metabolic disorder.

[80] The method of embodiment [77], wherein the condition is an inflammatory disorder.

[81] The method of embodiment [77], wherein the condition is an autoimmune disease.

[82] The method of embodiment [77], wherein the condition is an infectious disease.

[83] The method of embodiment [77], wherein the condition is a genetic disease.

Numbered Embodiments #2

[1] A composition comprising a circular polyribonucleotide comprising a conjugation moiety, wherein the conjugation moiety conjugates the circular polyribonucleotide to a chemical compound (e.g., a small molecule) that binds a target protein to modulate a substrate protein.

[2] A composition comprising a circular polyribonucleotide comprising a conjugation moiety, wherein the conjugation moiety conjugates the circular polyribonucleotide to a chemical compound (e.g., a small molecule) that binds a substrate protein for modulation.

[3] A composition comprising a circular polyribonucleotide comprising a first conjugation moiety and a second conjugation moiety, wherein the first conjugation moiety conjugates the circular polyribonucleotide to a first chemical compound (e.g., a small molecule) that binds to a target protein that modulates a substrate protein and wherein the second conjugation moiety conjugates the circular polyribonucleotide to a second chemical compound that binds the substrate protein.

[4] A composition comprising a circular polyribonucleotide comprising a conjugation moiety and a binding site, wherein the conjugation moiety conjugates the circular polyribonucleotide to a first chemical compound (e.g., a small molecule) that binds to a target protein that modulates a substrate protein and wherein the binding site (e.g., an aptamer) binds the substrate protein; or the conjugation moiety conjugates the circular polyribonucleotide to a first chemical compound (e.g., a small molecule) that binds to a substrate protein and wherein the binding site (e.g., an aptamer) binds a target protein that modulates the substrate protein.

[5] A composition comprising:

a) a circular polyribonucleotide comprising a conjugation moiety; and b) a chemical compound that binds a target protein;

wherein the circular polyribonucleotide is conjugated to the chemical compound by the conjugation moiety and the target protein modulates a substrate protein.

[6] A composition comprising:

a) a circular polyribonucleotide comprising a conjugation moiety; and b) a chemical compound that binds a substrate protein;

wherein the circular polyribonucleotide is conjugated to the chemical compound by the conjugation moiety.

[7] A composition comprising:

a) a circular polyribonucleotide comprising a first conjugation moiety and a second conjugation moiety;

b) a first chemical compound that binds a target protein; and c) a second chemical compound that binds a substrate protein;

wherein the circular polyribonucleotide is conjugated to the first chemical compound by the first conjugation moiety, the circular polyribonucleotide is conjugated to the second chemical compound by the second conjugation moiety, and the target protein modulates the substrate protein.

[8] A composition comprising:

a) a circular polyribonucleotide comprising a conjugation moiety and a binding site;

b) a chemical compound that binds a target protein;

wherein the circular polyribonucleotide is conjugated to the first chemical compound by the first conjugation moiety, the binding site binds to the substrate, and the target protein modulates the substrate protein.

[9] A composition comprising:

a) a circular polyribonucleotide comprising a conjugation moiety and a second conjugation moiety;

b) a first chemical compound that binds a target protein; and c) a second chemical compound that binds a substrate protein;

wherein the circular polyribonucleotide is conjugated to the first chemical compound by the first conjugation moiety, the circular polyribonucleotide is conjugated to the second chemical compound by the second conjugation moiety, and the target protein modulates the substrate protein.

[10] A composition of any one of the preceding embodiments, further comprising the target protein bound to the chemical compound to form a complex.

[11] A composition of any one of the preceding embodiments, further comprising the target protein bound to the first chemical compound and the substrate protein bound to the second chemical compound to form a complex.

[12] A composition comprising:

a) a circular polyribonucleotide comprising a conjugation moiety;

b) a chemical compound; and c) a target protein that modulates a substrate protein;

wherein the conjugation moiety is conjugated to the chemical compound and the chemical compound is bound to the target protein to form a complex.

[13] A composition comprising:

a) a circular polyribonucleotide comprising a conjugation moiety and a binding site;

b) a chemical compound; and c) a target protein that modulates a substrate protein;

wherein the binding site is bound to the target protein, the conjugation moiety is conjugated to the chemical compound, and the chemical compound is bound to the substrate protein to form a complex.

[14] A composition comprising:

a) a circular polyribonucleotide comprising a first conjugation moiety and a second conjugation moiety;

b) a first chemical compound that binds a target protein;

c) a second chemical compound that binds a substrate protein; and d) the target protein that modulates the substrate protein;

wherein the first conjugation moiety is conjugated to the first chemical compound, the second conjugation moiety is conjugated to the second chemical compound, and the first chemical compound is bound to the target protein to form a complex.

[15] A composition comprising:

a) a circular polyribonucleotide comprising a conjugation moiety;

b) a chemical compound that binds to a target protein that modulates a substrate protein;

c) the target protein; and d) the substrate protein;

wherein the conjugation moiety is conjugated to the chemical compound, the chemical compound is bound to the target protein, and the target protein is bound to the substrate protein to form a complex.

[16] A composition comprising:

a) a circular polyribonucleotide comprising a first conjugation moiety and a second conjugation moiety;

b) a first chemical compound that binds a target protein that modulates a substrate protein;

c) a second chemical compound that binds the substrate protein;

d) the target protein; and e) the substrate protein;

wherein the first conjugation moiety is conjugated to the first chemical compound, the second conjugation moiety is conjugated to the second the chemical compound, the first chemical compound is bound to the target protein, and second chemical compound is bound to the substrate protein to form a complex.

[17] A composition comprising a circular polyribonucleotide comprising a conjugation moiety, and a chemical compound that binds a substrate, wherein the conjugation moiety is conjugated to the chemical compound and the chemical compound is bound to the substrate protein.

[18] The composition of embodiment [17], wherein the circular polyribonucleotide comprises at least 1, 2, 3, 4, 5, 6, 7, 8, 9, 10, 11, 12, 13, 14, 15, 20, 25, 30, 35, 40, 45, 50, 60, 70, 80, 90, or 100 conjugation moieties.

[19] The composition of embodiment [17] or embodiment [18], the circular polyribonucleotide comprises at least, 2, 3, 4, 5, 6, 7, 8, 9, 10, 11, 12, 13, 14, 15, 20, 25, 30, 35, 40, 45, 50, 60, 70, 80, 90, or 100 chemical compounds.

[20] The composition of any one embodiments [1]-[19], wherein the circular polyribonucleotide further comprises a binding site that binds to the substrate protein or the target protein.

[21] A composition comprising a circular polyribonucleotide comprising a first conjugation moiety; a second conjugation moiety; a first chemical compound that binds a target protein that modulates a substrate protein; a second chemical compound that binds the substrate protein, wherein the first conjugation moiety is conjugated to the first chemical compound, the first chemical compound is bound to the target protein, the second conjugation moiety is conjugated to the second the chemical compound, and second chemical compound is bound to the substrate protein.

[22] A composition comprising a circular polyribonucleotide comprising a conjugation moiety; a binding site that binds to a substrate protein; a chemical compound that binds a target protein that modulates the substrate protein, wherein the conjugation moiety is conjugated to the chemical compound.

[23] The composition of embodiments [21] or [22], wherein the composition further comprises the target protein and/or the substrate protein.

[24] The composition of any one of embodiments [1]-[24], wherein substrate comprises a circular polyribonucleotide (circRNA)-binding motif.

[25] The composition of any one of embodiments [4], [8], [13], [20], or [22], wherein the binding site is an aptamer.

[26] The composition of any one of embodiments [1]-[25], wherein the circular polyribonucleotide is an exogenous, synthetic circular polyribonucleotide.

[27] The composition of any one of embodiments [1]-[26], wherein the circular polyribonucleotide lacks a poly-A sequence, a replication element, or both.

[28] A composition comprising:

a) a first circular polyribonucleotide comprising a first conjugation moiety;

b) a second circular polyribonucleotide comprising a second conjugation moiety;

c) a first chemical compound that binds a target protein that modulates a substrate protein;

d) a second chemical compound that binds the substrate protein;

e) the target protein; and f) the substrate protein;

wherein the first conjugation moiety is conjugated to the first chemical compound, the first chemical compound is bound to the target protein, the second conjugation moiety is conjugated to the second the chemical compound, and second chemical compound is bound to the substrate protein.

[29] The composition of embodiment [28], wherein the substrate protein is bound to the target protein to form a complex.

[30] The composition of any one of embodiments [1]-[29], wherein the conjugation moiety is a modified nucleotide.

[31] The composition of any one of embodiments [1]-[30], wherein the first conjugation moiety is a first modified nucleotide and the second conjugation moiety is a second modified nucleotide.

[32] The composition of embodiment [31], wherein the first modified nucleotide and second modified nucleotide are the same.

[33] The composition of embodiment [31], wherein the first modified nucleotide and second modified nucleotide are different.

[34] The composition of embodiment [30], wherein the modified nucleotide is a modified UTP analog, a modified ATP analog, modified CTP analog, or a modified GTP analog.

[35] The composition of embodiment [34], wherein the modified nucleotide comprises a click chemistry moiety.

[36] The composition of embodiments [34] or [35], wherein the modified UTP analog 5-Azidomethyl-UTP, 5-Azido-C3-UTP, 5-Azido-PEG4-UTP, 5-Ethynyl-UTP, DBCO-PEG4-UTP, Vinyl-UTP, 8-Azido-ATP, 3'-Azido-2',3'-ddATP, 5-Azido-PEG4-CTP, 5-DBCO-PEG4-CTP, N6-Azidohexyl-3'-dATP, 5-azidopropyl-UTP or 5-DBCO-PEG4-dCpG.

[37] The composition of embodiments [31] or [32], wherein the first modified nucleotide is a modified UTP analog, a modified ATP analog, modified CTP analog, or a modified GTP analog, and wherein the second modified nucleotide is a modified UTP analog, a modified ATP analog, modified CTP analog, or a modified GTP analog.

[38] The composition of embodiment [37], wherein the first modified nucleotide comprises a first click chemistry moiety and the second modified nucleotide comprises a second click chemistry moiety.

[39] The composition of embodiments [37] or [38], wherein the first a modified UTP analog, 5-Azidomethyl-UTP, 5-Azido-C3-UTP, 5-Azido-PEG4-UTP, 5-Ethynyl-UTP, DBCO-PEG4-UTP, Vinyl-UTP, 8-Azido-ATP, 3'-Azido-2',3'-ddATP, 5-Azido-PEG4-CTP, 5-DBCO-PEG4-CTP, N6-Azidohexyl-3'-dATP, 5-azidopropyl-UTP or 5-DBCO-PEG4-dCpG, and the second modified nucleotide is a modified UTP analog, 5-Azidomethyl-UTP, 5-Azido-C3-UTP, 5-Azido-PEG4-UTP, 5-Ethynyl-UTP, DBCO-PEG4-UTP, Vinyl-UTP, 8-Azido-ATP, 3'-Azido-2',3'-ddATP, 5-Azido-PEG4-CTP, 5-DBCO-PEG4-CTP, N6-Azidohexyl-3'-dATP, 5-azidopropyl-UTP or 5-DBCO-PEG4-dCpG.

[40] The composition of any one embodiment [1]-[39], wherein the chemical compound or the first chemical compound is a small molecule.

[41] The composition of any one embodiment [140], wherein the chemical compound or the first chemical compound recruits the target protein.

[42] The composition of any one embodiment [1]-[41], wherein the chemical compound or the first chemical compound is a target protein ligand.

[43] The composition of any one embodiment [1]-[42], wherein the chemical compound or the first chemical compound is an LCL161 derivative, VHL-1, pomalidomide, lenalidomide, thalidomide or a derivative thereof, a HIF-1a-derived (R)-hydroxyproline, VHL ligand 2, VL-269, a VH032 derivative, or a hydroxyproline-based ligand.

[44] The composition of any one embodiment [1]-[43], wherein the circular polyribonucleotide is conjugated to one or more additional chemical compounds.

[45] The composition of embodiment [44], wherein the one or more additional chemical compounds are the same.

[46] The composition of embodiment [44], wherein the one or more additional chemical compounds are different.

[47] The composition of any one of embodiments [3], [7], [9], [11], [14], [16], [21], or [28], wherein the second chemical compound is a small molecule.

[48] The composition of any one of embodiments [3], [7], [9], [11], [14], [16], [21], [28], or [47], wherein the second chemical compound binds to a misfolded protein.

[49] The composition of any one of embodiments [3], [7], [9], [1]1, [14], [16], [21], [28], or [47], wherein the second chemical compound binds to a disease-associated protein.

[50] The composition of any one of embodiments [3], [7], [9], [11], [14], [16], [21], [28], or [47], wherein the second chemical compound binds to a protein associated with cancer.

[51] The composition of any one of embodiments [3], [7], [9], [11], [14], [16], [21], [28], or [47], wherein the chemical compound or the second chemical compound is a Heat Shock Protein 90 (HSP90) inhibitor, Kinase and Phosphatase inhibitor, MDM2 inhibitor, HDAC inhibitor, Human Lysine Methyltransferase Inhibitor, Angiogenesis inhibitor, Immunosuppressive compound, or a compounds that binds to a Human BET Bromodomain-containing protein, the aryl hydrocarbon receptor (AHR), REF receptor kinase, FKBP, Androgen Receptor (AR), Estrogen receptor (ER), Thyroid Hormone Receptor, HIV Protease, HIV Integrase, HCV Protease, and Acyl-protein Thioesterase-1 and -2 (APTI and APT2).

[52] The composition of any one of embodiments [3], [7], [9], [11], [14], [16], [21], [28], or [47], wherein the second chemical compound binds to BCR-Abl, c-ABL, EGFR, c-Met, Sirt2, CDK9, FLT3, ALK, BTK, ERalpha, BRD2/3/4, PDE4, ERRalpha, RIPK2, FKBP12, TBK1, BRD9, HER2, AR, TRIM23, or MDM2.

[53] The composition of any one of embodiments [3], [7], [9], [11], [14], [16], [21], [28], or [47], wherein the second chemical compound binds to GFP-halotag7.

[54] The composition of any one of embodiments [3], [7], [9], [11], [14], [16], [21], [28], or [47], wherein the second chemical compound is dasatinib, lapatinib, gefitinib, foretinib, Sirt2 inhibitor 3b, Sirt2 inhibitor, SNS-032, AC220, ceritinib, ibrutinib, ibrutinib derivative, 4-OHT, Jq1, PDE4 inhibitor, thiazolidinedione-based ligand, ripk2 inhibitor, bosutinib, OTX015, steel factor, TBK1 inhibitor, HJB97, aminopyrazole analog, RN486, AR antagonist, IACS-73, or nutlin small molecule.

[55] The composition any one of embodiments [3], [7], [9], [11], [14], [16], [21], [28], or [47], wherein the second chemical compound is chloroalkane.

[56] The composition of any one of embodiments [1]-[55], wherein the target protein is an enzyme.

[57] The composition of any one of embodiments [1]-[56], wherein the target protein is a post-translational modification enzyme.

[58] The composition of any one of embodiments [1]-[57], wherein the target protein modifies the substrate by adding a functional group to the substrate protein.

[59] The composition of any one of embodiments [1]-[58], wherein the target protein modifies the substrate protein by acetylation, acylation, adenylylation, ADP-ribosylation, alkylation, amidation, amide bond formation, amino acid addition, arginylation, beta-lysine addition, butyrylation, carbamidation, carbonylation, carboxylation, citrullination, C-linked glycosylation, crotonylation, diphthamide formation, deacetylation, demethylation, ethanolamine phosphoglycerol attachment, farnesylation, flavin moiety attachment, formylation, gamma-carboxyglutamic acid, gamma-carboxylation, geranilgeranilation, glutarylation, glutathionylation, glycosylation, GPI-anchor formation, heme C attachment, hydroxylation, hypusine formation, iodination, ISGylation, isoprenylation, lipoylation, malonylation, methylation, myristoylation, N-acylation, N-linked glycosylation, neddylation, nitration, nitrosylation, nucleotide addition, O-acylation, O-linked glycosylation, oxidation, palmitoylation, phosphate ester formation, phosphoramidate formation, phosphorylation, phosphopantetheinylation, polyglutamylation, polyglycylation, polysialylation, prenylation, propionylation, pyroglutamate formation, pyrrolidone carboxylic acid, pyrrolylation, pyruvate, Retinylidene Schiff base formation, S-acylation, S-diacylglycerol, S-glutathionylation, S-linked glycosylation, S-nitrosylation, succinylation, sulfation, S-sulfenylation, S-sulfinylation, succinylation, sumoylation, or ubiquitination, uridylylation.

[60] The composition of any one of embodiments [1]-[59], wherein the target protein is a ubiquitin ligase.

[61] The composition of embodiment [60], wherein the ubiquitin ligase is a HECT, RING-finger, U-box, or PHD-finger ubiquitin ligase.

[62] The composition of any one of embodiment [60] or [61], wherein the ubiquitin ligase is selected from the group consisting of von Rippel-Lindau (VHL); cereblon; XIAP; E3A; MDM2; Anaphase-promoting complex (APC); UBR5 (EDDI); SOCS/BC-box/eloBC/CUL5/RING; LNXp80; CBX4; CBLLI; HACEI; HECTDI; HECTD2; HECTD3; HECWI; HECW2; HERCI; HERC2; HERC3; HERC4; HUWEI; ITCH; NEDD4; NEDD4L; PPIL2; PRPF19; PIASI; PIAS2; PIAS3; PIAS4; RANBP2; RNF4; RBXI; SMURFI; SMURF2; STUBI; TOPORS; TRIP12; UBE3A; UBE3B; UBE3C; UBE4A; UBE4B; UBOX5; UBR5; WWPI; WWP2; Parkin; A20/TNFAIP3; AMFR/gp78; ARA54; beta-TrCPI/BTRC; BRCAI; CBL; CHIP/STUB I; E6; E6AP/UBE3A; F-box protein 15/FBXOIS; FBXW7/Cdc4; GRAIL/RNF128; HOIP/RNF3 l; cIAP-1/HIAP-2; cIAP-2/HIAP-1; cIAP (pan); ITCH/AIP4; KAPI; MARCH8; Mind Bomb 1/MIBI; Mind Bomb 2/MIB2; MuRFl/TRIM63; NDFIPI; NEDD4; NleL; Parkin; RNF2; RNF4; RNF8; RNF168; RNF43; SARTI; Skp2; SMURF2; TRAF-1; TRAF-2; TRAF-3; TRAF-4; TRAF-5; TRAF-6; TRIMS; TRIM21; TRIM32; UBR5; and ZNRF3.

[63] The composition of any one of embodiments [1]-[62], wherein modulation of the substrate protein modulates a cellular process.

[64] The composition of any one of embodiments [1]-[63], wherein degradation of the substrate protein modulates a cellular process.

[65] The composition of any one of embodiments [1]-[64], wherein the cellular process is DNA damage repair, cell division, apoptosis, cell cycle regulation, signal transduction, transcriptional activity, or epigenetic regulation.

[66] The composition of any one of embodiments [1]-[65], wherein the cellular process is associated with pathogenesis of a disease or condition.

[67] The composition of any one of embodiments [1]-[66], wherein the substrate protein is a disease-associated protein.

[68] The composition of any one of embodiments [1]-[67], wherein the substrate protein is a misfolded protein.

[69] The composition of any one of embodiments [1]-[68], wherein the substrate protein comprises a mutation as compared to a wild-type version of the substrate protein.

[70] The composition of any one of embodiments [1]-[69], wherein the substrate protein is BCR-Abl, c-ABL, EGFR, c-Met, Sirt2, CDK9, FLT3, ALK, BTK, ERalpha, BRD2/3/4, PDE4, ERRalpha, RIPK2, FKBP12, TBK1, BRD9, HER2, AR, TRIM23, MDM2, FoxOl, HDAC, DP-1, E2F, ABL, ALK, AMPK, BRK, BRSK I, BRSK2, BTK, CAMKKI, CAMKK alpha, CAMKK beta, Rb, Suv39HI, SCF, pl9INK4D, GSK-3, pi 8 INK4, myc, cyclin E, CDK2, CDK9, CDG4/6, Cycline D, pl6 INK4A, cdc25A, BMII, SCF, Akt, CHK1/2, CI delta, CKI gamma, C 2, CLK2, CSK, DDR2, DYRKIA/2/3, EF2K, EPH-A2/A4/B1/B2/B3/B4, EIF2A 3, Smad2, Smad3, Smad4, Smad7, p53, p21 Cipl, PAX, Fyn, CAS, C3G, SOS, Tal, Raptor, RACK-I, CRK, Rapl, Rae, KRas, NRas, HRas, GRB2, FAK, PBK, spred, Spry, mTOR, MPK, LKB1, PAK 1/2/4/5/6, PDGFRA, PYK.2, Src, SRPKI, PLC, PKC, PKA, PKB, alpha/beta, PKC alpha/gamma/zeta, PKD, PLK1, PRAK, PRK2, RIPK2, WA VE-2, TSC2, DAPK1, BAD, IMP, C-TAKI, TAKI, TAO1, TBKI, TESKI, TGFBRI, TIE2, TLKI, TrkA, TSSKI, TTBKI/2, TTK, Tpl2/cotl, MEKI, MEK2, PLDL Erk1, Erk2, Erk5, Erk8, p90RSK, PEA-15, SRF, p27 KIPI, TIF 1a, HMGNI, ER81, MKP-3, c-Fos, FGF-Rl, GCK, GSK3 beta, HER4, HIPKI/2/3/, IGF-IR, cdc25, UBF, LAMTOR2, Statl, StaO, CREB, JAK, Src, SNCA, PTEN, NF-kappaB, HECTH9, Bax, HSP70, HSP90, Apaf-1, Cyto c, BCL-2, Bcl-xL, BCL-6, Smac, XIAP, Caspase-9, Caspase-3, Caspase-6, Caspase-7, CDC37, TAB, IKK, TRADD, TRAF2, RIPI, FLIP, TAKI, JNK1/2/3, Lek, A-Raf, B-Raf, C-Raf, MOS, MLK1/3, MN 1/2, MSK1, MST2/3/4, MPSKI, MEKK1, ME K4, MEL, ASKI, MINK I, MKK 1/2/3/4/6/7, NE, 2a/6/7, NUAKI, OSRI, SAP, STK33, Syk, Lyn, PDKI, PHK, PIM 1/2/3, Ataxin-1, mTORCl, MDM2, p21 Wafl, Cyclin D1, Lamin A, Tpl2, Myc, catenin, Wnt, IKK-beta, IKKgamma, IKK-alpha, IKK-epsilon, ELK, p65Re1A, IRAKI, IRA 2, IRAK4, IRR, FADD, TRAF6, TRAF3, MKK3, MKK6, ROCK2, RSKI/2, SGK 1, SmMLCK, SIK2/3, ULKI/2, VEGFRI, WNK 1, YESI, ZAP70, MAP4K3, MAP4K5, MAPKlb, MAPKAP-K2 K3, p38, alpha/beta/delta/gamma MAPK, Aurora A, Aurora B, Aurora C, MCAK, Clip, MAPKAPK, FAK, MARK 1/2/3/4, Mucl, SHC, CXCR4, Gap-I, Myc, beta-catenin/TCF, Cbl, BRM, Mel1, BRD2, BRD3, BRD4, AR, RAS, ErbB3, EGFR, IREI, HPKI, RIPK2, ERa, or PCAF/GCN5.

[71] The composition of any one of embodiments [10]-[16], or [29], wherein the complex alters substrate protein interactions with other proteins.

[72] The composition of any one of embodiments [10]-[16], or [29], wherein the complex increases activity of the substrate protein.

[73] The composition of any one of embodiments [10]-[16], or [29], wherein the complex decreases activity of the substrate protein.

[74] The composition of any one of embodiments [10]-[16], or [29], wherein the complex alters localization of the substrate protein.

[75] The composition of any one of embodiments [10]-[16], or [29], wherein the complex alters stability of the substrate protein.

[76] The composition of any one of embodiments [10]-[16], or [29], wherein the complex promotes degradation of the substrate protein.

[77] The composition of any one of embodiments [10]-[16], or [29], wherein the degradation of the substrate protein comprises proteasomal degradation.

[78] The composition of any one of embodiments [10]-[16], or [29], wherein the complex promotes ubiquitination of the substrate protein.

[79] The composition of any one of embodiments [4], [8], [13], [20], [22], or [25], wherein the binding site is an aptamer.

[80] The composition of any one of embodiments [4], [8], [13], [20], [22], or [25], wherein the binding site is a miRNA binding site.

[81] The composition of any one of embodiments [1]-[80], wherein the circular polyribonucleotide is translation incompetent or translation defective.

[82] The composition of any one of embodiments [1]-[81], wherein the circular polyribonucleotide further comprises at least one structural element selected from the group consisting of:

a) an encryptogen;
b) a splicing element;
c) a regulatory sequence;
d) a replication sequence;
e) a quasi-double-stranded secondary structure;
f) a quasi-helical structure; and
g) an expression sequence.

[83] The composition of embodiment [82], wherein the quasi-helical structure comprises at least one double-stranded RNA segment with at least one non-double-stranded segment.

[84] The composition of embodiment [82], wherein the quasi-helical structure comprises a first sequence and a second sequence linked with a repetitive sequence.

[85] The composition of embodiment [82], wherein the encryptogen comprises a splicing element.

[86] The composition of embodiment [82], wherein the encryptogen comprises at least one modified nucleic acid.

[87] The composition of embodiment [82], wherein the encryptogen comprises a protein binding site.

[88] The composition of embodiment [82], wherein the encryptogen comprises an immunoprotein binding site.

[89] The composition of any one of embodiments [1]-[88], wherein the circular polyribonucleic acid has at least 2× lower immunogenicity than a counterpart lacking the encryptogen, as assessed by expression, signaling, or activation of at least one of RIG-I, TLR-3, TLR-7, TLR-8, MDA-5, LGP-2, OAS, OASL, PKR, and IFN-beta.

[90] The composition of any one of embodiments [1]-[89], wherein the circular polyribonucleic acid has a size of about 20 bases to about 20 kb.

[91] The composition of any one of embodiments [1]-[90], wherein the circular polyribonucleic acid is synthesized through circularization of a linear polynucleotide.

[92] The composition of any one of embodiments [1]-[91], wherein the circular polyribonucleic acid is substantially resistant to degradation.

[93] The composition of any one of embodiments [1]-[92], wherein the circular polyribonucleic acid comprises one or more expression sequences.

[94] A pharmaceutical composition comprising the composition of any one of the preceding embodiments and a pharmaceutically acceptable carrier or excipient.

[95] A pharmaceutical composition comprising the composition of any one of the preceding embodiments and a pharmaceutically acceptable excipient and is free of any carrier.

[96] A method of treating a condition in a subject in need thereof, the method comprising administering to the subject the composition or the pharmaceutical composition of any one of the preceding embodiments.

[97] The method of embodiment [96], wherein the condition is a cancer or a hyperproliferative disease.

[98] The method of embodiment [97], wherein the cancer is a solid tumor or a liquid tumor.

[99] The method of embodiment [98], wherein the solid tumor is a reproductive tissue cancer (e.g., prostate cancer or cervical cancer).

[100] The method of embodiment [98], wherein the liquid tumor is a lymphoma (e.g., B cell lymphoma).

[101] The method of embodiment [96], wherein the condition is a neurodegenerative disease.

[102] The method of embodiment [96], wherein the condition is a metabolic disorder.

[103] The method of embodiment [96], wherein the condition is an inflammatory disorder.

[104] The method of embodiment [96], wherein the condition is an autoimmune disease.

[105] The method of embodiment [96], wherein the condition is an infectious disease.

[106] The method of embodiment [96], wherein the condition is a genetic disease.

[107] The method of any one of embodiments [96]-[106], wherein administering is intravenous administration.

[108] The method of any one of embodiments [96]-[107], wherein administering is intratumoral administration.

[109] A bifunctional circular polyribonucleotide, wherein the bifunctional circular polyribonucleotide comprises the following chemical structure:

$X^1$-circular polyribonucleotide-$X^2$ wherein $X^1$ and $X^2$ independently comprise a molecule comprising an E3 ubiquitin ligase binding moiety (UBM) or a molecule comprising a protein binding moiety (PBM).

[110] The bifunctional circular ribonucleotide of embodiment [109], wherein $X^1$ comprises an UBM.

[111] The bifunctional circular ribonucleotide of embodiment [109], wherein $X^1$ comprises an PBM.

[112] The bifunctional circular ribonucleotide of any one of embodiments [109]-[111], wherein the PBM is a Von Hippel-Lindau E3 ubiquitin ligase binding moiety, a cereblon E3 ubiquitin ligase binding moiety, an MDM2 E3 ubiquitin ligase binding moiety, an IAP binding moiety, or a combination thereof.

[113] The bifunctional circular ribonucleotide of any one of embodiments [109]-[112], wherein $X^1$ comprise one or more UBMs and one or more PBMs.

[114] The bifunctional circular ribonucleotide of any one of embodiments [109]-[112], wherein $X^2$ comprise one or more UBMs and one or more PBMs.

[115] The bifunctional circular ribonucleotide of any one of embodiments [109]-[114], wherein $X^1$ and $X^2$ independently comprise one or more UBMs and one or more PBMs.

[116] The bifunctional circular ribonucleotide of any one of embodiments [109]-[115], wherein the one or more UBMs are identical.

[117] The bifunctional circular ribonucleotide of any one of embodiments [109]-[115], wherein the one or more UBMs are different.

[118] The bifunctional circular ribonucleotide of any one of embodiments [109]-[117], wherein the one or more PBMs are identical.

[119] The bifunctional circular ribonucleotide of any one of embodiments [109]-[117], wherein the one or more UBMs are different.

[120] The bifunctional circular ribonucleotide of any one of embodiments [109]-[119], wherein $X^1$ and $X^2$ independently comprise up to 100 binding moieties.

EXAMPLES

Example 1: Circular RNA that Contains a Chemical Compound

This Example demonstrates circular RNA linked to a chemical compound to bind and recruit a protein of choice.

Thalidomide, a clinically approved drug (Thalomid), is known to associate with a member of the cells' protein degradation machinery, the E3 ubiquitin ligase. By conjugating thalidomide to circular RNA (e.g., via click chemistry), thalidomide-conjugated circular RNA can recruit cells' degradation machinery to a second, disease-causing protein (e.g., also targeted by the circular RNA). As shown in the following Example, a chemical compound, e.g., a small molecule was conjugated to a circular RNA to bind E3 ubiquitin ligase Cereblon for ubiquitination and subsequent degradation of a target protein.

Circular RNA was designed to include reactive uridine residues (e.g., 5-azido-C3-UTP) for conjugation of alkyne-functionalized small molecules, known to interact with an intracellular protein of interest.

Linear RNA was synthesized by in vitro transcription using T7 RNA polymerase (Lucigen). All UTP was substituted with 5-azido-C3-UTP (Jena Biosciences) in the in vitro transcription reaction to generate azide-functionalized RNA. Synthesized linear RNA was purified with an RNA clean up kit (New England Biolabs) and subjected to RNA 5' Pyrophosphohydrolase (RppH, New England Biolabs) treatment to remove pyrophosphate. RppH-treated linear RNA was purified with an RNA clean up kit (New England Biolabs).

Circular RNA was generated by splint ligation. RppH-treated linear RNA (100 uM) and splint DNA (200 uM) was annealed by heating at 75° C. for 5 min and gradual cooling at room temperature for 20 min. Ligation reaction was performed with T4 RNA ligase 2 (0.2 U/ul, New England Biolabs) for 4 hours at 37° C. The ligated mixture was purified by ethanol precipitation. To isolate circular RNA, the ligated mixture was separated on 4% denaturing UREA-PAGE. RNA on the gel was stained with SYBR-green (Thermo Fisher) and visualized with transilluminator (Transilluminators). Corresponding RNA bands for circular RNA were excised and crushed by gel breaker tubes (1st Engineering). For elution of circular RNA, crushed gels with circular RNA were incubated with elution buffer (0.5M Sodium Acetate, 1 mM EDTA, 0.1% SDS) at 37° C. for an hour and supernatant was carefully harvested. The remaining crushed gel elution was subjected to another round of elution, and repeated total three times. Elution buffer with circular RNA was filtrated through a 0.45 um cellulose acetate filter to remove gel debris and circular RNA was purified/concentrated by ethanol precipitation.

Figure 3:
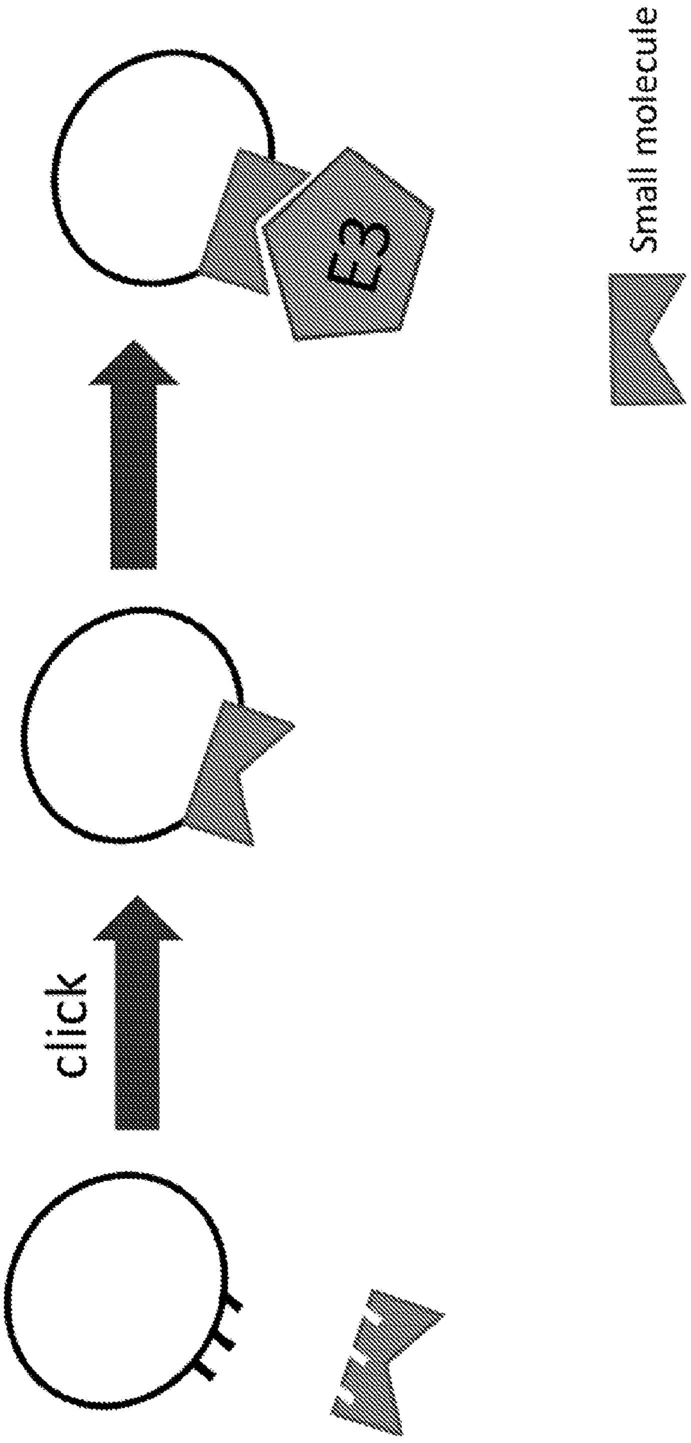
FIG. 3 illustrates click chemistry conjugation of a chemical compound (e.g., a small molecule) to a circular RNA to generate a circular RNA that can bind an E3 ubiquitin ligase.

FIG. 3 illustrates click chemistry conjugation of a chemical compound to a circular RNA to generate a circular RNA that can bind an E3 ubiquitin ligase.

Alkyne-functionalized thalidomide (Jena Bioscience) was conjugated to azide-functionalized circular RNA via Copper-catalyzed Azide-Alkyne click chemistry reactions (CuAAC) with the click chemistry reaction kit based on manufacturer's instructions (Jena Bioscience). Thalidomide-conjugated circular RNA was purified with an RNA clean up kit (New England Biolabs).

Binding properties of the thalidomide-conjugated circular RNA binding was analyzed using GST pull-down followed by qPCR for RNA detection. For GST pull-down assay, thalidomide-conjugated circular RNA (2 nM) was incubated with GST-E3 ubiquitin ligase Cereblon (50 nM), which interacts with thalidomide, for 2 hours at room temperature in the presence of 25 mM Tris-Cl (pH7.0), 100 mM NaCl, 1 mM EDTA, 0.5% NP-40, 5% Glycerol. Azide-functionalized circular RNA without thalidomide conjugation was used as a negative control.

The RNA-protein mixture was further incubated for an hour at room temperature with GSH-agarose beads to assess GST-GSH interactions. After washing three times with binding buffer, the RNA specifically bound to the GSH-beads was extracted with Trizol (Thermo Fisher). The extracted circular RNA was reverse transcribed and detected by quantitative RT-PCR with primers specific for circular RNA (forward: TACGCCTGCAACTGTGTTGT, reverse: TCGATGATCTTGTCGTCGTC).

Figure 4:
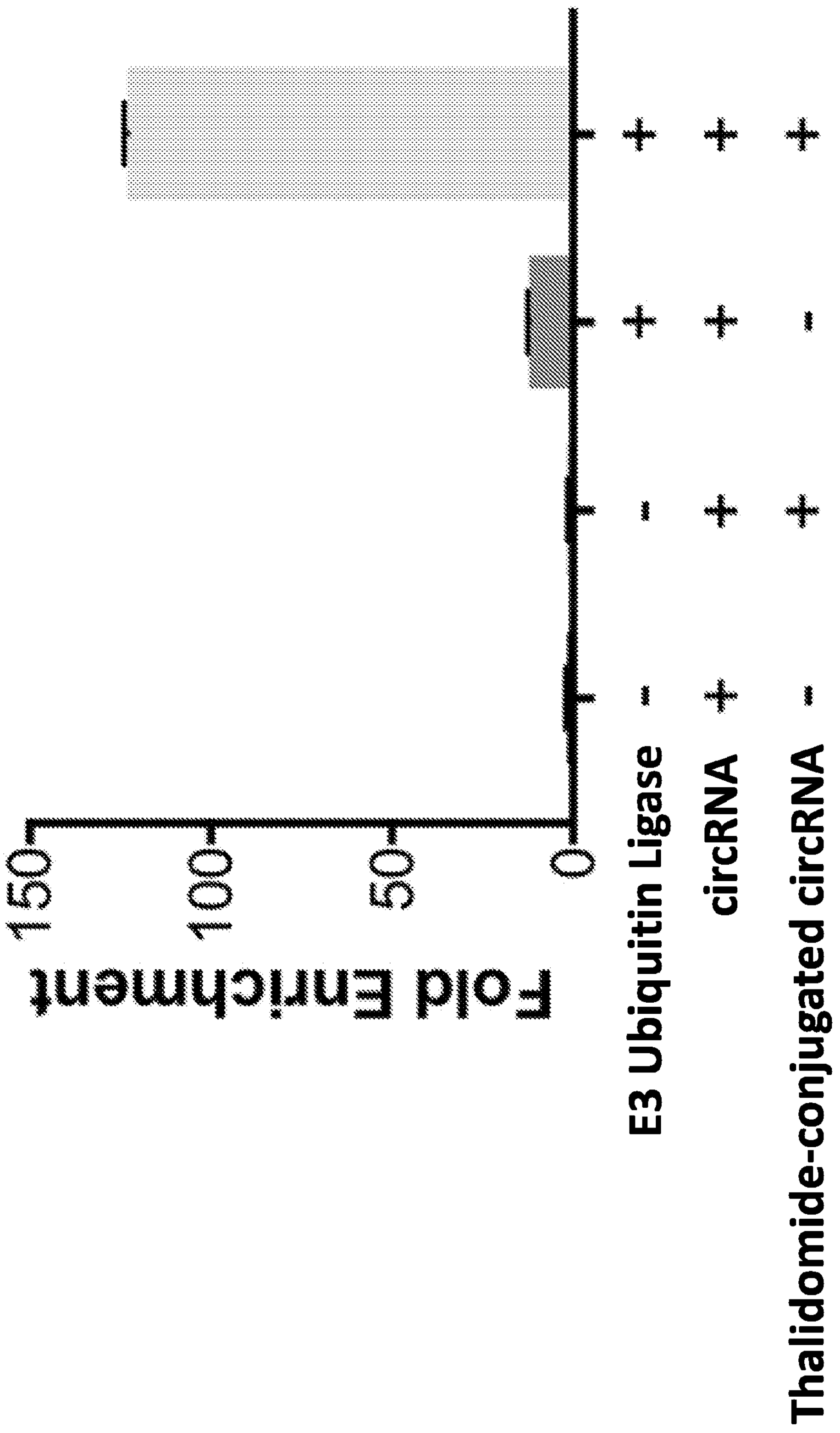
FIG. 4 demonstrates a small molecule-circular RNA conjugate (Thalidomide-conjugated circRNA) can bind to a protein targeted by the small molecule (Cereblon).
Figure 5:
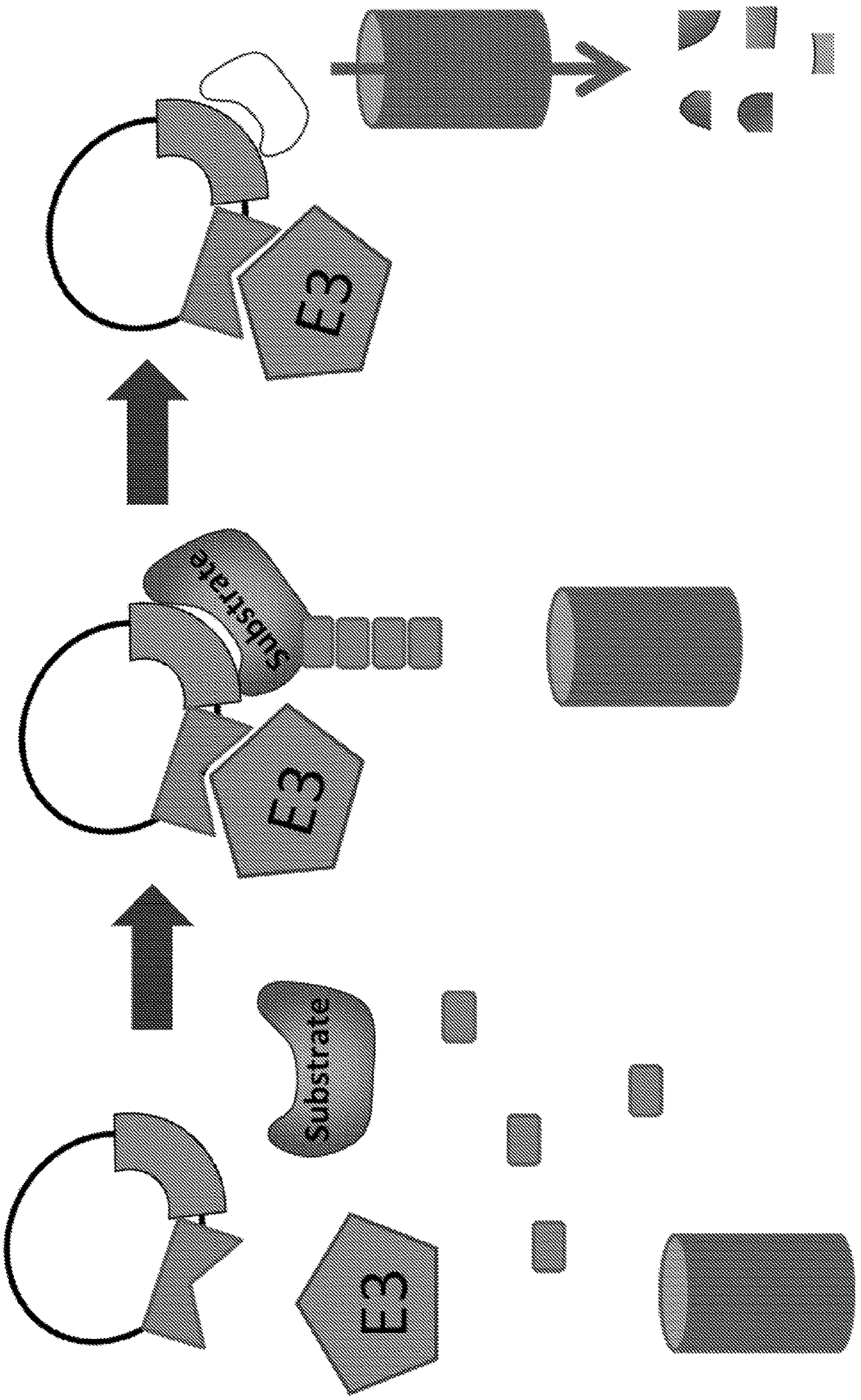
FIG. 5 illustrates a circular RNA containing a protein binding sequence and a conjugated small molecule that can recruit an E3 ubiquitin ligase and a second protein, and target the second protein for ubiquitination and degradation.

FIG. 4 demonstrates that circular RNA conjugated to the thalidomide small molecule was highly enriched in the GST pull-down, demonstrating that a circular RNA-chemical compound conjugate can bind a target protein via the small molecule, e.g., to promote degradation of the protein of choice.

Example 2: Circular RNA with a Chemical Compound

This Example demonstrates circular RNA linked to a chemical compound to induce specific bioactivity.

As shown in the following Example, a chemical compound, e.g., a small molecule, was clicked to a circular RNA to harness specific bioactivity, e.g., ubiquitination, for bioactivity on a specific protein.

Circular RNA was designed to include reactive uridine residues (e.g., 5-azido-C3-UTP or 5-ethyl-UTP) for conjugation of alkyne-functionalized or azide-functionalized small molecules, for any downstream functionality.

Linear RNA was synthesized by in vitro transcription using T7 RNA polymerase (Lucigen). All UTP was substituted with 5-azido-C3-UTP or 5-ethyl-UTP (Jena Biosciences) in the in vitro transcription reaction to generate azide-functionalized or alkyne functionalized RNA, respectively. Synthesized linear RNA was purified with an RNA clean up kit (New England Biolabs) and subjected to RNA 5' Pyrophosphohydrolase (RppH, New England Biolabs) treatment to remove pyrophosphate. RppH treated linear RNA was purified with an RNA clean up kit (New England Biolabs).

Circular RNA was generated by splint ligation. RppH-treated linear RNA (100 uM) and splint DNA (200 uM) was annealed by heating at 75° C. for 5 min and gradual cooling at room temperature for 20 min. Ligation reaction was performed with T4 RNA ligase 2 (0.2 U/ul, New England Biolabs) for 4 hours at 37° C. The ligated mixture was purified by ethanol precipitation.

To isolate circular RNA, the ligated mixture was separated on 6% denaturing UREA-PAGE. RNA on the gel was stained with SYBR-green (Thermo Fisher) and visualized with a transilluminator (Transilluminators). Corresponding RNA bands for circular RNA were excised and crushed by gel breaker tubes (Ist Engineering). For elution of circular RNA, crushed gels with circular RNA were incubated with elution buffer (0.5M Sodium Acetate, 1 mM EDTA, 0.1% SDS) at 37° C. for an hour and supernatant was carefully harvested. The remaining crushed gel elution was subjected to another round of elution, and repeated for a total of three times. Elution buffer with circular RNA was filtrated through a 0.45 um cellulose acetate filter to remove gel debris and circular RNA was purified/concentrated by ethanol precipitation.

Alkyne-functionalized Alex Fluor 488 dye or azide-functionalized Alex Fluor 488 dye (Jena Bioscience) was conjugated to azide-functionalized circular RNA or alkyne-funcitonalized RNA via Copper-catalyzed Azide-Alkyne click chemistry reactions (CuAAC) with the click chemistry reaction kit based on manufacturer's instructions (Jena Bioscience). Alexa Fluor 488-conjugated circular RNA was purified with an RNA clean up kit (New England Biolab).

The dye conjugation was monitored by separating circular RNA on 6% denaturing UREA-PAGE. Alexa Fluor dye-unconjugated and -conjugated circular RNA were separated on the gel in parallel for comparison. Fluorescence from the RNA on the gel was monitored by iBright Imaging System (Invitrogen). After monitoring fluorescence, the gel was stained with SYBR safe and RNA on the gel was visualized by iBright Imaging System (Invitrogen).

Circular RNA containing a chemical compound Alexa Fluor 488 was shown to fluoresce demonstrating that circular RNA can contain a functional chemical compound.

Figure 10:
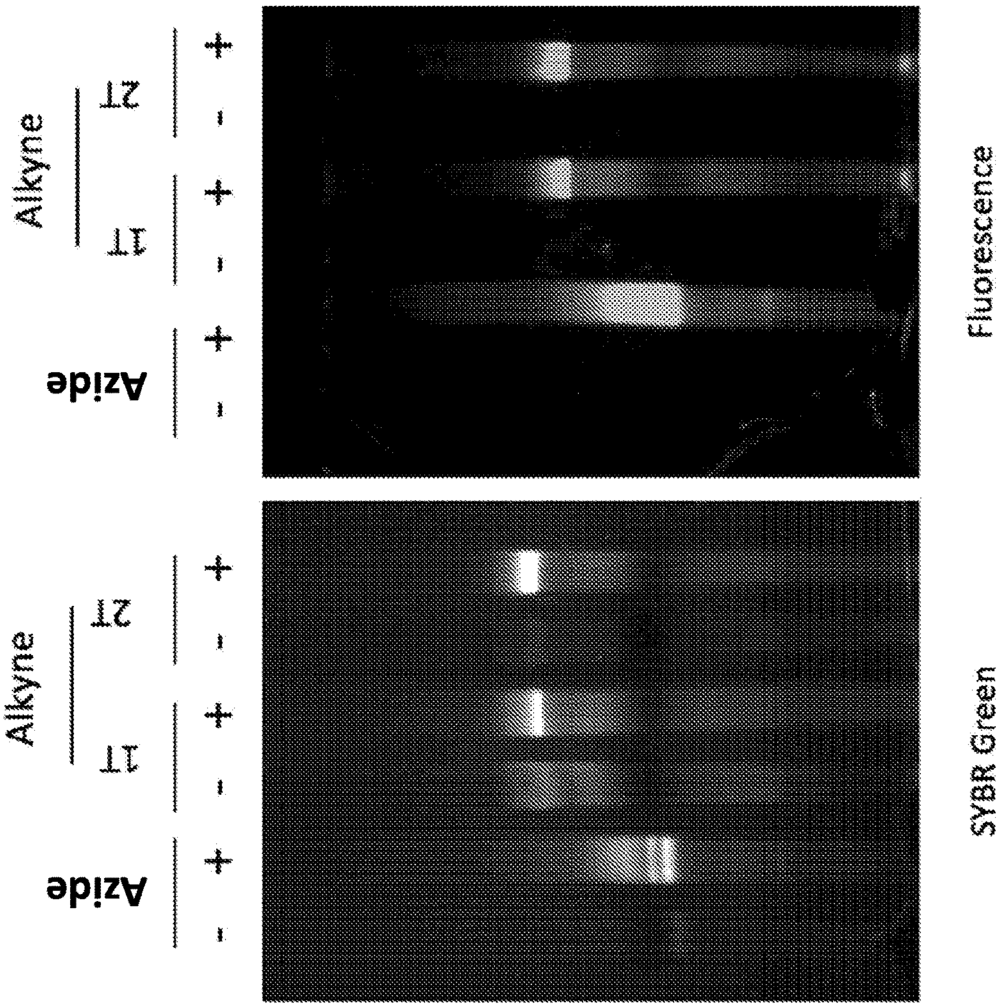
FIG. 10 demonstrates interaction of a circular RNA-small molecule conjugate with a specific bioactive molecule.

As illustrated in FIG. 10, circular RNA conjugated to the thalidomide small molecule produced a discrete PCR product as detected by fluorescence, demonstrating that circular RNA conjugated to a chemical compound interacted with a specific bioactive dye.

Example 3: Circular RNA with Two Chemical Compounds

This example describes a circular RNA containing two conjugated chemical compounds that can each recruit a protein.

VH 032 is a small molecule known to associate with the E3 ubiquitin ligase VHL. A VH 032-conjugated circular RNA that also contains a binding site for a second target protein could therefore recruit an E3 ubiquitin ligase and the second target protein, for example, to target the second (e.g., disease-causing) protein for ubiquitination and degradation.

Gefitinib is a drug that is known to bind to the epidermal growth factor receptor (EGFR). A gefitinib-conjugated circular RNA that also binds to a ubiquitin ligase could be used, for example, to target EGFR for ubiquitination and degradation.

The following Example describes a circular RNA that is synthesized containing two chemical compound conjugates, each of which can recruit a protein. In this example, the circular RNA can bind the E3 ubiquitin ligase VHL and EGFR, thereby targeting EGFR for ubiquitination and degradation.

A circular RNA is designed to include conjugated VH 032 and gefitinib.

Figure 6:
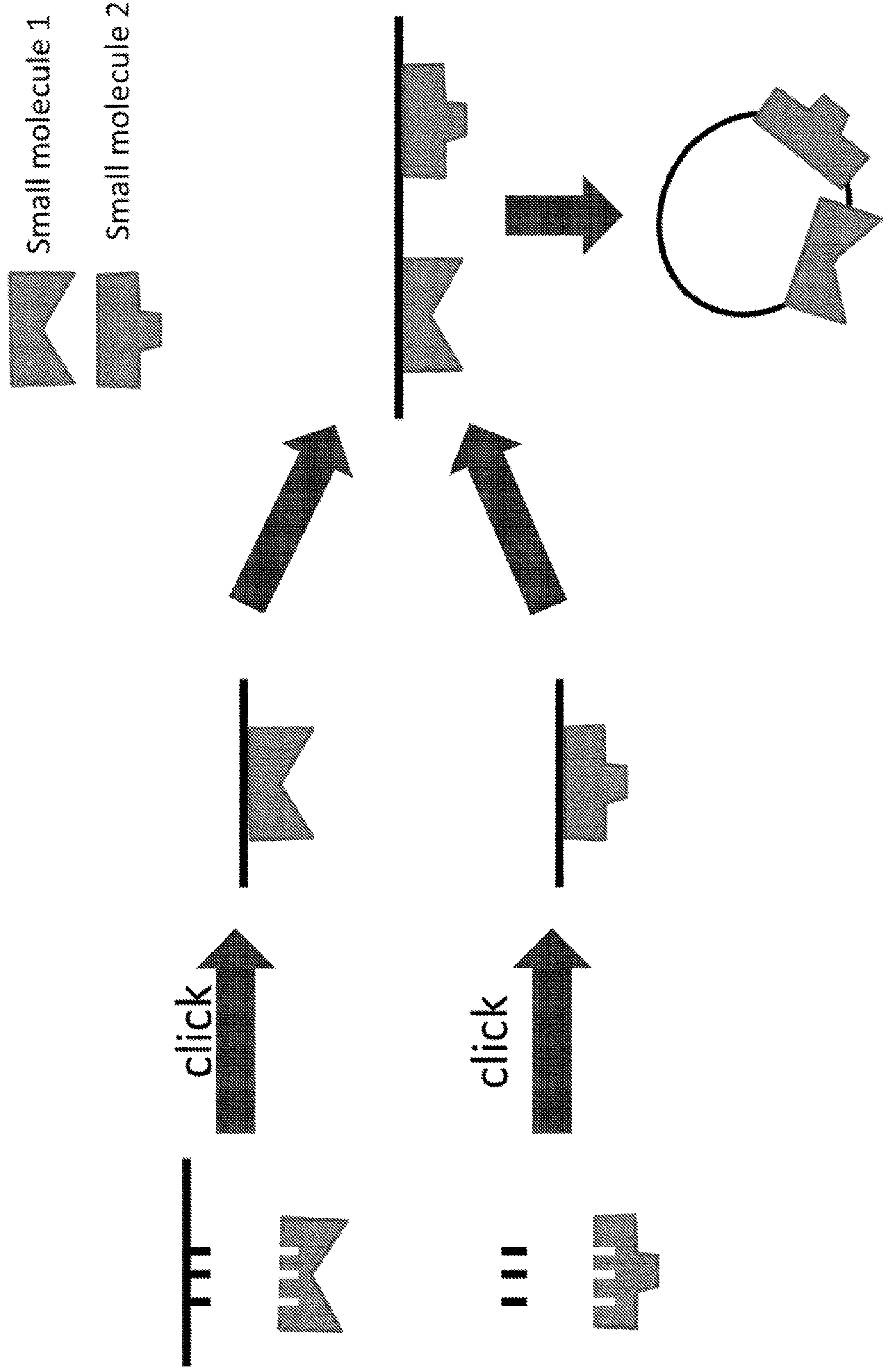
FIG. 6 provides a schematic for generation of a circular RNA comprising two small molecules.

Two linear RNA segments containing molecular handles are separately transcribed and conjugated to VH 032 or gefitinib. The two linear RNA segments are then ligated together and circularized as illustrated in FIG. 6.

A first linear RNA comprising a molecular handle is synthesized by in vitro transcription using T7 RNA polymerase (Lucigen). UTP is substituted with 5-azido-C3-UTP (Jena Biosciences) during the in vitro transcription reaction to generate azide-functionalized RNA. Synthesized linear RNA is purified with RNA clean up kit (New England Biolabs). Alkyne-functionalized VH 032 is conjugated to the azide-functionalized segment of the linear RNA via Copper-catalyzed Azide-Alkyne click chemistry reactions (CuAAC) with the CuAAC Biomolecule Reaction Buffer Kit based on manufacturer's instructions (Jena Bioscience). VH 032-conjugated linear RNA is purified with an RNA clean up kit (New England Biolab).

A second linear RNA comprising a molecular handle is synthesized by in vitro transcription using T7 RNA polymerase (Lucigen). UTP is substituted with 5-azido-C3-UTP (Jena Biosciences) during the in vitro transcription reaction to generate azide-functionalized RNA. Synthesized linear RNA is purified with RNA clean up kit (New England Biolabs). Alkyne-functionalized gefitinib is conjugated to the azide-functionalized segment of the linear RNA via Copper-catalyzed Azide-Alkyne click chemistry reactions (CuAAC) with the CuAAC Biomolecule Reaction Buffer Kit based on manufacturer's instructions (Jena Bioscience). Gefitinib-conjugated linear RNA is purified with an RNA clean up kit (New England Biolab).

The two oligonucleotides are ligated together using the T4 DNA ligase, then are subjected to RNA 5' Pyrophosphohydrolase (RppH, New England Biolabs) treatment to remove pyrophosphate. RppH treated linear RNA is purified with an RNA clean up kit (New England Biolabs).

Circular RNA is generated by splint ligation. RppH-treated linear RNA (100 uM) and splint DNA (200 uM) is annealed by heating at 75 C for 5 min and is gradually cooled at room temperature for 20 min. A ligation reaction is performed with T4 RNA ligase 2 (0.2 U/ul, New England Biolabs) for 4 hours at 37 C. Ligated mixture is purified by ethanol precipitation. To isolate circular RNA, ligated mixture is separated on 4% denaturing UREA-PAGE. RNA on the gel is stained with SYBR-green (Thermo Fisher) and visualized with a transilluminator (Transilluminators). Corresponding RNA bands for circular RNA are excised and crushed by gel breaker tubes (Ist Engineering). For elution of circular RNA, crushed gels containing circular RNA is incubated with elution buffer (0.5M Sodium Acetate, 1 mM EDTA, 0.1% SDS) at 37 C for an hour and supernatant is carefully harvested. Remaining crushed gel elution is subjected another round of elution, and repeated three times in total. Elution buffer containing circular RNA is filtrated with 0.45 um cellulose acetate filter to remove gel debris and purified/concentrated by ethanol precipitation.

Circular RNA binding to VHL is assessed, for example, by pull down of GST-VHL followed by RT-qPCR for circRNA detection.

Circular RNA binding to EGFR is assessed, for example, by pull down of poly-histidine tagged EGFR followed by RT-qPCR for circRNA detection.

Circular RNA binding to VHL and EGFR is assessed, for example, by pull down of GST-VHL followed by Western Blot for EGFR, or by pull-down of poly-histidine tagged EGFR followed by Western Blot for VHL.

Degradation of EGFR is quantified by, for example, Western Blot or Enzyme Linked Immunosorbent Assay (ELISA) after delivering the circular RNA to cells or an in vitro system comprising EGFR and components of the E3 ubiquitin ligase and proteasomal degradation pathway.

Figure 7:
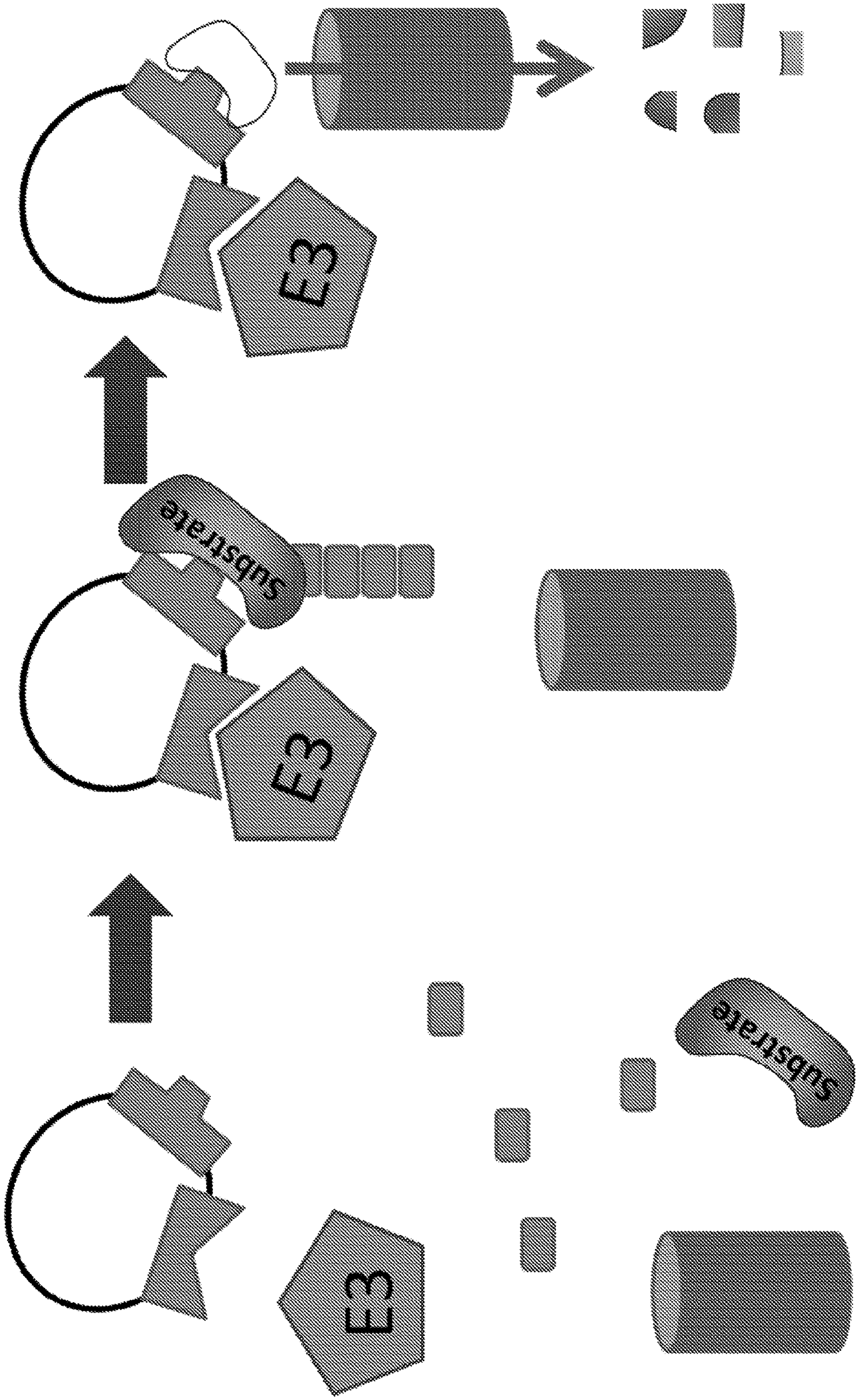
FIG. 7 illustrates a circular RNA comprising two conjugated small molecule that can target a protein for ubiquitination and degradation.

FIG. 7 illustrates a circular RNA with two chemical compound conjugates that can target a protein for ubiquitination and degradation.

Example 4: Circular RNA that Binds Two Proteins

This Example describes circular RNA simultaneously binding to two proteins.

The E3 ubiquitin ligase, MDM2, binds and ubiquitinates proteins, such as p53, marking them for degradation by the proteasome. The following example describes the circular RNA simultaneously binding to MDM2 and p53. This binding enhances the MDM2-dependent ubiquitination of p53.

Circular RNA is designed to include the sequence of FOX3 RNA that binds MDM2 and p53.

Unmodified linear RNA is synthesized by in vitro transcription using T7 RNA polymerase from a DNA segment having the appropriate sequence. Transcribed RNA is purified with an RNA purification system (QIAGEN), treated with alkaline phosphatase (ThermoFisher Scientific, EF0652) following the manufacturer's instructions, and purified again with the RNA purification system.

Splint ligation circular RNA is generated by treatment of the transcribed linear RNA and a DNA splint using T4 DNA ligase (New England Bio, Inc., M0202M) or T4 RNA ligase 2 (New England Bio, Inc., M0239S) and the circular RNA is isolated following enrichment with RNase R treatment. RNA quality is assessed by agarose gel or through automated electrophoresis (Agilent).

One method to assess circular RNA binding to MDM2 and p53 is by electrophoretic mobility shift assay to visualize each RNA-protein complex or alternatively by pull-down of circular RNA using a biotinylated oligo complementary to a region of the circular RNA followed by immunoblotting. Additionally, MDM2 ubiquitination of p53 through binding of circular RNA is assayed via immunoblotting with anti-ubiquitin antibodies or by mass-spectrometry. Degradation of p53 protein is quantified by, for example, Western Blot or Enzyme Linked Immunosorbent Assay (ELISA).

Figure 8:
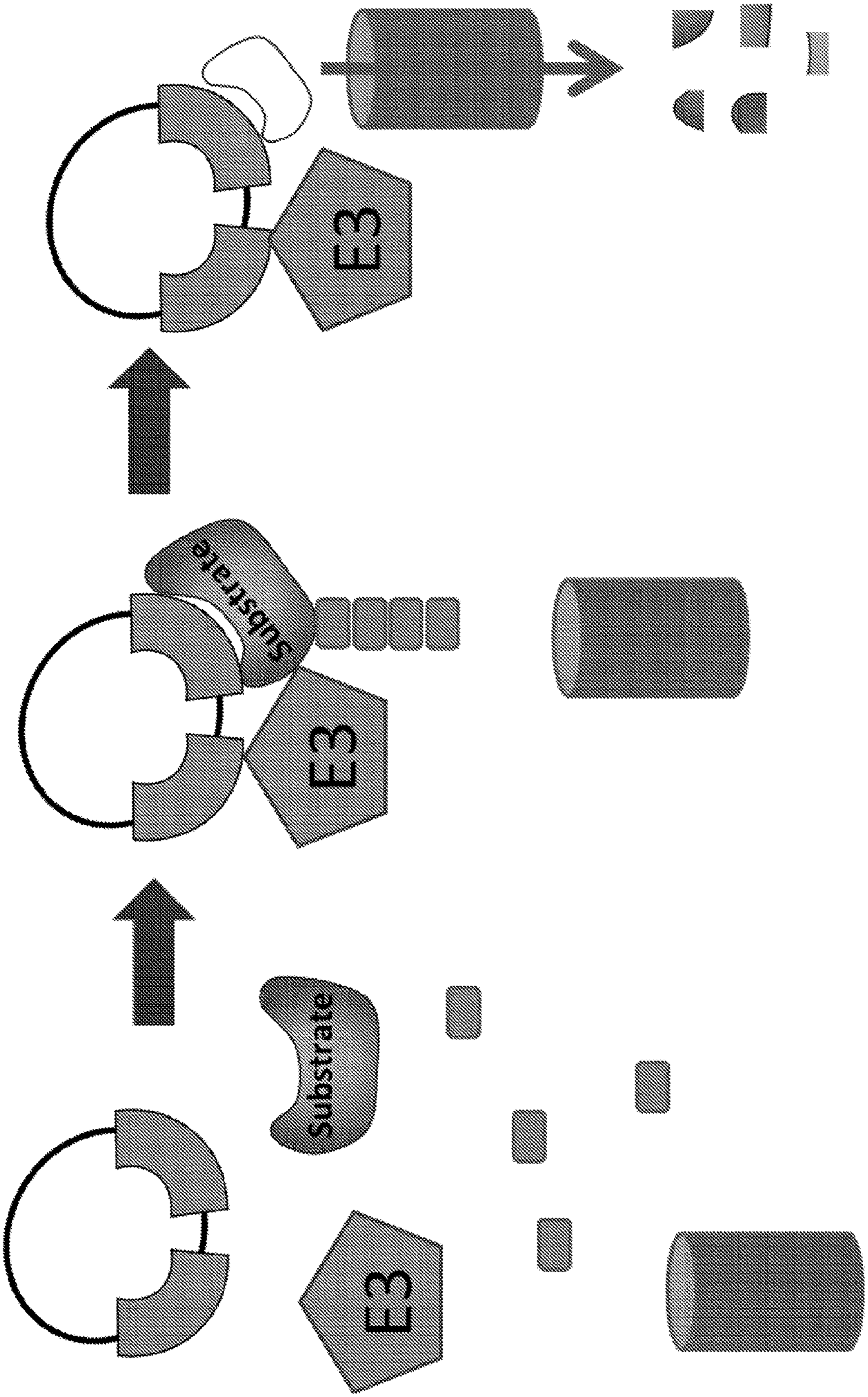
FIG. 8 illustrates a circular RNA that can bind two proteins and target one of the proteins for ubiquitination and degradation.

FIG. 8 illustrates a circular RNA that can bind two proteins and target one of the proteins for ubiquitination and degradation.

Example 5: Circular RNA Bound Protein

This Example demonstrates circular RNA comprising a protein binding site binds to protein.

Human antigen receptor (HuR) can be a pathogenic protein, e.g. it is known to bind and stabilize cancer related mRNA transcripts, such as mRNAs for proto-oncogenes, cytokines, growth factors, and invasion factors. HuR has a central tumorigenic activity by enabling multiple cancer phenotypes. Sequestration of HuR with circular RNA may attenuate tumorigenic growth in multiple cancers. As shown in the following Example, a circular RNA bound to to HuR for sequestration.

Circular RNA was designed to include the HuR RNA binding motifs: 5'-UCAUAAUCAA UUUAUUAUUUUC-UUUUAUUUUAUUCACAUAAUUUUGUUUUU-3', 5'-AUUUUGUUUUUAA CAUUUC-3', 5'-UCAUAAU-CAAUUUAUUAUUUUCUUUUAUUUUAUUCA-CAUAAUUUUGUUU UUAUUUUGUUUUUAA-CAUUUC-3' to competitively bind HuR and inhibit its binding/downstream functions.

Unmodified linear RNA was synthesized by in vitro transcription using T7 RNA polymerase from a DNA segment comprising the HuR RNA motif and protein binding sequence.

Transcribed RNA was purified with an RNA cleanup kit (New England Biolabs, T2050), treated with RNA 5'-phosphohydrolase (RppH, New England Biolabs, M0356) following the manufacturer's instructions, and purified again with the RNA purification column. RppH treated RNA was circularized using a splint DNA complementary to the circularization sequences and T4 RNA ligase 2 (New England Biolabs, M0239). Circular RNA was Urea-PAGE purified, eluted in a buffer containing (0.5M Sodium Acetate, 0.1% SDS, 1 mM EDTA, ethanol precipitated and resuspended in RNase free water. RNA quality was assessed by Urea-PAGE or through automated electrophoresis (Agilent).

Figure 9:
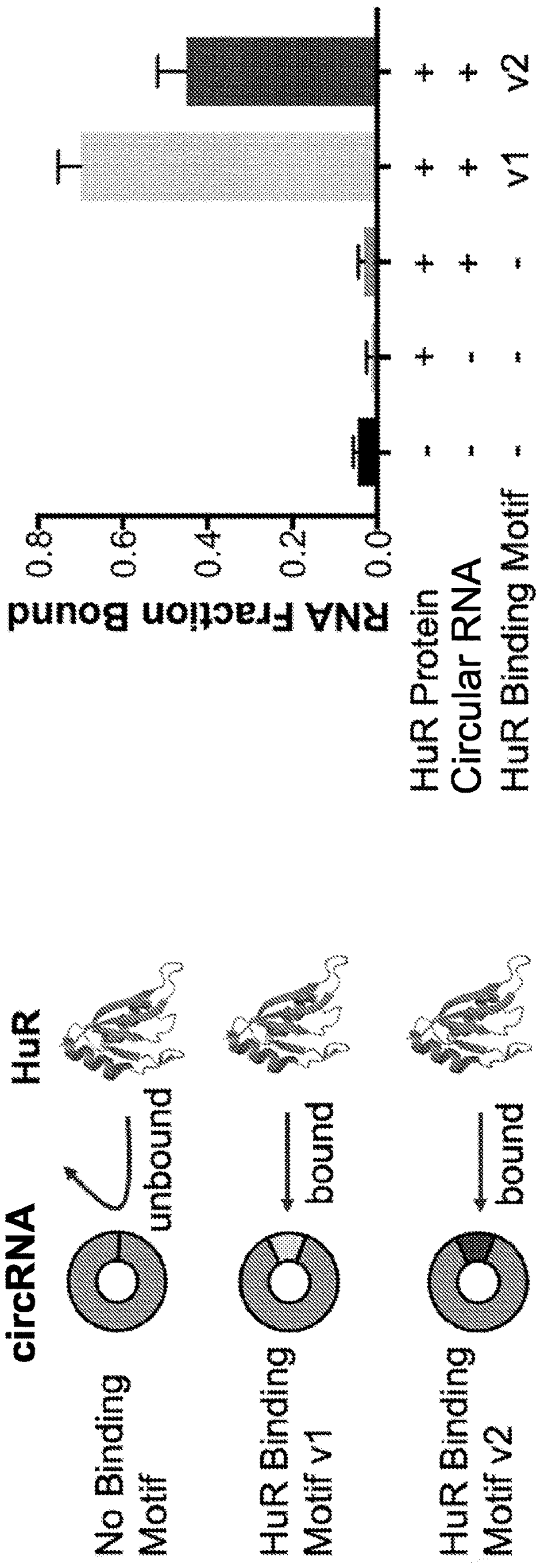
FIG. 9 illustrates binding of a circular RNA containing a protein-binding motif to the corresponding protein.

Circular RNA binding to HuR was evaluated in vitro by RNA immunoprecipitation (RIP) for HuR. Circular RNAs containing the HuR RNA-binding motif bound HuR protein, while circular RNAs lacking the HuR RNA-binding motif did not exhibit binding (FIG. 9).

This result demonstrated selective binding of a circRNA to a biomolecule of therapeutic interest.

Example 6: Circular RNA with Two Different Chemical Compounds

This Example describes circular RNA linked to chemical compounds that recruits two different proteins of choice.

The following Example describes two chemical compounds (thalidomide and JQ1) that are conjugated to a circular RNA to bind (1) E3 ubiquitin ligase Cereblon for ubiquitination and subsequent degradation of a neighboring protein and (2) BET family proteins through JQ1, which is a chemical compound inhibitor that binds to BET family proteins.

Circular RNA is designed to include reactive uridine residues (e.g., 5-azido-C3-UTP) for conjugation of alkyne-functionalized small molecules, known to interact with an intracellular protein of interest.

Linear RNA is synthesized by in vitro transcription using T7 RNA polymerase (Lucigen). All UTP are substituted with 5-azido-C3-UTP (Jena Biosciences) in the in vitro transcription reaction to generate azide-functionalized RNA. Synthesized linear RNA is purified with an RNA clean up kit (New England Biolabs) and subjected to RNA 5' Pyrophosphohydrolase (RppH, New England Biolabs) treatment to remove pyrophosphate. RppH-treated linear RNA is purified with an RNA clean up kit (New England Biolabs).

Circular RNA is generated by splint ligation. RppH-treated linear RNA (100 uM) and splint DNA (200 uM) was annealed by heating at 75° C. for 5 min and is gradually cooled at room temperature for 20 min. Ligation reaction is performed with T4 RNA ligase 2 (0.2 U/ul, New England Biolabs) for 4 hours at 37° C. The ligated mixture is purified by ethanol precipitation. To isolate circular RNA, the ligated mixture is separated on 4% denaturing UREA-PAGE. RNA on the gel is stained with SYBR-green (Thermo Fisher) and is visualized with transilluminator (Transilluminators). Corresponding RNA bands for circular RNA are excised and are crushed by gel breaker tubes (1st Engineering). For elution of circular RNA, crushed gels with circular RNA are incubated with elution buffer (0.5M Sodium Acetate, 1 mM EDTA, 0.1% SDS) at 37° C. for an hour and supernatant is carefully harvested. The remaining crushed gel elution is subjected to another round of elution, and is repeated total three times. Elution buffer with circular RNA is filtrated through a 0.45 um cellulose acetate filter to remove gel debris and circular RNA is purified/concentrated by ethanol precipitation.

Alkyne-functionalized thalidomide and alkyne-functionalized JQ1 (Jena Bioscience) is conjugated to azide-functionalized circular RNA via Copper-catalyzed Azide-Alkyne click chemistry reactions (CuAAC) with the click chemistry reaction kit based on manufacturer's instructions (Jena Bioscience). For comparison, three different kinds of chemical compound conjugated circular RNA are generated: RNA with both JQ1 and thalidomide, thalidomide only, and JQ1 only. Chemical compound-conjugated circular RNA is purified with an RNA clean up kit (New England Biolab).

Chemical compound-conjugated circular RNA binding to E3 ubiquitin ligase CRBN and BET family proteins is analyzed using GST pull-down. GST-CRBN (Abcam) and one of the BET family protein, Bromodomain containing protein 4 (BRD4, BPSBiosciences) are used for this experiment. For GST pull-down assay, thalidomide and JQ1 conjugated-circular RNA (2 nM) are incubated with GST-CRBN and BRD4 (50 nM each) for 2 hours at room temperature in the presence of 25 mM Tris-Cl (pH7.0), 100 mM NaCl, 1 mM EDTA, 0.5% NP-40, 5% Glycerol. Azide-functionalized circular RNA without conjugation, thalidomide conjugated RNA, and JQ1 conjugated RNA are used as negative controls. RNA-protein mixture are further incubated with GSH-agarose bead to allow GST-GSH interaction for an hour at room temperature. After wash three times with binding buffer, the bead is separated to two equal parts. To monitor protein binding, one part of the bead is boiled in the presence of Lammli Sample Buffer (Bio-Rad) and is subjected to western blot with BRD4 antibody (for detecting BRD4 protein) and GST antibody (for detecting GST-CRBN). To monitor RNA recruitment, the RNA on the bead is extracted with Trizol (Thermo Fisher) and the extracted circular RNA is reverse transcribed and is detected by quantitative RT-PCR with primers specific for circular form of RNA (forward: TACGCCTGCAACTGTGTTGT, reverse: TCGATGATCTTGTCGTCGTC).

It is expected that circular RNA containing the thalidomide and JQ1 small molecules is highly enriched in the GST pull down for both CRBN as well as BET domain protein BRD4, demonstrating that not only can circular RNA contain a chemical compound, but it can bind to two specific proteins using this chemical compound conjugate to degrade the protein of choice.

Example 7: Circular RNA with Specific M6A Modifications Affect its Function

This Example describes circular RNA with m6a modifications in specific areas affect its function.

Almost all non-coding RNAs functions are affected by their ability to adopt a secondary structure and bind proteins. Both of these aspects are likely affected by specific nucleotide modifications.

For example here we will engineer in a m6a modification of the appropriate site in circular metastasis-associated lung adenocarcinoma transcript 1 (MALAT1) to allow enhanced binding of Heterogeneous Nuclear Ribonucleoprotein C (HNRNPC). It is expected that enhanced HNRNPC-binding will affect the abundance and alternative splicing of target mRNAs.

Circular RNA is designed to include the MALAT1 sequence with and without m6a modified nucleotides on A2515 and A2577 (linear sequence can be found in N. Liu et al. RNA. 2013 December; 19(12): 1848-56).

Circular MALAT1 RNA containing m6a is expected to enhance HNRNPC binding and subsequently affect alternative splicing because an adenine is located in a stem-loop structure opposite a uridine stretch. Formation of m6a is predicted to result in a conformational change, allowing the enhanced binding of HNRNPC to the uridine region of MALAT1 in the modified circular RNA, and therefore affecting the abundance and alternative splicing of target mRNAs.

Example 8: Circular RNA that Contains Specific M5C Modifications Affect its Function This Example describes circular RNA containing m5c modifications in specific areas affect its function.

Almost all non-coding RNAs functions are affected by their ability to adopt a secondary structure and bind proteins. Both of these aspects are likely affected by specific nucleotide modifications.

In this example, a m5c modification of the appropriate site in circular XIST is engineered in to inhibit binding of XIST to the PRC2 complex. It is expected that inhibited binding to PRC2 will affect epigenetic processes. PRC2 is a chromatin modifying complex. XIST is a lncRNA derived from a regulatory locus termed X-inactivation center and functions to permanently inactivate one of the two X-chromosomes in female placental mammals. XIST is thought to interact with the PRC2 complex to affect silencing of the X chromosome.

Circular RNA is designed to include the XIST sequence with and without m5c modified nucleotides on the following 5 sites: C701, C702, C703, C711 and C712.

Circular XIST RNA containing m5c is expected to inhibit PRC2 binding.

Example 9: Circular RNA for Targeted RNA Degradation

This Example describes circular RNA binding to a target mRNA, creating a ribozyme cleavage site to degrade target mRNA.

A non-naturally occurring circular RNA is engineered to include a sequence that binds to the SRSF1 mRNA. Aggressive tumor cells overexpress SRSF1, and this results in enhanced cell mobility and invasiveness. SRSF1 target genes are involved in tumor initiation, progression, and survival.

The following Example describes the circular RNA binding to the target SRSF1 mRNA, resulting in its cleavage.

Figure 11:
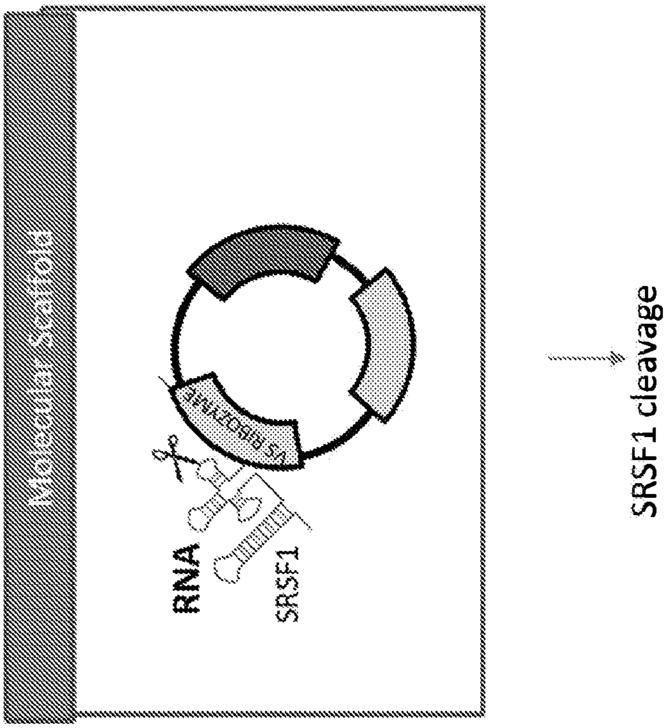
FIG. 11 shows an exemplary circular RNA engineered to include a sequence that binds to the Serine And Arginine Rich Splicing Factor 1 (SRSF1) mRNA.

Circular RNA containing sequences complementary to SRSF1 mRNA, including but not limited to 5'-CAAUAAUGGAGGCAAUGGUAUGACUC-CAAGUGCUAUUGUCACAGAU GAAAUUGGC-AGUAUUGACCUUAUACUAAAAGGCAGGG-GUUAAAAAUGAUUAUAUACA UUUUCCUUAAAACACU-3' (NM 006924.5), is designed to generate a VS ribozyme cleavage site in the target as shown in FIG. 11. Circular RNA additionally includes sequences for the trans-acting VS ribozyme (helices II-VI) (Guo and Collins 1995) and the coding sequence for the M1 isoform of pyruvate kinase (ENST00000319622). Other trans-acting ribozymes such as HDV, hammerhead, group I, and/or group II may be utilized.

Unmodified linear RNA is synthesized by in vitro transcription using T7 RNA polymerase from a DNA segment, having an SRSF1 complementary sequence and a VS ribozyme. Transcribed RNA is purified with an RNA purification system (New England Biolabs, Inc.), is treated with RNA 5' Pyrophosphohydrolase (RppH) (New England Biolabs, Inc., M0356) following the manufacturer's instructions, and is purified again with the RNA purification system.

Splint ligated circular RNA is generated by treatment of the transcribed linear RNA and a DNA splint with T4 RNA ligase 2 (New England Biolabs, Inc., M0239). To purify the circular RNAs, ligation mixtures are resolved on 4% denaturing PAGE and RNA bands corresponding to each of the circular and linear RNAs are excised. Excised RNA gel fragments (linear or circular) are crushed, and RNA is eluted with gel elution buffer (0.5M NaOAc, 1 mM EDTA and 0.1% SDS) for an hour at 37° C. Supernatant is harvested, and RNA is eluted once again by adding gel elution buffer to the crushed gel and incubated for an hour. Gel debris is removed by centrifuge filters and RNA is precipitated with ethanol.

Circular RNA binding to, and concomitant degradation of SRSF1 mRNA is evaluated by RT-PCR. Expression of SRSF1 protein is evaluated by western blotting to further support SRSF1 mRNA degradation. Additional evidence for changes induced following target RNA binding and cleavage include cell proliferation assays Example 10: Circular RNA for Degradation of mRNA and Subsequent mRNA Replacement This Example describes circular RNA binding to a target mRNA, creating a ribozyme cleavage site to specifically degrade this mRNA.

A non-naturally occurring circular RNA is engineered to include a sequence that binds to the M2 isoform of pyruvate kinase mRNA. In contrast to normal cells, which rely on oxidative phosphorylation, cancer cells rely on aerobic glycolysis—a phenomenon called the Warburg effect. The Warburg effect is the observation that most cancer cells rely on aerobic glycolysis to generate energy for cellular processes versus normal differentiated cells, which instead rely primarily on mitochrondrial oxidavitive phophorylation. (See, e.g., Vander Heiden et al., *Science*. 2009 May 22; 324(5930): 1029-1033). A key molecular feature associated with this abnormal metabolic change is the exclusive expression of the embryonic M2 isoform of pyruvate kinase. Restoring expression of the M1 (adult) isoform reverses the Warburg effect and reduced tumor growth.

The following Example describes the circular RNA binding to the target M2 isoform of pyruvate kinase, resulting in its cleavage.

Figure 12:
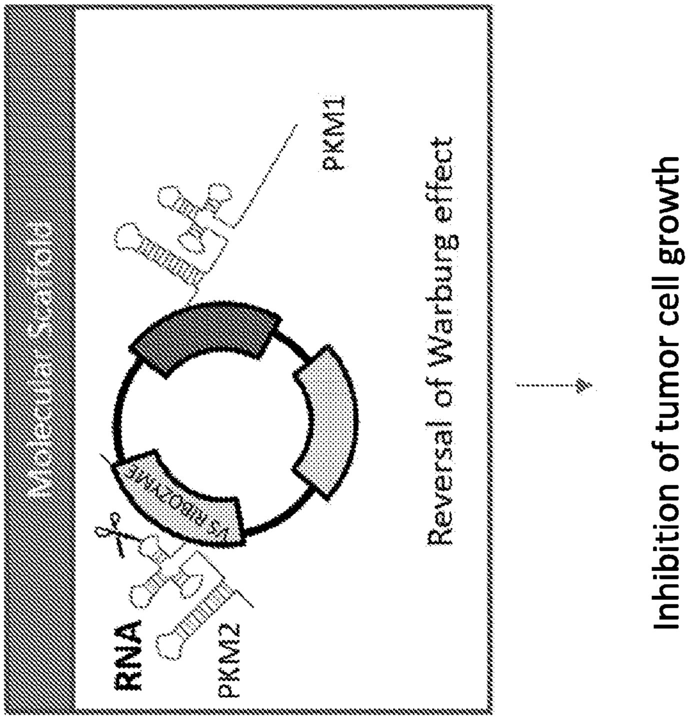
FIG. 12 shows an exemplary circular RNA designed to include a sequence complementary to the M2 isoform of pyruvate kinase that binds a VS ribozyme to bind to the target, a sequence for the trans-acting VS ribozyme, and the coding sequence for the M1 isoform of pyruvate kinase.

Circular RNA is designed to include sequences complementary to the M2 isoform of pyruvate kinase (ENST00000335181, NM 002654) that generates a VS ribozyme cleavage site in the target. Circular RNA additionally includes sequences for the trans-acting VS ribozyme (helices II-VI) (Guo and Collins 1995) and the coding sequence for the M1 isoform of pyruvate kinase (ENST00000319622). A schematic of this circular RNA is shown in FIG. 12.

Unmodified linear RNA is synthesized by in vitro transcription using T7 RNA polymerase from a DNA segment having the M2 isoform complementary sequence, VS ribozyme, and M1 coding sequence.

Transcribed RNA is purified with an RNA purification system (New England Biolabs, Inc.), is treated with RNA 5' Pyrophosphohydrolase (RppH) (New England Biolabs, Inc., M0356) following the manufacturer's instructions, and is purified again with the RNA purification system.

Splint ligated circular RNA is generated by treatment of the transcribed linear RNA and a DNA splint with T4 RNA ligase 2 (New England Biolabs, Inc., M0239). To purify the circular RNAs, ligation mixtures are resolved on 4% denaturing PAGE and RNA bands corresponding to each of the circular and linear RNAs are excised. Excised RNA gel fragments (linear or circular) are crushed, and RNA is eluted with gel elution buffer (0.5M NaOAc, 1 mM EDTA and 0.1% SDS) for an hour at 37° C. Supernatant is harvested, and RNA is eluted once again by adding gel elution buffer to the crushed gel and incubated for an hour. Gel debris is removed by centrifuge filters and RNA is precipitated with ethanol.

Circular RNA binding to, and concomitant degradation of, pk M2 mRNA is evaluated by RT-PCR. Restored expression of pk M1 mRNA is evaluated by RT-PCR. Additionally, expression of pk M1 and pk M2 proteins is evaluated by western blotting to further support pk M1 mRNA degradation.

Circular RNA binding to, and concomitant degradation of, PKM2 mRNA (ENST00000335181, NM 002654) is evaluated by quantitative RT-PCR. Restored expression of PKM1 mRNA (ENST00000319622) is evaluated by quantitative RT-PCR. Additionally, expression of PKM1 and PKM2 proteins is evaluated by western blotting to further support PKM1 mRNA degradation.

Additional evidence for functional metabolic changes induced following target RNA binding, cleavage, and replacement include changes in lactate production, increased oxygen consumption, and a decrease in ability to form tumors in mouse xenografts.

Example 11: Circular RNA Tagged the Target Protein for Degradation

This Example demonstrates circular RNA linked to small molecules recruited two different proteins of choice and thereby tagged the target protein for degradation.

Figure 13:
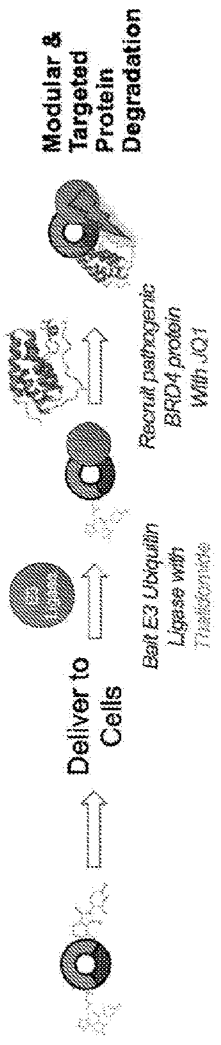
FIG. 13 is a schematic showing an exemplary circular RNA that is delivered into cells and tags a substrate BRD4 protein in the cells for degradation by ubiquitin system.

FIG. 13 is a schematic showing an exemplary circular RNA that is delivered into cells and tags a target BRD4 protein in the cells for degradation by ubiquitin system. As shown in the following Example, two small molecule (thalidomide and JQ1) were conjugated to a circular RNA to bind (1) E3 ubiquitin ligase Cereblon for ubiquitination and subsequent degradation of a neighboring protein; and (2) BET family proteins through JQ1 that is small molecule inhibitor that binds BET family proteins.

Circular RNA was designed to include multiple (49 residues) reactive uridine residues (e.g., 5-azido-C3-UTP) for conjugation of alkyne-functionalized small molecules, known to interact with an intracellular protein of interest.

Linear RNA was synthesized by in vitro transcription using T7 RNA polymerase (Lucigen). All UTP was substituted with 5-azido-C3-UTP (Jena Biosciences) in the in vitro transcription reaction to generate azide-functionalized RNA. Synthesized linear RNA was purified with an RNA clean up kit (New England Biolabs) and subjected to RNA 5' Pyrophosphohydrolase (RppH, New England Biolabs) treatment to remove pyrophosphate. RppH-treated linear RNA was purified with an RNA clean up kit (New England Biolabs).

Circular RNA was generated by splint ligation. RppH-treated linear RNA (100 uM) and splint DNA (200 uM) was annealed by heating at 75° C. for 5 min and gradual cooling at room temperature for 20 min. Ligation reaction was performed with T4 RNA ligase 2 (0.2 U/ul, New England Biolabs) for 4 hours at 37° C. The ligated mixture was purified by ethanol precipitation. To isolate circular RNA, the ligated mixture was separated on 4% denaturing UREA-PAGE. RNA on the gel was stained with SYBR-green (Thermo Fisher) and visualized with transilluminator (Transilluminators). Corresponding RNA bands for circular RNA were excised and crushed by gel breaker tubes (1st Engineering). For elution of circular RNA, crushed gels with circular RNA were incubated with elution buffer (0.5M Sodium Acetate, 1 mM EDTA, 0.1% SDS) at 37° C. for an hour and supernatant was carefully harvested. The remaining crushed gel was subjected to another round of elution, and repeated a total of three times. Elution buffer with circular RNA was filtrated through a 0.45 μm cellulose acetate filter to remove gel debris and circular RNA was purified/concentrated by ethanol precipitation.

Alkyne-functionalized thalidomide and/or JQ1 (thienotriazolodiazepine, Jena Bioscience) was conjugated to azide-functionalized circular RNA via Copper-catalyzed Azide-Alkyne click chemistry reactions (CuAAC) with the click chemistry reaction kit based on manufacturer's instructions (Jena Bioscience). For comparison, three different kinds of small molecules were conjugated to circular RNA; RNA with both JQ1 and thalidomide, thalidomide only, or JQ1 only. Small molecule-conjugated circular RNA was purified with an RNA clean up kit (New England Biolab).

These different RNAs were then transfected into HEK293T cells to monitor degradation of target protein using by lipid transfection reagent (Invitrogen) according to the manufacturer's instruction. 1 pmole of each RNA was used to transfect HEK293T cells and the cells were plated into 12 well plates (2 nM final). In the case of circular RNA conjugated with both JQ1 and thalidomide, 3 pmole of RNA was transfected into HEK293T cells to test the effect of different concentrations of circular RNA on BRD4 degradation (6 nM final). As a positive control, PROTAC dBET1 (Tocris Biosciences) that has both JQ1 and thalidomide, and is known to degrade BRD4 protein in cells through CRBN recruitment, was used (2 uM, 10 uM concentration). For a negative control, carrier only and circular RNA without conjugation were used. After 24 hours transfection, cells were harvested by adding RIPA buffer directly onto the plate.

Small molecule-conjugated circular RNA binding to E3 ubiquitin ligase CRBN and BET family proteins degrading ability was analyzed using western blot. Briefly, 12 ug of protein was resolved on 4%-12% gradient Bis-Tris gel (Thermo Fisher Scientific) and transferred to nitrocellulose membrane using a blot transfer system (Thermo Fisher Scientific). Rabbit anti-BRD4 antibody (Abcam) was used to detect BRD4 protein and rabbit anti-alpha tubulin antibody (Abcam) was used to detect alpha tubulin as a loading control. The chemiluminescence signal from protein bands of BRD4 and alpha tubulin were monitored by an Fc imaging system (LI-COR).

BRD4 protein levels as well as alpha tubulin as a loading control were also measured using densitometry using ImageJ.

Figure 14:
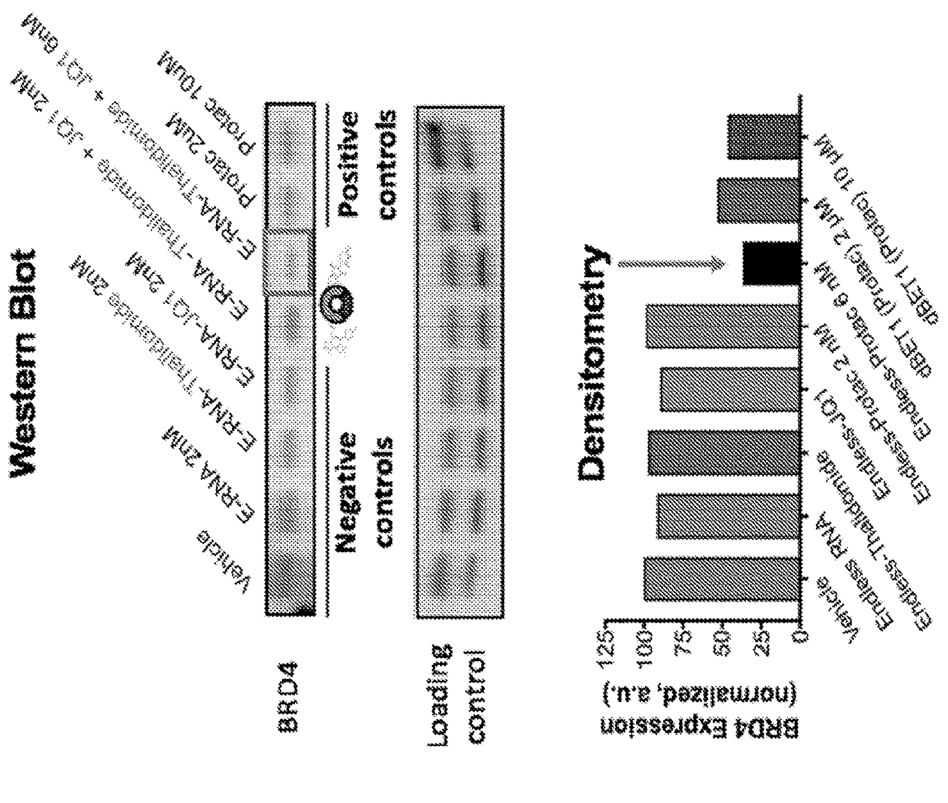
FIG. 14 shows Western blot images and quantitative chart demonstrating that circular RNA containing thalidomide and JQ1 small molecules was able to degrade BRD4 in cells.

As shown in FIG. 14, circular RNA containing the thalidomide and JQ1 small molecules was able to degrade BRD4, as demonstrated by the normalized levels of BRD4. This result demonstrated that circular RNA with a small molecule can bind to two specific proteins using the small molecule conjugate to degrade the target protein.

Example 12: Circular RNA Bound a Pathogenic Transcription Factor

This Example demonstrates circular RNA bound to protein for sequestration. NF-kB is a family of transcription factors that activate transcription and induce survival pathways. In cancerous cells, NF-kB can be pathogenic as it mediates survival and chemoresistance. As shown in the following Example, the circular RNA was modified with an aptamer sequence that bound NF-kB.

Circular RNA was designed to include the NF-kB binding aptamer motif: 5'-aaaaaaaaaaGATCTTGAAACTGTTTTAAGGTTGGCCGATCTTaaaaaa-3' to competitively bind NF-kB and inhibit its binding/downstream functions. Poly (A) stretches were added to the internal binding motif to (1) make the RNA oligo amenable to ligation and to maintain the secondary structure of the aptamer. Correct folding was checked using RNAfold WebServer. As a control, a scrambled RNA sequence was used (aaaaaaaTTCTCCGAACGTGTCACGTTTCAAGAGAACGTGACACGTTCGGAGAAaaaaaa). This scrambled RNA sequence folds into a 3D structure similar to the aptamer, but does not target any proteins, as described in Mi et al., Mol Ther. 2008 January; 16(1):66-73.

RNA with the NF-kB binding aptamer motif was synthesized by a commercial vendor (IDT) with a 5' monophosphate group and a 3' hydroxyl group. RNA ligase 1 (New England Biolabs, M0204S) was used to ligate the RNA oligo. RNase R was used to remove residual linear RNA from the samples, according to manufacturer's instructions (Lucigen, RNR07250). Additionally, circular mRNA was purified by extracting the circular RNA from a 15% Urea PAGE gel. Circular RNA was eluted from the gel in a buffer containing: 0.5M Sodium Acetate, 0.1% SDS, 1 mM EDTA. Residual gel debris or salts from the gel extraction were removed by running the elution through a spin column (New England Biolabs, T2030S). RNA was eluted in to RNA storage buffer (1 mM sodium citrate, Thermo Fisher, AM7000) and RNA integrity was assessed by Urea-PAGE or through automated gel capillary electrophoresis (Agilent).

Electrophoretic mobility shift assay (EMSA) was performed to assess circular RNA aptamer binding affinity to NF-kB. One pmole of linear or circular RNA was incubated with recombinant NF-kB p50 subunit (Caymen Chemical, 10009818) at varying concentrations over the RNA concentration (i.e., 0, 0.1, 1, 10 pmoles of protein) for 20 minutes at room temperature in a buffered reaction (20 mM Tris-HCl, pH 8.0, 50 mM NaCl, 1 mM MgCl2). Samples were run a 6% TBE Urea gel for 25 minutes at 200V. Gels were stained with SybrGold (Thermo Scientific, S11494) and imaged with a blue E-gel imaging system (Thermo Scientific, 4466612).

Figure 15:
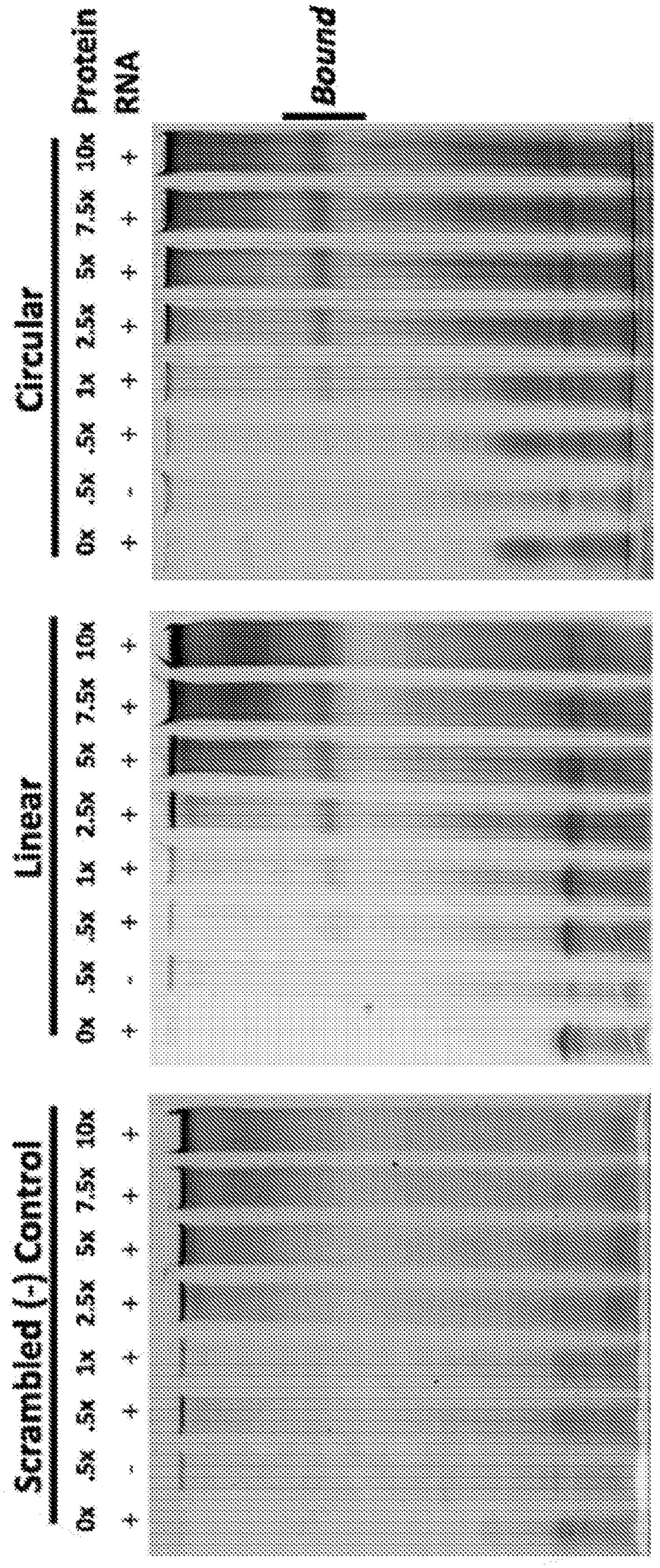
FIG. 15 shows images from electrophoretic mobility shift assay (EMSA) demonstrating that RNA with scrambled binding aptamer sequences did not show binding affinity to the p50 subunit of NF-kB, while both linear and circular RNAs with the NF-kB binding aptamer sequence bound to the p50 subunit with similar affinities.

As demonstrated in FIG. 15, RNA with scrambled binding aptamer sequences did not show binding affinity to the p50 subunit of NF-kB. Both linear and circular versions of the NF-kB binding aptamer bound to the p50 subunit with similar affinities.

Circular RNA aptamer binding to NF-kB was evaluated in vitro by EMSA for NF-kB. NF-kB selectively bound circular RNAs containing the NF-kB binding aptamer motif. This result demonstrated that biomolecules of interests were selectively bound by aptamer in circular RNA.

Example 13: Circular RNA Decreased Cell Viability Through Protein Sequestration

This Example demonstrates circular RNA binds to protein in cells and this sequestration leads to cell death of cancer cells. As shown in the following Example, the circular RNA bound to NF-kB for sequestration leading to cell death via NF-kB sequestration and inhibition in cells.

Circular RNA, linear, and linear scrambled RNA was designed and synthesized as previously described.

Figure 16:
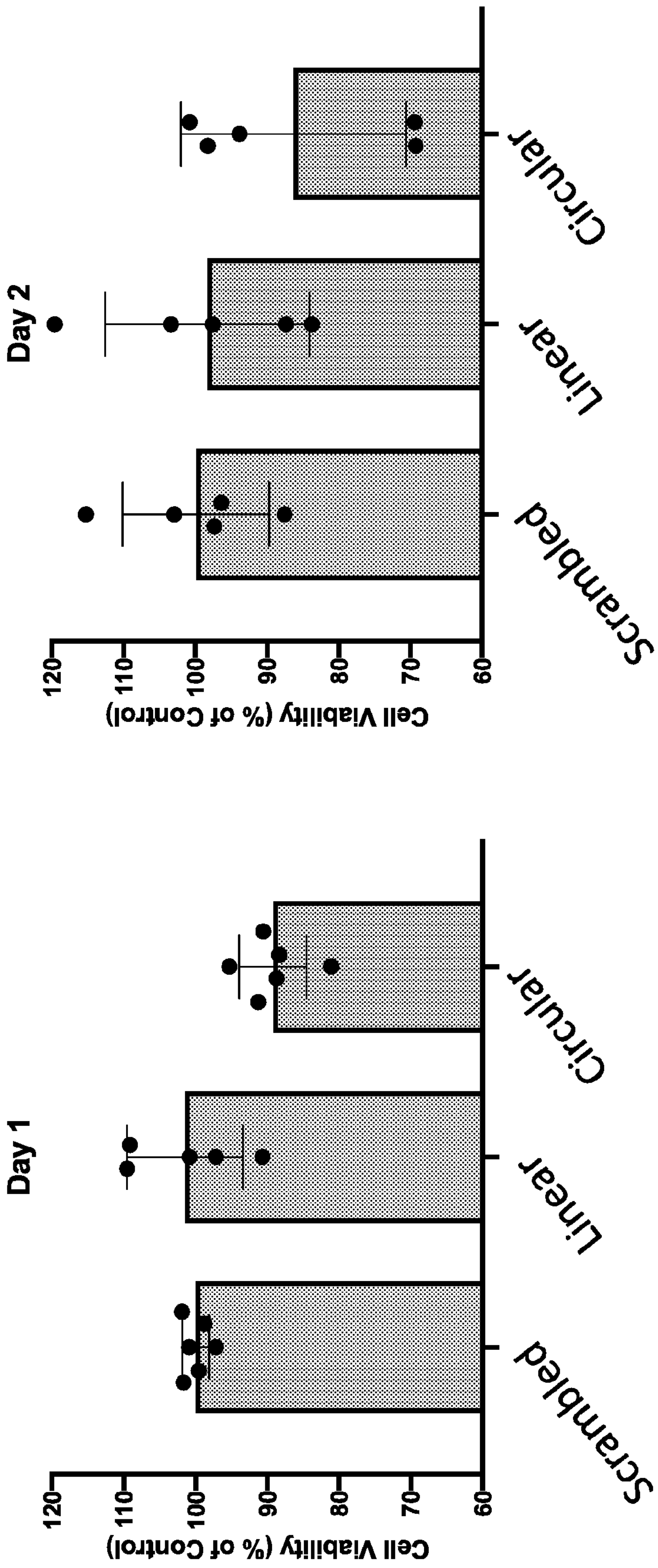
FIG. 16 shows that treatment with circular RNA with the NF-kB binding aptamer sequence led to a decrease in cell viability of A549 cells as compared to its linear counterpart.

The effect of NF-kB sequestration in non-small cell lung cancer (NSCLC) cell line, A549s, was was determined after delivery of a circular RNA targeting NF-kB for sequestration. Cell viability was determined by MTT Assay (Thermo Scientific, V13154). In short, A549 cells were transfected with 1 pmole of linear, linear scrambled, or circular RNA after complexation with lipid transfection reagent (Thermo Scientific, LMRNA003). Viability was measured by MTT assay performed according to the manufacturer's instructions As demonstrated in FIG. 16, cells treated with linear RNA demonstrated no change in viability at day 1 and a slight decrease in viability at day 2 (101% viability on Day 1, and 97% on Day 2). In contrast, cells treated with the circular RNA demonstrated a measurable decrease in viability at day 1 and greater increase by day 2 (89% on Day 1 and 86% on Day 2).

Overall, the results demonstrated that circular NFkB RNA aptamer in cells and inhibited NF-kB activation of survival pathways to affect cell viability.

Example 15: Circular RNA Increased Sensitivity of Cancer Cells to Chemotherapeutic Via Protein Sequestration This Example demonstrates circular RNA binds to a target protein in cells leading to the inhibition of signaling pathways. As shown in the following Example, the circular RNA re-sensitized cancer cells to a chemotherapeutic.

Linear, linear scrambled, and circular RNA were designed and synthesized as previously described.

Re-sensitization of doxorubicin to the NSCLC cell line, A549s, via a circular aptamer than inhibition NF-kB signaling was determined by measuring the cell killing by MTT Assay (Thermo Scientific, V13154). In short, A549 cells were transfected with 1 pmole of a scrambled linear control, linear, or circular RNA after complexation with lipid transfection reagent (Thermo Scientific, LMRNA003). 24 hours post-transfection cells were treated with 5 uM Doxorubicin for an additional 18 hours. Viability was measured by MTT assay performed according to the manufacturer's instructions. Doxorubicin treatment scheme was repeated and 48- and 72-hours post aptamer transfection.

Figure 17:
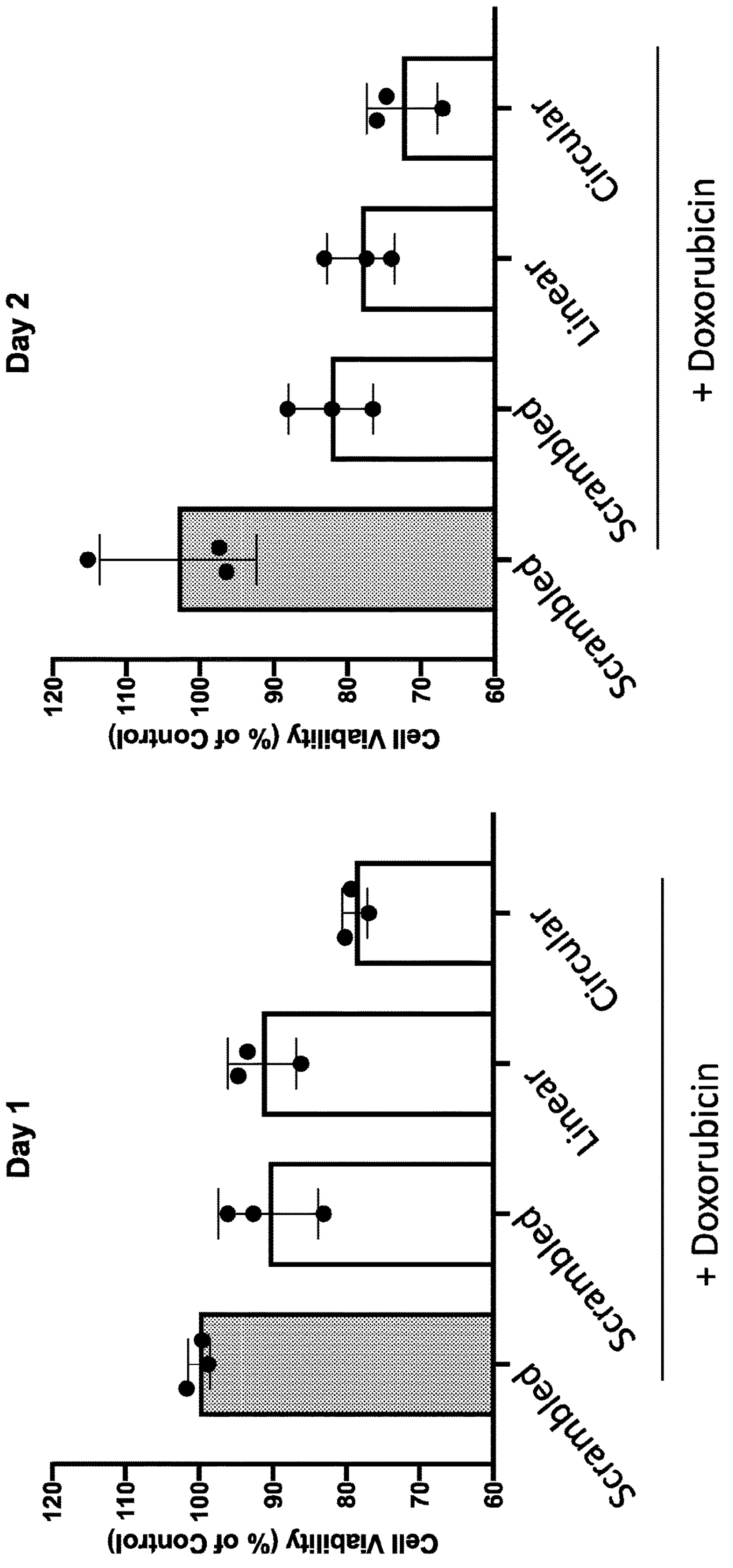
FIG. 17 shows co-treatment with linear RNA and doxorubicin (dox) decreased cell viability at day 2 and co-treatment with the circular aptamer and dox resulted in more cell death at both days 1 and 2 in the dox-resistant A549 lung cancer cell line.

As demonstrated in FIG. 17, Doxorubicin treatment with scrambled linear RNA (control) did not induce cell death in Dox-resistant A549 lung cancer cell line at day 1. Co-treatment of doxorubicin with linear RNA decreased cell viability at day 2 (78% survival). In contrast, co-treatment with the circular aptamer resulted in more cell death at both days 1 and 2 (79% survival at day 1 and 73% survival at day 2).

Overall, our results demonstrate that circular RNA binds NFkB in cells and thereby increasing sensitivity of cancer cells to the chemotherapeutic, Doxorubicin. Additionally, circular NFkB RNA aptamer was more stable than a linear RNA aptamer and thereby drove the cellular effect for a prolonged period.

Example 16: Circular RNA Bound a Small Molecule Longer than its Linear Counterpart This Example demonstrates circular RNA binding a small molecule for sequestration/bio-activity. As shown in the following Example, the circular RNA is more stable than its linear counterpart.

Linear mango RNA aptamers fluoresce when bound by a small molecule, TO-1 biotin dye. As shown in the following Example, circular Mango RNA bound to the thiazol orange derivative, TO-1 biotin for sequestration/bio-activity.

Circular RNA was designed to include the mango RNA small molecule binding sites and a stabilizing stem: 5'-AATAGCCG GUCUACGGCC AUACCACCCU GAACGCGCCC GAUCUCGUCU GAUCUCGGAAGC-UAAGCAGG GUCGGGCCUG GUUAGUACUU GGAUGGGAGA CCGCCUGGGAAUACCGGGUG CUGUAGGCGU CGACUUGCCA UGUGUAUGUG GGUACGAAGGAAGGAUUGGU AUGUGGUAUA UUCGUACCCA CAUACUCUGA UGAUCCUUCG GGAUCAUUCA UGGCAA CGGCTATT-3', as well as circularization sequences: 5'-AATAGCCG-3' and 5'-CGGCT-ATT-3'.

Unmodified linear RNA was synthesized by in vitro transcription using T7 RNA polymerase from a DNA segment comprising the Mango RNA motif, stems and circularization sequences. Transcribed RNA was purified with an RNA cleanup kit (New England Biolabs, T2050), treated with RNA 5'-phosphohydrolase (RppH, New England Biolabs, M0356) following the manufacturer's instructions, and purified again with the RNA purification column. RppH treated RNA was circularized using a splint DNA complementary to the circularization sequences and T4 RNA ligase 2 (New England Biolabs, M0239). Circular RNA was Urea-PAGE purified, eluted in a buffer containing (0.5M Sodium Acetate, 0.1% SDS, 1 mM EDTA, ethanol precipitated and resuspended in RNase free water. RNA quality was assessed by Urea-PAGE or through automated electrophoresis (Agilent).

Figure 18:
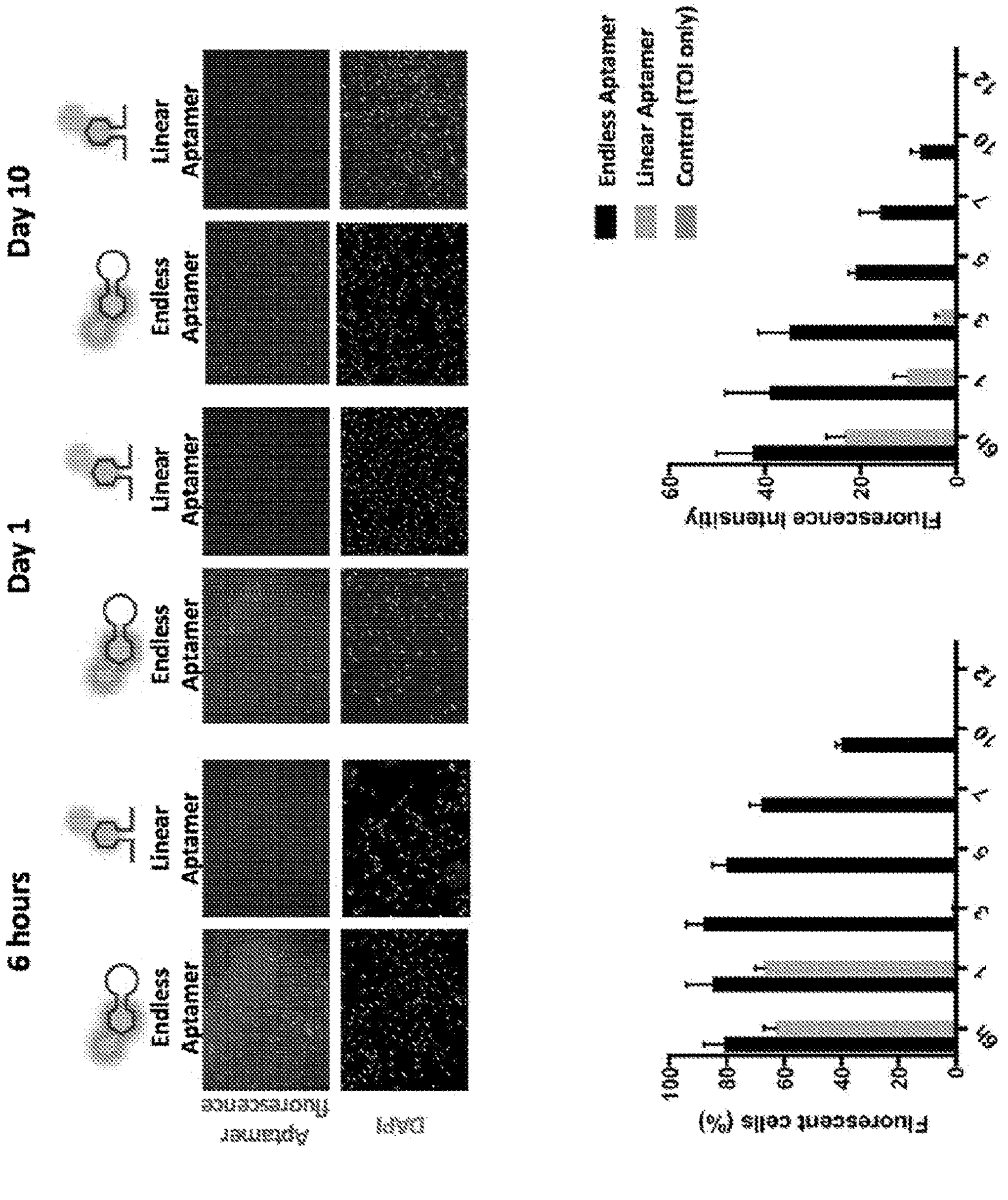
FIG. 18 shows aptamer fluorescence when bound to TO-1 biotin at different time points after delivery of the circular RNA (endless aptamer) or the linear RNA (linear aptamer) to HeLa cell cultures. The fluorescent images (top) show aptamer fluorescence when bound to TO-1 biotin at 6 hours, Day 1, and Day 10 after delivery of the the circular RNA (endless aptamer) or the linear RNA (linear aptamer). The graphs (bottom) show the percentage of fluorescent cells in the HeLa cell cultures at 6 hours, Day 1, Day 3, Day 5, Day 7, Day 10, and Day 12 after delivery of the the circular RNA (endless aptamer), the linear RNA (linear aptamer), or the TO-1 biotin only (control).

Circular RNA binding to TO-1 biotin was evaluated in vitro in HeLa cells, using fluorescent microscopy. When TO-1 biotin was bound to RNA it enhanced its fluorescence more than 100-fold. Linear or circular aptamers (50 nM) were added to the media of BJ fibroblast cultures, as well as a no-RNA control. A transfection reagent, lipofectamine, was added to ensure RNA delivery. Cultures were treated with TO-1 biotin and fluorescence was analyzed at 6 h and days 1-12. As shown in FIG. 18, increased fluorescence/stability was detected from the circular aptamer, with fluorescence detected at least for 10 days in culture.

Example 17: Circular RNA Brought Protein and RNA into Proximity

This Example demonstrates circular RNA binding to protein and RNA for sequestration.

Human antigen receptor (HuR) plays a central role in mRNA fate and a key role in post-transcriptional regulation of mRNA. HuR is an important protein in pathogenesis, e.g., it can alter the way cells react to apoptotic, differentiative, proliferative, stress, senescence, inflammatory and immune stimuli. It is known to bind and stabilize cancer related mRNA transcripts, such as mRNAs for proto-oncogenes, cytokines, growth factors, and invasion factors. HuR has a central tumorigenic activity by enabling multiple cancer phenotypes.

RNA plays a central role in cell metabolism and RNA molecules undergo multiple post-transcriptional processes such as splicing, editing, modification, translation, and degradation. A defect, mis-regulation, or malfunction of these processes often results in "RNA diseases", including cancer.

As shown in the following Example, circular RNA bound to HuR and RNA for sequestration.

Circular RNA was designed to include the HuR RNA binding aptamer motif: 5'-UCAUAAUCAA UUUAUUAUUUUCUUUUAUUUUAUUCA-CAUAAUUUUGUUUUU-3' to competitively bind HuR and inhibit its binding/downstream functions and the RNA binding aptamer motif: 5'-CGA GAC GCT ACG GAC TTA AAA TCC GTT GAC-3'.

Unmodified linear RNA was synthesized by in vitro transcription using T7 RNA polymerase from a DNA segment comprising the HuR RNA motif and protein binding sequence.

Transcribed RNA was purified with an RNA cleanup kit (New England Biolabs, T2050), treated with RNA 5'-phosphohydrolase (RppH, New England Biolabs, M0356) following the manufacturer's instructions, and purified again with the RNA purification column. RppH treated RNA was circularized using a splint DNA complementary to the circularization sequences and T4 RNA ligase 2 (New England Biolabs, M0239). Circular RNA was Urea-PAGE purified, eluted in a buffer containing (0.5M Sodium Acetate, 0.1% SDS, 1 mM EDTA, ethanol precipitated and resuspended in RNase free water. RNA quality was assessed by Urea-PAGE or through automated electrophoresis (Agilent).

Circular RNA binding to HuR and RNA was evaluated in vitro by a combination of HuR immunoprecipitation (IP) and Biotin RNA pull-down assay, followed by qPCR. HuR protein-coupled to Protein G-anti HuR antibody was incubated with circular RNA, washed and eluted at low pH. Bound material was incubated with biotinylated RNA, washed and pulled down with streptavidin dynabeads.

Figure 19:
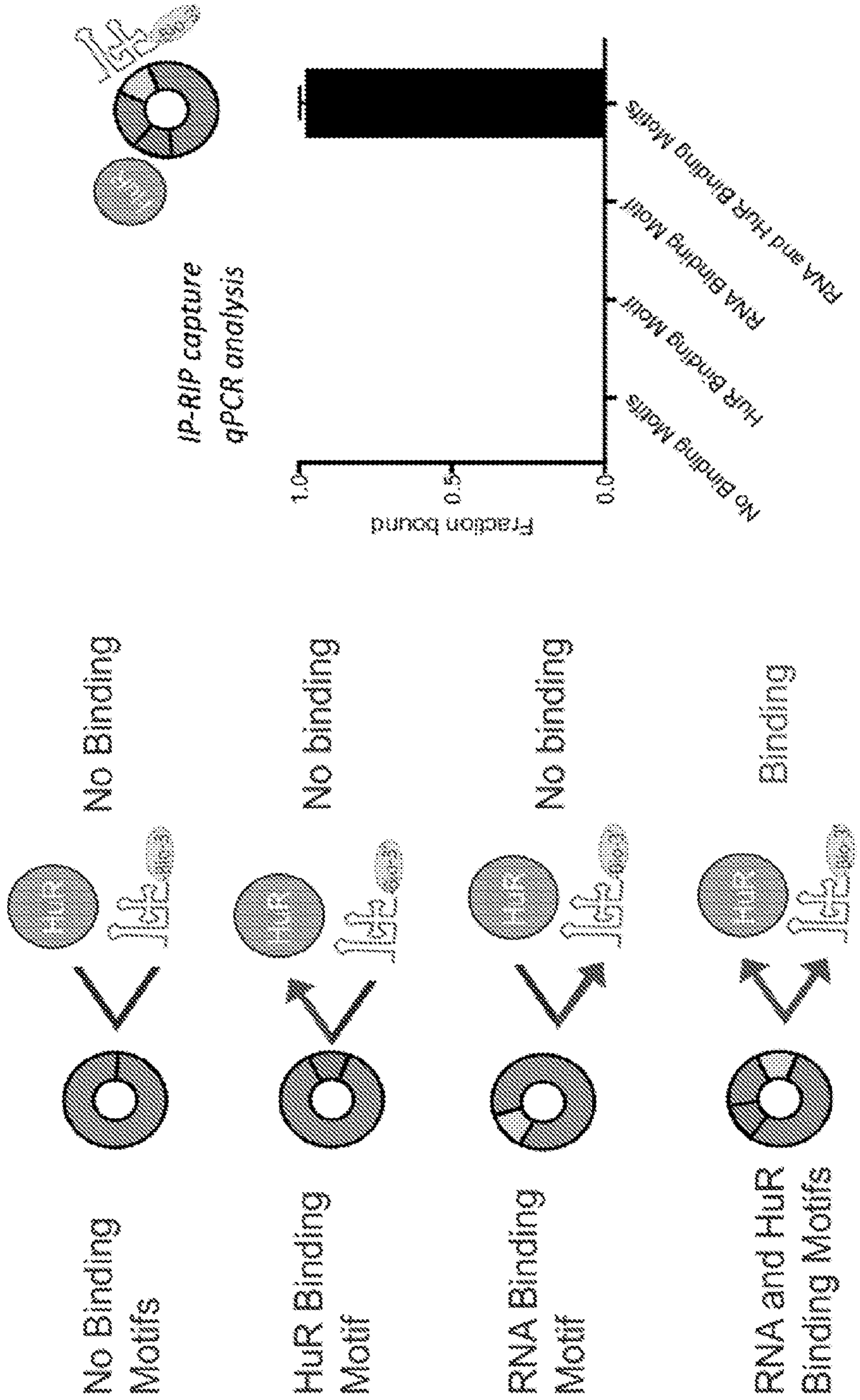
FIG. 19 shows HuR bound circular RNAs with a HuR RNA binding aptamer motif and the streptavidin pull-down yielded RNAs with the RNA binding aptamer motifs compared to a circular RNA with no binding aptamer motifs, a circular RNA with a HuR RNA binding aptamer motif, and a circular RNA with an RNA binding aptamer motif.

HuR bound circular RNAs with the HuR RNA binding aptamer motif and the streptavidin pull-down yielded RNAs with the RNA binding aptamer motifs as shown in FIG. 19. Thus binding was observed when the two, HuR and RNA, binding motifs were present. This result demonstrated that biomolecules of interests were selectively bound.

Example 18: Circular RNA Brought Protein and DNA into Proximity

This Example demonstrates circular RNA binding to protein and DNA for sequestration.

DNA binding by proteins and RNAs plays a pivotal role in different cellular processes, i.e., transcription.

Human antigen receptor (HuR) plays a central role in mRNA fate and a key role in post-transcriptional regulation of mRNA. HuR is an important protein in pathogenesis, e.g., it can alter the way cells react to apoptotic, differentiative, proliferative, stress, senescence, inflammatory and immune stimuli. It is known to bind and stabilize cancer related mRNA transcripts, such as mRNAs for proto-oncogenes, cytokines, growth factors, and invasion factors. HuR has a central tumorigenic activity by enabling multiple cancer phenotypes.

Targeting and competing these contacts with circular RNA could be used to modulate these interactions and control outcomes in disease and non-disease processes.

Circular RNA was designed to include the DNA binding aptamer motif: 5'-CGA GAC GCT ACG GAC TTA AAA TCC GTT GAC-3' RNA.

Unmodified linear RNA was synthesized by in vitro transcription using T7 RNA polymerase from a DNA segment. Transcribed RNA was purified with an RNA cleanup kit (New England Biolabs, T2050), treated with RNA 5'-phosphohydrolase (RppH, New England Biolabs, M0356) following the manufacturer's instructions, and purified again with the RNA purification column. RppH treated RNA was circularized using a splint DNA complementary to the circularization sequences and T4 RNA ligase 2 (New England Biolabs, M0239). Circular RNA was Urea-PAGE purified, eluted in a buffer containing (0.5M Sodium Acetate, 0.1% SDS, 1 mM EDTA, ethanol precipitated and resuspended in RNase free water. RNA quality was assessed by Urea-PAGE.

Circular RNA binding to DNA and HuR was evaluated in vitro by a combination of HuR immunoprecipitation (IP) and biotinylated DNA pull-down assay, followed by RT-qPCR. Circular RNA lacking the DNA binding motif or HuR motif was used as a specificity control. The biotinylated DNA bound circular RNAs with the DNA binding aptamer motif.

Figure 20:
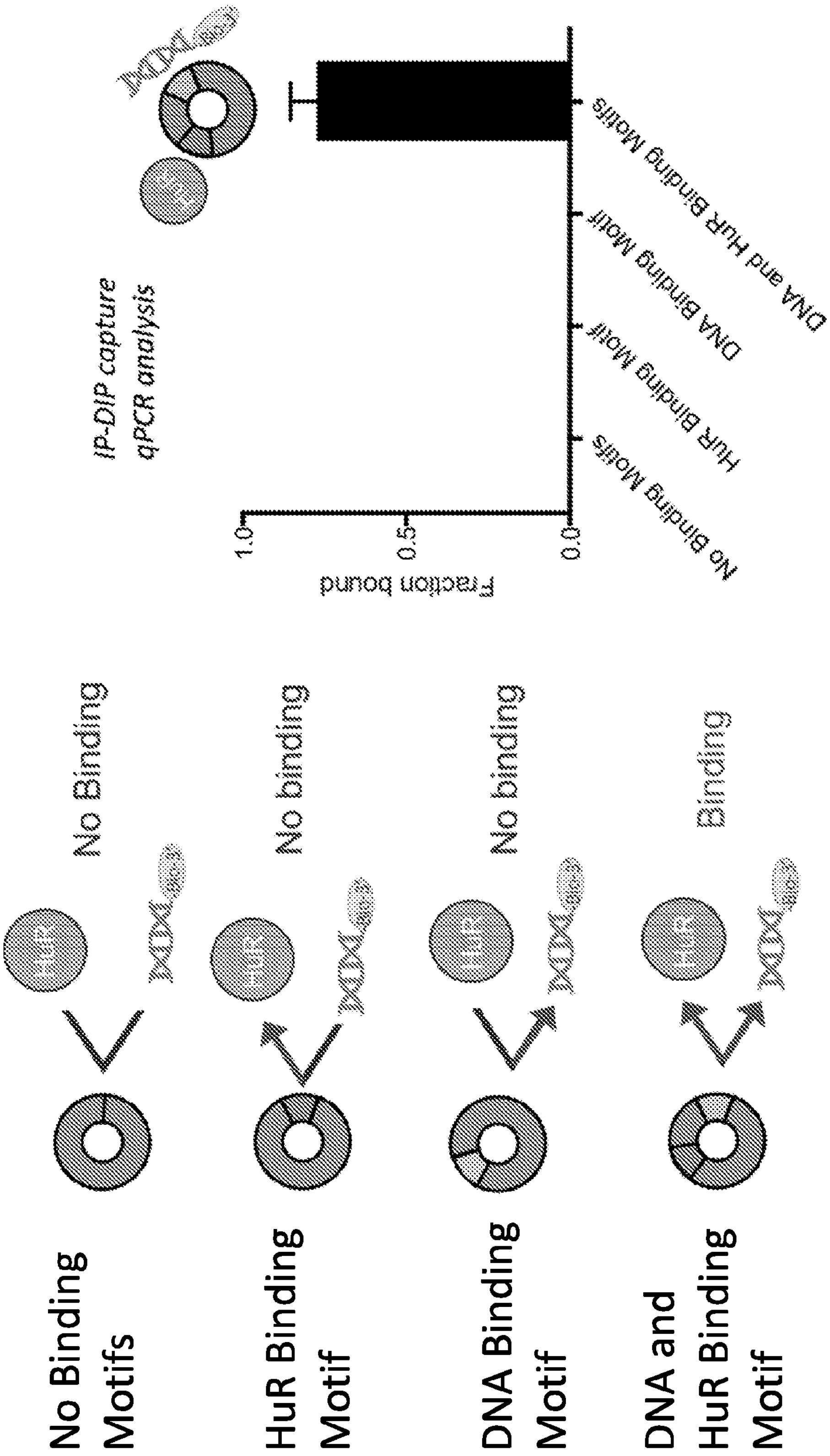
FIG. 20 shows HuR bound circular RNAs with the HuR DNA binding aptamer motif and the streptavidin pull-down yielded RNAs with the DNA binding aptamer motifs compared to a circular RNA with no binding apatmer motifs, a circular RNA with a HuR DNA binding aptamer motif, and a circular RNA with DNA.

HuR protein-coupled to Protein G-anti-HuR beads was incubated with the circular RNA, washed and eluted at low pH. Bound material was incubated with biotinylated DNA, washed and pulled down with streptavidin Dynabeads. HuR bound circular RNAs with the HuR DNA binding aptamer motif and the streptavidin pull-down yielded RNAs with the DNA binding aptamer motifs as shown in FIG. 20. Thus, binding was observed when the two, HuR and DNA, binding aptamer motifs were present. This result demonstrated protein and DNA molecules of interests were selectively bound to the same circular construct.

Example 19: Circular RNA Translated a Protein, and Bound to a Different Protein that Affected its Translation This Example demonstrates circular RNA encoding a protein and binding a different protein that has an effect in circular RNA translation.

Human antigen receptor (HuR) plays a central role in mRNA fate and plays a key role in post-transcriptional regulation of mRNA targets with central cellular functions. Thus, using HuR to control RNA expression may provide control over translated protein dosage.

As shown in the following Example, a non-naturally occurring circular RNA was engineered to encode *Gaussia* Luciferase (GLuc), a biologically active secreted protein and to bind HuR to regulate GLuc. translation. This circular RNA included an IRES, an ORF encoding *Gaussia* Luciferase, two spacer elements flanking the IRES-ORF and 1×, 2× or 3×HuR binding aptamer motifs: 5'-UCA UAA UCA AUU UAU UAU UUU CUU UUA UUU UAU UCA CAU AAU UUU GUU UUU-3', 5'-AUU UUG UUU UUA ACA UUUC-3', 5'-UCA UAA UCA AUU UAU UAU UUU CUU UUA UUU UAU UCA CAU AAU UUU GUU UUU AUU UUG UUU UUA ACA UUU C-3' to bind HuR.

Unmodified linear RNA was synthesized by in vitro transcription using T7 RNA polymerase from a DNA segment comprising the HuR RNA motif and protein binding sequence.

Transcribed RNA was purified with an RNA cleanup kit (New England Biolabs, T2050), treated with RNA 5'-phosphohydrolase (RppH, New England Biolabs, M0356) following the manufacturer's instructions, and purified again with the RNA purification column. RppH treated RNA was circularized using a splint DNA complementary to the circularization sequences and T4 RNA ligase 2 (New England Biolabs, M0239). Circular RNA was Urea-PAGE purified, eluted in a buffer containing (0.5M Sodium Acetate, 0.1% SDS, 1 mM EDTA, ethanol precipitated and resuspended in RNase free water. RNA quality was assessed by Urea-PAGE or through automated electrophoresis (Agilent).

Circular RNA binding to HuR was determined by in vitro RNA pull-down assay as described previously.

To evaluate the effect of HuR binding and its effect on circular RNA protein expression in cells, $5\times10^3$ HeLa cells were successfully reverse transfected with a lipid-based transfection reagent (Invitrogen) and 2 nM of circular RNA. *Gaussia* Luciferase activity was monitored daily for up to 96h in cell culture supernatants, as a measure of expression, using a *Gaussia* Luciferase assay kit and following manufacturer's instructions.

Figure 21:
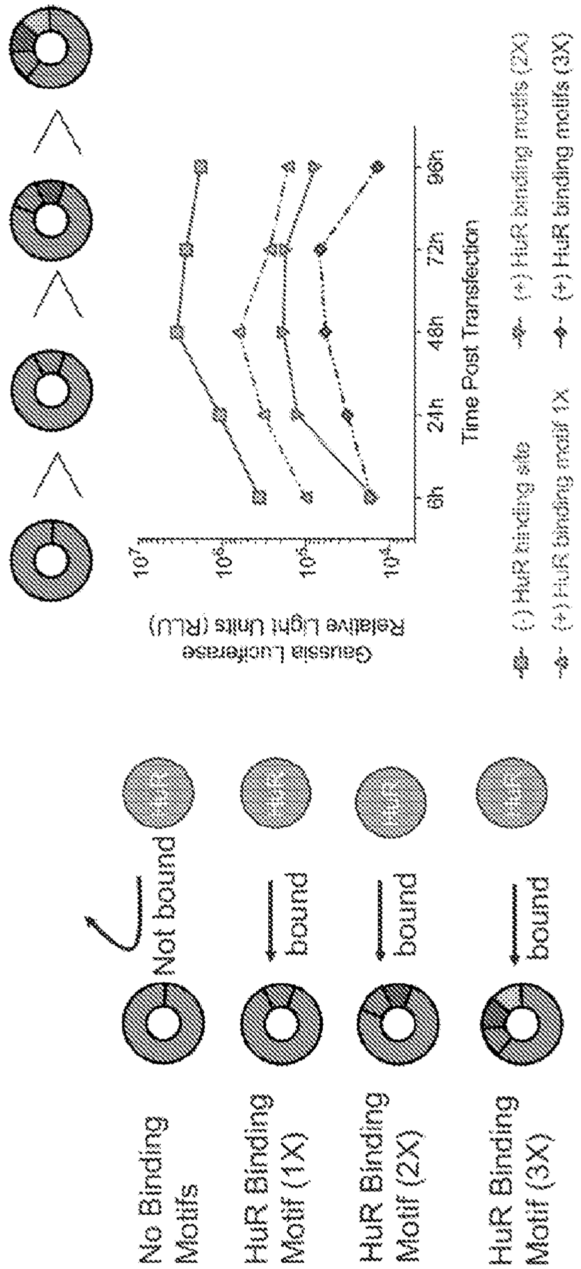
FIG. 21 shows lower secreted protein expression from circular RNA without a HuR binding motif compared to a circular RNA with 1×HuR binding motif, 2×HuR binding motifs, and 3×HuR binding motifs.

FIG. 21 shows lower secreted protein expression from circular RNA with HuR binding aptamer sites. Even more, the GLuc expression levels changed with the number of HuR binding aptamer motifs in the circular RNA. This example demonstrates that the level of translation from the engineered circular RNA was affected by additional protein binding aptamers.

Example 20: Circular RNA with that Tags the Target Protein for Degradation Leads to a Reduction of Cell Viability by Inducing Apoptosis in Cervical Cancer Cell This Example demonstrates circular RNA linked to small molecules that recruits two different proteins of choice and thereby tags the target protein for degradation and reduces cell viability by inducing apoptosis in tumor cell.

As shown in the following Example, two small molecule (thalidomide and JQ1) were conjugated to a circular RNA to bind (1) E3 ubiquitin ligase Cereblon [for ubiquitination and subsequent degradation of a neighboring protein] (2) BRD4 through JQ1 that is small molecule inhibitor to bind BET family proteins, respectively.

BRD4, member of the Bromodomain and Extraterminal (BET) protein family, is largely acknowledged in cancer for its role in super-enhancers (SEs) organization and oncogenes expression regulation. Inhibition of BRD4 shortcuts the communication between SEs and target promoters with a subsequent cell-specific repression of oncogenes to which cancer cells are addicted and cell death.

Circular RNA was designed to include 49 reactive was designed to include 49 reactive uridine residues (e.g., 5-azido-C3-UTP) for conjugation of alkyne-functionalized small molecules, known to interact with an intracellular protein of interest.

Linear RNA was synthesized by in vitro transcription using T7 RNA polymerase (Lucigen). All UTP was substituted with 5-azido-C3-UTP (Jena Biosciences) in the in vitro transcription reaction to generate azide-functionalized RNA. Synthesized linear RNA was purified with an RNA clean up kit (New England Biolabs) and subjected to RNA 5' Pyrophosphohydrolase (RppH, New England Biolabs) treatment to remove pyrophosphate. RppH-treated linear RNA was purified with an RNA clean up kit (New England Biolabs).

Circular RNA was generated by splint ligation. RppH-treated linear RNA (100 uM) and splint DNA (5'-GGTGGCTCCCTGGCGCTGTT-3') (200 uM) was annealed by heating at 75° C. for 5 min and gradual cooling at room temperature for 20 min. Ligation reaction was performed with T4 RNA ligase 2 (0.2 U/uL, New England Biolabs) for 4 hours at 37° C. The ligated mixture was purified by ethanol precipitation. To isolate circular RNA, the ligated mixture was separated on 4% denaturing UREA-PAGE. RNA on the gel was stained with SYBR-green (Thermo Fisher) and visualized with transilluminator (Transilluminators). Corresponding RNA bands for circular RNA were excised and crushed by gel breaker tubes (Ist Engineering). For elution of circular RNA, crushed gels with circular RNA were incubated with elution buffer (0.5 M Sodium Acetate, 1 mM EDTA, 0.1% SDS) at 37° C. for an hour and supernatant was carefully harvested. The remaining crushed gel was subjected to another round of elution, and repeated total three times. Elution buffer with circular RNA was filtrated through a 0.45 um cellulose acetate filter to remove gel debris and circular RNA was purified/concentrated by ethanol precipitation.

Alkyne-functionalized thalidomide and JQ1 (Jena Bioscience) was conjugated to azide-functionalized circular RNA via Copper-catalyzed Azide-Alkyne click chemistry reactions (CuAAC) with the click chemistry reaction kit based on manufacturer's instructions (Jena Bioscience). Small molecule-conjugated circular RNA was purified with an RNA clean up kit (New England Biolab).

Conjugated RNAs were then transfected into cervical cancer cells (HeLa cells) to monitor the consequence of degradation of target protein using by MessengerMax (Invitrogen) according to the manufacturer's instruction. Different concentration of RNA was used to transfect into 10,000 cells and plated to 96 well plates (0.01 pmole, 0.05 pmole, 0.1 pmole, 0.3 pmole). Carrier only and circular RNA without conjugation were used as negative controls.

48 hours after transfection, cell viability was monitored by CellTiter-Glo 2.0 (Promega, G9241) and caspase activity was monitored by Caspase Glo 3/7 assay system (Promega, G8090).

Figure 22:
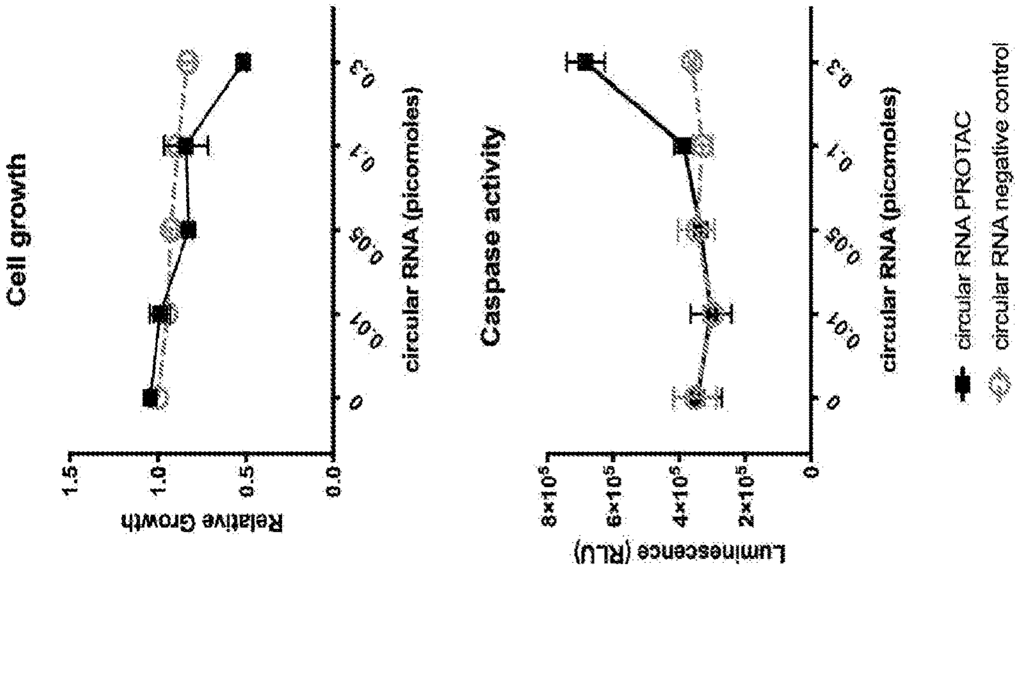
FIG. 22 shows circular RNA containing the thalidomide and JQ1 small molecules (PROTAC) activates caspase activity and reduces cervical cancer cell growth.

As shown in FIG. 22, circular RNA containing the thalidomide and JQ1 small molecules activated caspase activity about 2 folds when compared with same amount of transfected unconjugated circular RNA. Additionally, circular RNA containing the thalidomide and JQ1 reduced cell growth by 50% after 48 hour transfection indicating circular RNA designed to degrade BRD4 inhibits cervical cancer cell growth by activating apoptosis.

Example 21: Circular RNA Encoding an Aptamer to a Substrate Protein and Conjugated to an E3 Ubiquitin Ligase Recruiting Small Molecule Binds to Corresponding Proteins This Example demonstrates circular RNA conjugated to a small molecule and encoding an aptamer binds and recruits a protein of choice.

As shown in the following Example, a small molecule was conjugated to a circular RNA encoding an aptamer against NFkB protein to bind both E3 ubiquitin ligase Cereblon and NFkB protein.

Figure 23:
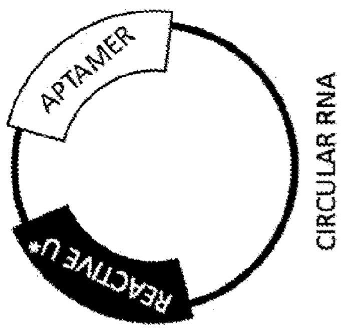
FIG. 23 shows circular RNA including an NFkB aptamer and 10 reactive uridine residues (e.g., 5-azido-C3-UTP) for conjugation of alkyne-functionalized thalidomide on a single circular RNA.

In the following Example, circular RNA was designed to include NFkB aptamer and a second RNA component with 10 reactive uridine residues (e.g., 5-azido-C3-UTP) for conjugation of alkyne-functionalized thalidomide (shown in FIG. 23). To generate circular RNA, two IVT templates were amplified separately. The aptamer component includes NFkB aptamer and two annealing regions (16 nt and 13 nt long) at each the 5' and 3' end, respectively. The reactive uridine component harbors 10 reactive uridine residues and two 15 nt long annealing region at each the 5' and 3' end. The NFkB aptamer component was generated as linear RNA with unmodified nucleotide through in vitro transcription. The reactive uridine component was generated as linear RNA and was fully substituted with 5-azido-C3-UTP.

Transcribed RNA was purified with an RNA cleanup kit (New England Biolabs, T2050) and RppH treated to generate monophosphated RNA (NEB, M0356). After purification with RNA cleanup kit (New England Biolabs, T2050) RNAs were subjected to RNA-RNA ligation. Aptamer component and reactive uridine component RNAs were annealed with the splint DNA in the presence of 2 uM of each component, 2.56 uM of splint DNA (5'-CCCGGTTGCCGTTCCAATAGCCGTTTTG-3'), 50 mM NaCl. This mixture was incubated at 75° C. for 10 min and then slowly cooled down to 37° C. The mixture was further incubated for ligation in the presence of 50 mM Tris-HCl, 10 mM $MgCl_2$, 1 mM ATP, 1 mM DTT, 0.16 U/uL RNase inhibitor (Promega, N2115) and 15 U/uL T4 DNA ligase (NEB, M0202M) for 4 hours. Ligated RNA was purified with Monarch RNA purification column (NEB, T2050). The efficiency of RNA-RNA ligation was monitored by separating on Urea-PAGE.

For circularization, ligation mixture was prepared with 1 uM of RNA-RNA ligated RNA, 2 uM of circularization splint DNA (5'-GTTTTTCGGCTATTCCGGTGGCTCTCGGTCT-3'), 50 mM Tris-HCl, 2 mM $MgCl_2$ and 400 uM ATP. This mixture was heated at 75° C. for 10 min and slowly cooled down at room temperature for 20 min. After cooled down, 0.2 U/uL of T4 RNA ligase 2 (NEB, M0239) and 0.4 U/uL of RNAse inhibitor (Promega, N2115) were added and incubated for 4 hours. Ligated RNA was purified with EtOH precipitation. Circular RNA was Urea-PAGE purified, eluted in a buffer (0.5 M Sodium Acetate, 0.1% SDS, 1 mM EDTA), ethanol precipitated and resuspended in RNase free-water.

Alkyne-functionalized thalidomide (Jena Bioscience) was conjugated to azide-functionalized circular RNA via Copper-catalyzed Azide-Alkyne click chemistry reactions (CuAAC) with the click chemistry reaction kit based on manufacturer's instructions (Jena Bioscience). Small molecule-conjugated circular RNA was purified with an RNA clean up kit (New England Biolab).

The thalidomide-conjugated circular RNA encoding an NFkB aptamer was assessed for binding to proteins of choice by GST pull-down followed by western blot. For the GST pull-down, thalidomide-conjugated circular RNA with aptamer (2 nM) was incubated with GST-E3 ubiquitin ligase Cereblon (10 nM) and NFkB p50 protein (10 nM) for 2 hours at room temperature in the presence of 25 mM Tris-Cl (pH 7.0), 100 mM NaCl, 1 mM MgCl2, 1 mM EDTA, 0.5% NP-40, 5% Glycerol.

GST protein instead of GST-Cereblon or azide-functionalized circular RNA without thalidomide conjugation in the presence of GST-Cereblon was used as a negative control.

The RNA-protein mixture was further incubated for an hour at room temperature with GSH-agarose beads to assess GST-GSH interactions. After washing three times with binding buffer, the proteins specifically bound to the GSH-beads was extracted with NuPAGE LSD sample buffer (Thermo Fisher Scientific).

The extracted protein was separated on 4-12% Bis-Tris gels (Thermo Fisher Scientific) and transferred to Nitrocellulose membrane by iBlot2 transfer system (Thermo Fisher Scientific). GST and GST-Celebron were detected by anti-GST antibody (Abcam) and NFkB was detected by anti-NFkB p50/p105 antibody (Abcam).

Figure 24:
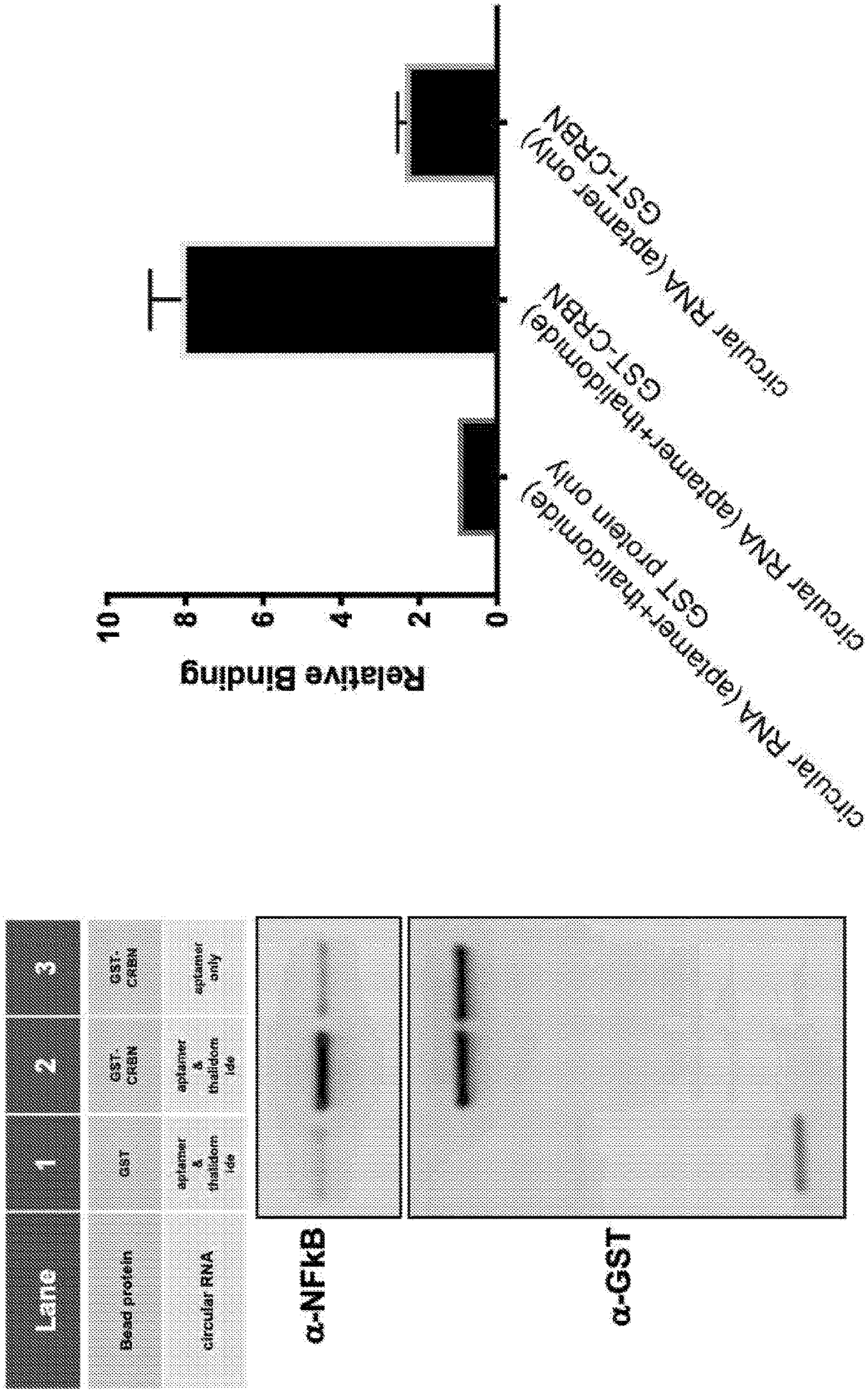
FIG. 24 shows circular RNA with a small molecule and aptamer can recruit target and substrate proteins simultaneously.

NFkB protein was highly enriched only when it was incubated with circular RNA conjugated to the thalidomide small molecule and GST-Celebron, demonstrating that circular RNA with a small molecule and aptamer can recruit aptamer binding protein and small molecule binding protein simultaneously (FIG. 24).

Example 22: Circular RNA Conjugated to Thalidomide and JQ1 Tags BRD4 for Degradation Leading to a Reduction of Cell Growth in Prostate Cancer Cells This Example demonstrates circular RNA conjugated to two small molecules that each recruit a protein of choice (a target protein and a degrader protein), is able to tag the target protein for degradation inducing apoptosis and resulting in a reduction of cell growth.

As shown in the following Example, two small molecule (thalidomide and JQ1) were conjugated to a circular RNA to bind (1) E3 ubiquitin ligase Cereblon [for ubiquitination and subsequent degradation of a neighboring protein], and (2) BRD4 through JQ1, a small molecule inhibitor to bind BET family proteins, respectively.

BRD4, a member of the Bromodomain and Extraterminal (BET) protein family, is known in cancer for its role in super-enhancers (SEs) organization and oncogenes expression regulation. Inhibition of BRD4 shortcuts the communication between SEs and target promoters with a subsequent cell-specific repression of oncogenes to which cancer cells are addicted and cell death.

In this example, circular RNA (SEQ ID NO: 1) was designed to include multiple (49 residues) reactive uridine residues (e.g., 5-azido-C3-UTP) for conjugation of alkyne-functionalized small molecules, known to interact with an intracellular protein of interest.

To generate circular RNA, linear RNA was synthesized by in vitro transcription using T7 RNA polymerase (Lucigen). All UTP was substituted with 5-azido-C3-UTP (Jena Biosciences) in the in vitro transcription reaction to generate azide-functionalized RNA. Synthesized linear RNA was purified with an RNA clean up kit (New England Biolabs) and subjected to RNA 5' Pyrophosphohydrolase (RppH, New England Biolabs) treatment to remove pyrophosphate. RppH-treated linear RNA was purified with an RNA clean up kit (New England Biolabs). RNA was circularized by splint ligation. RppH-treated linear RNA (100 uM) and splint DNA (5'-GGTGGCTCCCTGGCGCTGTT-3') (200 uM) was annealed by heating at 75° C. for 5 min and gradual cooling at room temperature for 20 min. Ligation reaction was performed with T4 RNA ligase 2 (0.2 U/uL, New England Biolabs) for 4 hours at 37° C. The ligated mixture was purified by ethanol precipitation.

To isolate circular RNA, the ligated mixture was separated on 4% denaturing UREA-PAGE. RNA on the gel was stained with SYBR-green (Thermo Fisher) and visualized with transilluminator (Transilluminators). Corresponding RNA bands for circular RNA were excised and crushed by gel breaker tubes (Ist Engineering). For elution of circular RNA, crushed gels with circular RNA were incubated with elution buffer (0.5 M Sodium Acetate, 1 mM EDTA, 0.1% SDS) at 37° C. for one hour and supernatant was harvested. The remaining crushed gel was subjected to another round of elution, and repeated total three times. Elution buffer with circular RNA was filtrated through a 0.45 um cellulose acetate filter to remove gel debris and circular RNA was purified/concentrated by ethanol precipitation.

Alkyne-functionalized thalidomide and JQ1 (Jena Bioscience) was conjugated to azide-functionalized circular RNA via Copper-catalyzed Azide-Alkyne click chemistry reactions (CuAAC) with the click chemistry reaction kit based on manufacturer's instructions (Jena Bioscience). Small molecule-conjugated circular RNA was purified with an RNA clean up kit (New England Biolab).

Conjugated RNAs were then transfected into prostate cancer cells (22Rv1 cells) to monitor the consequence of degradation of target protein using by MessengerMax (Invitrogen) according to the manufacturer's instruction. Briefly, cells were plated to the 96 well plate (10,000 cells per well) a day before transfection, and MessengerMax-RNA mixture were added to the well directly. Different concentration of RNA was used to transfect into cells (0.01 pmole, 0.05 pmole, 0.1 pmole, 0.3 pmole and 0.6 pmole). Vehicle only and circular RNA without small molecule conjugation were used as negative controls.

24 hours after transfection, caspase activity was monitored by Caspase Glo 3/7 assay system (Promega, G8090). 72 hours after transfection, cell viability was monitored by CellTiter-Glo 2.0 (Promega, G9241). Images of the cells were taken by EVOS Core XL cell imaging system (Thermo Fisher Scientific) at the same time point.

Figure 25:
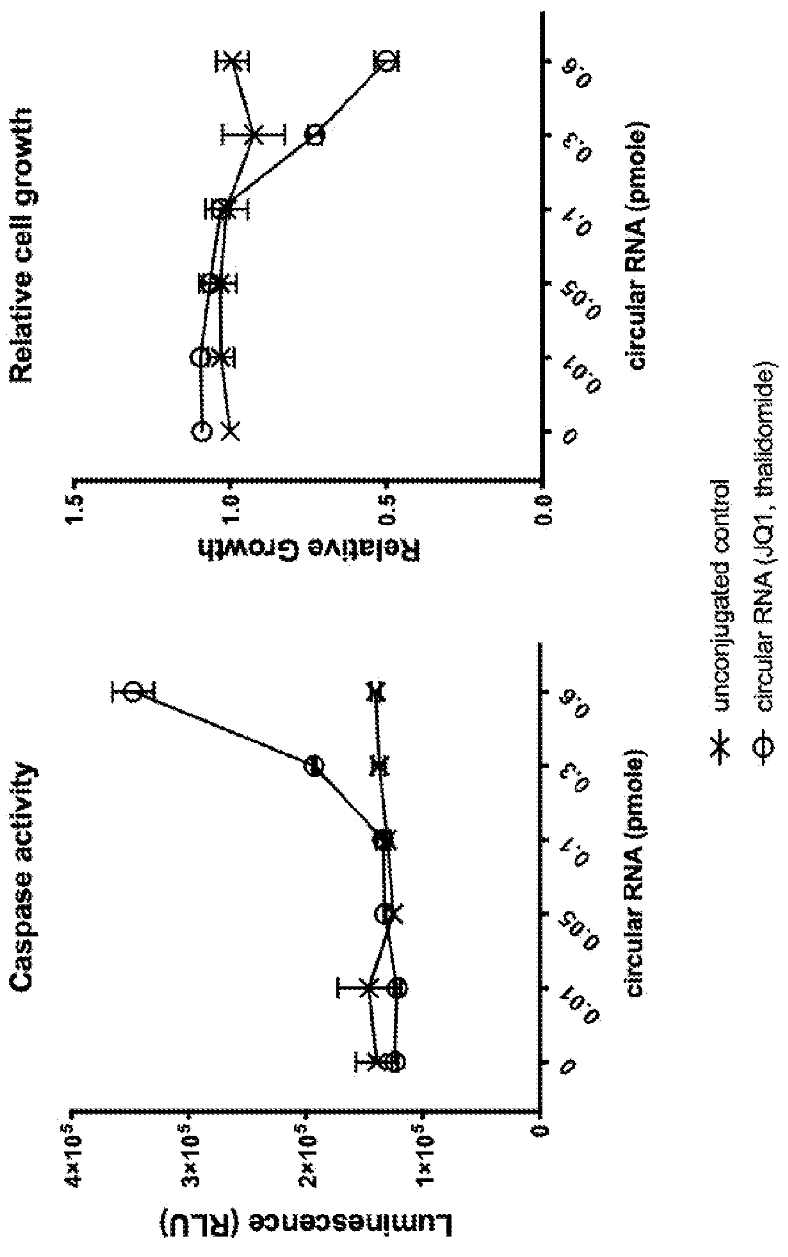
FIG. 25 shows circular RNA containing the thalidomide and JQ1 small molecules (PROTAC) activates caspase activity and reduces prostate cancer cell growth

As shown in Figure FIG. 25, circular RNA conjugated to thalidomide and JQ1 small molecules increases caspase activity ~2.5-fold compared to the unconjugated circular RNA control. Further, circular RNA conjugated to thalidomide and JQ1 reduces cell growth by 50% at 72 hours after transfection indicating that circular RNA designed to degrade BRD4 inhibits prostate cancer cell growth by activating apoptosis.

Circular RNA sequence

SEQ ID NO: 1

GGGAGCCACCATGGACTACAAGGACGACGACGACAAGATCATCGACTA

TAAAGACGACGACGATAAAGGTGGCGACTATAAGGACGACGACGACAA

AGCCATTAATAGTGACTCTGAGTGTCCCCTGTCCCACGACGGGTACTG

CCTCCACGACGGTGTGTGCATGTATATTGAAGCATTGGACAAGTACGC

CTGCAACTGTGTTGTTGGCTACATCGGGGAGCGCTGTCAGTACCGAGA

CCTGAAGTGGTGGGAACAGCGCCA

Reactive Ubiquitin Component

SEQ ID NO: 2

*GGAACGGCAACCGGG*CAAACAAACAATCAATCAATCAATCAATCAATC

AATCAATCAATCAATCAAACAAACAAAA*GACCGAGAGCCACC*

NFkB Aptamer Component

SEQ ID NO: 3

GGAATAGCCGAAAAACAAAAAGATCTTGAAACTGTTTTAAGGTTGGCC

GATCAAAAACAAAACGGCTATT

What is claimed is:

1. A complex comprising a circular polyribonucleotide bound to two or more copies of a target protein and to two or more copies of a substrate protein, wherein the target protein modulates the substrate protein thereby promoting degradation of the substrate protein, and wherein the target protein is a ubiquitin ligase.

2. The complex of claim 1, wherein the circular polyribonucleotide is bound to five or more copies of a target protein.

3. The complex of claim 2, wherein the circular polyribonucleotide is bound er to ten or more copies of the target protein.

4. The complex of claim 1, wherein the circular polyribonucleotide is bound to five or more copies of the substrate protein.

5. The complex of claim 4, wherein the circular polyribonucleotide is bound er to ten or more copies of the substrate protein.

6. The complex of claim 1, wherein the ubiquitin ligase is an E3 ubiquitin ligase.

7. The complex of claim 1, wherein the circular polyribonucleotide is bound to the two or more copies of the substrate protein by way of two or more modified nucleotides each comprising a functional group conjugated to a first chemical compound that binds the substrate protein.

8. The complex of claim 1, wherein the circular polyribonucleotide is bound to the two or more copies of the substrate protein by way of two or more modified nucleotides each comprising a functional group conjugated to a second chemical compound that binds the target protein.

9. The complex of claim 1, wherein the circular polyribonucleotide is bound to the two or more copies of the substrate protein by way of two or more binding moieties, wherein each binding moiety binds to the substrate protein.

10. The complex of claim 1, wherein the circular polyribonucleotide is bound to the two or more copies of the target protein by way of two or more binding moieties, wherein each binding moiety binds to the target protein.

11. The complex of claim 1, wherein the circular polyribonucleotide is bound to the two or more copies of the substrate protein by way of two or more modified nucleosides each comprising a functional group conjugated to a first chemical compound that binds the substrate protein, and wherein the circular polyribonucleotide is bound to the two or more copies of the target protein by way of two or more modified nucleosides each comprising a functional group conjugated to a second chemical compound that binds the target protein.

12. The complex of claim 1, wherein the circular polyribonucleotide is bound to the two or more copies of the substrate protein by way of two or more modified nucleosides each comprising a functional group conjugated to a first chemical compound that binds the substrate protein, and wherein the circular polyribonucleotide is bound to the two or more copies of the target protein by way of two or more binding moieties, wherein each binding moiety binds to the target protein.

13. A pharmaceutical composition comprising the complex according to claim 1.

14. The complex of claim 6, wherein the E3 ubiquitin ligase is a HECT ubiquitin ligase, RING-finger ubiquitin ligase, U-box ubiquitin ligase, or PHD-finger ubiquitin ligase.

* * * * *